(12) United States Patent
Goto et al.

(10) Patent No.: US 7,491,738 B2
(45) Date of Patent: Feb. 17, 2009

(54) PEST CONTROL AGENTS

(75) Inventors: Kimihiko Goto, Kanagawa-ken (JP);
Ryo Horikoshi, Kanagawa-ken (JP);
Mariko Tsuchida, Kanagawa-ken (JP);
Kazuhiko Oyama, Kanagawa-ken (JP);
Satoshi Omura, Tokyo-to (JP); Hiroshi Tomoda, Tokyo-to (JP); Toshiaki Sunazuka, Chiba-ken (JP)

(73) Assignees: Meiji Seika Kaisha, Ltd., Tokyo-to (JP);
The Kitasato Institute (A School Juridical Person), Minato-ku (JP)

( * ) Notice: Subject to any disclaimer, the term of this patent is extended or adjusted under 35 U.S.C. 154(b) by 281 days.

(21) Appl. No.: 11/443,299

(22) Filed: May 31, 2006

(65) Prior Publication Data

US 2006/0281780 A1    Dec. 14, 2006

Related U.S. Application Data

(60) Provisional application No. 60/687,318, filed on Jun. 6, 2005.

(30) Foreign Application Priority Data

Jun. 1, 2005 (JP) ............................. 2005-161019

(51) Int. Cl.
*A01N 43/40* (2006.01)
*A61K 31/44* (2006.01)
*C07D 405/00* (2006.01)

(52) U.S. Cl. .................................. 514/338; 546/282.7

(58) Field of Classification Search .................. None
See application file for complete search history.

(56) References Cited

U.S. PATENT DOCUMENTS 2,075,359 A * 3/1937 Bousquet et al. ............. 514/63
3,973,944 A * 8/1976 Erdmann et al. ............ 504/299

FOREIGN PATENT DOCUMENTS

| JP | H04-360895 | 12/1992 |
| JP | WO 94/09147 | * 4/1994 |
| JP | H06-184158 | 7/1994 |
| JP | H08-239385 | 9/1996 |
| JP | H08-259569 | 10/1996 |
| JP | H08-269062 | 10/1996 |
| JP | H08-269063 | 10/1996 |
| JP | H08-269064 | 10/1996 |
| JP | H08-269065 | 10/1996 |
| JP | H08-269066 | 10/1996 |
| JP | H08-291164 | 10/1996 |
| WO | WO 94/09147 A1 | 4/1994 |
| WO | WO2004/060065 A1 | 7/2004 |

OTHER PUBLICATIONS

Http://www.fzi.uni-freiburg.de/InsectPestKey-long%20version/hemipter.htm; last accessed on Jun. 16, 2008.*
Satoshi Omura et al., "Pyripyropenes, Highly Potent Inhibitors of Acyl-CoA: Cholesterol Acyltransferase Produced by Aspergillus fumigatus", The Journal of Antibiotics, Jul. 1993, pp. 1168-1169, vol. 46, No. 7.
Toshiaki Sunazuka et al., "Synthetic Study of α-Pyrone Meroterpenodis, Pyripyropens", 1998, pp. 478-488, vol. 56, No. 6.
Rika Obata et al., "Chemical Modification and Structure-activity Relationships of Pyripyropenes", The Journal of Antibiotics, 1997, pp. 229-236, vol. 50, No. 3.
Hui-Juan Wang et al., "Aflavinines and Other Antiinsectan Metabolites from the Ascostromata of Eupenicillium crustaceum and Related Species", Applifled and Environmental Microbiology, Dec. 1995, pp. 4429-4435, vol. 61, No. 12.
Rika Obata et al., "Chemical Modification and Structure-activity Relationships of Pyripyropenes", The Journal of Antibiotics, 1996, pp. 1133-11438, vol. 49, No. 11.

* cited by examiner

*Primary Examiner*—James O. Wilson
*Assistant Examiner*—Jeffrey H Murray
(74) *Attorney, Agent, or Firm*—Wenderoth, Lind & Ponack, L.L.P.

(57) ABSTRACT

There is provided a pest control agent comprising a compound represented by formula (I) as active ingredient.

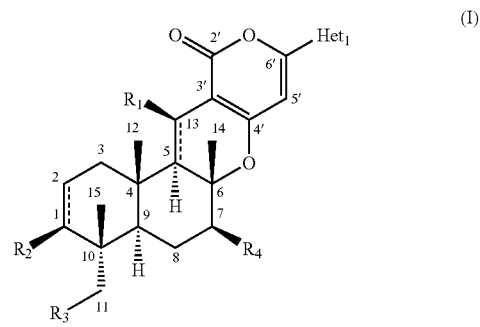

2 Claims, No Drawings

PEST CONTROL AGENTS

BACKGROUND OF THE INVENTION

1. Field of the Invention

The present invention relates to a pest control agent comprising a pyripyropene derivative as active ingredient.

2. Background Art

Pyripyropene A has inhibitory activity against ACAT (acyl-CoA: cholesterol acyltransferase) and is expected to be applied, for example, to the treatment of diseases induced by cholesterol accumulation, as described in Japanese Patent No. 2993767 (Japanese Patent Laid-Open Pub. No. 360895/1992) Publication and Journal of Antibiotics (1993), 46(7), 1168-9.

Further, pyripyropene analogues and derivatives and ACAT inhibitory activity thereof are described in Journal of Society of Synthetic Organic Chemistry, Japan (1998), Vol. 56, No. 6, pp. 478-488, Japanese Patent Laid-Open Pub. No. 184158/1994, Japanese Patent Laid-Open Pub. No. 239385/1996, Japanese Patent Laid-Open Pub. No. 259569/1996, Japanese Patent Laid-Open Pub. No. 269062/1996, Japanese Patent Laid-Open Pub. No. 269063/1996, Japanese Patent Laid-Open Pub. No. 269064/1996, Japanese Patent Laid-Open Pub. No. 269065/1996, Japanese Patent Laid-Open Pub. No. 269066/1996, Japanese Patent Laid-Open Pub. No. 291164/1996, and Journal of Antibiotics (1997), 50(3), 229-36.

Furthermore, *Applied and Environmental Microbiology* (1995), 61(12), 4429-35 describes that pyripyropene A has insecticidal activity against larvae of *Helicoverpa zea*. Furthermore, WO 2004/060065 Publication (Japanese version) describes that pyripyropene A has insecticidal activity against *Plutella xylostella* L larvae and *Tenebrio molitor* L. In these documents, however, there is no specific description on insecticidal activity of pyripyropene A against other pests.

Further, none of the above documents describes insecticidal activity of pyripyropene analogues and derivatives.

Up to now, many compounds having insecticidal activity have been reported and have been used as pest control agents, however, the presence of insect species, which are resistant to or can be hardly controlled by these compounds, has posed a problem. Accordingly, the development of a novel pest control agent having excellent insectidal activity has still been desired.

SUMMARY OF THE INVENTION

The present inventors have now found that pyripyropene derivatives represented by formula (I) have significant insecticidal activity.

The present inventors further found that pyripyropene A and its derivatives represented by formula (Ia) have significant insecticidal activity against hemipteran pests.

The present invention has been made based on such finding.

Accordingly, an object of the present invention is to provide a pest control agent, that comprises a pyripyropene derivative having significant insecticidal activity as active ingredient and can reliably exhibit the contemplated effect and can be used safely.

Another object of the present invention is to provide a hemipteran pest control agent that comprises pyripyropene A and its derivative as active ingredient and can reliably exhibit the contemplated effect and can be used safely.

And, the pest control agent according to the present invention comprises a compound represented by formula (I) as active ingredient:

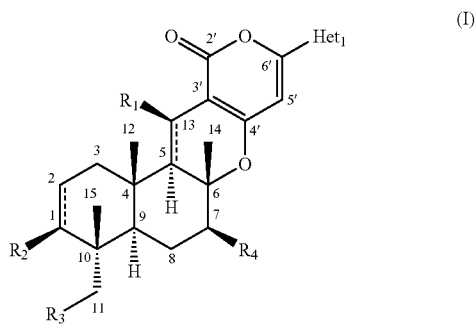

(I)

[wherein
$Het_1$ represents a saturated or unsaturated five- to six-membered heterocyclic ring,
$R_1$ represents a hydroxyl group,
an optionally substituted $C_{1-6}$ alkylcarbonyloxy group,
an optionally substituted $C_{2-6}$ alkenylcarbonyloxy group,
an optionally substituted $C_{2-6}$ alkynylcarbonyloxy group,
an optionally substituted $C_{1-6}$ alkyloxy group,
an optionally substituted $C_{2-6}$ alkenyloxy group,
an optionally substituted $C_{2-6}$ alkynyloxy group,
an optionally substituted benzyloxy group, or
an oxo group in the absence of a hydrogen atom at the 13-position, or
the bond between 5-position and 13-position represents a double bond in the absence of $R_1$ and a hydrogen atom at the 5-position,
$R_2$ represents a hydroxyl group,
an optionally substituted $C_{1-18}$ alkylcarbonyloxy group,
an optionally substituted $C_{2-6}$ alkenylcarbonyloxy group,
an optionally substituted $C_{2-6}$ alkynylcarbonyloxy group,
an optionally substituted benzoyloxy group,
an optionally substituted $C_{1-6}$ alkylsulfonyloxy group,
an optionally substituted $C_{1-6}$ alkyloxy group,
an optionally substituted $C_{2-6}$ alkenyloxy group,
an optionally substituted $C_{2-6}$ alkynyloxy group,
a $C_{1-6}$ alkyloxy-$C_{1-6}$ alkyloxy group,
a $C_{1-6}$ aklylthio-$C_{1-6}$ alkyloxy group,
an optionally substituted $C_{1-6}$ alkyloxycarbonyloxy group,
an optionally substituted $C_{1-6}$ alkylaminocarbonyloxy group, or
the bond between 1-position and 2-position represents a double bond in the absence of $R_2$, and
$R_3$ represents a hydrogen atom,
a hydroxyl group,
an optionally substituted $C_{1-18}$ alkylcarbonyloxy group,
an optionally substituted $C_{2-6}$ alkenylcarbonyloxy group,
an optionally substituted $C_{2-6}$ alkynylcarbonyloxy group,
an optionally substituted benzoyloxy group,
an optionally substituted $C_{1-6}$ alkylsulfonyloxy group,
an optionally substituted benzenesulfonyloxy group,
an optionally substituted $C_{1-6}$ alkyloxy group,
an optionally substituted $C_{2-6}$ alkenyloxy group,
an optionally substituted $C_{2-6}$ alkynyloxy group,
an optionally substituted $C_{1-6}$ alkyloxycarbonyloxy group,
an optionally substituted $C_{1-6}$ alkylaminocarbonyloxy group, or
an optionally substituted five- to six-membered heterocyclic thiocarbonyloxy group, or R$_2$ and R$_3$ together represent —O—CR$_2$'R$_3$'—O— (wherein R$_2$' and R$_3$', which may be the same or different, represent a hydrogen atom, C$_{1-6}$ alkyl, C$_{1-6}$ alkyloxy, C$_{2-6}$ alkenyl, optionally substituted phenyl, or optionally substituted benzyl, or R$_2$' and R$_3$' together represent oxo or C$_{2-6}$ alkylene), and R$_4$ represents a hydrogen atom,
a hydroxyl group,
an optionally substituted C$_{1-18}$ alkylcarbonyloxy group,
an optionally substituted C$_{2-6}$ alkenylcarbonyloxy group,
an optionally substituted C$_{2-6}$ alkynylcarbonyloxy group,
an optionally substituted benzoyloxy group,
an optionally substituted C$_{1-6}$ alkylsulfonyloxy group,
an optionally substituted benzenesulfonyloxy group,
an optionally substituted benzyloxy group,
an optionally substituted C$_{1-6}$ alkyloxy group,
an optionally substituted C$_{2-6}$ alkenyloxy group,
an optionally substituted C$_{2-6}$ alkynyloxy group,
a C$_{1-6}$ alkyloxy-C$_{1-6}$ alkyloxy group,
a C$_{1-6}$ alkylthio-C$_{1-6}$ alkyloxy group,
a C$_{1-6}$ alkyloxy-C$_{1-6}$ alkyloxy-C$_{1-6}$ alkyloxy group,
an optionally substituted C$_{1-6}$ alkyloxycarbonyloxy group,
an optionally substituted C$_{1-6}$ alkylaminocarbonyloxy group,
an optionally substituted saturated or unsaturated five- to six-membered heterocyclic oxy group,
an optionally substituted saturated or unsaturated five- to six-membered heterocyclic carbonyloxy group,
an optionally substituted saturated or unsaturated five- to six-membered heterocyclic thiocarbonyloxy group, or
an oxo group in the absence of a hydrogen atom at the 7-position, provided that
a compound wherein
Het$_1$ represents a 3-pyridyl group,
R$_1$ represents a hydroxyl group, and
all of R$_2$, R$_3$, and R$_4$ represent an acetyloxy group, is excluded.]

Further, the hemipteran pest control agent according to the present invention comprises a compound represented by formula (Ia) as active ingredient:

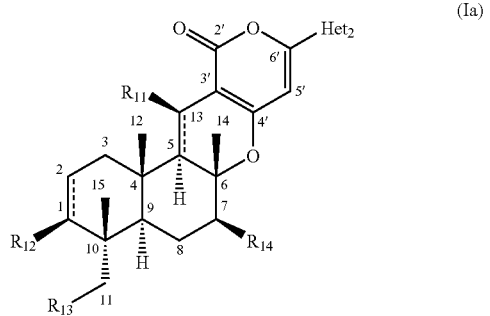

(Ia)

[wherein
Het$_2$ represents optionally substituted saturated or unsaturated five- to six-membered heterocyclic ring,
R$_{11}$ represents a hydroxyl group,
an optionally substituted C$_{1-6}$ alkylcarbonyloxy group,
an optionally substituted C$_{2-6}$ alkenylcarbonyloxy group,
an optionally substituted C$_{2-6}$ alkynylcarbonyloxy group,
an optionally substituted C$_{1-6}$ alkyloxy group,
an optionally substituted C$_{2-6}$ alkenyloxy group,
an optionally substituted C$_{2-6}$ alkynyloxy group,
an optionally substituted benzyloxy, or an oxo group in the absence of a hydrogen atom at the 13-position, or
the bond between 5-position and 13-position represents a double bond in the absence of R$_{11}$ and a hydrogen atom at the 5-position, R$_{12}$ represents a hydroxyl group,
an optionally substituted C$_{1-18}$ alkylcarbonyloxy group,
an optionally substituted C$_{2-6}$ alkenylcarbonyloxy gorup,
an optionally substituted C$_{2-6}$ alkynylcarbonyloxy group,
an optionally substituted benzoyloxy group, or
an optionally substituted C$_{1-6}$ alkylsulfonyloxy group,
an optionally substituted C$_{1-6}$ alkyloxy group,
an optionally substituted C$_{2-6}$ alkenyloxy group,
an optionally substituted C$_{2-6}$ alkynyloxy group,
a C$_{1-6}$ alkyloxy-C$_{1-6}$ alkyloxy group,
a C$_{1-6}$ alkylthio-C$_{1-6}$ alkyloxy group,
an optionally substituted C$_{1-6}$ alkyloxycarbnyloxy group,
an optionally substituted C$_{1-6}$ alkylaminocarbonyloxy group, or
the bond between 1-position and 2-position represents a double bond in the absence of R$_{12}$, and R$_{13}$ represents a hydrogen atom,
a hydroxyl group,
an optionally substituted C$_{1-18}$ alkylcarbonyloxy group,
an optionally substituted C$_{2-6}$ alkenylcarbonyloxy group,
an optionally substituted C$_{2-6}$ alkynylcarbonyloxy group,
an optionally substituted benzoyloxy group,
an optionally substituted C$_{1-6}$ alkylsulfonyloxy group,
an optionally substituted benzenesulfonyloxy group, or
an optionally substituted C$_{1-6}$ alkyloxy group,
an optionally substituted C$_{2-6}$ alkenyloxy group,
an optionally substituted C$_{2-6}$ alkynyloxy group,
an optionally substituted C$_{1-6}$ alkyloxycarbonyloxy group,
an optionally substituted C$_{1-6}$ alkylaminocabonyloxy group,
an optionally substituted five- to six-membered heterocyclic thiocarbonyloxy group, or
R$_{12}$ and R$_{13}$ together represent —O—CR$_{12}$'R$_{13}$'—O— (wherein R$_{12}$' and R$_{13}$', which may be the same or different, represent a hydrogen atom, a C$_{1-6}$ alkyl group, a C$_{1-6}$ alkyloxy, group, a C$_{2-6}$ alkenyl group, an optionally substituted phenyl group, or an optionally substituted benzyl group, or R$_{12}$' and R$_{13}$' together represent an oxo group or a C$_{2-6}$ alkylene group), and R$_{14}$ represents a hydrogen atom,
a hydroxyl group,
an optionally substituted C$_{1-18}$ alkylcarbonyloxy group,
an optionally substituted C$_{2-6}$ alkenylcarbonyloxy group,
an optionally substituted C$_{2-6}$ alkynylcarbonyloxy group,
an optionally substituted benzoyloxy group,
an optionally substituted C$_{1-6}$ alkylsulfonyloxy group,
an optionally substituted benzenesulfonyloxy group,
an optionally substituted benzyloxy,
an optionally substituted C$_{1-6}$ alkyloxy group,
an optionally substituted C$_{2-6}$ alkenyloxy group,
an optionally substituted C$_{2-6}$ alkynyloxy group,
a C$_{1-6}$ alkyloxy-C$_{1-6}$ alkyloxy group,
a C$_{1-6}$ alkylthio-C$_{1-6}$ alkyloxy group,
a C$_{1-6}$ alkyloxy-C$_{1-6}$ alkyloxy-C$_{1-6}$ alkyloxy group,
an optionally substituted C$_{1-6}$ alkyloxycarbonyloxy group,
an optionally substituted C$_{1-6}$ alkylaminocarbonyloxy group,
an optionally substituted saturated or unsaturated five- to six-membered heterocyclic oxy group,
an optionally substituted saturated or unsaturated five- to six-membered heterocyclic carbonyloxy group, an optionally substituted saturated or unsaturated five- to six-membered heterocyclic thiocarbonyloxy group, or an oxo group in the absence of a hydrogen atom at the 7-position.]

The pyripyropene derivatives represented by formula (I) according to the present invention have excellent control effect against agricultural and horiticultural pests, sanitary pests, parasites of animals, stored grain pests, clothing pests, and house pests and a compositions comprising the pyripyropene derivatives as active ingredient can be advantageously utilized as a novel pest control agent. Further, it is surprising that, among the compounds represented by formula (Ia), pyripyropene A has excellent control effect against hemipteran pests. Accordingly, a composition according to the present invention comprising the compounds represented by formula (Ia) including pyripyropene A, can be advantageously utilized particularly as a hemipteran pest control agent.

DETAILED DESCRIPTION OF THE INVENTION

The term "halogen" as used herein means fluorine, chlorine, bromine, or iodine, preferably fluorine, chlorine, or bromine.

Further, the terms "alkyl," "alkenyl," and "alkynyl" as used in this specification as a group or a part of a group respectively mean alkyl, alkenyl, and alkynyl that the group is of a straight chain, branched chain, or cyclic type or a type of a combination thereof unless otherwise specified. Further, for example, "$C_{1-6}$" in "$C_{1-6}$alkyl" as used herein as a group or a part of a group means that the number of carbon atoms in the alkyl group is 1 to 6.

Further, the term "heterocyclic ring" as used in this specification means a heterocyclic ring containing one or more, preferably one to four, heteroatoms, which may be the same or different, selected from the group consisting of nitrogen, oxygen, and sulfur atoms.

Further, the expression "optionally substituted" alkyl as used in this specification means that one or more hydrogen atoms on the alkyl group may be substituted by one or more substituents (which may be the same or different). It will be apparent to a person having ordinary skill in the art that the maximum number of substituents may be determined depending upon the number of substitutable hydrogen atoms on the alkyl group. This is also true for functional groups other than the alkyl group.

Examples of the "saturated or unsaturated five- to six-membered heterocyclic ring" represented by $Het_1$ and $Het_2$ include a thienyl group, a furyl group, a pyrrolyl group, an imidazolyl group, a pyrazolyl group, an isothiazoyl group, an isoxazolyl group, a thiazolyl group, an oxazolyl group, a pyridynyo group, a pyridyl group, a pyrimidinyl group, a pyrazinyl group, and a pyridazinyl group, and more specific examples thereof include a (2- or 3-)thienyl group, a (2- or 3-)furyl group, a (1-, 2- or 3-)pyrrolyl group, a (1-, 2-, 4- or 5-)imidazolyl group, a (1-, 3-, 4- or 5-)pyrazolyl group, a (3-, 4- or 5-)isothiazolyl group, a (3-, 4- or 5-)isoxazolyl group, a (2-, 4- or 5-)thiazolyl group, a (2-, 4- or 5-)oxazolyl group, a 1-oxydopyridynio group, a 1-methylpyridynyo group, a (2-, 3- or 4-)pyridyl group or, a (2-, 4-, 5- or 6-)pyrimidinyl group, a (2- or 3-)pyrazinyl group, and a (3- or 4-)pyridazinyl group, preferred are a pyridyl group, a thiazolyl group, a pyrazolyl group, a pyrimidinyl group, and a pyrrolyl group, and more preferred are a 3-pyridyl group. Here, this saturated or unsaturated five- to six-membered heteriocyclic ring may be substituted, and substituents include halogen atoms, a $C_{1-4}$ alkyl group, a $C_{1-4}$ alkyloxy group, a nitro group, a cyano group, a formyl group, a trifluoromethyl group, a trifluoromethoxy group, a trifluoromethylthio group, a trifluoromethylsulfinyl group, a trifluoromethylsulfonyl group, an acetyl group, and an acetyloxy group, preferred are halogen atoms and a trifluoromethyl group, and more preferred are a chlorine atom and a trifluoromethyl group.

The "$C_{1-6}$ alkylcarbonyloxy group" represented by $R_1$ and $R_{11}$ is optionally substituted, and substituents include halogen atoms, cyano, phenyl, trifluoromethoxy, and trifluoromethylthio groups.

The "$C_{1-18}$ alkylcarbonyloxy group" represented by $R_2$, $R_3$ and $R_4$, and $R_{12}$, $R_{13}$ and $R_{14}$ is preferably a $C_{1-6}$ alkylcarbonyloxy group. This $C_{1-18}$ alkylcarbonyloxy group is optionally substituted, and substituents include halogen atoms and cyano, phenyl, trifluoromethoxy, and trifluoromethylthio groups.

The "$C_{2-6}$ alkenylcarbonyloxy group" represented by $R_1$, $R_2$, $R_3$ and $R_4$, and $R_{11}$, $R_{12}$, $R_{13}$ and $R_{14}$ is optionally substituted, and substituents include halogen atoms, cyano, phenyl, trifluoromethoxy, and trifluoromethylthio.

The "$C_{2-6}$ alkynylcarbonyloxy group" represented by $R_1$, $R_2$, $R_3$ and $R_4$, and $R_{11}$, $R_{12}$, $R_{13}$ and $R_{14}$ is optionally substituted, and substituents include halogen atoms and cyano, phenyl, trifluoromethoxy, and trifluoromethylthio groups.

The "$C_{1-6}$ alkyloxy group" represented by $R_1$, $R_2$, $R_3$, $R_4$, and $R_{11}$, $R_{12}$, $R_{13}$, and $R_{14}$ is optionally substituted, and substituents include halogen atoms; a cyano group; a phenyl group; a trifluoromethoxy group; a trifluoromethylthio group; a $C_{1-6}$ alkylcarbonyl group optionally substituted by a halogen atom; and a $C_{1-6}$ alkylcarbonyloxy group optionally substituted by a halogen atom.

The "$C_{2-6}$ alkenyloxy group" represented by $R_1$, $R_2$, $R_3$, $R_4$, and $R_{11}$, $R_{12}$, $R_{13}$ and $R_{14}$ is optionally substituted, and substituents include halogen atoms; a cyano group; a phenyl group; a trifluoromethoxy group; a trifluoromethylthio group; a $C_{1-6}$ alkylcarbonyl group optionally substituted by a halogen atom; and a $C_{1-6}$ alkylcarbonyloxy group optionally substituted by a halogen atom.

The "$C_{2-6}$ alkynyloxy group" represented by $R_1$, $R_2$ $R_3$, $R_4$, and $R_{11}$, $R_{12}$, $R_{13}$ and $R_{14}$ is optionally substituted, and substituents include halogen atoms; a cyano group; a phenyl group; a trifluoromethoxy group; a trifluoromethylthio group; a $C_{1-6}$ alkylcarbonyl group optionally substituted by a halogen atom; and a $C_{1-6}$ alkylcarbonyloxy group optionally substituted by a halogen atom.

The phenyl group in the "benzyloxy group" represented by $R_1$ and $R_4$, and $R_{11}$ and $R_{14}$ is optionally substituted, and substituents include halogen atoms; a $C_{1-6}$ alkyloxy group optionally substituted by a halogen atom; a $C_{1-6}$ alkyl group optionally substituted by a halogen atom; a $C_{1-6}$ alkylcarbonyl group optionally substituted by a halogen atom; a $C_{1-6}$ alkylcarbonyloxy group optionally substituted by a halogen atom; a $C_{1-6}$ alkylcarbonylamino group optionally substituted by a halogen atom; a $C_{1-6}$ alkylaminocarbonyloxy group optionally substituted by a halogen atom; a $C_{1-6}$ alkylaminocarbonyl group optionally substituted by a halogen atom; a $C_{1-6}$ alkylsulfonyloxy group optionally substituted by a halogen atom; a $C_{1-6}$ alkylthio group optionally substituted by a halogen atom; a $C_{1-6}$ alkylsulfinyl group optionally substituted by a halogen atom; a $C_{1-6}$ alkylsulfonyl group optionally substituted by a halogen atom; a cyano group; formyl group; an azide group; a guanidyl group; group —C(═NH)—NH$_2$; or group —CH═N—O—CH$_3$.

The phenyl group in the "benzoyloxy group" represented by $R_2$, $R_3$ and $R_4$, and $R_{12}$, $R_{13}$ and $R_{14}$ is optionally substituted, and substituents include halogen atoms; a $C_{1-6}$ alkyloxy group optionally substituted by a halogen atom; a $C_{1-6}$ alkyl group optionally substituted by a halogen atom; a $C_{1-6}$ alkylcarbonyl group optionally substituted by a halogen atom; a $C_{1-6}$ alkylcarbonyloxy group optionally substituted by a halogen atom; a $C_{1-6}$ alkylcarbonylamino group optionally substituted by a halogen atom; a $C_{1-6}$ alkylaminocarbonyloxy group optionally substituted by a halogen atom; a $C_{1-6}$ alkylaminocarbonyl group optionally substituted by a halogen atom; a $C_{1-6}$ alkylsulfonyloxy group optionally substituted by a halogen atom; a $C_{1-6}$ alkylthio group optionally substituted by a halogen atom; a $C_{1-6}$ alkylsulfinyl group optionally substituted by a halogen atom; a $C_{1-6}$ alkylsulfonyl group optionally substituted by a halogen atom; a cyano group; a formyl group; an azide group; a guanidyl group; group —C(=NH)—NH$_2$; or group —CH=N—O—CH$_3$.

The phenyl group in the "benzenesulfonyloxy group" represented by $R_3$ and $R_4$, and $R_{13}$ and $R_{14}$ is optionally substituted, and substituents include halogen atoms; a $C_{1-6}$ alkyloxy group optionally substituted by a halogen atom; a $C_{1-6}$ alkyl group optionally substituted by a halogen atom; a $C_{1-6}$ alkylcarbonyl group optionally substituted by a halogen-atom; a $C_{1-6}$ alkylcarbonyloxy group optionally substituted by a halogen atom; a $C_{1-6}$ alkylcarbonylamino group optionally substituted by a halogen atom; a $C_{1-6}$ alkylaminocarbonyloxy group optionally substituted by a halogen atom; a $C_{1-6}$ alkylaminocarbonyl group optionally substituted by a halogen atom; a $C_{1-6}$ alkylsulfonyloxy group optionally substituted by a halogen atom; a $C_{1-6}$ alkylthio group optionally substituted by a halogen atom; a $C_{1-6}$ alkylsulfinyl group optionally substituted by a halogen atom; a $C_{1-6}$ alkylsulfonyl group optionally substituted by a halogen atom; a cyano group; a formyl group; an azide group; a guanidyl group; group —C(=NH)—NH$_2$; or group —CH=N—O—CH$_3$.

The "$C_{1-6}$ alkylsulfonyloxy group" represented by $R_2$, $R_3$, and $R_4$ and $R_{12}$, $R_{13}$ and $R_{14}$ is optionally substituted, and substituents include halogen atoms, a cyano group, a phenyl group, a trifluoromethoxy group, or a trifluoromethylthio group.

The "$C_{1-6}$ alkyloxycarbonyloxy group" represented by $R_2$, $R_3$, and $R_4$ and $R_{12}$, $R_{13}$, and $R_{14}$ is optionally substituted, and substituents include halogen atoms, a cyano group, a phenyl group, a trifluoromethyloxy group, or a trifluoromethylthio.

The "$C_{1-6}$ alkylaminocarbonyloxy group" represented by $R_2$, $R_3$, and $R_4$ and $R_{12}$, $R_{13}$, and $R_{14}$ is optionally substituted, and substituents include halogen atoms, a cyano group, a phenyl group, a trifluoromethyloxy, or trifluoromethylthio.

The "phenyl group" and the phenyl group in the "benzyl group" represented by $R_2'$ and $R_3'$, and $R_{12}'$ and $R_{13}'$ is optionally substituted, and substituents include halogen atoms, a $C_{1-4}$ alkyl group, a $C_{1-4}$ alkyloxy group, a nitro group, a cyano group, a formyl group, a trifluoromethyloxy group, an acetyl group, or an acetyloxy group.

Examples of the saturated or unsaturated five- to six-membered oxy group, the saturated or unsaturated five- to six-membered heterocyclic carbonyloxy group, and the "saturated or unsaturated five- to six-membered heterocyclic ring" in the saturated or unsaturated five- to six-membered heterocyclic thiocabonyloxy group represented by $R_3$ and $R_4$, and $R_{13}$, and $R_{14}$ include a thienyl group, a furyl group, a pyrrolyl group, an imidazolyl group, a pyrazolyl group, an isothiazoyl group, an isoxazolyl group, a thiazolyl group, an oxazolyl group, a pyridyl group, a pyrimidinyl group, a pyrazinyl group, a pyridazinyl group, a tetrahydropyranyl group, a piperidinyl group, a piperadinyl group, a morpholynyl group, a tetrahydropyranyl group, or mannosyl group, preferably a pyridyl group, a furanyl group, a thiazolyl group, an imidazolyl group, a tetrahydropyranyl group, or a mannosyl group, and more specific examples thereof include a (2- or 3-)thienyl group, a (2- or 3-)furyl group, a (1-, 2- or 3-)pyrrolyl group, a (1-, 2-, 4- or 5-)imidazolyl group, a (1-, 3-, 4- or 5-)pyrazolyl group, a (3-, 4- or 5-)isothiazolyl group, a (3-, 4- or 5-)isoxazolyl group, a (2-, 4- or 5-)thiazolyl group, a (2-, 4- or 5-)oxazolyl group, a (2-, 3- or 4-)pyridyl group or, a (2-, 4-, 5- or 6-)pyrimidinyl group, a (2- or 3-)pyrazinyl group, a (3- or 4-)pyridazinyl group, (2-, 3- or 4-)tetrahydropyranyl group, (1-, 2-, 3- or 4-)piperidinyl group, (1-, 2- or 3-)piperadinyl group, and (2-, 3- or 4-) morpholinyl group, and preferred are a 3-pyridyl group, a 2-furanyl group, a 5-thiazolyl group, a 1-imidazolyl group, a 5-imidazolyl group, or a 2-tetrahydropyranyl group.

The above heterocyclic ring in the saturated or unsaturated five- to six-membered heterocyclic carbonyloxy group and the saturated or unsaturated five- to six-membered heterocyclic thiocarbonyloxy group are optionally substituted, and substituents include halogen atoms, a $C_{1-4}$ alkyl group, a $C_{1-4}$ alkyloxy group, a nitro group, a cyano group, a formyl group, a trifluoromethyloxy group, a trifluoromethyl group, a trifluoromethylthio group, a trifluoromethylsulfinyl group, a trifluoromethylsulfonyl group, an acetyl group, and an acetyloxy group, and preferred are halogen atoms.

The heterocyclic ring in the above saturated or unsaturated five- to six-membered heterocyclic oxy group is optionally substituted, and substituents include a hydroxyl group, a benzyloxy group, a halogen atom, a $C_{1-4}$ alkyl group, a $C_{1-4}$ alkyloxy group, a nitro group, a cyano group, a formyl group, a trifluoromethoxy group, a trifluoromethyl group, a trifluoromethylthio group, a trifluoromethylsulfinyl group, a trifluoromethylsulfonyl group, an acetyl group, or an acetyloxy group, and preferred are a hydroxyl group or a benzyloxy group.

A composition represented by formula (I)

According to a preferred embodiment of the present invention, in the compound represented by formula (I), Het$_1$ represents an optionally substituted pyridyl group, a 1-oxydopyridinyo group, a 1-methylpyridinyo group, an optionally substituted thiazolyl group, a pyrazolyl group, a pyrimidinyl group, or a pyrrolyl group.

Further, according to a preferred embodiment of the present invention, in the compound represented by formula (I), $R_1$ represents a hydroxyl group, a $C_{1-6}$ alkylcarbonyloxy group, a $C_{1-3}$ alkyloxy group, a benzyloxy group, or an oxo group in the absence of a hydrogen atom at the 13-position, or the bond between 5-position and 13-position represents a double bond in the absence of $R_1$ and a hydrogen atom at the 5-position, more preferably, a hydroxyl group or a $C_{1-6}$ alkylcarbonyloxy group or the bond between 5-position and 13-position represents a double bond in the absence of $R_1$ and a hydrogen atom at the 5-position, still more preferably a hydroxyl group.

Further, according to a preferred embodiment of the present invention, in the compound represented by formula (I), $R_2$ represents a hydroxyl group, a $C_{1-18}$ alkylcarbonyloxy group, an optionally substituted benzoyloxy group, a $C_{1-3}$ alkylsulfonyloxy group, a $C_{1-3}$ alkyloxy group, a $C_{1-3}$ alkyloxy-$C_{1-3}$ alkyloxy group, a $C_{1-3}$ alkylthio-$C_{1-3}$ alkyloxy group, $C_{1-3}$ alkyloxycarbonyloxy group, a $C_{1-3}$ alkylaminocarbonyloxy group, or the bond between 1-position and 2-position represents a double bond in the absence of $R_2$, more preferably, a $C_{1-8}$ alkylcarbonyloxy group, still more preferably, a $C_{1-6}$ alkylcarbonyloxy group.

Further, in a preferred embodiment of the present invention, in the compound represented by formula (I), $R_3$ represents a hydrogen atom, a hydroxyl group, a $C_{1-18}$ alkylcarbonyloxy group, an optionally substituted benzoyloxy group, a $C_{1-6}$ alkylsulfonyloxy group, an optionally substituted benzenesulfonyloxy group, a $C_{1-6}$ alkyloxy group, a $C_{1-3}$ alkyloxycarbonyloxy group, a $C_{1-3}$ alkylaminocaronyloxy group, or a five- to six-membered heterocyclic thiocarbonyloxy group, more preferably, a $C_{1-8}$ alkylcarbonyloxy group or a $C_{1-6}$ alkylsulfonyloxy group, still more preferably, a $C_{1-6}$ alkylcarbonyloxy group, particularly preferably, a $C_{3-5}$ alkylcarbonyloxy group.

Further, according to a preferred embodiment of the present invention, in the compound represented by formula (I), $R_2$ and $R_3$ together represent —O—$CR_2'R_3'$—O— (wherein $R_2'$ and $R_3'$, which may be the same or different, represent a hydrogen atom, a $C_{1-6}$ alkyl group, a $C_{1-3}$ alkyloxy group, a $C_{2-3}$ alkenyl group, a benzyl group, or an optionally substituted phenyl group, or $R_2'$ and $R_3'$ together represent an oxo group or a $C_{2-6}$ alkylene group), more preferably, together represent —O—$CR_2'R_3'$—O— (wherein $R_2'$ and $R_3'$, which may be the same or different, represent a hydrogen atom, a $C_{1-6}$ alkyl group, or an optionally substituted phenyl group, or $R_2'$ and $R_3'$ together represent an oxo group or a $C_{2-6}$ alkylene group).

Further, according to a preferred embodiment of the present invention, in the compound represented by formula (I), $R_4$ represents a hydrogen atom, a hydroxyl group, an optionally substituted $C_{1-18}$ alkylcarbonyloxy group, a $C_{2-6}$ alkenylcarbonyloxy group, a $C_{2-6}$ alkynylcarbonyloxy group, a $C_{1-6}$ alkylsulfonyloxy group, a benzenesulfonyloxy group, a benzyloxy group, a $C_{1-3}$ alkyloxy group, a $C_{1-3}$ alkyloxy-$C_{1-3}$ alkyloxy group, a $C_{1-3}$ alkylthio-$C_{1-3}$ alkyloxy group, a $C_{1-3}$ alkyloxy-$C_{1-3}$ alkyloxy-$C_{1-3}$ alkyloxy-$C_{1-3}$ alkyloxy group, an optionally substituted $C_{1-3}$ alkyloxycarbonyloxy group, an optionally substituted $C_{1-3}$ alkylaminocarbonyloxy group, an optionally substituted benzoyloxy group, a saturated or unsaturated five- to six-membered heterocyclic oxy group, a saturated or unsaturated five- to six-membered heterocyclic carbonyloxy group, or saturated or unsaturated five- to six-membered heterocyclic thiocarbonyloxy group, or an oxo group in the absence of a hydrogen atom at the 7-position, more preferably, a hydroxyl group, a $C_{1-18}$ alkylcarbonyloxy group, a saturated or unsaturated five- to six-membered heterocyclic oxy group, an optionally substituted benzoyloxy group, an optionally substituted $C_{1-6}$ alkylaminocaronyloxy group, a saturated or unsaturated five- to six-membered heterocyclic carbonyloxy group, a saturated or unsaturated five- to six-membered heterocyclic thiocarbonyloxy group, or an oxo group in the absence of a hydrogen atom at the 7-position, still more preferably, a $C_{1-6}$ alkylcarbonyloxy group, a saturated or unsaturated five- to six-membered heterocyclic oxy group, or a benzoyloxy group, further more preferably, a $C_{3-5}$ alkylcarbonyloxy group, a 2-tetrahydropyranyl group, or a benzoyloxy group.

Further, according to another preferred embodiment of the present invention, in the compound represented by formula (I), $Het_1$ represents a 3-pyridyl group, $R_1$ represents a hydroxyl group or a $C_{1-6}$ alkylcarbonyloxy group, or the bond between 5-position and 13-position represents a double bond in the absence of $R_1$ and a hydrogen atom at the 5-position, $R_2$ represents a $C_{1-6}$ alkylcarbonyloxy group, $R_3$ represents a $C_{1-6}$ alkylcarbonyloxy group or a $C_{1-6}$ alkylsulfonyloxy group, or $R_2$ and $R_3$ together represent —O—$CR_2'R_3'$—O— (wherein $R_2'$ and $R_3'$, which may be the same or different, represent a hydrogen atom, a $C_{1-6}$ alkyl group, or an optionally substituted phenyl group, or $R_2'$ and $R_3'$ together represent an oxo group or a $C_{2-6}$ alkylene group), and $R_4$ represents a hydroxyl group, a $C_{1-6}$ alkylcarbonyloxy group, a saturated or unsaturated five- to six-membered heterocyclic oxy group, an optionally substituted benzoyloxy group, an optionally substituted $C_{1-6}$ alkylaminocarbonyloxy group, a saturated or unsaturated five- to six-membered heterocyclic carbonyloxy group, a saturated or unsaturated five- to six-membered heterocyclic thiocarbonyloxy group, or an oxo group in the absence of a hydrogen atom at the 7-position.

Further, according to another preferred embodiment of the present invention, in the compound represented by formula (I), $Het_1$ represents a 3-pyridyl group, $R_1$ represents a hydroxyl group, $R_2$ represents a $C_{1-6}$ alkylcarbonyloxy group, and $R_3$ and/or $R_4$ represents a $C_{3-5}$ alkylcarbonyloxy group.

Further, according to another preferred embodiment of the present invention, in the compound represented by formula (I), Het represents a 3-pyridyl group, $R_1$ represents a hydroxyl group, $R_2$ represents a $C_{1-6}$ alkylcarbonyloxy group, $R_3$ represents a $C_{1-6}$ alkylcarbonyloxy group or a $C_{1-6}$ alkylsulfonyloxy group, and $R_4$ represents a $C_{1-6}$ alkylcarbonyloxy, an optionally substituted benzoyloxy group, a saturated or unsaturated five- to six-membered heterocyclic oxy group, a saturated or unsaturated five- to six-membered heterocyclic carbonyloxy group, or a saturated or unsaturated five- to six-membered heterocyclic thiocarbonyloxy group.

Further, according to another preferred embodiment of the present invention, in the compound represented by formula (I), $R_1$ represents a hydroxyl group, and $R_2$, $R_3$, and $R_4$ represent a $C_{1-6}$ alkylcarbonyloxy group.

Further, according to another preferred embodiment of the present invention, in the compound represented by formula (I), $R_1$, $R_2$, $R_3$, and $R_4$ represent a $C_{1-6}$ alkylcarbonyloxy group.

Further, according to another preferred embodiment of the present invention, in the compound represented by formula (I), $R_1$ represents a hydroxyl group and $R_2$ and $R_3$ represent a $C_{1-6}$ alkylcarbonyloxy group and $R_4$ represents a saturated or unsaturated five- to six-membered heterocyclic oxy group.

A compound represented by formula (Ia)

According to a preferred embodiment of the present invention, in the compound represented by formula (Ia), $Het_2$ represents an optionally substituted pyridyl group, a 1-oxydopyridinyo group, a 1-methylpyridinyo group, an optionally substituted thiazolyl group, a pyrazolyl group, a pyrimidinyl group, or a pyrrolyl group.

Further, according to a preferred embodiment of the present invention, in the compound represented by formula (Ia), $R_{11}$ represents a hydroxyl group, a $C_{1-6}$ alkylcarbonyloxy group, a $C_{1-3}$ alkyloxy group, a benzyloxy group, or an oxo group in the absence of a hydrogen atom at the 13-position, or the bond between 5-position and 13-position represents a double bond in the absence of $R_{11}$ and a hydrogen atom at the 5-position, more preferably, a hydroxyl group or a $C_{1-6}$ alkylcarbonyloxy group, or the bond between 5-position and 13-position represents a double bond in the absence of $R_{11}$ and a hydrogen atom at the 5-position, still more preferably a hydroxyl group.

Further, according to a preferred embodiment of the present invention, in the compound represented by formula (Ia), $R_{12}$ represents a hydroxyl group, a $C_{1-8}$ alkylcarbonyloxy group, an optionally substituted benzoyloxy group, a $C_{1-3}$ alkylsulfonyloxy group, a $C_{1-3}$ alkyloxy group, a $C_{1-3}$ alkyloxy-$C_{1-3}$ alkyloxy group, a $C_{1-3}$ alkylthio-$C_{1-3}$ alkyloxy group, a $C_{1-3}$ alkyloxycarbonyloxy group, or a $C_{1-3}$ alkylaminocarbonyloxy group, or the bond between 1-position and 2-position represents a double bond in the absence of $R_2$, more preferably, a $C_{1-8}$ alkylcarbonyloxy group, still more preferably, a $C_{1-6}$ alkylcarbonyloxy group.

Further, according to a preferred embodiment of the present invention, in the compound represented by formula (Ia), $R_{13}$ represents a hydrogen atom, a hydroxyl group, a $C_{1-18}$ alkylcarbonyloxy group, an optionally substituted benzoyloxy group, a $C_{1-6}$ alkylsulfonyloxy group, an optionally substituted benzenesulfonyloxy group, a $C_{1-6}$ alkyloxy group, a $C_{1-3}$ alkyloxycarbonyloxy group, a $C_{1-3}$ alkylaminocabonyloxy group, or a five- to six-membered thiocarbonyloxy group, more preferebly, a $C_{1-18}$ alkylcarbonyloxy group or $C_{1-6}$ alkylsulfonyloxy group, still more preferably, a $C_{1-6}$ alkylcabonyloxy group, particularly preferably, a $C_{3-5}$ alkylcaronyloxy group.

According to a preferred embodiment of the present invention, in the compound represented by formula (Ia), $R_{12}$ and $R_{13}$ together represent —O—$CR_{12}'R_{13}'$—O— (wherein $R_{12}'$ and $R_{13}'$, which may be the same or different, represent a hydrogen atom, a $C_{1-6}$ alkyl group, a $C_{1-3}$ alkyloxy group, a $C_{2-3}$ alkenyl group, a benzyl group, or an optionally substituted phenyl group, or $R_{12}'$ and $R_{13}'$ together represent an oxo group or a $C_{2-6}$ alkylene group), more preferably, together represent —O—$CR_{12}'R_{13}'$—O— (wherein $R_{12}'$ and $R_{13}'$, which may be the same or different, represent a hydrogen atom, a $C_{1-6}$ alkyl group, or an optionally substituted phenyl group, or $R_{12}'$ and $R_{13}'$ together represent an oxo group or a $C_{2-6}$ alkylene group).

Further, according to a preferred embodiment of the present invention, in the compound represented by formula (Ia), $R_{14}$ represents a hydrogen atom, a hydroxyl group, an optionally substituted $C_{1-18}$ alkylcarbonyloxy group, a $C_{2-6}$ alkenylcarbonyloxy group, a $C_{2-6}$ alkynylcarbonyloxy group, a $C_{1-6}$ alkylsulfonyloxy group, a benzenesulfonyloxy group, a benzyloxy group, a $C_{1-3}$ alkyloxy group, a $C_{1-3}$ alkyloxy-$C_{1-3}$ alkyloxy group, a $C_{1-3}$ alkylthio-$C_{1-3}$ alkyloxy group, a $C_{1-3}$ alkyloxy-$C_{1-3}$ alkyloxy-$C_{1-3}$ alkyloxy group, an optionally substituted $C_{1-3}$ alkyloxycarbonyloxy group, an optionaly substituted $C_{1-3}$ alkylaminocarbonyloxy group, an optionally substituted benzoyloxy group, a saturated or unsaturated five- to six-membered heterocyclic oxy group, a saturated or unsaturated five- to six-membered heterocyclic carbonyloxy group, or saturated or unsaturated five- to six-membered heterocyclic thiocarbonyloxy group, or an oxo group in the absence of a hydrogen atom at the 7-position, more preferably, a hydroxyl group, a $C_{1-18}$ alkylcarbonyloxy group, an optionally substituted benzoyloxy group, a saturated or unsaturated five- to six-membered heterocyclic oxy group, a $C_{1-6}$ alkylaminocarbonyloxy group, a saturated or unsaturated five- to six-membered heterocyclic carbonyloxy group, a saturated or unsaturated five- to six-membered heterocyclic thiocarbonyloxy group, or an oxo group in the absence of a hydrogen atom at the 7-position, still more preferably, a $C_{1-6}$ alkylcarbonyloxy group, a saturated or unsaturated five- to six-membered heterocyclic oxy group, or benzoyloxy group, still more preferably, a $C_{3-5}$ alkylcarbonyloxy group, a 2-tetrahydropyranyl group, or a benzoyloxy group.

Further, according to another preferred embodiment of the present invention, in the compound represented by formula (Ia), $Het_2$ represents a 3-pyridyl group, $R_{11}$ represents a hydroxyl group, a $C_{1-6}$ alkylcarbonyloxy group, or the bond between 5-position and 13-position represents a double bond in the absence of $R_{11}$ and a hydrogen atom at the 5-position, $R_{12}$ represents a $C_{1-6}$ alkylcarbonyloxy group, and $R_{13}$ represents a $C_{1-6}$ alkylcarbonyloxy group, a $C_{1-6}$ alkylsulfonyloxy group, or $R_{12}$ and $R_{13}$ together represent —O—$CR_{12}'R_{13}'$—O— (wherein $R_{12}'$ and $R_{13}'$, which may be the same or different, represent a hydrogen atom, a $C_{1-6}$ alkyl group, or an optionally substituted phenyl group, or $R_{12}'$ and $R_{13}'$ together represent an oxo group or a $C_{2-6}$ alkylene group), and $R_{14}$ represents a hydroxyl group, a $C_{1-6}$ alkylcarbonyloxy group, a saturated or unsaturated five- to six-membered heterocyclic oxy group, an optionally substituted benzoyloxy group, an optionally substituted $C_{1-6}$ alkylaminocarbonyloxy group, a saturated or unsaturated five- to six-membered heterocyclic carbonyloxy group, a saturated or unsaturated five- to six-membered heterocyclic thiocarbonyloxy group, or, an oxo group in the absence of a hydrogen atom at the 7-position.

Further, according to another preferred embodiment of the present invention, in the compound represented by formula (Ia), $Het_2$ represents a 3-pyridyl group, $R_{11}$ represents a hydroxyl group, $R_{12}$ represents a $C_{1-6}$ alkylcarbonyloxy group, $R_{13}$ and/or $R_{14}$ represents a $C_{3-5}$ alkylcarbonyloxy group.

Further, according to still another preferred embodiment of the present invention, in the compound represented by formula (Ia), $Het_2$ represents a 3-pyridyl group, $R_{11}$ represents a hydroxyl group, $R_{12}$ represents a $C_{1-6}$ alkylcarbonyloxy group, $R_{13}$ represents a $C_{1-6}$ alkylcarbonyloxy group, or $C_{1-6}$ alkylsulfonyloxy group, and $R_{14}$ represents a $C_{1-6}$ alkylcarbonyloxy group, an optionally substituted benzoyloxy group, a saturated or unsaturated five- to six-membered heterocyclic oxy group, a saturated or unsaturated five- to six-membered heterocyclic carbonyloxy group, or a saturated or unsaturated five- to six-membered thiocarbonyloxy group, and $R_{14}$ represents a $C_{1-6}$ alkylcarbonyloxy group, a saturated or unsaturated five- to six-membered heterocyclic oxy group, an optionally substituted benzoyloxy group, a saturated or unsaturated five- to six-membered heterocyclic carbonyloxy group, or a saturated or unsaturated five- to six-membered heterocyclic thiocabonyloxy group.

Further, according to another preferred embodiment of the present invention, in the compound represented by formula (Ia), $R_{11}$ represents a hydroxyl group, and $R_{12}$, $R_{13}$, and $R_{14}$ represent a $C_{1-6}$ alkylcarbonyloxy group.

Further, according to another preferred embodiment of the present invention, in the compound represented by formula (Ia), $R_{11}$, $R_{12}$, $R_{13}$, and $R_{14}$ represent a $C_{1-6}$ alkylcarbonyloxy group.

Further, according to another preferred embodiment of the present invention, in the compound represented by formula (Ia), $R_{11}$ represents a hydroxyl group, $R_{12}$ and $R_{13}$ represent $C_{1-6}$ alkylcarbonyloxy group, and $R_{14}$ represents a saturated or unsaturated five- to six-membered heterocyclic oxy group.

Specific examples of the compounds represented by formula (I) or (Ia) above include compounds shown in Tables 1 to 14 below. In addition, in the following tables, H(=) means that the bond between 5-position and 13-position represents a double bond in the absence of $R_1$ and a hydrogen atom at the 5-position.

TABLE 1

| Compound No. | $R_1$ | $R_2$ | $R_3$ | $R_4$ | $Het_1$ |
|---|---|---|---|---|---|
| 1 | OH | OCOCH3 | OCOCH3 | OCOCH2CH3 | 3-pyridyl |
| 2 | OH | OCOCH3 | OCOCH3 | OCOCH2CF3 | 3-pyridyl |
| 3 | OH | OCOCH3 | OCOCH3 | OCOCH2OCH3 | 3-pyridyl |
| 4 | OH | OCOCH3 | OCOCH3 | OCOCH2OCOCH3 | 3-pyridyl |
| 5 | OH | OCOCH3 | OCOCH3 | OCOCH2CH2CN | 3-pyridyl |

TABLE 1-continued

| Compound No. | R$_1$ | R$_2$ | R$_3$ | R$_4$ | Het$_1$ |
|---|---|---|---|---|---|
| 6 | OH | OCOCH3 | OCOCH3 | OCO(CH2)2CH3 | 3-pyridyl |
| 7 | OH | OCOCH3 | OCOCH3 | OCO(CH2)3CH3 | 3-pyridyl |
| 8 | OH | OCOCH3 | OCOCH3 | OCO(CH2)4CH3 | 3-pyridyl |
| 9 | OH | OCOCH3 | OCOCH3 | OCO(CH2)5CH3 | 3-pyridyl |
| 10 | OH | OCOCH3 | OCOCH3 | OCO(CH2)6CH3 | 3-pyridyl |
| 11 | OH | OCOCH3 | OCOCH3 | OCO(CH2)16CH3 | 3-pyridyl |
| 12 | OH | OCOCH3 | OCOCH3 | OCOCH(CH3)2 | 3-pyridyl |
| 13 | OH | OCOCH3 | OCOCH3 | OCOC(CH3)3 | 3-pyridyl |
| 14 | OH | OCOCH3 | OCOCH3 | OCOCH2CH(CH3)2 | 3-pyridyl |
| 15 | OH | OCOCH3 | OCOCH3 | OCO(CH2)2CH(CH3)2 | 3-pyridyl |
| 16 | OH | OCOCH3 | OCOCH3 | OCO-trans-CH=CHCH2CH3 | 3-pyridyl |
| 17 | OH | OCOCH3 | OCOCH3 | OCOCH2C≡CCH3 | 3-pyridyl |
| 18 | OH | OCOCH3 | OCOCH3 | OCOC≡CCH2CH3 | 3-pyridyl |
| 19 | OH | OCOCH3 | OCOCH3 | OCO(CH2)2C≡CH | 3-pyridyl |

TABLE 2

| Compound No. | R$_1$ | R$_2$ | R$_3$ | R$_4$ | Het1 |
|---|---|---|---|---|---|
| 20 | OH | OCOCH3 | OCOCH3 | OCO(CH2)2CH=CH2 | 3-pyridyl |
| 21 | OH | OCOCH3 | OCOCH3 | OCOCH2C6H5 | 3-pyridyl |
| 22 | OH | OCOCH3 | OCOCH3 | OCO(CH2)2C6H5 | 3-pyridyl |
| 23 | OH | OCOCH3 | OCOCH3 | OCOC6H5 | 3-pyridyl |
| 24 | OH | OCOCH3 | OCOCH3 | OCO-(p-Br—C6H4) | 3-pyridyl |
| 25 | OH | OCOCH3 | OCOCH3 | OCO-(p-N3-C6H4) | 3-pyridyl |
| 26 | OH | OCOCH3 | OCOCH3 | OCO-(p-OCF3-C6H4) | 3-pyridyl |
| 27 | OH | OCOCH3 | OCOCH3 | OCO-(p-SO2CF3-C6H4) | 3-pyridyl |
| 28 | OH | OCOCH3 | OCOCH3 | OCO-(3-pyridyl) | 3-pyridyl |
| 29 | OH | OCOCH3 | OCOCH3 | OCO-(2-Cl-3-pyridyl) | 3-pyridyl |
| 30 | OH | OCOCH3 | OCOCH3 | OCO-(2-franyl) | 3-pyridyl |
| 31 | OH | OCOCH3 | OCOCH3 | OCO-(2-thiazolyl) | 3-pyridyl |
| 32 | OH | OCOCH3 | OCOCH3 | OCO-(2-Cl-5-thiazolyl) | 3-pyridyl |
| 33 | OH | OCOCH3 | OCOCH3 | OCO-(5-imidazolyl) | 3-pyridyl |
| 34 | OH | OCOCH3 | OCOCH3 | OCS-(1-imidazolyl) | 3-pyridyl |
| 35 | OH | OCOCH3 | OCOCH3 | OCOOCH2C6H5 | 3-pyridyl |
| 36 | OH | OCOCH3 | OCOCH3 | OSO2CH3 | 3-pyridyl |
| 37 | OH | OCOCH3 | OCOCH3 | OSO2C6H5 | 3-pyridyl |
| 38 | OH | OCOCH3 | OCOCH3 | OCONHCH2CH3 | 3-pyridyl |

TABLE 3

| Compound No. | R$_1$ | R$_2$ | R$_3$ | R$_4$ | Het1 |
|---|---|---|---|---|---|
| 39 | OH | OCOCH3 | OCOCH3 | OCONH(CH2)2CH3 | 3-pyridyl |
| 40 | OH | OCOCH3 | OCOCH3 | OCONHCH2C6H5 | 3-pyridyl |
| 41 | OH | OCOCH3 | OCOCH3 | OCH2C6H5 | 3-pyridyl |
| 42 | OH | OCOCH3 | OCOCH3 | OCH2SCH3 | 3-pyridyl |
| 43 | OH | OCOCH3 | OCOCH3 | OCH2OCH3 | 3-pyridyl |
| 44 | OH | OCOCH3 | OCOCH3 | OCH2OCH2CH2OCH3 | 3-pyridyl |
| 45 | OH | OCOCH3 | OCOCH3 | O-(2-tetrahydropyranyl) | 3-pyridyl |
| 46 | OH | OCOCH3 | OCOCH3 | O-tetra-O-benzyl-mannosyl | 3-pyridyl |
| 47 | OH | OCOCH3 | OCOCH3 | H | 3-pyridyl |
| 48 | OH | OCOCH3 | OCOCH3 | OCO—c—C3H5 | 3-pyridyl |
| 49 | OH | OCOCH3 | OCOCH3 | OH | 3-pyridyl |
| 50 | OH | OCOCH3 | OCOCH3 | =O | 3-pyridyl |
| 51 | OH | OCOCH3 | OCOCH2CH3 | OCOCH3 | 3-pyridyl |
| 52 | OH | OCOCH3 | OCOCH2CH3 | OCOCH2CH3 | 3-pyridyl |
| 53 | OH | OCOCH3 | OCOCH2CH3 | H | 3-pyridyl |
| 54 | OH | OCOCH3 | OCO(CH2)2CH3 | OCOCH3 | 3-pyridyl |
| 55 | OH | OCOCH3 | OCO(CH2)2CH3 | OH | 3-pyridyl |
| 56 | OH | OCOCH3 | OCO(CH2)3CH3 | OCOCH3 | 3-pyridyl |
| 57 | OH | OCOCH3 | OCOCH(CH3)2 | OCOCH3 | 3-pyridyl |
| 58 | OH | OCOCH3 | OCOC6H5 | OCOCH3 | 3-pyridyl |

TABLE 4

| Compound No. | R$_1$ | R$_2$ | R$_3$ | R$_4$ | Het1 |
|---|---|---|---|---|---|
| 59 | OH | OCOCH3 | OCOC6H5 | OH | 3-pyridyl |
| 60 | OH | OCOCH3 | OCS-(1-imidazolyl) | OCOCH3 | 3-pyridyl |

TABLE 4-continued

| Compound No. | R₁ | R₂ | R₃ | R₄ | Het1 |
|---|---|---|---|---|---|
| 61 | OH | OCOCH3 | OSO2CH3 | OCOCH3 | 3-pyridyl |
| 62 | OH | OCOCH3 | OSO2CH3 | OCO(CH2)3CH3 | 3-pyridyl |
| 63 | OH | OCOCH3 | OSO2C6H5 | OCOCH3 | 3-pyridyl |
| 64 | OH | OCOCH3 | OSO2CH2CH3 | OCOCH3 | 3-pyridyl |
| 65 | OH | OCOCH3 | OSO2CH2CH2CH3 | OCOCH3 | 3-pyridyl |
| 66 | OH | OCOCH3 | OCH2CH3 | OCOCH3 | 3-pyridyl |
| 67 | OH | OCOCH3 | C(H2)3CH3 | OCOCH3 | 3-pyridyl |
| 68 | OH | OCOCH3 | OH | OH | 3-pyridyl |
| 69 | OH | OCOCH3 | OH | OCOCH3 | 3-pyridyl |
| 70 | OH | OCOCH3 | H | H | 3-pyridyl |
| 71 | OH | OCOCH3 | H | OCOCH2CH3 | 3-pyridyl |
| 72 | OH | OCOCH2CH3 | OCOCH3 | OCOCH3 | 3-pyridyl |
| 73 | OH | OCOCH2CH3 | OCOCH2CH3 | OH | 3-pyridyl |
| 74 | OH | OCOCH2CH3 | OCOCH2CH3 | OCOCH3 | 3-pyridyl |
| 75 | OH | OCOCH2CH3 | OCOCH3 | OCOCH2CH3 | 3-pyridyl |
| 76 | OH | OCOCH2CH3 | OCOCH2CH3 | OCOCH2CH3 | 3-pyridyl |
| 77 | OH | OCOCH2CH3 | OCOCH2CH3 | OCOC6H5 | 3-pyridyl |
| 78 | OH | OCOCH2CH3 | OCOCH2CH3 | H | 3-pyridyl |

TABLE 5

| Compound No. | R₁ | R₂ | R₃ | R₄ | Het1 |
|---|---|---|---|---|---|
| 79 | OH | OCOCH2CH3 | H | H | 3-pyridyl |
| 80 | OH | OCO(CH2)2CH3 | OCOCH3 | OCOCH3 | 3-pyridyl |
| 81 | OH | OCO(CH2)2CH3 | OCO(CH2)2CH3 | OH | 3-pyridyl |
| 82 | OH | OCO(CH2)2CH3 | OCO(CH2)2CH3 | OCO(CH2)2CH3 | 3-pyridyl |
| 83 | OH | OCO(CH2)2CH3 | OCO(CH2)2CH3 | OCOCH3 | 3-pyridyl |
| 84 | OH | OCO(CH2)3CH3 | OCOCH3 | OCOCH3 | 3-pyridyl |
| 85 | OH | OCO(CH2)3CH3 | OCO(CH2)3CH3 | OCO(CH2)3CH3 | 3-pyridyl |
| 86 | OH | OCO(CH2)3CH3 | OSO2CH3 | OCO(CH2)3CH3 | 3-pyridyl |
| 87 | OH | OCO(CH2)3CH3 | OSO2CH3 | OH | 3-pyridyl |
| 88 | OH | OCO(CH2)16CH3 | OCO(CH2)16CH3 | OCO(CH2)16CH3 | 3-pyridyl |
| 89 | OH | OCOCH(CH3)2 | OCOCH3 | OCOCH3 | 3-pyridyl |
| 90 | OH | OCOCH(CH3)2 | OCOCH(CH3)2 | OCOCH(CH3)2 | 3-pyridyl |
| 91 | OH | OCOC(CH3)3 | OCOC(CH3)3 | OCOC(CH3)3 | 3-pyridyl |
| 92 | OH | OCOC6H5 | OCOCH3 | OCOCH3 | 3-pyridyl |
| 93 | OH | OCOC6H5 | OSO2CH3 | OH | 3-pyridyl |
| 94 | OH | OCOC6H5 | OSO2CH3 | OCOCH3 | 3-pyridyl |
| 95 | OH | OCOC6H5 | OSO2CH3 | OCO(CH2)3CH3 | 3-pyridyl |
| 96 | OH | OCO-p-Br—C6H4 | OCO-p-Br—C6H4 | OCO-p-Br—C6H4 | 3-pyridyl |
| 97 | OH | OCO-p-N3-C6H4 | OSO2CH3 | OCOCH3 | 3-pyridyl |

TABLE 6

| Compound No. | R₁ | R₂ | R₃ | R₄ | Het1 |
|---|---|---|---|---|---|
| 98 | OH | OSO2CH3 | OSO2CH3 | OH | 3-pyridyl |
| 99 | OH | OSO2CH3 | OSO2CH3 | OSO2CH3 | 3-pyridyl |
| 100 | OH | OSO2CH3 | OSO2CH3 | OCOCH3 | 3-pyridyl |
| 101 | OH | OSO2CH3 | OH | OH | 3-pyridyl |
| 102 | OH | OH | OH | OH | 3-pyridyl |
| 103 | OH | OH | OH | OCOCH3 | 3-pyridyl |
| 104 | OH | OH | OH | OCO(CH2)3CH3 | 3-pyridyl |
| 105 | OH | OH | OH | OCH2OCH2CH2OCH3 | 3-pyridyl |
| 106 | OH | OH | OCOCH3 | OH | 3-pyridyl |
| 107 | OH | OH | OCOCH2CH3 | OH | 3-pyridyl |
| 108 | OH | OH | OCO(CH2)2CH3 | OH | 3-pyridyl |
| 109 | OH | OH | OCO(CH2)3CH3 | OH | 3-pyridyl |
| 110 | OH | OH | OCOCH(CH3)2 | OH | 3-pyridyl |
| 111 | OH | OH | OSO2CH3 | OH | 3-pyridyl |
| 112 | OH | OH | OSO2CH2CH3 | OH | 3-pyridyl |
| 113 | OH | OH | OSO2CH2CH2CH3 | OH | 3-pyridyl |
| 114 | OH | OH | OSO2CH(CH3)2 | OH | 3-pyridyl |
| 115 | OH | OH | OSO2C6H5 | OH | 3-pyridyl |
| 116 | OH | OH | OSO2-(p-CH3-C6H5) | OH | 3-pyridyl |

TABLE 7

| Compound No. | R₁ | R₂ | R₃ | R₄ | Het1 |
|---|---|---|---|---|---|
| 117 | OH | OH | OCO-p-Br—C6H4 | OH | 3-pyridyl |
| 118 | OH | OH | OCO(CH2)3CH3 | OCO(CH2)3CH3 | 3-pyridyl |
| 119 | OH | OH | OSO2CH3 | OSO2CH3 | 3-pyridyl |
| 120 | OH | OH | OSO2CH3 | OCOCH3 | 3-pyridyl |
| 121 | OH | OH | OSO2CH3 | OCOCH3 | 3-pyridyl |
| 122 | OH | OH | OSO2CH3 | OCO(CH2)3CH3 | 3-pyridyl |
| 123 | OH | OH | OSO2C6H5 | OCOCH3 | 3-pyridyl |
| 124 | OH | OH | OSO2C6H5 | OSO2C6H5 | 3-pyridyl |
| 125 | OH | —O—CH(CH3)-O— | | OCO(CH2)3CH3 | 3-pyridyl |
| 126 | OH | —O—CH(C2H5)-O— | | OH | 3-pyridyl |
| 127 | OH | —O—CH(C2H5)-O— | | OCO(CH2)3CH3 | 3-pyridyl |
| 128 | OH | —O—CH(CH=CH2)-O— | | OH | 3-pyridyl |
| 129 | OH | —O—CH(CH=CH2)-O— | | OCO(CH2)3CH3 | 3-pyridyl |
| 130 | OH | —O—CH(i-Pr)—O— | | OH | 3-pyridyl |
| 131 | OH | —O—CH(i-Pr)—O— | | OCO(CH2)3CH3 | 3-pyridyl |
| 132 | OH | —O—CH(OCH3)-O— | | OH | 3-pyridyl |
| 133 | OH | —O—CH(t-Bu)—O— | | OCO(CH2)3CH3 | 3-pyridyl |
| 134 | OH | —O—CH(CH2C6H5)-O— | | OH | 3-pyridyl |
| 135 | OH | —O—C(CH3)2-O— | | OH | 3-pyridyl |

TABLE 8

| Compound No. | R₁ | R₂ | R₃ | R₄ | Het₁ |
|---|---|---|---|---|---|
| 136 | OH | —O—C(CH3)2-O— | | OCOCH3 | 3-pyridyl |
| 137 | OH | —O—C(CH3)2-O— | | OCO(CH2)3CH3 | 3-pyridyl |
| 138 | OH | —O—C(CH3)(C6H5)-O— | | OH | 3-pyridyl |
| 139 | OH | —O—C(CH3)(C6H5)-O— | | OCO(CH2)3CH3 | 3-pyridyl |
| 140 | OH | —O—CH(C6H5)-O— | | OH | 3-pyridyl |
| 141 | OH | —O—CH(C6H5)-O— | | OCOCH3 | 3-pyridyl |
| 142 | OH | —O—CH(OCH3)-O— | | OCO(CH2)3CH3 | 3-pyridyl |
| 143 | OH | —O—CH(C6H5)-O— | | OCO(CH2)3CH3 | 3-pyridyl |
| 144 | OH | —O—CH(m-CH3-C6H4)-O— | | OH | 3-pyridyl |
| 145 | OH | —O—CH(m-CH3-C6H4)-O— | | OCO(CH2)3CH3 | 3-pyridyl |
| 146 | OH | —O—CH(o-CH3-C6H4)-O— | | OH | 3-pyridyl |
| 147 | OH | —O—CH(p-CH3-C6H4)-O— | | OCO(CH2)3CH3 | 3-pyridyl |
| 148 | OH | —O—CH(m-F—C6H4)-O— | | OH | 3-pyridyl |
| 149 | OH | —O—CH(o-F—C6H4)-O— | | OCO(CH2)3CH3 | 3-pyridyl |
| 150 | OH | —O—CH(p-F—C6H4)-O— | | OCO(CH2)3CH3 | 3-pyridyl |
| 151 | OH | —O—CH(p-NO2-C6H4)-O— | | OH | 3-pyridyl |
| 152 | OH | —O—CH(p-NO2-C6H4)-O— | | OCO(CH2)3CH3 | 3-pyridyl |
| 153 | OH | —O—CH(p-OCH3-C6H4)-O— | | OH | 3-pyridyl |
| 154 | OH | —O—CH(p-OCH3-C6H4)-O— | | OCO(CH2)3CH3 | 3-pyridyl |

TABLE 9

| Compound No. | R₁ | R₂ | R₃ | R₄ | Het₁ |
|---|---|---|---|---|---|
| 155 | OH | —O—C(spiro-c-Pen)-O— | | OH | 3-pyridyl |
| 156 | OH | —O—C(spiro-c-Pen)-O— | | OCO(CH2)3CH3 | 3-pyridyl |
| 157 | OH | —O—C(spiro-c-Hex)-O— | | OH | 3-pyridyl |
| 158 | OH | —O—C(spiro-c-Hex)-O— | | OCO(CH2)3CH3 | 3-pyridyl |
| 159 | OH | —O—CO—O— | | OH | 3-pyridyl |
| 160 | OH | —O—CO—O— | | OCO-imidazolyl | 3-pyridyl |
| 161 | OH | —O—CO—O— | | OCO(CH2)3CH3 | 3-pyridyl |
| 162 | OCOCH3 | OCOCH3 | OCOCH3 | OCOCH3 | 3-pyridyl |
| 163 | OCOCH3 | OCOCH3 | OCOCH3 | OH | 3-pyridyl |
| 164 | OCOCH3 | OCOCH3 | OCO(CH2)2CH3 | OCOCH3 | 3-pyridyl |
| 165 | OCOCH3 | OH | OH | OCOCH3 | 3-pyridyl |
| 166 | OCOCH3 | OCOCH2CH3 | OCOCH2CH3 | OCOCH2CH3 | 3-pyridyl |
| 167 | OCOCH2CH3 | OCOCH2CH3 | OCOCH2CH3 | OCOCH2CH3 | 3-pyridyl |
| 168 | OCOCH2CH3 | OCOCH3 | OCOCH3 | OCOCH3 | 3-pyridyl |
| 169 | OCO(CH2)3CH3 | OCOCH3 | OCOCH3 | OCOCH3 | 3-pyridyl |
| 170 | OCO(CH2)3CH3 | OCOCH3 | OCOCH3 | OCO(CH2)3CH3 | 3-pyridyl |
| 171 | OCO(CH2)2CH3 | OCOCH3 | OCOCH3 | OCOCH3 | 3-pyridyl |
| 172 | OCH3 | OCOCH3 | OCOCH3 | OCOCH3 | 3-pyridyl |
| 173 | H(=) | OSO2CH3 | OSO2CH3 | OH | 3-pyridyl |

TABLE 10

| Compound No. | R₁ | R₂ | R₃ | R₄ | Het₁ |
|---|---|---|---|---|---|
| 174 | H(=) | OCOC6H5 | OSO2CH3 | OCOCH3 | 3-pyridyl |
| 175 | H(=) | OH | OH | OCOCH3 | 3-pyridyl |
| 176 | H(=) | OCOCH3 | OCOCH3 | =O | 3-pyridyl |
| 177 | H(=) | —O—CH(C6H5)-O— | | OCOCH3 | 3-pyridyl |
| 178 | H(=) | —O—CH(i-Pr)—O— | | OH | 3-pyridyl |
| 179 | H(=) | —O—CH(p-NO2-C6H4)-O— | | OH | 3-pyridyl |
| 180 | H(=) | OCOCH3 | OCOCH3 | OCOCH3 | 3-pyridyl |
| 181 | H(=) | OH | OH | OH | 3-pyridyl |
| 182 | H(=) | OCOCH3 | OCOCH3 | OH | 3-pyridyl |
| 183 | H(=) | OCOCH3 | OCOCH3 | OCH2SCH3 | 3-pyridyl |
| 184 | H(=) | OCOCH3 | OCOCH3 | OCH2OCH3 | 3-pyridyl |
| 185 | H(=) | OCOCH3 | OCOCH3 | OCO(CH2)3CH3 | 3-pyridyl |
| 186 | H(=) | OCOCH3 | OCOCH3 | OCO(CH2)2Ph | 3-pyridyl |
| 187 | H(=) | OCOCH3 | OSO2CH3 | OCOCH3 | 3-pyridyl |
| 188 | H(=) | OCOCH2CH3 | OCOCH2CH3 | OCOCH2CH3 | 3-pyridyl |
| 189 | H(=) | OCOCH2CH3 | OCOCH2CH3 | OH | 3-pyridyl |
| 190 | H(=) | OH | OSO2CH3 | OH | 3-pyridyl |
| 191 | H(=) | OH | OH | OCO(CH2)3CH3 | 3-pyridyl |
| 192 | H(=) | —O—C(CH3)2-O— | | OH | 3-pyridyl |

TABLE 11

| Compound No. | R₁ | R₂ | R₃ | R₄ | Het₁ |
|---|---|---|---|---|---|
| 193 | H(=) | —O—C(CH₃)₂—O— | | OCO(CH₂)₃CH₃ | 3-pyridyl |
| 194 | H(=) | —O—CH(C₆H₅)—O— | | OH | 3-pyridyl |
| 195 | H(=) | —O—CH(C₆H₅)—O— | | OCO(CH₂)₃CH₃ | 3-pyridyl |
| 196 | H(=) | —O—CH(p-OCH₃—C₆H₄)—O— | | OH | 3-pyridyl |
| 197 | H(=) | —O—CH(C₂H₅)—O— | | OH | 3-pyridyl |
| 198 | H(=) | —O—CH(t-Bu)—O— | | OH | 3-pyridyl |
| 199 | H(=) | —O—CH(CH₂.C₆H₅)—O— | | OH | 3-pyridyl |
| 200 | =O | OH | OH | OH | 3-pyridyl |
| 201 | =O | OCOCH3 | OCOCH3 | =O | 3-pyridyl |
| 202 | =O | OCOCH3 | OCOCH3 | OH | 3-pyridyl |
| 203 | =O | OCOCH3 | OCOCH3 | | 3-pyridyl |
| 204 | =O | OCOCH2CH3 | OCOCH2CH3 | OCOCH2CH3 | 1-CH3-3 |
| 205 | OH | OCOCH3 | OCOCH3 | OCOCH3 | 1-CH3-pyridynio |
| 206 | OH | OCOCH3 | OCOCH3 | OCOCH3 | 1-oxydo-3-pyridynio |
| 207 | OH | OCOCH3 | OCOCH3 | OH | 1-oxydo-3-pyridynio |
| 208 | OH | OCOCH3 | OCOCH3 | OCOH2C6H5 | 1-oxydo-3-pyridynio |
| 209 | OCH3 | OCOCH3 | OCOCH3 | OCH3 | 1-oxydo-3-pyridynio |
| 210 | OCH3 | OCOCH3 | OCOCH3 | OCOCH3 | 1-oxydo-3-pyridynio |
| 211 | OCH2C6H5 | OCOCH3 | OCOCH3 | OCH2C6H5 | l-oxydo-3-pyridynio |

TABLE 12

| Compound No. | R₁ | R₂ | R₃ | R₄ | Het₁ |
|---|---|---|---|---|---|
| 212 | =O | OCOCH3 | OCOCH3 | OCOC3 | 1-oxydo-pyridynio |
| 213 | OH | OCOCH3 | OCOCH3 | OCOC3 | 4-pyridyl |
| 214 | OH | OCOCH3 | OCOCH3 | OH | 4-pyridyl |
| 215 | OH | OCOCH2CH3 | OCOCH2CH3 | OCOCH2CH3 | 4-pyridyl |
| 216 | OH | OCOCH3 | OCOCH3 | OCOC6H5 | 4-pyridyl |
| 217 | OH | OCO(CH2)3CH3 | OSOCH3 | OCO(CH2)3CH3 | 4-pyridyl |
| 218 | =O | OH | OH | OH | 4-pyridyl |
| 219 | =O | OCOCH3 | OCOCH3 | OCOCH3 | 4-pyridyl |
| 220 | OH | OCOCH3 | OCOCH3 | OCOCH3 | 2-pyridyl |
| 221 | OH | OCOCH2CH3 | OCOCH2CH3 | OCOCH2CH3 | 2-pyridyl |
| 222 | OH | OCOCH2CH3 | OCOCH2CH3 | OH | 2-pyridyl |
| 223 | OH | OCO(CH2)3CF3 | OSO2CH3 | OCO(CH2)3CH3 | 2-pyridyl |
| 224 | OH | OCOCH3 | OCOCH3 | OCH2SCH3 | 2-pyridyl |
| 225 | =O | OCOCH3 | OCOCH3 | OCOH3 | 6-Cl-3-pyridyl |
| 226 | OH | OCOCH3 | OCOCH3 | OH | 6-Cl-3-pyridyl |
| 227 | OH | OCOCH2CH3 | OCOCH2CH3 | OCOCH2CH3 | 6-Cl-3-pyridyl |
| 228 | OH | OCOCH2CH3 | OCOCH2CH3 | OH | 6-Cl-3-pyridyl |
| 229 | OH | DCOCH3 | OCOCH3 | OCO-(3-pyridyl) | 6-Cl-3-pyridyl |
| 230 | OH | OCOCH3 | OCOCH3 | OCH2SCH3 | 6-Cl-3-pyridyl |

TABLE 13

| Compound No. | R₁ | R₂ | R₃ | R₄ | Het₁ |
| --- | --- | --- | --- | --- | --- |
| 231 | OCOCH3 | OCOCH2CH3 | OCOCH2CH3 | OCOCH2CH3 | 6-Cl-3-pyridyl |
| 232 | OH | OCO(CH2)3CH3 | OSO2CH3 | OH | 6-Cl-3-pyridyl |
| 233 | H(=) | OCOCH3 | OCOCH3 | OCOCH3 | 6-Cl-3-pyridyl |
| 234 | H(=) | OCOCH2CH3 | OCOCH2CH3 | OH | 6-Cl-3-pyridyl |
| 235 | =O | OCOCH2CH3 | OCOCH2CH3 | OCOCH2CH3 | 6-Cl-3-pyridyl |
| 236 | OH | OCOCH3 | OCOCH3 | OCOCH3 | 4-CF3-3-pyridyl |
| 237 | OH | OCOCH3 | OCOCH3 | OH | 4-CF3-3-pyridyl |
| 238 | OH | OCOCH2CH3 | OCOCH2CH3 | OCOCH2CH3 | 4-CF3-3-pyridyl |
| 239 | OH | OCOCH2CH3 | OCOCH2CH3 | OH | 4-CF3-3-pyridyl |
| 240 | OH | OCOCH3 | OCOCH3 | OCOC6H5 | 4-CF3-3-pyridyl |
| 241 | OH | OCO(CH2)3CH3 | OSO2CH3 | OCO(CH2)3CH3 | 4-CF3-3-pyridyl |
| 242 | OCOCH3 | OCOCH2CH3 | OCOCH2CH3 | OCH2SCH3 | 4-CF3-3-pyridyl |
| 243 | H(=) | OCOCH3 | OCOCH3 | OCOCH3 | 4-CF3-3-pyridyl |
| 244 | =O | OCOCH2CH3 | OCOCH2CH3 | OCOH2CH3 | 4-CF3-3-pyridyl |
| 245 | OH | OCOCH3 | OCOCH3 | OCOCH3 | 2-Ci-5-thiazolyl |
| 246 | OH | OCOCH3 | OCOCH3 | OH | 2-Ci-5-thiazolyl |
| 247 | OH | OCOCH2CH3 | OCOCH2CH3 | OCOCH2CH3 | 2-Ci-5-thiazolyl |
| 248 | OH | OCOCH2CH3 | OCOCH2CH3 | OH | 2-Ci-5-thiazolyl |
| 249 | OH | OCOCH3 | OCOCH3 | OCOC6H5 | 2-Ci-5-thiazolyl |
| 250 | OH | OCOCH3 | OCOCH3 | OCH2SCH3 | 2-Ci-5-thiazolyl |

TABLE 14

| Compound No. | R₁ | R₂ | R₃ | R₄ | Het₁ |
| --- | --- | --- | --- | --- | --- |
| 251 | H(=) | OCOCH3 | OCOCH3 | OCOCH3 | 2-Ci-5-thiazolyl |
| 252 | H(=) | OCOCH2CH3 | OCOCH2CH3 | OH | 2-Ci-5-thiazolyl |
| 253 | =O | OCOCH2CH3 | OCOCH2CH3 | OCOCH2CH3 | 2-Ci-5-thiazolyl |
| 254 | OH | OCOCH3 | OCOCH3 | OCOCH3 | 3-pyrazolyl |
| 255 | OH | OCOCH3 | OCOCH3 | OCOC6H5 | 3-pyrazolyl |
| 256 | OH | OCOCH3 | OCOCH3 | OCH2SCH3 | 3-pyrazolyl |
| 257 | =O | OCOCH2CH3 | OCOCH2CH3 | OCOCH2CH3 | 3-pyrazolyl |
| 258 | OH | OCOCH3 | OCOCH3 | OCOCH3 | 4-pyrimidinyl |
| 259 | OH | OCOCH2CH3 | OCOCH2CH3 | OCOCH2CH3 | 4-pyrimidinyl |
| 260 | OH | OCOCH2CH3 | OCOCH2CH3 | OH | 4-pyrimidinyl |
| 261 | OH | OCOCH3 | OCOCH3 | OCOC6H5 | 4-pyrimidinyl |
| 262 | OH | OCO(CH2)3CH3 | OSO2CH3 | OCO(CH2)3CH3 | 4-pyrimidinyl |
| 263 | OH | OCOCH3 | OCOCH3 | OCOH2CH3 | 4-pyrimidinyl |
| 264 | H(=) | OCOCH3 | OCOCH3 | OCOCH3 | 4-pyrimidinyl |
| 265 | OH | OCOCH3 | OCOCH3 | OCOCH3 | 3-pyrrolyl |
| 266 | OH | OCOCH3 | OCOCH3 | OH | 3-pyrrolyl |

Production Process

The compound represented by formula (I) or (Ia) according to the present invention can be produced according to the following procedure.

Among the compounds according to the present invention, the compounds represented by formula (II) can be synthesized by the method described in Japanese Patent Laid-Open Pub. No. 259569/1996, Japanese Patent Laid-Open Pub. No. 269062/1996, or Japanese Patent Laid-Open Pub. No. 269065/1996.

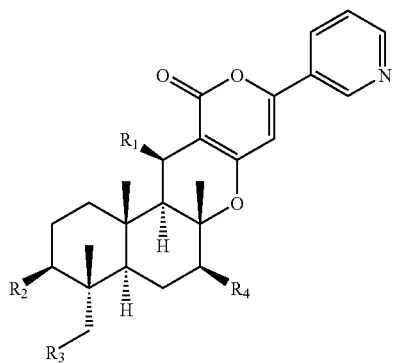

(II)

[wherein

R$_1$ represents a hydroxyl group, an optionally substituted C$_{1-6}$ alkylcarbonyloxy group, an optionally substituted C$_{2-6}$ alkenylcarbonyloxy group, an optionally substituted C$_{2-6}$ alkynylcarbonyloxy group, an optionally substituted C$_{1-6}$ alkyloxy group, an optionally substituted C$_{2-6}$ alkenyloxy group, an optionally substituted C$_{2-6}$ alkynyloxy group, an optionally substituted benzyloxy group, or an oxo group in the absence of a hydrogen atom at the 13-position, and R$_2$, R$_3$ and R$_4$ are as defined in formula (I).]

Further, among the compounds according to the present invention, the compounds represented by formula (III) can be synthesized by the method described in Japanese Patent Laid-Open Pub. No. 269063/1996, or Japanese Patent Laid-Open Pub. No. 269066/1996.

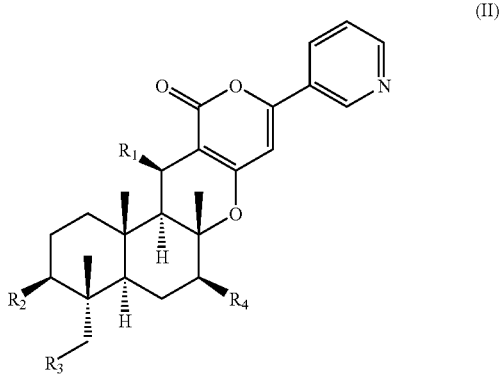

(II)

[wherein R$_2$, R$_3$ and R$_4$ are as defined in formula (I).]

Further, among the compounds according to the present invention, the compounds represented by formula (IV) can be synthesized by those skilled in the art by combining the method described in *Journal of Antibiotics* (1997), Vol. 50, pp. 229-36 and the synthesizing methods represented by formulae (II) and (III) above.

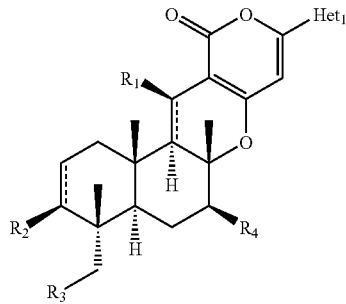

[wherein Het$_1$, R$_1$, R$_2$, R$_3$, and R$_4$ are as defined in formula (I), however, a compound wherein Het$_1$ represents a 3-pyridyl group is excluded.]

Use

Insect species against which pyripyropene derivatives of formula (I) according to the present invention have control effect include: lepidopteran pests (for example, *Spodoptera litura*, *Mamestra brassicae*, *Pseudaletia separata*, green caterpillar, *Plutella xylostella*, *Spodoptera exigua*, *Chilo suppressalis*, *Cnaphalocrocis medinalis*, *Tortricidae*, *Carposinidae*, *Lyonetiidae*, *Lymantriidae*, pests belonging to the genus (*Agrotis* spp), pests belonging to the genus (*Helicoverpa* spp), and pests belonging to the genus (*Heliothis* spp); hemipteran pests (for example, *Aphididae* such as *Myzus persicae*, *Aphis gossypii*, *Aphis fabae*, *Aphis maidis*, *Acyrthosiphon pisum*, *Aulacorthum solani*, *Aphis craccivora*, *Macrosiphum euphorbiae*, *Macrosiphum avenae*, *Metopolophium dirhodum*, *Rhopalosiphum padi*, *Schizaphis graminum*, *Brevicoryne brassicae*, *Lipaphis erysimi*, *Aphis citricola*, Apple aphid, Rosy apple aphid, Apple cotton aphid, *Eriosoma lanigerum*, *Toxoptera aurantii*, and *Toxoptera citricidus*; *Deltocephalidae* such as *Nephotettix cincticeps*; *Delphacidae* such as *Laodelphax striatellus*, *Nilaparvata lugens*, and *Sogatella furcifera*; *Pentatornidae* such as *Eysarcoris ventralis*, *Nezara viridula*, and *Trigonotylus coelestialium*; *Aleyrodidae* such as *Bemisia argentifolii*, *Bemisia tabaci*, and *Trialeurodes vaporariorum*; *Cerococcidae*, such as *Pseudococcus comstocki* and *Planococcus citri Risso*); Coleoptera pests (for example, *Lissorhoptrus oryzophilus*, *Callosobruchuys chienensis*, *Tenebrio molitor*, *Diabrotica virgifera*, *Diabrotica undecimpunctata howardi*, *Anomala cuprea*, *Anomala rufocuprea*, *Phyllotreta striolata*, *Aulacophora femoralis*, *Leptinotarsa decemlineata*, *Oulema oryzae*, *Carposinidae*, and *Cerambycidae*); Acari (for example, *Tetranychus urticae*, *Tetranychus kanzawai*, and *Panonychus citri*); Hymenopteran pests (for example, *Tenthredinidae*); Orthopteran pests (for example, *Acrididae*); Dipteran pests (for example, *Muscidae* and *Agromyzidae*); Thysanopteran pests (for example, *Thrips palmi* and *Frankliniella occidentalis*); Plant Parasitic Nematodes (for example, *Meloidogyne hapla*, *Pratylenchus* spp., *Aphelenchoides besseyi* and *Bursaphelenchus xylophilus*); and parasites of animals for example, *Siphonaptera*, *Anoplura*, mites (*Boophilus microplus*, *Haemaphysalis longicomis*, *Rhipicephalus sanguineus*, and *Scarcoptes scabiei*), and preferred are hemipteran pests.

Further, the compound represented by formula (Ia) according to the present invention has significant control effect against hemipteran pests. And, preferred hemipteran pests are preferably selected from *Aphidoidea*, *Coccoidea* and *Aleyrodidae*. More preferred are *Myzus persicae*, *Aphis gossypii*, *Aphis fabae*, *Aphis maidis*, *Acyrthosiphon pisum*, *Aulacorthum solani*, *Aphis craccivora*, *Macrosiphum euphorbiae*, *Macrosiphum avenae*, *Metopolophium dirhodum*, *Rhopalosiphum padi*, *Schizaphis graminum*, *Brevicoryne brassicae*, *Lipaphis erysimi*, *Aphis citricola*, Apple aphid, Rosy apple aphid, Apple cotton aphid, *Eriosoma lanigerum*, *Toxoptera aurantii*, *Toxoptera citricidus*, or *Pseudococcus comstocki*.

When the compound according to formula (I) and (Ia) can be used as an effective ingredient of a pest control agent, the above compound can be used as such, however, the compound is usually used in any suitable formulation, such as emulsifiable concentrates, liquid formulations, suspension, wettable powder, flowables, dust, granules, tablets, oil solutions, aerosols, or smoking agents by using suitable carriers including solid carriers, liquid carriers, gaseous carriers, surfactants, dispersants and/or other adjuvants for formulations, and the like.

Solid carriers usable herein include, for example, talc, bentonite, clay, kaolin, diatomaceous earth, vermiculite, white carbon, and calcium carbonate and the like.

Examples of liquid carriers include, for example: alcohols, such as methanol, n-hexanol, and ethylene glycol; ketones, such as acetone, methyl ethyl ketone, and cyclohexanone; aliphatic hydrocarbons, such as n-hexane, kerosine, and kerosene; aromatic hydrocarbons, such as toluene, xylene, and methylnaphthalene; ethers, such as diethyl ether, dioxane, and tetrahydrofuran; esters, such as ethyl acetate; nitriles, such as acetonitrile and isobutyronitrile; acid amides, such as dimethylformamide and dimethylacetamide; vegetable oils, such as soy bean oil and cotton seed oil; dimethylsulfoxide; and water.

Further, gaseous carriers include, for example, LPQ air, nitrogen, carbon dioxide, and dimethyl ether.

Surfactants or dispersants usable, for example, for emulsifying, dispersing, or spreading include, for example, alkylsulfonic esters, alkyl(aryl)sulfonic acid salts, polyoxyalkylene alkyl(aryl) ethers, polyhydric alcohol esters, and lignin sulfonic acid salts.

Further, adjuvants usable for improving the properties of formulations include, for example, carboxymethylcellulose, gum arabic, polyethylene glycol, and calcium stearate.

The above carriers, surfactants, dispersants, and adjuvant may be used either solely or in combination according to need.

The content of the active ingredient in the formulation is not particularly limited, however, in general, the content of the active ingredient is 1 to 75% by weight for emulsifiable concentrates, 0.3 to 25% by weight for dust, 1 to 90% by weight for wettable powder, and 0.5 to 10% by weight for granules.

The compound represented by formula (I), (Ia), or the above formualtions comprising the same may be applied as such or after dilution to plants or soil. Therefore, according to another aspect of the present invention, there is provided a method for controlling a pest, comprising applying an effective amount of a compound represented by formula (I) to a plant or soil. Further, according to still another aspect of the present invention, there is provided a method for controlling a hemipteran pest, comprising applying an effective amount of a compound represented by formula (Ia) to a plant or soil. Preferred methods usable for applying the above compound and formulation to plants or soil include spreading treatment, soil treatment, surface treatment, or fumigation treatment.

Spreading treatments include, for example, spreading, spraying, misting, atomizing, granule application, and submerged application. Further, soil treatments include, soil effusion and soil mixing. Further, examples of surface treatments include, for example, coating, dust coating, and covering. Further, fumigation treatments include, for example, covering of soil with a polyethylene film after soil injection. Accordingly, the control method according to the present invention comprises a method in which the compound represented by formula (I) or (Ia) or a formulation comprising the same is applied by fumigation in a sealed space.

The composition according to the present invention may be used as a mixture or in a combination with, for example, other, fungicides, insecticides, miticides, herbicides, plant growth-regulating agents, or fertilizers. Agents which may be mixed or used in combination include those described, for example, in The Pesticide Manual (13th edition, published by The British Crop Protection Council); and SHIBUYA INDEX (9th edition, 2002, published by SHIBUYA INDEX RESEARCH GROUP). More specifically, insecticides, miticides, or nematocides include, for example: organic ester phosphate compounds such as O-(4-boromo-2-chlorophenyl) O-ethyl S-propylfosphorothioate (general name: profenofos), O-(2,2-dichlorovinyl) O,O-dimethylphosphate (general name: dichlorovos), O-ethyl O-[3-methyl-4-(methylthio)phenyl] N-isopropylphosphoroamidate (general name: fanamifos), O,O-dimethyl O-(4-nirto-m-tryl)phosphorothioate (general name: fenitrothion), O-ethyl O-(4-nitrophenyl)phosphorothioate (general name: EPN), O,O-diethyl O-(2-isopropyl-6-methylpyrimidin-4-yl)phosphoroate (general name: diazinon), O,O-dimethyl O-(3,5,6-trichloro-2-pyridyl)phosphorothioate (general name: chloropyrifosmethyl), O,S-dimenylN-acetylphosphoroamidethioate (general name: acephate), and O-(2,4-dichlorophenyl) O-ethyl S-propylphosphorodioate (general name: prothiophos); carbamate compounds such as 1-naphthyl N-methylcarbamate (general name: carbaryl), 2-isopropoxyphenyl N-methylcarbamate (general name: propoxur), 2-methyl-2-(methylthio) propyonaldehyde O-methylcarbamoyloxym (general name: Aldicarb), 2,3-dihydro-2,2-dimethylbenzofuran-7-yl N-methylcarbamate (general name: carbofuran), dimethylN,N'-[thiobis{(methylimino) carbonyloxy}] gisetahneimidothiate (general name: thiodicarb), S-methyl N-(methylcarbamoyloxy) thioacetoimidate (general name: methomyl), N,N-dimethyl-2-methylcarbamoyloxyimino-2-(methylthio) acetoamide (general name: Oxamyl), 2(ethylthiomethyl) phenyl N-methylcarbamate (general name: ethyofencarb), and 2-dimethylamino-5,6-dimethylpyrimidin-4-yl N,N-dimethylcarbamate (general name: fenothiocarb); 2-sec-butylphenyl N-methylcarbamate (general name: fenobucarb); nereistoxin derivatives such as S,S'-2-dimethylaminotrimethylenebis (thiocarbamate) (general name: cartap) and N,N-dimethyl-1,2,3-trithian-5-ylamine (general name: thiocyclam); organochlorine compounds such as 2,2,2-trichloro-1,1-bis(4-chlorophenyl) ethanol (general name: dicofol) and 4-chlorophenyl-2,4,5-trichlorophenylsulfon (general name: tetradifon); organometallic compounds such as bis[tris(2-methyl-2-phenylpropyl) thin] oxyde (general name: phenbutatin oxide); pyrethoroid compounds such as (RS)-α-cyano-3-phenoxybenzyl (RS)-2-(4-chlorophenyl)-3-methylbutylate (general name: fenvalerate), 3-phenoxybenzyl (1RS)-sys, trans-3-(2,2-dichlorovinyl)-2,2-dimethylcyclopopanecarboxylate (general name: permethrin), (RS)-α-cyano-3-phenoxybenzyl (1RS)-sys, trans-3-(2,2-dichlorovinyl)-2,2-dimethylcyclopropanecarboxylate (general name: cypermethrin), (S)-α-cyano-3-phenoxybenzyl (1R)-sys-3-(2,2-dibromovinyl)-2,2-dimethylcyclopropnecarboxylate (general name: deltamethorin), (RS)-α-cyano-3-phenoxybenzyl (1RS)-sys, trans-3-(2-chloro-3,3,3-trifluoropropenyl)-2,2-dimethylchloropropanecarboxylate (general name: cyhalothrin), 4-methyl-2,3,5,6-tetrafluorobenzyl-3-(2-chloro-3,3,3-trifluoro-1-propenyl)-2,2-dimethylchloropropanecarboxylate (general name: tefluthrin), and 2-(4-ethoxyphenyl)-2-methylpropyl 3-phenoxybenzylether (general name: ethofenprox); benzoylurea compounds such as 1-(4-chlorophenyl)-3-(2,6-difluorobenzoyl)urea (general name: diflubenzuron), 1-[3,5-dichloro-4-(3-chloro-5-trifluoromethyl-2-pyridyloxy)phenyl]-3-2,6-difluorobenzoyl)-urea (general name: chlorofluazuron), and 1-(3,5-dichloro-2,4-difluorophenyl)-3-(2,6-difluorobenzoyl)urea (general name: teflubenzuron); juvenile hormone-like compounds such as isopropyl(2E,4E)-11-methoxy-3,7,11-trimethyl-2,4-dotecadienoate (general name: methoprene); pyridadinone compounds such as 2-t-butyl-5-(4-t-butylbenzylthio)-4-chloro-3 (2H)-pyridadinone (general name: pyridaben); pyrazole compounds such as t-butyl 4-[(1,3-dimethyl-5-phenoxypyrazole-4-yl) methyleneaminooxymethyl] benzoate (general name: fenpyroxymate); nitro compounds such as 1-(6-chloro-3-pyridylmethyl)-N-nitro-imidazoridin-2-iridenamine (general name: imidachloprid); or dinitro compounds, organosulfur compounds, urea compounds, triazine compounds, hydrazine compounds, and other compounds include compounds such as 2-tert-butylimino-3-isopropyl-5-phenyl-3,4,5,6-tetrahydro-2H-1,3,5-thiadiazine-4-on (general name: buprofezin), trans-(4-chlorophenyl)-N-cyclohexyl-4-methyl-2-oxothiazoridinone-3-carboxamide (general name: hexythiazox), N-methylbis(2,4-xyrylimi-nomethyl) amine (general name: amitraz), N'-(4-chloro-o-tryl)-N,N-dimethylfomramidine (general name: chlorodimeform), and (4-ethyxyphenyl)-[3-(4-fluoro-3-phenoxyphenyl) propyl](dimethyl) silane (general name: silafluofen).

Furthermore, the control agent according to the present invention may also be used as a mixture or in a combination with microbial pesticides such as BT formulations and entomopathogenic viral agents, and antibiotic agents such as avermectin and milbemycin.

Fungicides usable herein include, for example, anilinopyrimidine compounds such as 2-anilino-4-methyl-6-(1-propynyl) pyrimidine (general name: mepanipyrim) and 4,6-dimethyl-N-phenyl-2-pyrimidinamine (general name: pyrimethanil); azole compounds such as 1-(4-chlorophenoxy)-3,3-dimethyl-1-(1H-1,2,4-triazole-1-yl) butanone (general name: triadimefon), 1-(biphenyl-4-yloxy)-3,3-dimethyl-1-(1H,1,2,4-triazole-1-yl) butane-2-ol (general name: bitertanol), 1-[N-(4-chloro-2-trifluoromethylphenyl)-2-propoxyacetoimidoyl] imidazole (general name: triflumizole), 1-[2-(2,4-dichlorophenyl)-4-ethyl-1,3-dioxoran-2-ylmethyl]-1H-1,2,4-triazole (general name: etaconazole), 1-[2-(2,4-dichlorophenyl)-4-propyl-1,3-dioxoran-2-ylmethyl]-1H-1,2,4-triazole (general name: propiconazole), 1-[2-(2,4-dichlorophenyl) pentyl]-1H-1,2,4-triazole (general name: penconazole), bis (4-fluorophenyl) (methyl) (1H-1,2,4-triazole-1-ylmethyl) silane (general name: flusilazole), 2-(4-chlorphenyl)-2-(1H-1,2,4-triazole-1-ylmethyl) hexanenitryl (general name: myclobutanil), (2RS,3RS-2-4-chlorophenyl)-3-cyclopropyl-1-(1H-1,2,4-triazole-1-yl) butane-2-ol (general name: cyproconazole), (RS)-1-(4-chlorophenyl)-4,4-dimethyl-3-(1H-1,2,4-triazole-1-ylmethyl) pentane-3-ol (general name: tebuconazole), (RS)-2-(2,4-dichlorophenyl)-1-(1H-1,2,4-triazole-1-yl) hexane-2-ol (general name: hexaconazole), (2RS,5RS)-5-(2,4-dichlorophenyl) tetrahydro-5-(1H-1,2,4-triazole-1-ylmethyl)-2-furyl 2,2,2-trifluoroethylether (general name: farconazolesys), N-propyl-N-[2-(2,4,6-trichlorophenoxy) ethyl] imidazole-1-carboxamide (general name: prochloraz), and 2-(4-fluorophenyl-1-(1H-1,2,4 triazole-1-yl)-3-trimethylsilylpropane-2-ol (general name: simeconazole; quinoxaline compounds such as 6-methyl-1,3-dithiolo [4,5-b] quinoxaline-2-on (general name: quinomethonate); manganezeethylenebis (dithiocabamate) compounds (general name: maneb), zincethylenebis (dimethyldiocarbamate) compounds (general name: zineb), complex compounds of zinc and manganeseethylenebis(dithiocarbamate) (maneb) (general name: manzeb); ditiocarbamate compounds such as dizincbis (dimethylditiocarbamate) ethylenebis (diocarbamate) (general name: propineb); organochlorine compounds such as 4,5,6,7-tetrachlorofutharide (general name: futharide), tetrachloroisofuitharonitril (general name: chlorothalonil), and pentachloronitrobenzene (general name: quitozene); benzimidazole compounds such as methyl 1-(butylcarbamoyl) benzimidazole-2-ylcarbamate (general name: benomyl), dimetyl 4,4'-(o-phenylene) bis (3-thioarophanete) (general name: thiophanate-methyl), and methylbenzimidazole-2-ylcarbamate (general name: carbendazym); pyridinamine compounds such as 3-chloro-N-(3-chloro-2,6-dinitro-4-α,α,α-trifluorotryl)-5-trifluoromethyl-2-pyridinamine (general name: fluazinam); cyanoacetoamide compounds such as 1-(2-cyano-2-methoxyiminoacetyl)-3-ethylurea (general name: cymoxanil); phenylamide compounds such as methyl N-(2-methoxyacetyl)-N-5(2,6-xylyl)-DL-araninate (general name: metalaxyl), 2-methoxy-N-(2-oxo-1,3-oxazolyzine-3-yl) aceto-2',6'-xylidide (general name: oxadixyl), (±)-α-2-chloro-N-(2,6-xylylacetoamide)-γ-butyloractone (general name: ofurace), methyl N-phenylacetyl-N-(2,6-xylyl)-DL-araninate (general name: benalaxyl), methyl N-(2-floyl)-N-(2,6-xylyl)-DL-araninate (general name: furalaxyl), and (±)-α-[N-(3-chlorophenyl) cyclopropnecarboxamide]-γ-butyloractone (general name: cyprofuran); sulfenic acid compounds such as N-dichlorofluoromethylthio-N',N'-dimethyl-N-phenylsulfamide (general name: dichlofluanid); copper compounds such as copper hydroxide (general name: copper hydroxide) and copper-8-quinolynolate (general name: organocopper); isoxazole compounds such as 5-methylisoxazole-3-ol (general name: hydroxyisoxazole); organophosphorous compounds such as aluminumtris (ethylphosphnate) (general name: fosetylaluminum), O-2,6-dichloro-p-tril-O,O-dimethylphosphorothioate (general name: tolclofos-methyl), S-benzyl O,O-diisopropylphosphorothioate, O-ethyl S,S-diphenylphosphorodithioate, and aluminumethylhydrogenphosphonate; N-halogenothioalkyl compounds such as N-(trichloromethylthio) cyclohexy-4-en-1,2-dicarboxyimide (general name: captan), N-(1,1,2,2-tetrachloroethylthio) cyclohexy-4-en-1,2-dicarboxyimide (general name: captafol), and dicarboxyimide compounds such as N-(3,5-dichlorophenyl)-1,2-dimethylcyclopropane-1,2-dicarboxyimide (general name: procymidone), 3-(3,5-dichlorophenyl)-N-isopropyl-2,4-dioxoimidazolidine-1-caroxamide (general name: iprodione), and (RS)-3-(3,5-dichlorophenyl)-5-methyl-5-vinyl-1,3-oxazolidine-2,4-dione (general name: vinchlozolin); benzoanilide compounds such as α,α,α-trifluoro-3'-isopropoxy-o-tolualynide (general name: flutolanil), and 3'-isopropoxy-o-tolanilide (general name: mepronil); piperadine compounds such as N,N'-[piperadine-1,4-diylbis [(trichloromethyl) methylene]] diformamide (general name: triforine); pyridine compounds such as 2',4'-dichloro-2-(3-pyridyl) acetophenone O-methyloxym (general name: pyrifenox); carbinol compounds such as (±)-2,4'-dichloro-α-(pyrimidine-5-yl) benzhydrylalcohol (general name: fenarimol) and (±)-2,4'-difluoro-α-(1H-1,2,4-triazole-1-ylmethyl) benzhydrylalcohol (general name: flutoliafol); piperidine compounds such as (RS)-1-[3-(4-tertiallybutylphenyl)-2-methylpropyl] piperidine (general name: fenpropidin); morpholine compounds such as (±)-sys-4-[3-(4-tertiallybutylphenyl)-2-methylpropyl]-2,6-dimethylmorpholine (general name: fenpropimorf); organotin compounds such as triphenylthinhydroxyde (general name: phenthinhydroxide), and triphenylthinacetate (genral name: phenthinacetate); urea compounds such as 1-(4-chlorobenzyl)-1-cyclopentyl-3-phenylurea (general name: pencycuron); cynnamic acid compounds such as (E,Z) 4-[3-(4-chlorophenyl)-3-(3,4-dimethoxyphenyl) acryloyl] morpholine (general name: dimethomorph); phenylcarbamate compounds such as isopropyl 3,4-diethoxycarbanilate (general name: diethofencarb); or cyanopyrrole compounds such as 3-cyano-4-(2,2-difluoro-1,3-benzooxol-4-yl) pyrrol (general name: fludioxonil), 3-(2',3'-dichlorophenyl)-4-cyano-pyrrol (general name: fenpiclonyl).

According to another aspect of the present invention, there is provided use of a compound represented by formula (I). Further, according to still another aspect of the present invention, there is provided use of a compound represented by formula (Ia) as a hemipteran pest control agent.

EXAMPLES

The present invention will be specifically described hereunder with reference to examples, however, the present invention is not limited to these examples.

Preparation Example 1 [Wettable Powder]

| | |
|---|---|
| Compound according to the present invention (Compound No. 82) | 30 wt % |
| Clay | 30 wt % |
| Diatomaceous earth | 35 wt % |
| Calcium lignin sulfonate | 4 wt % |
| Sodium laurylsulfate | 1 wt % |

The above ingredients were homogeneously mixed together, and the mixture was ground to prepare wettable powder.

Preparation Example 2 [Dust]

| | |
|---|---|
| Compound according to the present invention (Compound No. 82) | 2 wt % |
| Clay | 60 wt % |
| Talc | 37 wt % |
| Calcium stearate | 1 wt % |

The above ingredients were homogeneously mixed together to prepare dust.

Preparation Example 3 [Emulsifiable Concentrate]

| | |
|---|---|
| Compound according to the present invention (Compound No. 82) | 20 wt % |
| N,N-Dimethylformamide | 20 wt % |
| Solvesso 150 (Exxon Mobil Corporation) | 50 wt % |
| Polyoxyethylenealkylarylether | 10 wt % |

The above ingredients were homogeneously mixed and dissolved to prepare emulsifiable concentrate.

Preparation Example 4 [Granules]

| | |
|---|---|
| Compound according to the present invention (Compound No. 28) | 5 wt % |
| Bentonite | 40 wt % |
| Talc | 10 wt % |
| Clay | 43 wt % |
| Calcium lignin sulfonate | 2 wt % |

The above ingredients were homogeneously ground and homogeneously mixed together and water was added to the mixture, followed by thorough kneading, then the kneaded product was granulated and dried to prepare granules.

Preparation Example 5 [Floables]

| | |
|---|---|
| Compound according to the present invention (Compound No. 28) | 25 wt % |
| POE polystyrylphenyl ether sulfate | 5 wt % |
| Propyleneglycol | 6 wt % |
| Bentonite | 1 wt % |
| 1% aqueous xanthan gum solution | 3 wt % |
| PRONAL EX-300 (Toho Chemical Industry Co., Ltd.) | 0.05 wt % |
| ADDAC 827 (K.I. Chemical Industry Co., Ltd.) | 0.02 wt % |
| Water | To 100 wt % |

All the above ingredients except for the 1% aqueous xanthan gum solution and a suitable amount of water were premixed together, and the mixture was then ground by a wet grinding mill. Thereafter, the 1% aqueous xanthan gum solution and the remaining water were added to the ground product to prepare 100 wt % floables.

Test Example 1: Pesticidal Effect Against *Myzus persicae*

Among the compounds of formula (I) produced by the conventional method described above, the compounds shown in Tables 1 to 14 were tested for pesticidal effect.

A leaf disk having a diameter of 2.8 cmφ was cut out from a cabbage grown in a pot and was placed in a 5.0 cm-Schale. Four adult aphids of *Myzus persicae* were released in this Schale. One day after the release of the adult aphids, the adult aphids were removed. The number of larvae at the first instar born in the leaf disk was adjusted to 10, and a test solution, which had been adjusted to a concentration of 20 ppm by the addition of a 50% aqueous acetone solution (0.05% Tween 20 added) was spread over the cabbage leaf disk. The cabbage leaf disk was then air dried and thereafter, the Schale was lidded and was allowed to stand in a temperature-controlled room (light period 16 hr—dark period 8 hr) (25° C.). Three days after the initiation of standing of the Schale, the larvae were observed for survival or death, and the death rate of larvae was calculated by the following equation.

Death rate (%) {number of dead larvae/(number of survived larvae+number of dead larvae)}×100

As result, it was found that the death rate was not less than 80% for compounds of Nos: 1, 6, 8, 9, 10, 12, 14, 16, 18, 20, 23, 25, 28, 34, 35, 36, 37, 38, 39, 40, 44, 45, 49, 54, 56, 57, 61, 69, 76, 82, 85, 86, 88, 90, 91, 98, 103, 106, 107, 108, 109, 111, 125, 128, 133, 135, 137, 139, 142, 153, 160, 161, 162, 164, 167, 169, 170, 171, 172, 176, 180, 182, 183, 186, 187, 190, 196, 201, 207.

What is claimed is:

1. A compound represented by formula (Ib) or an agriculturally and horticulturally acceptable salt thereof:

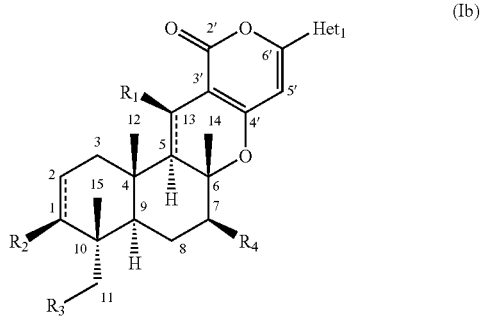

wherein
Het$_1$ represents 3-pyridyl,
R$_1$ represents hydroxyl,
R$_2$ and R$_3$ represent cyclopropylcarbonyloxy, and
R$_4$ represents hydroxyl, cyclopropylcarbonyloxy, or 2-cyanobenzoyloxy.

2. An agricultural or horticultural composition, comprising the compound according to claim 1 or an agriculturally and horticulturally acceptable salt thereof as an active ingredient and an agriculturally and horticulturally acceptable carrier.

* * * * *

UNITED STATES PATENT AND TRADEMARK OFFICE
CERTIFICATE OF CORRECTION

| | |
|---|---|
| PATENT NO. | : 7,491,738 B2 |
| APPLICATION NO. | : 11/443299 |
| DATED | : February 17, 2009 |
| INVENTOR(S) | : Kimihiko Goto et al. |

It is certified that error appears in the above-identified patent and that said Letters Patent is hereby corrected as shown below:

In the specification, abstract and claims:

*Please replace the specification and abstract of the subject patent with the attached specification and abstract.*

ABSTRACT

Disclosed is a composition for use as a pest control agent, comprising a compound represented by formula (I) or an agriculturally and horticulturally acceptable salt thereof as active ingredient and an agriculturally and horticulturally acceptable carrier:

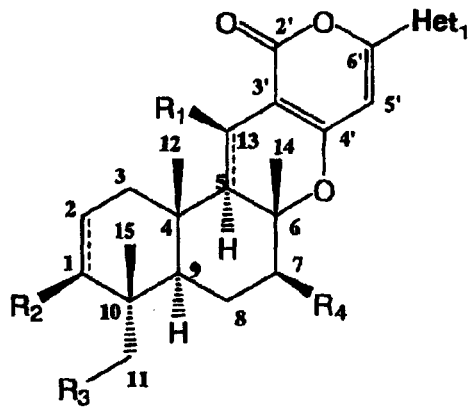

(I)

Signed and Sealed this
Twenty-sixth Day of April, 2011

David J. Kappos
*Director of the United States Patent and Trademark Office*

[BACKGROUND OF THE INVENTION]

Field of Invention

The present invention relates to a composition for use as a pest control agent comprising a pyripyropene derivative as active ingredient.

Background Art

Pyripyropene A has inhibitory activity against ACAT (acyl-CoA: cholesterol acyltransferase) and is expected to be applied, for example, to the treatment of diseases induced by cholesterol accumulation, as described in Japanese Patent No. 2993767 (Japanese Patent Laid-Open Publication No. 360895/1992) and Journal of Antibiotics (1993), 46(7), 1168-9.

Further, pyripyropene analogues and derivatives and ACAT inhibitory activity thereof are described in Journal of Society of Synthetic Organic Chemistry, Japan (1998), Vol. 56, No. 6, pp. 478-488, WO 94/09417, Japanese Patent Laid-Open Publication No. 184158/1994, Japanese Patent Laid-Open Publication No. 239385/1996, Japanese Patent Laid-Open Publication No. 259569/1996, Japanese Patent Laid-Open Publication No. 269062/1996, Japanese Patent Laid-Open Publication No. 269063/1996, Japanese Patent Laid-Open Publication No. 269064/1996, Japanese Patent Laid-Open Publication No. 269065/1996, Japanese Patent Laid-Open Publication No. 269066/1996, Japanese Patent Laid-Open Publication No. 291164/1996, and Journal of Antibiotics (1997), 50(3), 229-36.

Furthermore, Applied and Environmental Microbiology (1995), 61(12), 4429-35 describes that pyripyropene A has insecticidal activity against larvae of Helicoverpa zea. Furthermore, WO 2004/060065 describes that pyripyropene A has insecticidal activity against Plutella xylostella L larvae and Tenebrio molitor L. In these documents, however, there is no specific description on insecticidal activity of pyripyropene A against other pests.

Further, none of the above documents describes insecticidal activity of pyripyropene analogues and derivatives.

Up to now, many compounds having insecticidal activity have been reported and have been used as pest control agents. However, the presence of insect species, which are resistant to or can be hardly controlled by these compounds, has posed a problem. Accordingly, the development of a novel pest control agent having excellent insectidal activity has still been desired.

[SUMMARY OF THE INVENTION]

The present inventors have now found that pyripyropene derivatives represented by formula (I) have significant insecticidal activity.

The present inventors further found that pyripyropene A and its derivatives represented by formula (Ia) have significant insecticidal activity against hemipteran pests.

Furthermore, the present inventors have found novel pyripyropene derivatives represented by formula (Ib) having significant insecticidal activity.

The present invention has been made based on such finding.

Accordingly, an object of the present invention is to provide a composition useful as a pest control agent, that comprises a pyripyropene derivative having significant insecticidal activity as active ingredient and can reliably exhibit the contemplated effect and can be used safely. Another object of the present invention is to provide a hemipteran pest control agent that comprises pyripyropene A and its derivative as active ingredient and can reliably exhibit the contemplated effect and can be used safely. A further object of the present invention is to provide a novel pyripyropene derivative having significant insecticidal activity.

According to one aspect of the present invention, there is provided a composition for use as a pest control agent, comprising a compound represented by formula (I) or an agriculturally and horticulturally acceptable salt thereof as active ingredient and an agriculturally and horticulturally acceptable carrier:

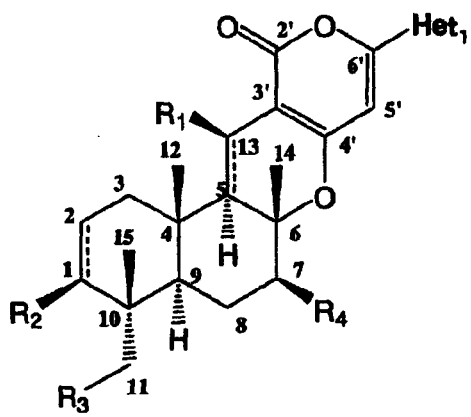

(I)

wherein
Het$_1$ represents optionally substituted 3-pyridyl,
R$_1$ represents hydroxyl,
optionally substituted C$_{1-6}$ alkylcarbonyloxy,
optionally substituted C$_{2-6}$ alkenylcarbonyloxy,
optionally substituted C$_{2-6}$ alkynylcarbonyloxy,
optionally substituted C$_{1-6}$ alkyloxy,
optionally substituted C$_{2-6}$ alkenyloxy,
optionally substituted C$_{2-6}$ alkynyloxy,
optionally substituted benzyloxy, or
oxo in the absence of a hydrogen atom at the 13-position,
or the bond between 5-position and 13-position represents a double bond in the absence of $R_1$ and a hydrogen atom at the 5-position, $R_2$ represents hydroxyl,
- optionally substituted $C_{1-18}$ alkylcarbonyloxy,
- optionally substituted $C_{2-6}$ alkenylcarbonyloxy,
- optionally substituted $C_{2-6}$ alkynylcarbonyloxy,
- optionally substituted benzoyloxy, or
- optionally substituted $C_{1-6}$ alkylsulfonyloxy, $R_3$ represents a hydrogen atom,
- hydroxyl,
- optionally substituted $C_{1-18}$ alkylcarbonyloxy,
- optionally substituted $C_{2-6}$ alkenylcarbonyloxy,
- optionally substituted $C_{2-6}$ alkynylcarbonyloxy,
- optionally substituted benzoyloxy,
- optionally substituted $C_{1-6}$ alkylsulfonyloxy,
- optionally substituted benzenesulfonyloxy, or
- optionally substituted five- or six-membered heterocyclic thiocarbonyloxy, or $R_2$ and $R_3$ together represent -O-$CR_2'R_3'$-O- wherein $R_2'$ and $R_3'$, which may be the same or different, represent a hydrogen atom, $C_{1-6}$ alkyl, $C_{1-6}$ alkyloxy, $C_{2-6}$ alkenyl, optionally substituted phenyl, or optionally substituted benzyl, or $R_2'$ and $R_3'$ together represent oxo or $C_{2-6}$ alkylene, and $R_4$ represents a hydrogen atom,
- hydroxyl,
- optionally substituted $C_{1-18}$ alkylcarbonyloxy,
- optionally substituted $C_{2-6}$ alkenylcarbonyloxy,
- optionally substituted $C_{2-6}$ alkynylcarbonyloxy,
- optionally substituted benzoyloxy,
- optionally substituted $C_{1-6}$ alkylsulfonyloxy,
- optionally substituted benzenesulfonyloxy,
- optionally substituted benzyloxy,
- optionally substituted $C_{1-6}$ alkyloxy,
- optionally substituted $C_{2-6}$ alkenyloxy,
- optionally substituted $C_{2-6}$ alkynyloxy,
- $C_{1-6}$ alkyloxy-$C_{1-6}$ alkyloxy,
- $C_{1-6}$ alkylthio-$C_{1-6}$ alkyloxy,
- $C_{1-6}$ alkyloxy-$C_{1-6}$ alkyloxy-$C_{1-6}$ alkyloxy,
- optionally substituted $C_{1-6}$ alkyloxycarbonyloxy,
- optionally substituted $C_{1-6}$ alkylaminocarbonyloxy,
- optionally substituted saturated or unsaturated five- or six-membered heterocyclic oxy,
- optionally substituted saturated or unsaturated five- or six-membered heterocyclic carbonyloxy, optionally substituted thieno[3,2-b]pyridylcarbonyloxy,
optionally substituted 1H-indolylcarbonyloxy,
optionally substituted saturated or unsaturated five- or six-membered heterocyclic thiocarbonyloxy, or
oxo in the absence of a hydrogen atom at the 7-position,
provided that
a compound wherein
$Het_1$ represents 3-pyridyl,
$R_1$ represents hydroxyl, and
all of $R_2$, $R_3$, and $R_4$ represent acetyloxy,
is excluded.

Further, according to another aspect of the present invention, there is provided a composition for use as a a hemipteran pest control agent, comprising a compound represented by formula (Ia) or an agriculturally and horticulturally acceptable salt thereof as active ingredient and an agriculturally and horticulturally acceptable carrier:

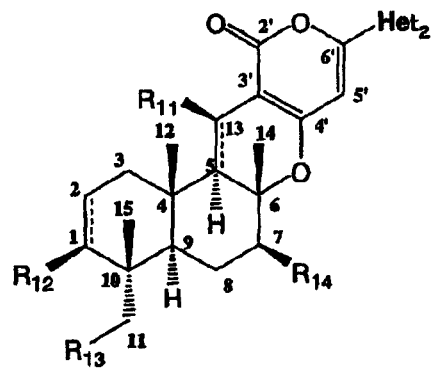

(Ia)

wherein
$Het_2$ represents optionally substituted 3-pyridyl,
$R_{11}$ represents hydroxyl,
optionally substituted $C_{1-6}$ alkylcarbonyloxy,
optionally substituted $C_{2-6}$ alkenylcarbonyloxy,
optionally substituted $C_{2-6}$ alkynylcarbonyloxy,
optionally substituted $C_{1-6}$ alkyloxy,
optionally substituted $C_{2-6}$ alkenyloxy,
optionally substituted $C_{2-6}$ alkynyloxy,
optionally substituted benzyloxy, or
oxo in the absence of a hydrogen atom at the 13-position,
or
the bond between 5-position and 13-position represents a double bond in the absence of $R_{11}$ and a hydrogen atom at the 5-position,

CERTIFICATE OF CORRECTION (continued)
U.S. Pat. No. 7,491,738 B2

$R_{12}$ represents hydroxyl,
    optionally substituted $C_{1-18}$ alkylcarbonyloxy,
    optionally substituted $C_{2-6}$ alkenylcarbonyloxy,
    optionally substituted $C_{2-6}$ alkynylcarbonyloxy,
    optionally substituted benzoyloxy, or
    optionally substituted $C_{1-6}$ alkylsulfonyloxy,
$R_{13}$ represents a hydrogen atom,
    hydroxyl,
    optionally substituted $C_{1-18}$ alkylcarbonyloxy,
    optionally substituted $C_{2-6}$ alkenylcarbonyloxy,
    optionally substituted $C_{2-6}$ alkynylcarbonyloxy,
    optionally substituted benzoyloxy,
    optionally substituted $C_{1-6}$ alkylsulfonyloxy,
    optionally substituted benzenesulfonyloxy, or
    optionally substituted five- or six-membered heterocyclic
thiocarbonyloxy, or
$R_{12}$ and $R_{13}$ together represent -O-$CR_{12}'R_{13}'$-O- wherein $R_{12}'$ and $R_{13}'$, which may be the same or different, represent a hydrogen atom, $C_{1-6}$ alkyl, $C_{1-6}$ alkyloxy, $C_{2-6}$ alkenyl, optionally substituted phenyl, or optionally substituted benzyl, or $R_{12}'$ and $R_{13}'$ together represent oxo or $C_{2-6}$ alkylene, and
$R_{14}$ represents a hydrogen atom,
    hydroxyl,
    optionally substituted $C_{1-18}$ alkylcarbonyloxy,
    optionally substituted $C_{2-6}$ alkenylcarbonyloxy,
    optionally substituted $C_{2-6}$ alkynylcarbonyloxy,
    optionally substituted benzoyloxy,
    optionally substituted $C_{1-6}$ alkylsulfonyloxy,
    optionally substituted benzenesulfonyloxy,
    optionally substituted benzyloxy,
    optionally substituted $C_{1-6}$ alkyloxy,
    optionally substituted $C_{2-6}$ alkenyloxy,
    optionally substituted $C_{2-6}$ alkynyloxy,
    $C_{1-6}$ alkyloxy-$C_{1-6}$ alkyloxy,
    $C_{1-6}$ alkylthio-$C_{1-6}$ alkyloxy,
    $C_{1-6}$ alkyloxy-$C_{1-6}$ alkyloxy-$C_{1-6}$ alkyloxy,
    optionally substituted $C_{1-6}$ alkyloxycarbonyloxy,
    optionally substituted $C_{1-6}$ alkylaminocarbonyloxy,
    optionally substituted saturated or unsaturated five- or
six-membered heterocyclic oxy,
    optionally substituted saturated or unsaturated five- or
six-membered heterocyclic carbonyloxy,
    optionally substituted thieno[3,2-b]pyridylcarbonyloxy,
    optionally substituted 1H-indolylcarbonyloxy, optionally substituted saturated or unsaturated five- or six-membered heterocyclic thiocarbonyloxy, or oxo in the absence of a hydrogen atom at the 7-position.

Further, the pyripyropene derivative according to the present invention comprises a compound represented by formula (Ib) or an agriculturally and horticulturally acceptable salt thereof.

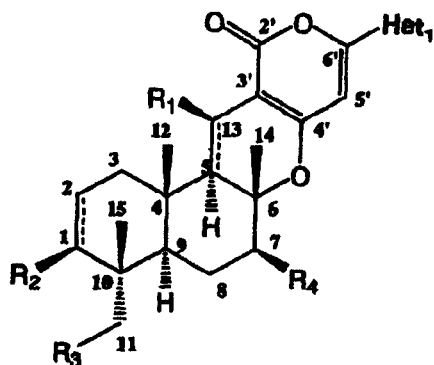

( I b )

wherein

Het$_1$ represents 3-pyridyl,

R$_1$ represents hydroxyl,

R$_2$ and R$_3$ represent propionyloxy or optionally substituted cyclic C$_{3-6}$ alkylcarbonyloxy, and R$_4$ represents hydroxyl, optionally substituted cyclic C$_{3-6}$ alkylcarbonyloxy, optionally substituted benzoyloxy, or optionally substituted saturated or unsaturated five- or six-membered heterocyclic carbonyloxy.

The pyripyropene derivatives reprsented by formula (I) or formula (Ib) according to the present invention have excellent control effect against agricultural and horiticultural pests, sanitary pests, parasites of animals, stored grain pests, clothing pests, and house pests and a compositions comprising the pyripyropene derivatives as active ingredient can be advantageously utilized as a novel pest control agent.

Further, it is surprising that, among the compounds represented by formula (Ia), pyripyropene A has excellent control effect against hemipteran pests. Accordingly, a composition according to the present invention comprising the compounds represented by formula (Ia) including pyripyropene A, can be advantageously utilized particularly a hemipteran pest control agent.

[DETAILED DESCRIPTION OF THE INVENTION]

The term "halogen" as used herein means fluorine, chlorine, bromine, or iodine, preferably fluorine, chlorine, or bromine.

The terms "alkyl," "alkenyl," and "alkynyl" as used herein as a group or a part of a group respectively mean alkyl, alkenyl, and alkynyl that the group is of a straight chain, branched chain, or cyclic type or a type of a combination thereof unless otherwise specified. Further, for example, "$C_{1-6}$" in "$C_{1-6}$ alkyl" as used herein as a group or a part of a group means that the number of carbon atoms in the alkyl group is 1 to 6. Further, in the case of cyclic alkyl, the number of carbon atoms is at least three.

The term "heterocyclic ring" as used herein means a heterocyclic ring containing one or more, preferably one to four, heteroatoms, which may be the same or different, selected from the group consisting of nitrogen, oxygen, and sulfur atoms. Further, the expression "optionally substituted" alkyl as used herein means that one or more hydrogen atoms on the alkyl group may be substituted by one or more substituents which may be the same or different. It will be apparent to a person having ordinary skill in the art that the maximum number of substituents may be determined depending upon the number of substitutable hydrogen atoms on the alkyl group. This is true of functional groups other than the alkyl group.

3-Pyridyl represented by $Het_1$ and $Het_2$ is optionally substituted, and substituents include halogen atoms, $C_{1-4}$ alkyl, $C_{1-4}$ alkyloxy, nitro, cyano, formyl, trifluoromethyl, trifluoromethoxy, trifluoromethylthio, trifluoromethylsulfinyl, trifluoromethylsulfonyl, acetyl, and acetyloxy. Preferred are halogen atoms and trifluoromethyl. A chlorine atom and trifluoromethyl are more preferred.

"$C_{1-6}$ alkylcarbonyloxy" represented by $R_1$ and $R_{11}$ is optionally substituted, and substituents include halogen atoms, cyano, phenyl, trifluoromethoxy, and trifluoromethylthio.

"$C_{1-18}$ alkylcarbonyloxy" represented by $R_2$, $R_3$ and $R_4$, and $R_{12}$, $R_{13}$ and $R_{14}$ is preferably $C_{1-6}$ alkylcarbonyloxy, more preferably propionyloxy or cyclic $C_{3-6}$ alkylcarbonyloxy. The $C_{1-18}$ alkylcarbonyloxy group is optionally substituted, and substituents include halogen atoms, cyano, cyclic $C_{3-6}$ alkyl, phenyl, trifluoromethoxy, trifluoromethylthio, pyridyl, and pyridylthio. More preferred are halogen atoms, cyclic $C_{3-6}$ alkyl, and pyridyl.

"$C_{2-6}$ alkenylcarbonyloxy" represented by $R_1$, $R_2$, $R_3$ and $R_4$, and $R_{11}$, $R_{12}$, $R_{13}$ and $R_{14}$ is optionally substituted, and substituents include halogen atoms, cyano, phenyl, trifluoromethoxy, and trifluoromethylthio.

"$C_{2-6}$ alkynylcarbonyloxy" represented by $R_1$, $R_2$, $R_3$ and $R_4$, and $R_{11}$, $R_{12}$, $R_{13}$ and $R_{14}$ is optionally substituted, and substituents include halogen atoms, cyano, phenyl, trifluoromethoxy, and trifluoromethylthio.

"$C_{1-6}$ alkyloxy" represented by $R_1$ and $R_4$, and $R_{11}$ and $R_{14}$ is optionally substituted, and substituents include halogen atoms; cyano; phenyl; trifluoromethoxy; trifluoromethylthio; $C_{1-6}$ alkylcarbonyl optionally substituted by a halogen atom; and $C_{1-6}$ alkylcarbonyloxy optionally substituted by a halogen atom.

"$C_{2-6}$ alkenyloxy" represented by $R_1$ and $R_4$, and $R_{11}$ and $R_{14}$ is optionally substituted, and substituents include halogen atoms; cyano; phenyl; trifluoromethoxy; trifluoromethylthio; $C_{1-6}$ alkylcarbonyl optionally substituted by a halogen atom; and $C_{1-6}$ alkylcarbonyloxy optionally substituted by a halogen atom.

"$C_{2-6}$ alkynyloxy" represented by $R_1$ and $R_4$, and $R_{11}$ and $R_{14}$ is optionally substituted, and substituents include halogen atoms; cyano; phenyl; trifluoromethoxy; trifluoromethylthio; $C_{1-6}$ alkylcarbonyl optionally substituted by a halogen atom; and $C_{1-6}$ alkylcarbonyloxy optionally substituted by a halogen atom.

Phenyl in "benzyloxy" represented by $R_1$ and $R_4$, and $R_{11}$ and $R_{14}$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; formyl; azide; guanidyl; group -C(=NH)-NH$_2$; and group -CH=N-O-CH$_3$.

Phenyl in "benzoyloxy" represented by $R_2$, $R_3$ and $R_4$, and $R_{12}$, $R_{13}$ and $R_{14}$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; nitro; formyl; azide; guanidyl; group -C(=NH)-NH$_2$; and group -CH=N-O-CH$_3$. Preferred are halogen atoms, $C_{1-6}$ alkyl substituted by a halogen atom, cyano, and nitro.

Phenyl in "benzenesulfonyloxy" represented by $R_3$ and $R_4$, and $R_{13}$ and $R_{14}$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; formyl; azide; guanidyl; group -C(=NH)-NH$_2$; and group -CH=N-O-CH$_3$.

"$C_{1-6}$ alkylsulfonyloxy" represented by $R_2$, $R_3$ and $R_4$, and $R_{12}$, $R_{13}$ and $R_{14}$ is optionally substituted, and substituents include halogen atoms, cyano, phenyl, trifluoromethoxy, and trifluoromethylthio.

"$C_{1-6}$ alkyloxycarbonyloxy" represented by $R_4$ and $R_{14}$ is optionally substituted, and substituents include halogen atoms, cyano, phenyl, trifluoromethoxy, and trifluoromethylthio.

"$C_{1-6}$ alkylaminocarbonyloxy" represented by $R_4$ and $R_{14}$ is optionally substituted, and substituents include halogen atoms, cyano, phenyl, trifluoromethoxy, and trifluoromethylthio.

"Phenyl" represented by $R_2$' and $R_3$', and $R_{12}$' and $R_{13}$' and phenyl in "benzyl" represented by $R_2$' and $R_3$', and $R_{12}$' and $R_{13}$' is optionally substituted, and substituents include halogen atoms, $C_{1-4}$ alkyl, $C_{1-4}$ alkyloxy, nitro, cyano, formyl, trifluoromethoxy, acetyl, and acetyloxy.

"Saturated or unsaturated five- or six-membered heterocyclic ring" in "saturated or unsaturated five- or six-membered heterocyclic thiocarbonyloxy" represented by $R_3$ and $R_{13}$, and "saturated or unsaturated five- or six-membered heterocyclic oxy," "saturated or unsaturated five- or six-membered heterocyclic carbonyloxy," and "saturated or unsaturated five- or six-membered heterocyclic thiocarbonyloxy" represented by $R_4$ and $R_{14}$, is preferably, saturated or unsaturated five- or six-membered heterocyclic ring containing one to three heteroatoms selected from the group consisting of nitrogen, oxygen, and sulfur atoms, more preferably, saturated or unsaturated five- or six-membered heterocyclic ring containing one or two heteroatoms selected from the group consisting of nitrogen, oxygen, and sulfur atoms, more preferably, saturated or unsaturated five- or six-membered heterocyclic ring containing one or two nitrogen atoms, saturated or unsaturated five- or six-membered heterocyclic ring containing one or two oxygen atoms, saturated or unsaturated five- or six-membered heterocyclic ring containing one or two sulfur atoms, saturated or unsaturated five- or six-membered heterocyclic ring containing one nitrogen atom and one oxigen atom, or saturated or unsaturated five- or six-membered heterocyclic ring containing one nitrogen atom and one sulfur atom.

More specifically, examples of the "saturated or unsaturated five- or six-membered heterocyclic ring" include thienyl, furyl, pyrrolyl, imidazolyl, pyrazolyl, isothiazoyl, isoxazolyl, thiazolyl, oxazolyl, pyridyl, pyrimidinyl, pyrazinyl, pyridazinyl, tetrahydropyranyl, piperidinyl, piperazinyl, morpholinyl, and mannosyl. Preferred are pyridyl, furanyl, thiazolyl, imidazolyl, tetrahydropyranyl, and mannosyl. More specific examples thereof include (2- or 3-)thienyl, (2- or 3-)furyl, (1-, 2- or 3-)pyrrolyl, (1-, 2-, 4- or 5-)imidazolyl, (1-, 3-, 4- or 5-)pyrazolyl, (3-, 4- or 5-)isothiazoyl, (3-, 4- or 5-)isoxazolyl, (2-, 4- or 5-)thiazolyl, (2-, 4- or 5-)oxazolyl, (2-, 3- or 4-)pyridyl or, (2-, 4-, 5- or 6-)pyrimidinyl, (2- or 3-)pyrazinyl, (3- or 4-)pyridazinyl, (2-, 3- or 4-)tetrahydropyranyl, (1-, 2-, 3- or 4-)piperidinyl, (1-, 2- or 3-)piperazinyl, and (2-, 3- or 4-)morpholinyl, preferably 3-pyridyl, 2-franyl, 5-thiazolyl, 1-imidazolyl, 5-imidazolyl, and 2-tetrahydropyranyl, more preferably 2-tetrahydropyranyl, 2-pyrazinyl, and 3-pyridyl, particularly preferably 3-pyridyl.

The heterocyclic ring in the "saturated or unsaturated five- or six-membered heterocyclic carbonyloxy" and "saturated or unsaturated five- or six-membered heterocyclic thiocarbonyloxy" and "thieno[3,2-b]pyridylcarbonyloxy" and "1H-indolylcarbonyloxy" represented by $R_4$ and $R_{14}$ are optionally substituted, and substituents include halogen atoms, $C_{1-4}$ alkyl, $C_{1-4}$ alkyloxy, $C_{1-4}$ alkylthio, nitro, cyano, formyl, trifluoromethoxy, trifluoromethyl, trifluoromethylthio, trifluoromethylsulfinyl, trifluoromethylsulfonyl, acetyl, acetyloxy, benzoyl, and $C_{1-4}$ alkyloxycarbonyl. Preferred are halogen atoms, $C_{1-4}$ alkyl, $C_{1-4}$ alkyloxy, and trifluoromethyl.

The heterocyclic ring in the "saturated or unsaturated five- or six-membered heterocyclic oxy" is optionally substituted, and substituents include hydroxyl, benzyloxy, a halogen atom, $C_{1-4}$ alkyl, $C_{1-4}$ alkyloxy, nitro, cyano, formyl, trifluoromethoxy, trifluoromethyl, trifluoromethylthio, trifluoromethylsulfinyl, trifluoromethylsulfonyl, acetyl, and acetyloxy. Preferred are hydroxyl and benzyloxy.

<u>A composition for use as a pest control agent, comprising a compound represented by formula (I)</u>

According to a preferred embodiment of the present invention, in the compound represented by formula (I), preferably, $Het_1$ represents 3-pyridyl.

Further, according to a preferred embodiment of the present invention, in the compound represented by formula (I), $R_1$ represents hydroxyl, $C_{1-6}$ alkylcarbonyloxy, $C_{1-3}$ alkyloxy, or benzyloxy, or oxo in the absence of a hydrogen atom at the 13-position, or the bond between 5-position and 13-position represents a double bond in the absence of $R_1$ and a hydrogen atom at the 5-position. More preferably, $R_1$ represents hydroxyl or $C_{1-6}$ alkylcarbonyloxy, or the bond between 5-position and 13-position represents a double bond in the absence of $R_1$ and a hydrogen atom at the 5-position, still more preferably $R_1$ represents hydroxyl.

According to a preferred embodiment of the present invention, in the compound represented by formula (I), $R_2$ represents hydroxyl, optionally substituted $C_{1-18}$ alkylcarbonyloxy, optionally substituted benzoyloxy, or $C_{1-3}$ alkylsulfonyloxy, more preferably optionally substituted $C_{1-18}$ alkylcarbonyloxy, still more preferably optionally substituted $C_{1-6}$ alkylcarbonyloxy, still more preferably straight chain or branched chain $C_{1-6}$ alkylcarbonyloxy (particularly propionyloxy) or optionally substituted cyclic $C_{3-6}$ alkylcarbonyloxy.

In a preferred embodiment of the present invention, in the compound represented by formula (I), $R_3$ represents a hydrogen atom, hydroxyl, optionally substituted $C_{1-18}$ alkylcarbonyloxy, optionally substituted benzoyloxy, $C_{1-6}$ alkylsulfonyloxy, optionally substituted benzenesulfonyloxy, or saturated or unsaturated five- or six-membered heterocyclic thiocarbonyloxy, more preferably optionally substituted $C_{1-6}$ alkylcarbonyloxy or $C_{1-6}$ alkylsulfonyloxy, still more preferably optionally substituted $C_{1-6}$ alkylcarbonyloxy, still more preferably straight chain or branched chain $C_{2-4}$ alkylcarbonyloxy (particularly propionyloxy) or optionally substituted cyclic $C_{3-6}$ alkylcarbonyloxy.

According to a preferred embodiment of the present invention, in the compound represented by formula (I), $R_2$ and $R_3$ together represent -O-$CR_2'R_3'$-O-, wherein $R_2'$ and $R_3'$ which may be the same or different, represent a hydrogen atom, $C_{1-6}$ alkyl, $C_{1-3}$ alkyloxy, $C_{2-3}$ alkenyl, benzyl, or optionally substituted phenyl, or $R_2'$ and $R_3'$ together represent oxo or $C_{2-6}$ alkylene. More preferably, $R_2$ and $R_3$ together represent -O-$CR_2'R_3'$-O-, wherein $R_2'$ and $R_3'$ which may be the same or different, represent a hydrogen atom, $C_{1-6}$ alkyl, or optionally substituted phenyl, or $R_2'$ and $R_3'$ together represent oxo or $C_{2-6}$ alkylene.

According to a preferred embodiment of the present invention, in the compound represented by formula (I), $R_4$ represents a hydrogen atom, hydroxyl, optionally substituted $C_{1-18}$ alkylcarbonyloxy, $C_{2-6}$ alkenylcarbonyloxy, $C_{2-6}$ alkynyl carbonyloxy, $C_{1-6}$ alkylsulfonyloxy, benzenesulfonyloxy, benzyloxy, $C_{1-3}$ alkyloxy, $C_{1-3}$ alkyloxy-$C_{1-3}$ alkyloxy, $C_{1-3}$ alkylthio-$C_{1-3}$ alkyloxy, $C_{1-3}$ alkyloxy-$C_{1-3}$ alkyloxy-$C_{1-3}$ alkyloxy, optionally substituted $C_{1-3}$ alkyloxycarbonyloxy, optionally substituted $C_{1-6}$ alkylaminocarbonyloxy, optionally substituted benzoyloxy, saturated or unsaturated five- or six-membered heterocyclic oxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. More preferably, $R_4$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. Still more preferably, $R_4$ represents hydroxyl, optionally substituted $C_{1-6}$ alkylcarbonyloxy, saturated or unsaturated five- or six-membered heterocyclic oxy, optionally substituted benzoyloxy, optionally substituted saturated or unsaturated five- or six-membered heterocyclic carbonyloxy, or saturated or unsaturated five- or six-membered heterocyclic thiocarbonyloxy. Still more preferably, $R_4$ represents hydroxyl, straight chain or branched chain $C_{2-4}$ alkylcarbonyloxy (particularly propionyloxy), optionally substituted cyclic $C_{3-6}$ alkylcarbonyloxy, or optionally substituted saturated or unsaturated five- or six-membered heterocyclic carbonyloxy.

According to another preferred embodiment of the present invention, in the compound represented by formula (I), $Het_1$ represents 3-pyridyl, $R_1$ represents hydroxyl or $C_{1-6}$ alkylcarbonyloxy, or the bond between 5-position and 13-position represents a double bond in the absence of and a hydrogen atom at the 5-position, $R_2$ represents optionally substituted $C_{1-6}$ alkylcarbonyloxy, $R_3$ represents optionally substituted $C_{1-6}$ alkylcarbonyloxy or $C_{1-6}$ alkylsulfonyloxy, or $R_2$ and $R_3$ together represent -O-$CR_2'R_3'$-O- wherein $R_2'$ and $R_3'$, which may be the same or different, represent a hydrogen atom, $C_{1-6}$ alkyl, or optionally substituted phenyl, or $R_2'$ and $R_3'$ together represent oxo or $C_{2-6}$ alkylene, and $R_4$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (I), $Het_1$ represents 3-pyridyl, $R_1$ represents hydroxyl, $R_2$ represents optionally substituted $C_{1-6}$ alkylcarbonyloxy, and $R_3$ represents optionally substituted $C_{1-6}$ alkylcarbonyloxy or $C_{1-6}$ alkylsulfonyloxy, and $R_4$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six- membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (I), $Het_1$ represents 3-pyridyl, represents hydroxyl, $R_2$ represents optionally substituted $C_{1-6}$ alkylcarbonyloxy, $R_3$ represents optionally substituted $C_{1-6}$ alkylcarbonyloxy or $C_{1-6}$ alkylsulfonyloxy, and $R_4$ represents hydroxyl, optionally substituted $C_{1-6}$ alkylcarbonyloxy, optionally substituted benzoyloxy, saturated or unsaturated five- or six-membered heterocyclic oxy, optionally substituted saturated or unsaturated five- or six-membered heterocyclic carbonyloxy, or saturated or unsaturated five- or six-membered heterocyclic thiocarbonyloxy.

According to another preferred embodiment of the present invention, in the compound represented by formula (I), $Het_1$ represents 3-pyridyl, $R_1$ represents hydroxyl, and $R_2$ and $R_3$ represent optionally substituted cyclic $C_{3-6}$ alkylcarbonyloxy.

According to another preferred embodiment of the present invention, in the compound represented by formula (I),
 $Het_1$ represents 3-pyridyl,
 $R_1$ represents hydroxyl or
  optionally substituted $C_{1-6}$ alkylcarbonyloxy or
 the bond between 5-position and 13-position represents a double bond in the absence of $R_1$ and a hydrogen atom at the 5-position,
  $R_2$ represents optionally substituted $C_{1-18}$ alkylcarbonyloxy or
   optionally substituted benzoyloxy,
  $R_3$ represents optionally substituted $C_{1-18}$ alkylcarbonyloxy or
   optionally substituted $C_{1-6}$ alkylsulfonyloxy, and
  $R_4$ represents hydroxyl,
   optionally substituted $C_{1-18}$ alkylcarbonyloxy,
   optionally substituted $C_{2-6}$ alkenylcarbonyloxy,
   optionally substituted benzoyloxy,
   optionally substituted $C_{1-6}$ alkylaminocarbonyloxy,
   optionally substituted saturated or unsaturated five- or
  six-membered heterocyclic oxy,
   optionally substituted saturated or unsaturated five- or
   six-membered heterocyclic carbonyloxy,
   optionally substituted thieno[3,2-b]pyridylcarbonyloxy
   optionally substituted 1H-indolylcarbonyloxy, or
   oxo in the absence of a hydrogen atom at the 7-position.

According to another preferred embodiment of the present invention, in the compound represented by formula (I),
$Het_1$ represents 3-pyridyl,
$R_1$ represents hydroxyl or
optionally substituted $C_{1-6}$ alkylcarbonyloxy, or
the bond between 5-position and 13-position represents a double bond in the absence of $R_1$ and a hydrogen atom at the 5-position,
$R_2$ represents optionally substituted $C_{1-18}$ alkylcarbonyloxy,
$R_3$ represents optionally substituted $C_{1-18}$ alkylcarbonyloxy or
optionally substituted $C_{1-6}$ alkylsulfonyloxy, and
$R_4$ represents hydroxyl,
optionally substituted $C_{1-18}$ alkylcarbonyloxy,
optionally substituted $C_{2-6}$ alkenylcarbonyloxy,
optionally substituted benzoyloxy,
optionally substituted $C_{1-6}$ alkylaminocarbonyloxy,
optionally substituted saturated or unsaturated five- or six-membered heterocyclic oxy,
optionally substituted saturated or unsaturated five- or six-membered heterocyclic carbonyloxy, or
oxo in the absence of a hydrogen atom at the 7-position.

According to another preferred embodiment of the present invention, in the compound represented by formula (I),
$Het_1$ represents 3-pyridyl,
$R_1$ represents hydroxyl or
optionally substituted $C_{1-6}$ alkylcarbonyloxy, or
the bond between 5-position and 13-position represents a double bond in the absence of $R_1$ and a hydrogen atom at the 5-position,
$R_2$ represents optionally substituted $C_{1-18}$ alkylcarbonyloxy,
$R_3$ represents optionally substituted $C_{1-18}$ alkylcarbonyloxy,
$R_4$ represents hydroxyl,
optionally substituted $C_{1-18}$ alkylcarbonyloxy,
optionally substituted benzoyloxy,
optionally substituted saturated or unsaturated five- or six-membered heterocyclic oxy, or
optionally substituted saturated or unsaturated five- or six-membered heterocyclic carbonyloxy.

According to another preferred embodiment of the present invention, in the compound represented by formula (I), $Het_1$ represents 3-pyridyl, $R_1$ represents hydroxyl, $R_2$ represents $C_{1-6}$ alkylcarbonyloxy, and $R_3$ and/or $R_4$ represent $C_{2-4}$ alkylcarbonyloxy.

Further, an agriculturally and horticulturally acceptable salt of the compound represented by formula (I) include the same as that of the compound represented by formula (Ib) described below.

A composition for use as a hemipteran pest control agent, comprising a compound represented by formula (Ia)

According to a preferred embodiment of the present invention, in the compound represented by formula (Ia), preferably, $Het_2$ represents 3-pyridyl.

Further, according to a preferred embodiment of the present invention, in the compound represented by formula (Ia), $R_{11}$ represents hydroxyl, $C_{1-6}$ alkylcarbonyloxy, $C_{1-3}$ alkyloxy, or benzyloxy, or oxo in the absence of a hydrogen atom at the 13-position, or the bond between 5-position and 13-position represents a double bond in the absence of $R_{11}$ and a hydrogen atom at the 5-position. More preferably, $R_{11}$ represents hydroxyl or $C_{1-6}$ alkylcarbonyloxy, or the bond between 5-position and 13-position represents a double bond in the absence of $R_{11}$ and a hydrogen atom at the 5-position, still more preferably $R_{11}$ represents hydroxyl.

According to a preferred embodiment of the present invention, in the compound represented by formula (Ia), $R_{12}$ represents hydroxyl, optionally substituted $C_{1-18}$ alkylcarbonyloxy, optionally substituted benzoyloxy, or $C_{1-3}$ alkylsulfonyloxy, more preferably optionally substituted $C_{1-18}$ alkylcarbonyloxy, still more preferably optionally substituted $C_{1-6}$ alkylcarbonyloxy, still more preferably straight chain or branched chain $C_{1-6}$ alkylcarbonyloxy (particularly propionyloxy) or optionally substituted cyclic $C_{3-6}$ alkylcarbonyloxy.

In a preferred embodiment of the present invention, in the compound represented by formula (Ia), $R_{13}$ represents a hydrogen atom, hydroxyl, optionally substituted $C_{1-18}$ alkylcarbonyloxy, optionally substituted benzoyloxy, $C_{1-6}$ alkylsulfonyloxy, optionally substituted benzenesulfonyloxy, or saturated or unsaturated five- or six-membered heterocyclic thiocarbonyloxy, more preferably optionally substituted $C_{1-6}$ alkylcarbonyloxy or $C_{1-6}$ alkylsulfonyloxy, still more preferably optionally substituted $C_{1-6}$ alkylcarbonyloxy, still more preferably straight chain or branched chain $C_{2-4}$ alkylcarbonyloxy (particularly propionyloxy) or optionally substituted cyclic $C_{3-6}$ alkylcarbonyloxy.

According to a preferred embodiment of the present invention, in the compound represented by formula (Ia), $R_{12}$ and $R_{13}$ together represent $-O-CR_{12}'R_{13}'-O-$, wherein $R_{12}'$ and $R_{13}'$, which may be the same or different, represent a hydrogen atom, $C_{1-6}$ alkyl, $C_{1-3}$ alkyloxy, $C_{2-3}$ alkenyl, benzyl, or optionally substituted phenyl, or $R_{12}'$ and $R_{13}'$ together represent oxo or $C_{2-6}$ alkylene. More preferably, $R_{12}$ and $R_{13}$ together represent $-O-CR_{12}'R_{13}'-O-$, wherein $R_{12}'$ and $R_{13}'$, which may be the same or different, represent a hydrogen atom, $C_{1-6}$ alkyl, or optionally substituted phenyl, or $R_{12}'$ and $R_{13}'$ together represent oxo or $C_{2-6}$ alkylene.

According to a preferred embodiment of the present invention, in the compound represented by formula (Ia), $R_{14}$ represents a hydrogen atom, hydroxyl, optionally substituted $C_{1-18}$ alkylcarbonyloxy, $C_{2-6}$ alkenylcarbonyloxy, $C_{2-6}$ alkynyl carbonyloxy, $C_{1-6}$ alkylsulfonyloxy, benzenesulfonyloxy, benzyloxy, $C_{1-3}$ alkyloxy, $C_{1-3}$ alkyloxy-$C_{1-3}$ alkyloxy, $C_{1-3}$ alkylthio-$C_{1-3}$ alkyloxy, $C_{1-3}$ alkyloxy-$C_{1-3}$ alkyloxy-$C_{1-3}$ alkyloxy, optionally substituted $C_{1-3}$ alkyloxycarbonyloxy, optionally substituted $C_{1-6}$ alkylaminocarbonyloxy, optionally substituted benzoyloxy, saturated or unsaturated five- or six-membered heterocyclic oxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. More preferably, $R_{14}$ represents hydroxyl, optionally substituted $C_{1-6}$ alkylcarbonyloxy, optionally substituted benzoyloxy, saturated or unsaturated five- or six-membered heterocyclic oxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. Still more preferably, $R_{14}$ represents hydroxyl, optionally substituted $C_{1-6}$ alkylcarbonyloxy, saturated or unsaturated five- or six-membered heterocyclic oxy, optionally substituted benzoyloxy, optionally substituted saturated or unsaturated five- or six-membered heterocyclic carbonyloxy, or saturated or unsaturated five- or six-membered heterocyclic thiocarbonyloxy. Still more preferably, $R_{14}$ represents straight chain or branched chain $C_{2-4}$ alkylcarbonyloxy (particularly propionyloxy), optionally substituted cyclic $C_{3-6}$ alkylcarbonyloxy, or optionally substituted saturated or unsaturated five- or six-membered heterocyclic carbonyloxy.

According to another preferred embodiment of the present invention, in the compound represented by formula (Ia), $Het_2$ represents 3-pyridyl, $R_{11}$ represents hydroxyl or $C_{1-6}$ alkylcarbonyloxy, or the bond between 5-position and 13-position represents a double bond in the absence of $R_{11}$ and a hydrogen atom at the 5-position, $R_{12}$ represents optionally substituted $C_{1-6}$ alkylcarbonyloxy, $R_{13}$ represents optionally substituted $C_{1-6}$ alkylcarbonyloxy or $C_{1-6}$ alkylsulfonyloxy, or $R_{12}$ and $R_{13}$ together represent -O-$CR_{12}'R_{13}'$-O- wherein $R_{12}'$ and $R_{13}'$, which may be the same or different, represent a hydrogen atom, $C_{1-6}$ alkyl, or optionally substituted phenyl, or $R_{12}'$ and $R_{13}'$ together represent oxo or $C_{2-6}$ alkylene, and $R_{14}$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (Ia), $Het_2$ represents 3-pyridyl, $R_{11}$ represents hydroxyl, $R_{12}$ represents optionally substituted $C_{1-6}$ alkylcarbonyloxy, and $R_{13}$ represents optionally substituted $C_{1-6}$ alkylcarbonyloxy or $C_{1-6}$ alkylsulfonyloxy, and $R_{14}$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six- membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (Ia), $Het_2$ represents 3-pyridyl, $R_{11}$ represents hydroxyl, $R_{12}$ represents optionally substituted $C_{1-6}$ alkylcarbonyloxy, $R_{13}$ represents optionally substituted $C_{1-6}$ alkylcarbonyloxy or $C_{1-6}$ alkylsulfonyloxy, and $R_{14}$ represents hydroxyl, optionally substituted $C_{1-6}$ alkylcarbonyloxy, optionally substituted benzoyloxy, saturated or unsaturated five- or six-membered heterocyclic oxy, optionally substituted saturated or unsaturated five- or six-membered heterocyclic carbonyloxy, or saturated or unsaturated five- or six-membered heterocyclic thiocarbonyloxy.

According to another preferred embodiment of the present invention, in the compound represented by formula (Ia), $Het_2$ represents 3-pyridyl, $R_{11}$ represents hydroxyl, and $R_{12}$ and $R_{13}$ represent optionally substituted cyclic $C_{3-6}$ alkylcarbonyloxy.

According to another preferred embodiment of the present invention, in the compound represented by formula (Ia),
$Het_2$ represents 3-pyridyl,
$R_{11}$ represents hydroxyl or
optionally substituted $C_{1-6}$ alkylcarbonyloxy, or
the bond between 5-position and 13-position represents a double bond in the absence of $R_{11}$ and a hydrogen atom at the 5-position, $R_{12}$ represents optionally substituted $C_{1-18}$ alkylcarbonyloxy or
  optionally substituted benzoyloxy,
$R_{13}$ represents optionally substituted $C_{1-18}$ alkylcarbonyloxy or
  optionally substituted $C_{1-6}$ alkylsulfonyloxy, and
$R_{14}$ represents hydroxyl,
  optionally substituted $C_{1-18}$ alkylcarbonyloxy,
  optionally substituted $C_{2-6}$ alkenylcarbonyloxy,
  optionally substituted benzoyloxy,
  optionally substituted $C_{1-6}$ alkylaminocarbonyloxy,
  optionally substituted saturated or unsaturated five- or
six-membered heterocyclic oxy,
  optionally substituted saturated or unsaturated five- or
six-membered heterocyclic carbonyloxy,
  optionally substituted thieno[3,2-b]pyridylcarbonyloxy,
  optionally substituted 1H-indolylcarbonyloxy, or
  oxo in the absence of a hydrogen atom at the 7-position.

According to another preferred embodiment of the present invention, in the compound represented by formula (Ia),
$Het_2$ represents 3-pyridyl,
$R_{11}$ represents hydroxyl or
  optionally substituted $C_{1-6}$ alkylcarbonyloxy, or
the bond between 5-position and 13-position represents a double bond in the absence of $R_{11}$ and a hydrogen atom at the 5-position,
$R_{12}$ represents optionally substituted $C_{1-18}$ alkylcarbonyloxy,
$R_{13}$ represents optionally substituted $C_{1-18}$ alkylcarbonyloxy or
  optionally substituted $C_{1-6}$ alkylsulfonyloxy, and
$R_{14}$ represents hydroxyl,
  optionally substituted $C_{1-18}$ alkylcarbonyloxy,
  optionally substituted $C_{2-6}$ alkenylcarbonyloxy,
  optionally substituted benzoyloxy,
  optionally substituted $C_{1-6}$ alkylaminocarbonyloxy,
  optionally substituted saturated or unsaturated five- or
six-membered heterocyclic oxy,
  optionally substituted saturated or unsaturated five- or
six-membered heterocyclic carbonyloxy, or
  oxo in the absence of a hydrogen atom at the 7-position.

According to another preferred embodiment of the present invention, in the compound represented by formula (Ia),
$Het_2$ represents 3-pyridyl,
$R_{11}$ represents hydroxyl or
  optionally substituted $C_{1-6}$ alkylcarbonyloxy, or
the bond between 5-position and 13-position represents a double bond in the absence of $R_{11}$ and a hydrogen atom at the 5-position, $R_{12}$ represents optionally substituted $C_{1-18}$ alkylcarbonyloxy,
$R_{13}$ represents optionally substituted $C_{1-18}$ alkylcarbonyloxy,
$R_{14}$ represents hydroxyl,
> optionally substituted $C_{1-18}$ alkylcarbonyloxy,
> optionally substituted benzoyloxy,
> optionally substituted saturated or unsaturated five- or six-membered heterocyclic oxy, or
> optionally substituted saturated or unsaturated five- or six-membered heterocyclic carbonyloxy.

According to another preferred embodiment of the present invention, in the compound represented by formula (Ia), $Het_2$ represents 3-pyridyl, $R_{11}$ represents hydroxyl, $R_{12}$ represents $C_{1-6}$ alkylcarbonyloxy, and $R_{13}$ and/or $R_{14}$ represent $C_{2-4}$ alkylcarbonyloxy.

Further, an agriculturally and horticulturally acceptable salt of the compound represented by formula (Ia) include the same as that of the compound represented by formula (Ib) described below.

Compunds of formula (Ib) or its agriculturally and horticulturally acceptable salts Compounds of formula (Ib) are novel pyripyropene derivatives that are comprised as a part in the compound represented by formula (I). In particular, they have significant insecticidal activity.

According to an embodiment of the present invention, there is provided the compounds of formula (Ib), excluding a compound wherein $Het_1$ represents 3-pyridyl, $R_1$ represents hydroxyl, and $R_2$ and $R_3$ represent propionyloxy, and $R_4$ represents hydroxyl.

According to another preferred embodiment of the present invention, in the compound represented by formula (Ib), $R_2$ and $R_3$ represent optionally substituted cyclic $C_{3-6}$ alkylcarbonyloxy, $R_4$ represents hydroxyl, optionally substituted cyclic $C_{3-6}$ alkylcarbonyloxy, or optionally substituted benzoyloxy. Alternatively, $R_2$ and $R_3$ represent propionyloxy, $R_4$ represents optionally substituted cyclic $C_{3-6}$ alkylcarbonyloxy, or optionally substituted saturated or unsaturated five- or six-membered heterocyclic carbonyloxy.

According to another preferred embodiment of the present invention, in the compounds represented by formula (Ib), $R_2$ and $R_3$ represent optionally substituted cyclic $C_{3-6}$ alkylcarbonyloxy, $R_4$ represents hydroxyl, optionally substituted cyclic $C_{3-6}$ alkylcarbonyloxy, or optionally substituted benzoyloxy.

According to another preferred embodiment of the present invention, in the compounds represented by formula (Ib), $R_2$ and $R_3$ represent propionyloxy, $R_4$ represents optionally substituted cyclic $C_{3-6}$ alkylcarbonyloxy or optionally substituted saturated or unsaturated five- or six-membered heterocyclic carbonyloxy.

According to still another preferred embodiment of the present invention, there is provided a pest control agent comprising a compound represented by formula (Ib) or an agriculturally and horticulturally acceptable salt thereof as an active ingredient.

Agriculturally and horticulturally acceptable salts in the compounds of formula (Ib) include, for example, acid addition salts such as hydrochlorides, nitrates, sulfates, phosphates, or acetates.

Specific examples of the compounds represented by formula (I), (Ia), or (Ib) include compounds shown in Tables 1 to 14 below. In the following tables, H(=) means that the bond between 5-position and 13-position represents a double bond in the absence of $R_1$ and a hydrogen atom at the 5-position.

Table 1

| Compound No. | $R_1$ | $R_2$ | $R_3$ | $R_4$ | $Het_1$ |
|---|---|---|---|---|---|
| 1 | OH | $OCOCH_3$ | $OCOCH_3$ | $OCOCH_2CH_3$ | 3-pyridyl |
| 2 | OH | $OCOCH_3$ | $OCOCH_3$ | $OCOCH_2CF_3$ | 3-pyridyl |
| 3 | OH | $OCOCH_3$ | $OCOCH_3$ | $OCOCH_2OCH_3$ | 3-pyridyl |
| 4 | OH | $OCOCH_3$ | $OCOCH_3$ | $OCOCH_2OCOCH_3$ | 3-pyridyl |
| 5 | OH | $OCOCH_3$ | $OCOCH_3$ | $OCOCH_2CH_2CN$ | 3-pyridyl |
| 6 | OH | $OCOCH_3$ | $OCOCH_3$ | $OCO(CH_2)_2CH_3$ | 3-pyridyl |
| 7 | OH | $OCOCH_3$ | $OCOCH_3$ | $OCO(CH_2)_3CH_3$ | 3-pyridyl |
| 8 | OH | $OCOCH_3$ | $OCOCH_3$ | $OCO(CH_2)_4CH_3$ | 3-pyridyl |
| 9 | OH | $OCOCH_3$ | $OCOCH_3$ | $OCO(CH_2)_5CH_3$ | 3-pyridyl |
| 10 | OH | $OCOCH_3$ | $OCOCH_3$ | $OCO(CH_2)_6CH_3$ | 3-pyridyl |
| 11 | OH | $OCOCH_3$ | $OCOCH_3$ | $OCO(CH_2)_{16}CH_3$ | 3-pyridyl |
| 12 | OH | $OCOCH_3$ | $OCOCH_3$ | $OCOCH(CH_3)_2$ | 3-pyridyl |
| 13 | OH | $OCOCH_3$ | $OCOCH_3$ | $OCOC(CH_3)_3$ | 3-pyridyl |
| 14 | OH | $OCOCH_3$ | $OCOCH_3$ | $OCOCH_2CH(CH_3)_2$ | 3-pyridyl |
| 15 | OH | $OCOCH_3$ | $OCOCH_3$ | $OCO(CH_2)_2CH(CH_3)_2$ | 3-pyridyl |
| 16 | OH | $OCOCH_3$ | $OCOCH_3$ | OCO-trans-$CH=CHCH_2CH_3$ | 3-pyridyl |
| 17 | OH | $OCOCH_3$ | $OCOCH_3$ | $OCOCH_2C\equiv CCH_3$ | 3-pyridyl |
| 18 | OH | $OCOCH_3$ | $OCOCH_3$ | $OCOC\equiv CCH_2CH_3$ | 3-pyridyl |
| 19 | OH | $OCOCH_3$ | $OCOCH_3$ | $OCO(CH_2)_2C\equiv CH$ | 3-pyridyl |
| 20 | OH | $OCOCH_3$ | $OCOCH_3$ | $OCO(CH_2)_2CH=CH_2$ | 3-pyridyl |

Table 2

| Compound No. | $R_1$ | $R_2$ | $R_3$ | $R_4$ | $Het_1$ |
|---|---|---|---|---|---|
| 21 | OH | OCOCH$_3$ | OCOCH$_3$ | OCOCH$_2$C$_6$H$_5$ | 3-pyridyl |
| 22 | OH | OCOCH$_3$ | OCOCH$_3$ | OCO(CH$_2$)$_2$C$_6$H$_5$ | 3-pyridyl |
| 23 | OH | OCOCH$_3$ | OCOCH$_3$ | OCOC$_6$H$_5$ | 3-pyridyl |
| 24 | OH | OCOCH$_3$ | OCOCH$_3$ | OCO-(4-Br-C$_6$H$_4$) | 3-pyridyl |
| 25 | OH | OCOCH$_3$ | OCOCH$_3$ | OCO-(4-N$_3$-C$_6$H$_4$) | 3-pyridyl |
| 26 | OH | OCOCH$_3$ | OCOCH$_3$ | OCO-(4-OCF$_3$-C$_6$H$_4$) | 3-pyridyl |
| 27 | OH | OCOCH$_3$ | OCOCH$_3$ | OCO-(4-SO$_2$CF$_3$-C$_6$H$_4$) | 3-pyridyl |
| 28 | OH | OCOCH$_3$ | OCOCH$_3$ | OCO-(3-pyridyl) | 3-pyridyl |
| 29 | OH | OCOCH$_3$ | OCOCH$_3$ | OCO-(2-Cl-3-pyridyl) | 3-pyridyl |
| 30 | OH | OCOCH$_3$ | OCOCH$_3$ | OCO-(2-franyl) | 3-pyridyl |
| 31 | OH | OCOCH$_3$ | OCOCH$_3$ | OCO-(2-thiazolyl) | 3-pyridyl |
| 32 | OH | OCOCH$_3$ | OCOCH$_3$ | OCO-(2-Cl-5-thiazolyl) | 3-pyridyl |
| 33 | OH | OCOCH$_3$ | OCOCH$_3$ | OCO-(5-imidazolyl) | 3-pyridyl |
| 34 | OH | OCOCH$_3$ | OCOCH$_3$ | OCS-(1-imidazolyl) | 3-pyridyl |
| 35 | OH | OCOCH$_3$ | OCOCH$_3$ | OCOOCH$_2$C$_6$H$_5$ | 3-pyridyl |
| 36 | OH | OCOCH$_3$ | OCOCH$_3$ | OSO$_2$CH$_3$ | 3-pyridyl |
| 37 | OH | OCOCH$_3$ | OCOCH$_3$ | OSO$_2$C$_6$H$_5$ | 3-pyridyl |
| 38 | OH | OCOCH$_3$ | OCOCH$_3$ | OCONHCH$_2$CH$_3$ | 3-pyridyl |
| 39 | OH | OCOCH$_3$ | OCOCH$_3$ | OCONH(CH$_2$)$_2$CH$_3$ | 3-pyridyl |
| 40 | OH | OCOCH$_3$ | OCOCH$_3$ | OCONHCH$_2$C$_6$H$_5$ | 3-pyridyl |

Table 3

| Compound No. | $R_1$ | $R_2$ | $R_3$ | $R_4$ | $Het_1$ |
|---|---|---|---|---|---|
| 41 | OH | OCOCH$_3$ | OCOCH$_3$ | OCH$_2$C$_6$H$_5$ | 3-pyridyl |
| 42 | OH | OCOCH$_3$ | OCOCH$_3$ | OCH$_2$SCH$_3$ | 3-pyridyl |
| 43 | OH | OCOCH$_3$ | OCOCH$_3$ | OCH$_2$OCH$_3$ | 3-pyridyl |
| 44 | OH | OCOCH$_3$ | OCOCH$_3$ | OCH$_2$OCH$_2$CH$_2$OCH$_3$ | 3-pyridyl |
| 45 | OH | OCOCH$_3$ | OCOCH$_3$ | O-(2-tetrahydropyranyl) | 3-pyridyl |
| 46 | OH | OCOCH$_3$ | OCOCH$_3$ | O-(tetra-O-benzyl-mannosyl) | 3-pyridyl |
| 47 | OH | OCOCH$_3$ | OCOCH$_3$ | H | 3-pyridyl |
| 48 | OH | OCOCH$_3$ | OCOCH$_3$ | OCO-c-C$_3$H$_5$ | 3-pyridyl |
| 49 | OH | OCOCH$_3$ | OCOCH$_3$ | OH | 3-pyridyl |
| 50 | OH | OCOCH$_3$ | OCOCH$_3$ | =O | 3-pyridyl |
| 51 | OH | OCOCH$_3$ | OCOCH2CH3 | OCOCH$_3$ | 3-pyridyl |
| 52 | OH | OCOCH$_3$ | OCOCH2CH3 | OCOCH$_2$CH$_3$ | 3-pyridyl |

| | | | | | |
|---|---|---|---|---|---|
| 53 | OH | OCOCH$_3$ | OCOCH$_2$CH$_3$ | H | 3-pyridyl |
| 54 | OH | OCOCH$_3$ | OCO(CH$_2$)$_2$CH$_3$ | OCOCH$_3$ | 3-pyridyl |
| 55 | OH | OCOCH$_3$ | OCO(CH$_2$)$_2$CH$_3$ | OH | 3-pyridyl |
| 56 | OH | OCOCH$_3$ | OCO(CH$_2$)$_3$CH$_3$ | OCOCH$_3$ | 3-pyridyl |
| 57 | OH | OCOCH$_3$ | OCOCH(CH$_3$)$_2$ | OCOCH$_3$ | 3-pyridyl |
| 58 | OH | OCOCH$_3$ | OCOC$_6$H$_5$ | OCOCH$_3$ | 3-pyridyl |
| 59 | OH | OCOCH$_3$ | OCOC$_6$H$_5$ | OH | 3-pyridyl |
| 60 | OH | OCOCH$_3$ | OCS-(1-imidazolyl) | OCOCH$_3$ | 3-pyridyl |

Table 4

| Compound No. | R$_1$ | R$_2$ | R$_3$ | R$_4$ | Het$_1$ |
|---|---|---|---|---|---|
| 61 | OH | OCOCH$_3$ | OSO$_2$CH$_3$ | OCOCH$_3$ | 3-pyridyl |
| 62 | OH | OCOCH$_3$ | OSO$_2$CH$_3$ | OCO(CH$_2$)$_3$CH$_3$ | 3-pyridyl |
| 63 | OH | OCOCH$_3$ | OSO$_2$C$_6$H$_5$ | OCOCH$_3$ | 3-pyridyl |
| 64 | OH | OCOCH$_3$ | OSO$_2$CH$_2$CH$_3$ | OCOCH$_3$ | 3-pyridyl |
| 65 | OH | OCOCH$_3$ | OSO$_2$CH$_2$CH$_2$CH$_3$ | OCOCH$_3$ | 3-pyridyl |
| 66 | OH | OCOCH$_3$ | OSO$_2$CH$_2$CH$_3$ | OH | 3-pyridyl |
| 67 | OH | OCOCH$_3$ | OSO$_2$CH$_2$CH$_2$CH$_3$ | OH | 3-pyridyl |
| 68 | OH | OCOCH$_3$ | OH | OH | 3-pyridyl |
| 69 | OH | OCOCH$_3$ | OH | OCOCH$_3$ | 3-pyridyl |
| 70 | OH | OCOCH$_3$ | H | H | 3-pyridyl |
| 71 | OH | OCOCH$_3$ | H | OCOCH$_2$CH$_3$ | 3-pyridyl |
| 72 | OH | OCOCH$_2$CH$_3$ | OCOCH$_3$ | OCOCH$_3$ | 3-pyridyl |
| 73 | OH | OCOCH$_2$CH$_3$ | OCOCH$_2$CH$_3$ | OH | 3-pyridyl |
| 74 | OH | OCOCH$_2$CH$_3$ | OCOCH$_2$CH$_3$ | OCOCH$_3$ | 3-pyridyl |
| 75 | OH | OCOCH$_2$CH$_3$ | OCOCH$_3$ | OCOCH$_2$CH$_3$ | 3-pyridyl |
| 76 | OH | OCOCH$_2$CH$_3$ | OCOCH$_2$CH$_3$ | OCOCH$_2$CH$_3$ | 3-pyridyl |
| 77 | OH | OCOCH$_2$CH$_3$ | OCOCH$_2$CH$_3$ | OCOC$_6$H$_5$ | 3-pyridyl |
| 78 | OH | OCOCH$_2$CH$_3$ | OCOCH$_2$CH$_3$ | H | 3-pyridyl |
| 79 | OH | OCOCH$_2$CH$_3$ | H | H | 3-pyridyl |
| 80 | OH | OCO(CH$_2$)$_2$CH$_3$ | OCOCH$_3$ | OCOCH$_3$ | 3-pyridyl |

Table 5

| Compound No. | R$_1$ | R$_2$ | R$_3$ | R$_4$ | Het$_1$ |
|---|---|---|---|---|---|
| 81 | OH | OCO(CH$_2$)$_2$CH$_3$ | OCO(CH$_2$)$_2$CH$_3$ | OH | 3-pyridyl |
| 82 | OH | OCO(CH$_2$)$_2$CH$_3$ | OCO(CH$_2$)$_2$CH$_3$ | OCO(CH$_2$)$_2$CH$_3$ | 3-pyridyl |
| 83 | OH | OCO(CH$_2$)$_2$CH$_3$ | OCO(CH$_2$)$_2$CH$_3$ | OCOCH$_3$ | 3-pyridyl |
| 84 | OH | OCO(CH$_2$)$_2$CH$_3$ | OCOCH$_3$ | OCOCH$_3$ | 3-pyridyl |
| 85 | OH | OCO(CH$_2$)$_3$CH$_3$ | OCO(CH$_2$)$_3$CH$_3$ | OCO(CH$_2$)$_3$CH$_3$ | 3-pyridyl |
| 86 | OH | OCO(CH$_2$)$_3$CH$_3$ | OSO$_2$CH$_3$ | OCO(CH$_2$)$_3$CH$_3$ | 3-pyridyl |
| 87 | OH | OCO(CH$_2$)$_3$CH$_3$ | OSO$_2$CH$_3$ | OH | 3-pyridyl |

| | | | | | |
|---|---|---|---|---|---|
| 88 | OH | OCO(CH$_2$)$_{10}$CH$_3$ | OCO(CH$_2$)$_{10}$CH$_3$ | OCO(CH$_2$)$_{10}$CH$_3$ | 3-pyridyl |
| 89 | OH | OCOCH(CH$_3$)$_2$ | OCOCH$_3$ | OCOCH$_3$ | 3-pyridyl |
| 90 | OH | OCOCH(CH$_3$)$_2$ | OCOCH(CH$_3$)$_2$ | OCOCH(CH$_3$)$_2$ | 3-pyridyl |
| 91 | OH | OCOC(CH$_3$)$_3$ | OCOC(CH$_3$)$_3$ | OCOC(CH$_3$)$_3$ | 3-pyridyl |
| 92 | OH | OCOC$_6$H$_5$ | OCOCH$_3$ | OCOCH$_3$ | 3-pyridyl |
| 93 | OH | OCOC$_6$H$_5$ | OSO$_2$CH$_3$ | OH | 3-pyridyl |
| 94 | OH | OCOC$_6$H$_5$ | OSO$_2$CH$_3$ | OCOCH$_3$ | 3-pyridyl |
| 95 | OH | OCOC$_6$H$_5$ | OSO$_2$CH$_3$ | OCO(CH$_2$)$_3$CH$_3$ | 3-pyridyl |
| 96 | OH | OCO-(4-Br-C$_6$H$_4$) | OCO-(4-Br-C$_6$H$_4$) | OCO-(4-Br-C$_6$H$_4$) | 3-pyridyl |
| 97 | OH | OCO-(4-N$_3$-C$_6$H$_4$) | OSO$_2$CH$_3$ | OCOCH$_3$ | 3-pyridyl |
| 98 | OH | OSO$_2$CH$_3$ | OSO$_2$CH$_3$ | OH | 3-pyridyl |
| 99 | OH | OSO$_2$CH$_3$ | OSO$_2$CH$_3$ | OSO$_2$CH$_3$ | 3-pyridyl |
| 100 | OH | OSO$_2$CH$_3$ | OSO$_2$CH$_3$ | OCOCH$_3$ | 3-pyridyl |

Table 6

| Compound No. | R$_1$ | R$_2$ | R$_3$ | R$_4$ | Het$_1$ |
|---|---|---|---|---|---|
| 101 | OH | OSO$_2$CH$_3$ | OH | OH | 3-pyridyl |
| 102 | OH | OH | OH | OH | 3-pyridyl |
| 103 | OH | OH | OH | OCOCH$_3$ | 3-pyridyl |
| 104 | OH | OH | OH | OCO(CH$_2$)$_3$CH$_3$ | 3-pyridyl |
| 105 | OH | OH | OH | OCH$_2$OCH$_2$CH$_2$OCH$_3$ | 3-pyridyl |
| 106 | OH | OH | OCOCH$_3$ | OH | 3-pyridyl |
| 107 | OH | OH | OCOCH$_2$CH$_3$ | OH | 3-pyridyl |
| 108 | OH | OH | OCO(CH$_2$)$_2$CH$_3$ | OH | 3-pyridyl |
| 109 | OH | OH | OCO(CH$_2$)$_3$CH$_3$ | OH | 3-pyridyl |
| 110 | OH | OH | OCOCH(CH$_3$)$_2$ | OH | 3-pyridyl |
| 111 | OH | OH | OSO$_2$CH$_3$ | OH | 3-pyridyl |
| 112 | OH | OH | OSO$_2$CH$_2$CH$_3$ | OH | 3-pyridyl |
| 113 | OH | OH | OSO$_2$CH$_2$CH$_2$CH$_3$ | OH | 3-pyridyl |
| 114 | OH | OH | OSO$_2$CH(CH$_3$)$_2$ | OH | 3-pyridyl |
| 115 | OH | OH | OSO$_2$C$_6$H$_5$ | OH | 3-pyridyl |
| 116 | OH | OH | OSO$_2$-(4-CH$_3$-C$_6$H$_4$) | OH | 3-pyridyl |
| 117 | OH | OH | OCO-(4-Br-C$_6$H$_4$) | OH | 3-pyridyl |
| 118 | OH | OH | OCO(CH$_2$)$_3$CH$_3$ | OCO(CH$_2$)$_3$CH$_3$ | 3-pyridyl |
| 119 | OH | OH | OSO$_2$CH$_3$ | OSO$_2$CH$_3$ | 3-pyridyl |
| 120 | OH | OH | OSO$_2$CH$_3$ | OCOCH$_3$ | 3-pyridyl |

Table 7

| Compound No. | R$_1$ | R$_2$ | R$_3$ | R$_4$ | Het$_1$ |
|---|---|---|---|---|---|
| 121 | OH | OH | OSO$_2$CH$_3$ | OCOCH$_3$ | 3-pyridyl |
| 122 | OH | OH | OSO$_2$CH$_3$ | OCO(CH$_2$)$_3$CH$_3$ | 3-pyridyl |
| 123 | OH | OH | OSO$_2$C$_6$H$_5$ | OCOCH$_3$ | 3-pyridyl |

| | | | | | |
|---|---|---|---|---|---|
| 124 | OH | OH | OSO$_2$C$_6$H$_5$ | OSO$_2$C$_6$H$_5$ | 3-pyridyl |
| 125 | OH | -O-CH(CH$_3$)-O- | | OCO(CH$_2$)$_3$CH$_3$ | 3-pyridyl |
| 126 | OH | -O-CH(C$_2$H$_5$)-O- | | OH | 3-pyridyl |
| 127 | OH | -O-CH(C$_2$H$_5$)-O- | | OCO(CH$_2$)$_3$CH$_3$ | 3-pyridyl |
| 128 | OH | -O-CH(CH=CH$_2$)-O- | | OH | 3-pyridyl |
| 129 | OH | -O-CH(CH=CH$_2$)-O- | | OCO(CH$_2$)$_3$CH$_3$ | 3-pyridyl |
| 130 | OH | -O-CH(CH(CH$_3$)$_2$)-O- | | OH | 3-pyridyl |
| 131 | OH | -O-CH(CH(CH$_3$)$_2$)-O- | | OCO(CH$_2$)$_3$CH$_3$ | 3-pyridyl |
| 132 | OH | -O-CH(OCH$_3$)-O- | | OH | 3-pyridyl |
| 133 | OH | -O-CH(C(CH$_3$)$_3$)-O- | | OCO(CH$_2$)$_3$CH$_3$ | 3-pyridyl |
| 134 | OH | -O-CH(CH$_2$C$_6$H$_5$)-O- | | OH | 3-pyridyl |
| 135 | OH | -O-C(CH$_3$)$_2$-O- | | OH | 3-pyridyl |
| 136 | OH | -O-C(CH$_3$)$_2$-O- | | OCOCH$_3$ | 3-pyridyl |
| 137 | OH | -O-C(CH$_3$)$_2$-O- | | OCO(CH$_2$)$_3$CH$_3$ | 3-pyridyl |
| 138 | OH | -O-C(CH$_3$)(C$_6$H$_5$)-O- | | OH | 3-pyridyl |
| 139 | OH | -O-C(CH$_3$)(C$_6$H$_5$)-O- | | OCO(CH$_2$)$_3$CH$_3$ | 3-pyridyl |
| 140 | OH | -O-CH(C$_6$H$_5$)-O- | | OH | 3-pyridyl |

Table 8

| Compound No. | R$_1$ | R$_2$ | R$_3$ | R$_4$ | Het$_1$ |
|---|---|---|---|---|---|
| 141 | OH | | -O-CH(C$_6$H$_5$)-O- | OCOCH$_3$ | 3-pyridyl |
| 142 | OH | | -O-CH(OCH$_3$)-O- | OCO(CH$_2$)$_3$CH$_3$ | 3-pyridyl |
| 143 | OH | | -O-CH(C$_6$H$_5$)-O- | OCO(CH$_2$)$_3$CH$_3$ | 3-pyridyl |
| 144 | OH | | -O-CH(3-CH$_3$-C$_6$H$_4$)-O- | OH | 3-pyridyl |
| 145 | OH | | -O-CH(3-CH$_3$-C$_6$H$_4$)-O- | OCO(CH$_2$)$_3$CH$_3$ | 3-pyridyl |
| 146 | OH | | -O-CH(2-CH$_3$-C$_6$H$_4$)-O- | OH | 3-pyridyl |
| 147 | OH | | -O-CH(4-CH$_3$-C$_6$H$_4$)-O- | OCO(CH$_2$)$_3$CH$_3$ | 3-pyridyl |
| 148 | OH | | -O-CH(3-F-C$_6$H$_4$)-O- | OH | 3-pyridyl |
| 149 | OH | | -O-CH(2-F-C$_6$H$_4$)-O- | OCO(CH$_2$)$_3$CH$_3$ | 3-pyridyl |
| 150 | OH | | -O-CH(4-F-C$_6$H$_4$)-O- | OCO(CH$_2$)$_3$CH$_3$ | 3-pyridyl |
| 151 | OH | | -O-CH(4-NO$_2$-C$_6$H$_4$)-O- | OH | 3-pyridyl |
| 152 | OH | | -O-CH(4-NO$_2$-C$_6$H$_4$)-O- | OCO(CH$_2$)$_3$CH$_3$ | 3-pyridyl |
| 153 | OH | | -O-CH(4-OCH$_3$-C$_6$H$_4$)-O- | OH | 3-pyridyl |
| 154 | OH | | -O-CH(4-OCH$_3$-C$_6$H$_4$)-O- | OCO(CH$_2$)$_3$CH$_3$ | 3-pyridyl |
| 155 | OH | | -O-C(spiro-c-C$_5$H$_8$)-O- | OH | 3-pyridyl |
| 156 | OH | | -O-C(spiro-c-C$_5$H$_8$)-O- | OCO(CH$_2$)$_3$CH$_3$ | 3-pyridyl |
| 157 | OH | | -O-C(spiro-c-C$_6$H$_{10}$)-O- | OH | 3-pyridyl |
| 158 | OH | | -O-C(spiro-c-C$_6$H$_{10}$)-O- | OCO(CH$_2$)$_3$CH$_3$ | 3-pyridyl |
| 159 | OH | | -O-CO-O- | OH | 3-pyridyl |
| 160 | OH | | -O-CO-O- | OCO-1-imidazolyl | 3-pyridyl |

Table 9

| Compound No. | $R_1$ | $R_2$ | $R_3$ | $R_4$ | $Het_1$ |
|---|---|---|---|---|---|
| 161 | OH | -O-CO-O- | | $OCO(CH_2)_3CH_3$ | 3-pyridyl |
| 162 | $OCOCH_3$ | $OCOCH_3$ | $OCOCH_3$ | $OCOCH_3$ | 3-pyridyl |
| 163 | $OCOCH_3$ | $OCOCH_3$ | $OCOCH_3$ | OH | 3-pyridyl |
| 164 | $OCOCH_3$ | $OCOCH_3$ | $OCO(CH_2)_2CH_3$ | $OCOCH_3$ | 3-pyridyl |
| 165 | $OCOCH_3$ | OH | OH | $OCOCH_3$ | 3-pyridyl |
| 166 | $OCOCH_3$ | $OCOCH_2CH_3$ | $OCOCH_2CH_3$ | $OCOCH_2CH_3$ | 3-pyridyl |
| 167 | $OCOCH_2CH_3$ | $OCOCH_2CH_3$ | $OCOCH_2CH_3$ | $OCOCH_2CH_3$ | 3-pyridyl |
| 168 | $OCOCH_2CH_3$ | $OCOCH_3$ | $OCOCH_3$ | $OCOCH_3$ | 3-pyridyl |
| 169 | $OCO(CH_2)_3CH_3$ | $OCOCH_3$ | $OCOCH_3$ | $OCOCH_3$ | 3-pyridyl |
| 170 | $OCO(CH_2)_3CH_3$ | $OCOCH_3$ | $OCOCH_3$ | $OCO(CH_2)_3CH_3$ | 3-pyridyl |
| 171 | $OCO(CH_2)_2CH_3$ | $OCOCH_3$ | $OCOCH_3$ | $OCOCH_3$ | 3-pyridyl |
| 172 | $OCH_3$ | $OCOCH_3$ | $OCOCH_3$ | $OCOCH_3$ | 3-pyridyl |
| 173 | H(=) | $OSO_2CH_3$ | $OSO_2CH_3$ | OH | 3-pyridyl |
| 174 | H(=) | $OCOC_6H_5$ | $OSO_2CH_3$ | $OCOCH_3$ | 3-pyridyl |
| 175 | H(=) | OH | OH | $OCOCH_3$ | 3-pyridyl |
| 176 | H(=) | $OCOCH_3$ | $OCOCH_3$ | =O | 3-pyridyl |
| 177 | H(=) | $-O-CH(C_6H_5)-O-$ | | $OCOCH_3$ | 3-pyridyl |
| 178 | H(=) | $-O-CH(CH(CH_3)_2)-O-$ | | OH | 3-pyridyl |
| 179 | H(=) | $-O-CH(4-NO_2-C_6H_4)-O-$ | | OH | 3-pyridyl |
| 180 | H(=) | $OCOCH_3$ | $OCOCH_3$ | $OCOCH_3$ | 3-pyridyl |

Table 10

| Compound No. | $R_1$ | $R_2$ | $R_3$ | $R_4$ | $Het_1$ |
|---|---|---|---|---|---|
| 181 | H(=) | OH | OH | OH | 3-pyridyl |
| 182 | H(=) | $OCOCH_3$ | $OCOCH_3$ | OH | 3-pyridyl |
| 183 | H(=) | $OCOCH_3$ | $OCOCH_3$ | $OCH_2SCH_3$ | 3-pyridyl |
| 184 | H(=) | $OCOCH_3$ | $OCOCH_3$ | $OCH_2OCH_3$ | 3-pyridyl |
| 185 | H(=) | $OCOCH_3$ | $OCOCH_3$ | $OCO(CH_2)_3CH_3$ | 3-pyridyl |
| 186 | H(=) | $OCOCH_3$ | $OCOCH_3$ | $OCO(CH_2)_2Ph$ | 3-pyridyl |
| 187 | H(=) | $OCOCH_3$ | $OSO_2CH_3$ | $OCOCH_3$ | 3-pyridyl |
| 188 | H(=) | $OCOCH_2CH_3$ | $OCOCH_2CH_3$ | $OCOCH_2CH_3$ | 3-pyridyl |
| 189 | H(=) | $OCOCH_2CH_3$ | $OCOCH_2CH_3$ | OH | 3-pyridyl |
| 190 | H(=) | OH | $OSO_2CH_3$ | OH | 3-pyridyl |
| 191 | H(=) | OH | OH | $OCO(CH_2)_3CH_3$ | 3-pyridyl |
| 192 | H(=) | $-O-C(CH_3)_2-O-$ | | OH | 3-pyridyl |
| 193 | H(=) | $-O-C(CH_3)_2-O-$ | | $OCO(CH_2)_3CH_3$ | 3-pyridyl |
| 194 | H(=) | $-O-CH(C_6H_5)-O-$ | | OH | 3-pyridyl |
| 195 | H(=) | $-O-CH(C_6H_5)-O-$ | | $OCO(CH_2)_3CH_3$ | 3-pyridyl |
| 196 | H(=) | $-O-CH(4-OCH_3-C_6H_4)-O-$ | | OH | 3-pyridyl |
| 197 | H(=) | $-O-CH(C_2H_5)-O-$ | | OH | 3-pyridyl |
| 198 | H(=) | $-O-CH(C(CH_3)_3)-O-$ | | OH | 3-pyridyl |
| 199 | H(=) | $-O-CH(CH_2C_6H_5)-O-$ | | OH | 3-pyridyl |
| 200 | =O | OH | OH | OH | 3-pyridyl |

Table 11

| Compound No. | $R_1$ | $R_2$ | $R_3$ | $R_4$ | $Het_1$ |
|---|---|---|---|---|---|
| 201 | =O | $OCOCH_3$ | $OCOCH_3$ | =O | 3-pyridyl |
| 202 | =O | $OCOCH_3$ | $OCOCH_3$ | OH | 3-pyridyl |
| 203 | =O | $OCOCH_3$ | $OCOCH_3$ | $OCOCH_3$ | 3-pyridyl |
| 204 | =O | $OCOCH_2CH_3$ | $OCOCH_2CH_3$ | $OCOCH_2CH_3$ | 3-pyridyl |
| 205 | OH | $OCOCH_2CH_3$ | $OCOCH_2CH_3$ | OCO-(3-Pyridyl) | 3-pyridyl |
| 206 | OH | $OCOCH_2CH_3$ | $OCOCH_2CH_3$ | $OCOCH(CH_3)_2$ | 3-pyridyl |
| 207 | OH | $OCOCH_2CH_3$ | $OCOCH_2CH_3$ | $OCOC(CH_3)_3$ | 3-pyridyl |
| 208 | OH | $OCOCH_2CH_3$ | $OCOCH_2CH_3$ | $OCO-(4-CF_3-C_6H_4)$ | 3-pyridyl |
| 209 | OH | $OCOCH_2CH_3$ | $OCOCH_2CH_3$ | OCO-(1-imidazolyl) | 3-pyridyl |
| 210 | OH | $OCOCH_2CH_3$ | $OCOCH_2CH_3$ | $OCONH(CH_2)_2CH_3$ | 3-pyridyl |
| 211 | OH | $OCOCH_2CH_3$ | $OCOCH_2CH_3$ | O-(2-tetrahydropyranyl) | 3-pyridyl |
| 212 | OH | $OCOCH_2CH_3$ | $OCOCH_2CH_3$ | OCO-(6-Cl-3-pyridyl) | 3-pyridyl |
| 213 | OH | $OCOCH_2CH_3$ | $OCOCH_2CH_3$ | $OCO-c-C_3H_5$ | 3-pyridyl |
| 214 | OH | $OCOCH_2CH_3$ | $OCOCH_2CH_3$ | $OCO-c-C_4H_7$ | 3-pyridyl |
| 215 | OH | $OCOCH_2CH_3$ | $OCOCH_2CH_3$ | $OCOCH=CH$ | 3-pyridyl |
| 216 | OH | $OCOCH_2CH_3$ | $OCOCH_2CH_3$ | OCO-(4-pyridyl) | 3-pyridyl |
| 217 | OH | $OCOCH_2CH_3$ | $OCOCH_2CH_3$ | OCO-(2-pyridyl) | 3-pyridyl |
| 218 | OH | $OCO-c-C_3H_5$ | $OCO-c-C_3H_5$ | $OCO-c-C_3H_5$ | 3-pyridyl |
| 219 | OH | $OCO-c-C_4H_7$ | $OCO-c-C_4H_7$ | $OCO-c-C_4H_7$ | 3-pyridyl |
| 220 | OH | $OCOC_6H_5$ | $OCOC_6H_5$ | $OCOC_6H_5$ | 3-pyridyl |

Table 12

| Compound No. | $R_1$ | $R_2$ | $R_3$ | $R_4$ | $Het_1$ |
|---|---|---|---|---|---|
| 221 | OH | $OCOCH_2CH_3$ | $OCOCH_2CH_3$ | $OCO-(6-CF_3-3-pyridyl)$ | 3-pyridyl |
| 222 | OH | $OCOCH_2CH_3$ | $OCOCH_2CH_3$ | $OCO-(4-CF_3-3-pyridyl)$ | 3-pyridyl |
| 223 | OH | $OCOCH_2CF_3$ | $OCOCH_2CF_3$ | $OCOCH_2CF_3$ | 3-pyridyl |
| 224 | OH | $OCOCH_2CH_3$ | $OCOCH_2CH_3$ | $OCOCH_2CF_3$ | 3-pyridyl |
| 225 | =O | $OCOCH_2CH_3$ | $OCOCH_2CH_3$ | $OCOCH_2CH_3$ | 6-Cl-3-pyridyl |
| 226 | OH | $OCOCH_2CH_3$ | $OCOCH_2CH_3$ | $OCOCH_2CH_3$ | 6-Cl-3-pyridyl |
| 227 | OH | $OCOCH_2CH_3$ | $OCOCH_2CH_3$ | OCO-(3-F-4-pyridyl) | 3-pyridyl |
| 228 | OH | $OCOCH_2CH_3$ | $OCOCH_2CH_3$ | OCO-(3-Cl-4-pyridyl) | 3-pyridyl |
| 229 | OH | $OCOCH_2CH_3$ | $OCOCH_2CH_3$ | $OCO-(3-CH_3-2-pyridyl)$ | 3-pyridyl |
| 230 | OH | $OCOCH_2CH_3$ | $OCOCH_2CH_3$ | $OCO-(3-COC_6H_5-2-pyridyl)$ | 3-pyridyl |
| 231 | OH | $OCOCH_2CH_3$ | $OCOCH_2CH_3$ | $OCO-(3-OCH_2CH_2CH_3-2-pyridyl)$ | 3-pyridyl |
| 232 | OH | $OCOCH_2CH_3$ | $OCOCH_2CH_3$ | OCO-(6-F-3-pyridyl) | 3-pyridyl |
| 233 | OH | $OCO-c-C_5H_9$ | $OCO-c-C_5H_9$ | $OCO-c-C_5H_9$ | 3-pyridyl |
| 234 | OH | $OCO-c-C_6H_{11}$ | $OCO-c-C_6H_{11}$ | $OCO-c-C_6H_{11}$ | 3-pyridyl |
| 235 | OH | $OCOCH_2CN$ | $OCOCH_2CN$ | $OCOCH_2CN$ | 3-pyridyl |

| | | | | | |
|---|---|---|---|---|---|
| 236 | OCOCH$_2$-c-C$_3$H$_5$ | OCOCH$_2$-c-C$_3$H$_5$ | OCOCH$_2$-c-C$_3$H$_5$ | OCOCH$_2$-c-C$_3$H$_5$ | 3-pyridyl |
| 237 | OH | OCOCH$_2$-c-C$_3$H$_5$ | OCOCH$_2$-c-C$_3$H$_5$ | OCOCH$_2$-c-C$_3$H$_5$ | 3-pyridyl |
| 238 | OH | OCO-(1-CH$_3$-2,2-diF-c-C$_3$H$_2$) | OCO-(1-CH$_3$-2,2-diF-c-C$_3$H$_2$) | OCO-(1-CH$_3$-2,2-diF-c-C$_3$H$_2$) | 3-pyridyl |
| 239 | OH | OCOCH$_2$CH$_3$ | OCOCH$_2$CH$_3$ | OCO-(4-CH$_3$-3-pyridyl) | 3-pyridyl |
| 240 | OH | OCOCH$_2$CH$_3$ | OCOCH$_2$CH$_3$ | OCO-(4-Cl-3-pyridyl) | 3-pyridyl |

Table 13

| Compound No. | R$_1$ | R$_2$ | R$_3$ | R$_4$ | Het$_1$ |
|---|---|---|---|---|---|
| 241 | OH | OCOCH$_2$CH$_3$ | OCOCH$_2$CH$_3$ | OCO-(4-COOCH$_3$-3-pyridyl) | 3-pyridyl |
| 242 | OH | OCOCH$_2$CH$_3$ | OCOCH$_2$CH$_3$ | OCO-[5-(CF$_3$)-thieno[3,2-b]pyridin-6-yl] | 3-pyridyl |
| 243 | OH | OCOCH$_2$CH$_3$ | OCOCH$_2$CH$_3$ | OCO-(2-CN-C$_6$H$_4$) | 3-pyridyl |
| 244 | OH | OCOCH$_2$CH$_3$ | OCOCH$_2$CH$_3$ | OCO-(2-CF$_3$-C$_6$H$_4$) | 3-pyridyl |
| 245 | OH | OCOCH$_2$CH$_3$ | OCOCH$_2$CH$_3$ | OCO-(2-F-C$_6$H$_4$) | 3-pyridyl |
| 246 | OH | OCOCH$_2$CH$_3$ | OCOCH$_2$CH$_3$ | OCO-(2-NO$_2$-C$_6$H$_4$) | 3-pyridyl |
| 247 | OH | OCOCH$_2$CH$_3$ | OCOCH$_2$CH$_3$ | OCO-(2-Cl-3-pyridyl) | 3-pyridyl |
| 248 | OH | OCOCH$_2$CH$_3$ | OCOCH$_2$CH$_3$ | OCO(2-Cl-6-CH$_3$-3-pyridyl) | 3-pyridyl |
| 249 | OH | OCOCH$_2$CH$_3$ | OCOCH$_2$CH$_3$ | OCH$_2$OCH$_3$ | 3-pyridyl |
| 250 | OH | OCO-(2,2-diF-c-C$_3$H$_3$) | OCO-(2,2-diF-c-C$_3$H$_3$) | OCO-(2,2-diF-c-C$_3$H$_3$) | 3-pyridyl |
| 251 | OH | OCOCH$_2$CH$_3$ | OCOCH$_2$CH$_3$ | OCO-(3-SC(CH$_3$)$_3$-2-pyridyl) | 3-pyridyl |
| 252 | OH | OCOCH$_2$CH$_3$ | OCOCH$_2$CH$_3$ | OCO-(3,5-diF-2-pyridyl) | 3-pyridyl |
| 253 | OH | OCOCH$_2$CH$_3$ | OCOCH$_2$CH$_3$ | OCO-2-pyrazinyl | 3-pyridyl |
| 254 | OH | OCOCH$_2$CH$_3$ | OCOCH$_2$CH$_3$ | OCO-4-thiazolyl | 3-pyridyl |
| 255 | OH | OCOCH$_2$CH$_3$ | OCOCH$_2$CH$_3$ | OCO-(3-Cl-2-thienyl) | 3-pyridyl |
| 256 | OH | OCOCH$_2$CH$_3$ | OCOCH$_2$CH$_3$ | OCO-(6-CH$_3$-3-pyridyl) | 3-pyridyl |
| 257 | OH | OCOCH$_2$CH$_3$ | OCOCH$_2$CH$_3$ | OCO-(6-Cl-2-pyridyl) | 3-pyridyl |
| 258 | OH | OCOCH$_2$CH$_3$ | OCOCH$_2$CH$_3$ | OCO-(6-F-2-pyridyl) | 3-pyridyl |
| 259 | OH | OCOCH$_2$CH$_3$ | OCOCH$_2$CH$_3$ | OCO-(1-CH$_3$-1H-indolyl) | 3-pyridyl |
| 260 | OH | OCOCH$_2$CH$_3$ | OCOCH$_2$CH$_3$ | OCO-(3-Cl-2-pyridyl) | 3-pyridyl |

Table 14

| Compound No. | R$_1$ | R$_2$ | R$_3$ | R$_4$ | Het$_1$ |
|---|---|---|---|---|---|
| 261 | OH | OCO-c-C$_3$H$_5$ | OCO-c-C$_3$H$_5$ | OH | 3-pyridyl |
| 262 | OH | OCOCH$_2$CH$_3$ | OCOCH$_2$CH$_3$ | OCO-(2-F-3-pyridyl) | 3-pyridyl |
| 263 | OH | OCOCH$_2$CH$_3$ | OCOCH$_2$CH$_3$ | OCO-(4-CN-C$_6$H$_4$) | 3-pyridyl |
| 264 | OH | OCOCH2CH3 | OCOCH$_2$CH$_3$ | OCO-(3-CN-C$_6$H$_4$) | 3-pyridyl |
| 265 | OH | OCOCH$_2$CH$_3$ | OCOCH$_2$CH$_3$ | OCO-(3-CF$_3$-C$_6$H$_4$) | 3-pyridyl |
| 266 | OH | OCOCH$_2$CH$_3$ | OCOCH$_2$CH$_3$ | OCOCH$_2$(2-pyridyl) | 3-pyridyl |
| 267 | OH | OCOCH$_2$CH$_3$ | OCOCH$_2$CH$_3$ | OCOCH$_2$(3-pyridyl) | 3-pyridyl |
| 268 | OH | OCOCH$_2$CH$_3$ | OCOCH$_2$CH$_3$ | OCOCH$_2$S(4-pyridyl) | 3-pyridyl |
| 269 | OH | OCO-c-C$_3$H$_5$ | OCO-c-C$_3$H$_5$ | OCO-(2-CN- | 3-pyridyl |

| | | | | $C_6H_4$) | |
|---|---|---|---|---|---|
| 270 | OH | OCO-c-$C_3H_5$ | OCO-c-$C_3H_5$ | OCO(4-$CF_3$-3-pyridyl) | 3-pyridyl |
| 271 | OH | OCO-c-$C_3H_5$ | OCO-c-$C_3H_5$ | OCO(3-Cl-2-pyridyl) | 3-pyridyl |
| 272 | OH | -O-CH($C_6H_5$)-O- | | =O | 3-pyridyl |
| 273 | OH | -O-CH(4-$OCH_3$-$C_6H_4$)-O- | | =O | 3-pyridyl |
| 274 | OCO($CH_2$)$_3$$CH_3$ | -O-CO-O- | | OCO($CH_2$)$_3$CH3 | 3-pyridyl |
| 275 | $OCOCH_3$ | -O-CH($C_6H_5$)-O- | | $OCOCH_3$ | 3-pyridyl |
| 276 | =O | -O-CH(4-$OCH_3$-$C_6H_4$)-O- | | OH | 3-pyridyl |

Production process

The compositon according to the present invention can be prepared by mixing the compound represented by formula (I), (Ia), or (Ib) as active ingredient with an agriculturally and horticulturally acceptable carrier. The compound represented by formula (I), (Ia), or (Ib) according to the present invention can be produced according to the following procedure.

Among the compounds according to the present invention, the compounds represented by formula (II) can be synthesized by the method described in Japanese Patent Laid-Open Publication No. 259569/1996, Japanese Patent Laid-Open Publication No. 269062/1996, Japanese Patent Laid-Open Publication No. 269065/1996, or Journal of Antibiotics (1997), 50(3), pp. 229-36. When pyripyropene A is used as a starting material, pyripyropene A, produced by the method described in Journal of SoClety of Synthetic Organic Chemistry, Japan (1998), Vol. 56, No. 6, pp. 478-488 or WO 94/09417, may be used as the starting material.

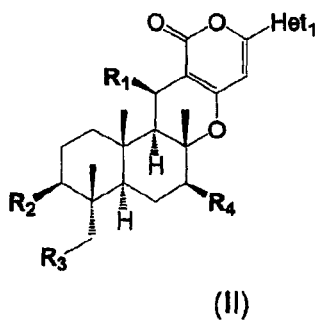

(II)

wherein $R_1$ represents hydroxyl, optionally substituted $C_{1-6}$ alkylcarbonyloxy, optionally substituted $C_{2-6}$ alkenylcarbonyloxy, optionally substituted $C_{2-6}$ alkynyl carbonyloxy, optionally substituted $C_{1-6}$ alkyloxy, optionally substituted $C_{2-6}$ alkenyloxy, optionally substituted $C_{2-6}$ alkynyloxy, optionally substituted benzyloxy, or oxo in the absence of a hydrogen atom at the 13-position, and $R_2$, $R_3$ and $R_4$ are as defined in formula (I).

Further, among the compounds according to the present invention, the compounds represented by formula (III) can be synthesized by the method described in Japanese Patent Laid-Open Publication No. 269063/1996, or Japanese Patent Laid-Open Publication No. 269066/1996.

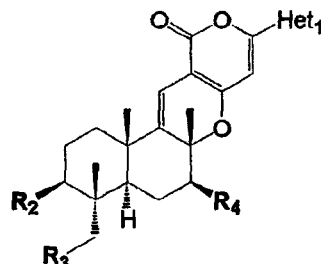

(III)

wherein $R_2$, $R_3$ and $R_4$ are as defined in formula (I).

Use

Insect species against which pyripyropene derivatives of formula (I) or (Ib) according to the present invention have control effect include: lepidopteran pests, for example, Spodoptera litura, Mamestra brassicae, Pseudaletia separata, green caterpillar, Plutella xylostella, Spodoptera exigua, Chilo suppressalis, Cnaphalocrocis medinalis, Tortricidae, Carposinidae, Lyonetiidae, Lymantriidae, pests belonging to the genus Agrotis spp., pests belonging to the genus Helicoverpa spp., and pests belonging to the genus Heliothis spp.; hemipteran pests, for example, Aphidoidea including Aphididae, Adelgidae and Phylloxeridae such as Myzus persicae, Aphis gossypii, Aphis fabae, Aphis maidis (corn-leaf aphid), Acyrthosiphon pisum, Aulacorthum solani, Aphis craccivora, Macrosiphum euphorbiae, Macrosiphum avenae, Metopolophium dirhodum, Rhopalosiphum padi, Schizaphis graminum, Brevicoryne brassicae, Lipaphis erysimi, Aphis citricola, Rosy apple aphid, Eriosoma lanigerum, Toxoptera aurantii, and Toxoptera citricidus; Deltocephalidae such as Nephotettix cincticeps, Delphacidae such as Laodelphax striatellus, Nilaparvata lugens, and Sogatella furcifera; Pentatomidae such as Eysarcoris ventralis, Nezara viridula, and Trigonotylus coelestialium; Aleyrodidae such as Bemisia argentifolii, Bemisia tabaci, and Trialeurodes vaporariorum; Diaspididae, Margarodidae, Ortheziidae, Aclerdiae, Dactylopiidae, Kerridae, Pseudococcidae, Coccidae, Eriococcidae, Asterolecaniidae, Beesonidae, Lecanodiaspididae, or Cerococcidae, such as Pseudococcus comstocki and Planococcus citri Risso; Coleoptera pests, for example, Lissorhoptrus oryzophilus, Callosobruchuys chienensis, Tenebrio molitor, Diabrotica virgifera virgifera, Diabrotica undecimpunctata howardi, Anomala cuprea, Anomala rufocuprea, Phyllotreta striolata, Aulacophora femoralis, Leptinotarsa decemlineata, Oulema oryzae, Carposinidae, and Cerambycidae; Acari, for example, Tetranychus urticae, Tetranychus kanzawai, and Panonychus citri; Hymenopteran pests, for example, Tenthredinidae; Orthopteran pests, for example, Acrididae; Dipteran pests, for example, Muscidae and Agromyzidae; Thysanopteran pests, for example, Thrips palmi and Frankliniella occidentalis; Plant Parasitic Nematodes, for example, Meloidogyne hapla, Pratylenchus spp., Aphelenchoides besseyi and Bursaphelenchus xylophilus; and parasites of animals, for example, Siphonaptera, Anoplura, mites such as Boophilus microplus, Haemaphysalis longicornis, Rhipicephalus sanguineus, and Scarcoptes scabiei. Preferred are hemipteran pests.

The compound represented by formula (Ia) accordingly to the present invention has significant control effect against hemipteran pests. Preferred hemipteran pests are selected from Aphidoidea such as Aphididae, Adelgidae, and Phylloxeridae, particularly preferably Aphididae; Coccoidea such as Diaspididae, Margarodidae, Ortheziidae, Aclerdiae, Dactylopiidae, Kerridae, Pseudococcidae, Coccidae, Eriococcidae, Asterolecaniidae, Beesonidae, Lecanodiaspididae, and Cerococcidae; and Aleyrodidae. More preferred are Myzus persicae, Aphis gossypii, Aphis fabae, Aphis maidis (corn-leaf aphid), Acyrthosiphon pisum, Aulacorthum solani, Aphis craccivora, Macrosiphum euphorbiae, Macrosiphum avenae, Metopolophium dirhodum, Rhopalosiphum padi, Schizaphis graminum, Brevicoryne brassicae, Lipaphis erysimi, Aphis citricola, Rosy apple aphid, Eriosoma lanigerum, Toxoptera aurantii, Toxoptera citricidus, and Pseudococcus comstocki.

The composition according to the present invention can be prescribed in any suitable formulation, such as emulsifiable concentrates, liquid formulations, suspension, wettable powder, flowables, dust, granules, tablets, oil solutions, aerosols, or smoking agents by using suitable agriculturally and horticulturally acceptable carriers. Accordingly, the carrier include solid carriers, liquid carriers, gaseous carriers, surfactants, dispersants and/or other adjuvants for formulations, and the like.

Solid carriers usable herein include, for example, talc, bentonite, clay, kaolin, diatomaceous earth, vermiculite, white carbon, and calcium carbonate.

Examples of liquid carriers include: alcohols, such as methanol, n-hexanol, and ethylene glycol; ketones, such as acetone, methyl ethyl ketone, and cyclohexanone; aliphatic hydrocarbons, such as n-hexane, kerosine, and kerosene; aromatic hydrocarbons, such as toluene, xylene, and methylnaphthalene; ethers, such as diethyl ether, dioxane, and tetrahydrofuran; esters, such as ethyl acetate; nitriles, such as acetonitrile and isobutyronitrile; acid amides, such as dimethylformamide and dimethylacetamide; vegetable oils, such as soy bean oil and cotton seed oil; dimethylsulfoxide; and water.

Gaseous carriers include, for example, LPG, air, nitrogen, carbon dioxide, and dimethyl ether.

Surfactants or dispersants usable, for example, for emulsifying, dispersing, or spreading include, for example, alkylsulfonic esters, alkyl(aryl)sulfonic acid salts, polyoxyalkylene alkyl(aryl) ethers, polyhydric alcohol esters, and lignin sulfonic acid salts.

Adjuvants usable for improving the properties of formulations include, for example, carboxymethylcellulose, gum arabic, polyethylene glycol, and calcium stearate.

The above carriers, surfactants, dispersants, and adjuvant may be used either solely or in combination according to need.

The content of the active ingredient in the formulation is not particularly limited. In general, however, the content of the active ingredient is 1 to 75% by weight for emulsifiable concentrates, 0.3 to 25% by weight for dust, 1 to 90% by weight for wettable powder, and 0.5 to 10% by weight for granules.

The compound represented by formula (I), (Ia), (Ib), or an agriculturally and horticulturally acceptable salt thereof and the above formualtions comprising the same may be applied as such or after dilution to plants or soil. Therefore, according to another aspect of the present invention, there is provided a method for controlling a pest, comprising applying an effective amount of a compound represented by formula (I) or an agriculturally and horticulturally acceptable salt thereof to a plant or soil. According to still another aspect of the present invention, there is provided a method for controlling a hemipteran pest, comprising applying an effective amount of a compound represented by formula (Ia) or an agriculturally and horticulturally acceptable salt thereof to a plant or soil. According to a further aspect of the present invention, there is provided a method for controlling a pest, comprising applying an effective amount of a compound represented by formula (Ib) or an agriculturally and horticulturally acceptable salt thereof to a plant or soil. Preferred methods usable for applying the compound or formulation to plants or soil include spreading treatment, soil treatment, surface treatment, and fumigation treatment.

Spreading treatments include, for example, spreading, spraying, misting, atomizing, granule application, and submerged application. Soil treatments include, for example, soil affusion and soil mixing. Examples of surface treatments include, for example, coating, dust coating, and covering. Fumigation treatments include, for example, covering of soil with a polyethylene film after soil injection. Accordingly, the control method according to the present invention comprises a method in which the compound represented by formula (I), (Ia), or (Ib) or a formulation comprising the same is applied by fumigation in a sealed space.

The composition according to the present invention may be used as a mixture or in a combination with, for example, other insecticides, fungicides, miticides, herbicides, plant growth-regulating agents, or fertilizers. Agents which may be mixed or used in combination include those described, for example, in The Pesticide Manual, 13th edition, published by The British Crop Protection Council; and SHIBUYA INDEX, the 10th edition, 2005, published by SHIBUYA INDEX RESEARCH GROUP. More specifically, insecticides usable herein include, for example, organophosphate ester compounds such as acephate, dichlorvos, EPN, fenitrothion, fenamifos, prothiofos, profenofos, pyraclofos, chlorpyrifos-methyl, and diazinon; carbamate compounds such as methomyl, thiodicarb, aldicarb, oxamyl, propoxur, carbaryl, fenobucarb, ethiofencarb, fenothiocarb, pirimicarb, carbofuran, and benfuracarb; nereistoxin derivatives such as cartap and thiocyclam; organochlorine compounds such as dicofol and tetradifon; pyrethroid compounds such as permethrin, tefluthrin, cypermethrin, deltamethrin, cyhalothrin, fenvalerate, fluvalinate, ethofenprox, and silafluofen; benzoylurea compounds such as diflubenzuron, teflubenzuron, flufenoxuron, and chlorfluazuron; juvenile hormone-like compounds such as methoprene; and molting hormone-like compounds such as chromafenozide. Other compounds usable herein include buprofezin, hexythiazox, amitraz, chlordimeform, pyridaben, fenpyroximate, pyrimidifen, tebufenpyrad, fluacrypyrim, acequinocyl, cyflumetofen, flubendiamide, ethiprole, fipronil, ethoxazole, imidacloprid, chlothianidin, pymetrozine, bifenazate, spirodiclofen, spiromesifen, flonicamid, chlorfenapyr, pyriproxyfene, indoxacarb, pyridalyl, or spinosad, avermectin, milbemycin, organometallic compounds, dinitro compounds, organosulfur compounds, urea compounds, triazine compounds, hydrazine compounds.

The composition according to the present invention may also be used as a mixture or in a combination with microbial pesticides such as BT formulations and entomopathogenic viral agents.

Fungicides usable herein include, for example, strobilurin compounds such as azoxystrobin, kresoxym-methyl, and trifloxystrobin; anilinopyrimidine compounds such as mepanipyrim, pyrimethanil, and cyprodinil; azole compounds such as triadimefon, bitertanol, triflumizole, etaconazole, propiconazole, penconazole, flusilazole, myclobutanil, cyproconazole, tebuconazole, hexaconazole, prochloraz, and simeconazole; quinoxaline compounds such as quinomethionate; dithiocarbamate compounds such as maneb, zineb, mancozeb, polycarbamate, and propineb; phenylcarbamate compounds such as diethofencarb; organochlorine compounds such as chlorothalonil and quintozene; benzimidazole compounds such as benomyl, thiophanate-methyl, and carbendazole; phenylamide compounds such as metalaxyl, oxadixyl, ofurace, benalaxyl, furalaxyl, and cyprofuram; sulfenic acid compounds such as dichlofluanid; copper compounds such as copper hydroxide and oxine-copper; isoxazole compounds such as hydroxyisoxazole; organophosphorus compounds such as fosetyl-aluminium and tolclofos-methyl; N-halogenothioalkyl compounds such as captan, captafol, and folpet; dicarboxyimide compounds such as procymidone, iprodione, and vinchlozolin; benzanilide compounds such as flutolanil and mepronil; morpholine comopounds such as fenpropimorph and dimethomorph; organotin compounds such as fenthin hydroxide, and fenthin acetate; and cyanopyrrole compounds such as fludioxonil and fenpiclonil. Other compounds usable herein include fthalide, fluazinam, cymoxanil, triforine, pyrifenox, fenarimol, fenpropidin, pencycuron, cyazofamid, iprovalicarb, and benthiavalicarb-isopropyl and the like.

According to another aspect of the present invention, there is provided use of a compound represented by formula (I) or an agriculturally and horticulturally acceptable salt thereof as a pest control agent. According to still another aspect of the present invention, there is provided use of a compound represented by formula (Ia) or an agriculturally and horticulturally acceptable salt thereof as a hemipteran pest control agent. According to still another aspect of the present invention, there is provided use of a compound represented by formula (Ib) or an agriculturally and horticulturally acceptable salt thereof as a pest control agent.

[EXAMPLES]

The present invention is further illustrated by the following Examples that are not intended as a limitation of the invention. The compound Nos. correspond to the compound Nos. in Tables 1 to 14.

Example 1: Synthesis of compound 73

Compound 76 (890 mg) synthesized by the method described in Japanese Patent Laid-Open Publication No. 259569/1996 was dissolved in an 80% aqueous methanol solution. Next, 1,8-diazabicyclo[5.4.0]-undeca-7-ene (216 mg) was added to the solution, and the mixture was stirred at room temperature for 1.5 hr. The reaction mixture was added with acetic acid to quench the reaction, and the solvent was removed by evaporation under the reduced pressure. Water was added to the precipitated crystal, followed by extraction with chloroform. The chloroform layer was washed with saturated brine, was dried over anhydrous magnesium sulfate, and the solvent was removed by evaporation under the reduced pressure to give a crude product of compound 73. The crude product was purified by chromatography on silica gel (Mega Bond Elut (Varian), acetone : hexane = 1 : 1) to give compound 73 (451 mg).

Mass spectrometric data (FAB$^+$): 570(M+H)$^+$

Example 2: Synthesis of compound 218

Compound 102 (30 mg) synthesized by the method described in Japanese Patent Laid-Open Publication No. 259569/1996 and cyclopropanecarboxylic acid (112 mg) were dissolved in anhydrous N,N-dimethylformamide (2 ml), and 1-ethyl-3-(3-dimethylaminopropyl)-carbodiimide hydrochloride (76 mg) and 4-(dimethylamino)pyridine (32 mg) were added to the solution. The reaction solution was stirred at room temperature for 68 hr and was then poured into water, followed by extraction with ethyl acetate. The ethyl acetate layer was washed with saturated brine and was dried over anhydrous magnesium sulfate, and the solvent was removed by evaporation under the reduced pressure to give a crude product of compound 218. The crude product was purified by preparative thin-layer chromatography (Merck Silica Gel 60 $F_{254}$ 0.5mm, acetone : hexane = 1 : 1) to give compound 218 (33 mg).
Mass spectrometric data ($FAB^+$): $662(M+H)^+$ Example 3: Synthesis of compound 261

Compound 218 (1.07 g) prepared in Example 2 was dissolved in an 80% aqueous methanol solution. 1,8-Diazabicyclo[5.4.0]-undeca-7-ene (271 mg) was added to the solution, and the mixture was stirred at room temperature for 24.5 hr. The reaction mixture was added with acetic acid to quench the reaction, and the solvent was removed by evaporation under the reduced pressure. Water was added to the precipitated crystal, followed by extraction with chloroform. The chloroform layer was washed with saturated brine and was dried over anhydrous magnesium sulfate, and the solvent was removed by evaporation under the reduced pressure to give a crude product of compound 261.   The crude product was purified by chromatography on silica gel (Mega Bond Elut (Varian), acetone : hexane = 1 : 1) to give compound 261 (233 mg).
Mass spectrometric data ($ESI^+$): $594(M+H)^+$ Example 4: Synthesis of compound 222

Compound 73 (30 mg) prepared in Example 1 and 4-(trifluoromethyl)nicotinic acid (30 mg) was dissolved in anhydrous N,N-dimethylformamide (3 ml). Next, 1-ethyl-3-(3-dimethylaminopropyl)-carbodiimide hydrochloride (15 mg) and 4-(dimethylamino)pyridine (4 mg) were added to the solution, and the reaction solution was stirred at room temperature for 15 hr and was then poured into water, followed by extraction with ethyl acetate. The ethyl acetate layer was washed with saturated brine and was dried over anhydrous magnesium sulfate, and the solvent was removed by evaporation under the reduced pressure to give a crude produce of compound 222. The crude product was purified by preparative thin-layer chromatography (Merck Silica Gel 60 $F_{254}$ 0.5mm, acetone : hexane = 1 : 1) to give compound 222 (19 mg).
Mass spectrometric data ($FAB^+$): $743(M+H)^+$ Example 5: Synthesis of compound 269

Compound 261 (20 mg) prepared in Example 3 and 2-cyanobenzoic acid (30 mg) were dissolved in anhydrous N,N-dimethylformamide (1 ml), and 1-ethyl-3-(3-dimethylaminopropyl)-carbodiimide hydrochloride (26 mg) and 4-(dimethylamino)pyridine (4 mg) were added to the solution. The reaction solution was stirred at room temperature for 12 hr, and the reaction solution was added to water, followed by extraction with ethyl acetate. The ethyl acetate layer was washed with saturated brine and was dried over anhydrous magnesium sulfate. The solvent was removed by evaporation under the reduced pressure to give a crude product of compound 269. The crude product was purified by preparative thin-layer chromatography (Merck Silica Gel 60 $F_{254}$ 0.5mm, acetone : hexane = 1 :1) to give compound 269 (18 mg).
Mass spectrometric data (ESI$^+$): 723 (M+H)$^+$ Example 6: Synthesis of compound 225

1,7,11-Trideacetyl-13-oxo-6"-chloropyripyropene A (10 mg) described in Journal of Antibiotics (1997), 50 (3), 229-36 was dissolved in anhydrous N,N-dimethylformamide (1 ml). Triethylamine (24 mg) and 4-(dimethylamino)pyridine (0.5 mg) were added to the solution, and the mixture was stirred at room temperature for 30 min. Thereafter, propionic acid anhydride (8 mg) was added. The reaction solution was stirred at the same temperature for 4 hr. The reaction solution was added to water, and the mixture was extracted with ethyl acetate. The ethyl acetate layer was washed with saturated brine and was dried over anhydrous magnesium sulfate, and the solvent was then removed by evaporation under the reduced pressure to give a crude product of compound 225. The crude product was purified by preparative thin-layer chromatography (Merck Silica Gel 60 $F_{254}$ 0.5mm, acetone: hexane = 1 : 1) to give compound 225 (5.6 mg).
Mass spectrometric data (ESI$^+$): 658 (M+H)$^+$ Example 7: Synthesis of compound 226

Compound 225 (10 mg) prepared in Example 6 was dissolved in methanol (1 ml). Cerium(III) chloride heptahydrate (57 mg) and sodium borohydride (6 mg) were added to the solution. The mixture was stirred at 0°C for 7 hr, and water was added to the reaction solution, followed by extraction with ethyl acetate. The ethyl acetate layer was washed with saturated brine and was dried over anhydrous magnesium sulfate, and the solvent was removed by evaporation under the reduced pressure to give a crude product of compound 226. The crude product was purified by preparative thin-layer chromatography (Merck Silica Gel 60 $F_{254}$ 0.5mm, acetone : hexane = 1 :1) to give compound 226 (8.5 mg).
Mass spectrometric data (ESI$^+$): 660 (M+H)$^+$ Example 8: Synthesis of compound 273

1,7,11-Trideacetyl-1,11-o-p-methoxybenzylidene pyripyropen A (10 mg) described in Japanese Patent Laid-Open Publication No. 269065/1996 was dissolved in anhydrous dichloromethane (0.5 ml), and pyridinium dichromate (PDC) (39 mg) was added to the solution. The reaction solution was stirred at room temperature for 4 hr, and the reaction solution was added to water. The dichloromethane layer was washed with saturated brine, and was dried over anhydrous sodium sulfate, and the solvent was then removed by evaporation under the reduced pressure to give a crude product of compound 273. The crude product was purified by preparative thin-layer chromatography (Merck Silica Gel 60 $F_{254}$ 0.5mm, chloroform : methanol = 12.5 :1) to give compound 273 (4.4 mg).
Mass spectrometric data (ESI$^+$): 574 (M+H)$^+$ Example 9: Synthesis of compound 274

1,11-o-Cyclic carbonate1,7,11-trideacetyl-pyripyropene A (4 mg) described in Japanese Patent Laid-Open Publication No. 269065/1996 was dissolved in anhydrous dichloromethane (1 ml). Triethylamine (5 μl) and 4-(dimethylamino)pyridine (1 mg) were added to the solution. The reaction solution was stirred at room temperature for 30 min, and valeric acid anhydride (5 μl) was added thereto. Next, the reaction solution was stirred at room temperature for 3 hr. The reaction solution was added to water, and the dichloromethane layer was washed with saturated brine and was dried over anhydrous sodium sulfate. The solvent was then removed by evaporation under the reduced pressure to give a crude product of compound 274. The crude product was purified by preparative thin-layer chromatography (Merck Silica Gel 60 $F_{254}$ 0.5mm, chloroform : methanol = 25 :1) to give compound 274 (0.1 mg).
Mass spectrometric data (ESI$^+$): 652 (M+H)$^+$ Example 10

Compounds shown in Tables 15 to 17 were synthesized using starting materials, reaction reagents 1 and 2 and solvents described in these tables. Further, the $^1$H-NMR data about some of the compounds in Tables 15 to 17 was described in Tables 18 to 29. In addition, CDCl$_3$ was used as the solvent for the $^1$H-NMR measurement. Tetramethylsilane was used as a standard substance for the $^1$H-NMR measurement.

Table 15

| Compound No. | Starting material (Compound No.) | Amount | Reaction reagent 1 | Amount | Reaction reagent 2 | Solvent | Yield | Mass spectrometric data Measuring Method | Data |
|---|---|---|---|---|---|---|---|---|---|
| 74 | 73 | 30 mg | acetic anhydride | 32.7 mg | $Et_3N$ 64.0 mg, DMAP 12.8 mg | DMF | 13.6 mg | FAB | 612 $(M+H)^+$ |
| 77 | 73 | 30 mg | benzoic acid | 84.8 mg | EDCI 49.2 mg, DMAP 46.4 mg | DMF | 36.4 mg | FAB | 674 $(M+H)^+$ |
| 91 | 102 | 30 mg | pivalic anhydride | 220 mg | $Et_3N$ 60.0 mg, DMAP 8.0 mg | DMF | 27.7 mg | FAB | 710 $(M+H)^+$ |
| 205 | 73 | 30 mg | nicotinic acid | 12.9 mg | EDCI 15.1 mg, DMAP 6.4 mg | DMF | 27.1 mg | FAB | 675 $(M+H)^+$ |
| 206 | 73 | 30 mg | isobutyric anhydride | 50.0 mg | $Et_3N$ 64.0 mg, DMAP 12.8 mg | DMF | 11.4 mg | FAB | 640 $(M+H)^+$ |
| 207 | 73 | 30 mg | pivalic anhydride | 58.9 mg | $Et_3N$ 64.0 mg, DMAP 12.8 mg | DMF | 23.4 mg | FAB | 654 $(M+H)^+$ |
| 208 | 73 | 30 mg | 4-(trifluoromethyl)benzoic anhydride | 114 mg | $Et_3N$ 64.0 mg, DMAP 12.8 mg | DMF | 32.2 mg | FAB | 742 $(M+H)^+$ |
| 209 | 73 | 40 mg | 1,1'-carbonyl diimidazole | 34.0 mg | | toluene | 5.1 mg | FAB | 664 $(M+H)^+$ |
| 210 | 73 | 30 mg | propyl isocyanate | 26.9 mg | $Et_3N$ 64.0 mg, DMAP 12.8 mg | DMF | 3.2 mg | FAB | 655 $(M+H)^+$ |
| 211 | 73 | 30 mg | 3,4-dihydro-2H-pyran | 155 mg | pyridine hydrochloride | $CH_2Cl_2$ | 22.7 mg | FAB | 654 $(M+H)^+$ |
| 212 | 73 | 30 mg | 6-chloro nicotinic acid | 16.5 mg | EDCI 15.2 mg, DMAP 6.4 mg | DMF | 39.8 mg | FAB | 709 $(M+H)^+$ |
| 213 | 73 | 30 mg | cyclopropane carboxylic acid | 27 mg | EDCI 15.2 mg, DMAP 6.4 mg | DMF | 18.2 mg | FAB | 638 $(M+H)^+$ |
| 214 | 73 | 30 mg | cyclobutane carboxylic acid | 31 mg | EDCI 15.2 mg, DMAP 6.4 mg | DMF | 14.9 mg | FAB | 652 $(M+H)^+$ |
| 215 | 73 | 30 mg | acrylic acid | 22.5 mg | EDCI 15.2 mg, DMAP 6.4 mg | DMF | 5.6 mg | FAB | 624 $(M+H)^+$ |
| 216 | 73 | 30 mg | isonicotinic acid | 12.9 mg | EDCI 15.2 mg, DMAP 6.4 mg | DMF | 8.2 mg | FAB | 675 $(M+H)^+$ |
| 217 | 73 | 30 mg | picolinic acid | 12.9 mg | EDCI 15.2 mg, DMAP 8.4 mg | DMF | 40.8 mg | FAB | 675 $(M+H)^+$ |
| 219 | 102 | 30 mg | cyclobutane carboxylic acid | 131 mg | EDCI 76 mg, DMAP 32 mg | DMF | 38.9 mg | FAB | 704 $(M+H)^+$ |
| 220 | 102 | 30 mg | benzoic acid | 160 mg | EDCI 126 mg, DMAP 80 mg | DMF | 37.9 mg | FAB | 770 $(M+H)^+$ |
| 221 | 73 | 30 mg | 6-(trifluoromethyl)nicotinic acid | 30 mg | EDCI 15.2 mg, DMAP 6.4 mg | DMF | 35.4 mg | FAB | 743 $(M+H)^+$ |
| 223 | 102 | 30 mg | 3,3,3-trifluoropropionic acid | 168 mg | EDCI 126 mg, DMAP 80 mg | DMF | 10.4 mg | FAB | 788 $(M+H)^+$ |
| 224 | 73 | 30 mg | 3,3,3-trifluoropropionic acid | 20 mg | EDCI 15.2 mg, DMAP 6.4 mg | DMF | 8.0 mg | FAB | 680 $(M+H)^+$ |

Table16

| Compound No. | Starting material (Compound No.) | Amount | Reaction reagent 1 | Amount | Reaction reagent 2 | Solvent | Yield | Mass spectrometric data Measuring Method | Data |
|---|---|---|---|---|---|---|---|---|---|
| 227 | 73 | 20 mg | 3-fluoro-isonicotinic acid | 15 mg | EDCI 14 mg, DMAP 4 mg | DMF | 5.4 mg | FAB | 693 (M+H)+ |
| 228 | 73 | 20 mg | 3-chloro-isonicotinic acid | 17 mg | EDCI 14 mg, DMAP 4 mg | DMF | 7.8 mg | FAB | 709 (M+H)+ |
| 229 | 73 | 20 mg | 3-methyl picolinic acid | 14 mg | EDCI 28 mg, DMAP 8 mg | DMF | 16.7 mg | FAB | 689 (M+H)+ |
| 230 | 73 | 20 mg | 3-benzoyl-2-pyridine carboxylic acid | 48 mg | EDCI 28 mg, DMAP 8 mg | DMF | 16.4 mg | FAB | 779 (M+H)+ |
| 231 | 73 | 20 mg | 3-n-propoxy picolinic acid | 38 mg | EDCI 28 mg, DMAP 8 mg | DMF | 17.3 mg | FAB | 733 (M+H)+ |
| 232 | 73 | 20 mg | 6-fluoro nicotinic acid | 30 mg | EDCI 28 mg, DMAP 8 mg | DMF | 5.3 mg | FAB | 693 (M+H)+ |
| 233 | 102 | 20 mg | cyclopentane carboxylic acid | 99 mg | EDCI 84 mg, DMAP 5 mg | DMF | 28.3 mg | FAB | 746 (M+H)+ |
| 234 | 102 | 20 mg | cyclohexane carboxylic acid | 112 mg | EDCI 84 mg, DMAP 5 mg | DMF | 21.5 mg | FAB | 788 (M+H)+ |
| 235 | 102 | 20 mg | cyano acetic acid | 74 mg | EDCI 84 mg, DMAP 5 mg | DMF | 3.3 mg | FAB | 659 (M+H)+ |
| 236 | 102 | 20 mg | cyclopropyl acetic acid | 87 mg | EDCI 84 mg, DMAP 5 mg | DMF | 16.7 mg | FAB | 786 (M+H)+ |
| 237 | 102 | 20 mg | cyclopropyl acetic acid | 87 mg | EDCI 84 mg, DMAP 5 mg | DMF | 8.2 mg | FAB | 704 (M+H)+ |
| 238 | 102 | 20 mg | 2,2-difluoro-1-methylcyclopropanecarboxylic acid | 118 mg | EDCI 84 mg, DMAP 5 mg | DMF | 6.1 mg | FAB | 812 (M+H)+ |
| 239 | 73 | 20 mg | 4-methyl nicotinic acid | 36 mg | EDCI 28 mg, DMAP 8 mg | DMF | 16.1 mg | FAB | 689 (M+H)+ |
| 240 | 73 | 20 mg | 4-chloro nicotinic acid | 33 mg | EDCI 28 mg, DMAP 8 mg | DMF | 13.8 mg | FAB | 709 (M+H)+ |
| 241 | 73 | 20 mg | (4-methoxy carbonyl) nicotinic acid | 38 mg | EDCI 28 mg, DMAP 8 mg | DMF | 18.8 mg | FAB | 733 (M+H)+ |
| 242 | 73 | 20 mg | 5-(trifluoromethyl)thieno[3,2-b]pyridine-6-carboxylic acid | 38 mg | EDCI 28 mg, DMAP 8 mg | DMF | 20.3 mg | FAB | 799 (M+H)+ |
| 243 | 73 | 20 mg | 2-cyano benzoic acid | 31 mg | EDCI 28 mg, DMAP 8 mg | DMF | 6.8 mg | FAB | 699 (M+H)+ |
| 244 | 73 | 20 mg | 2-(trifluoromethyl)benzoic acid | 40 mg | EDCI 28 mg, DMAP 8 mg | DMF | 10.2 mg | FAB | 742 (M+H)+ |
| 245 | 73 | 20 mg | 2-fluoro benzoic acid | 29 mg | EDCI 28 mg, DMAP 8 mg | DMF | 16.1 mg | FAB | 692 (M+H)+ |
| 246 | 73 | 20 mg | 2-nitro benzoic acid | 35 mg | EDCI 28 mg, DMAP 8 mg | DMF | 9.8 mg | FAB | 719 (M+H)+ |
| 247 | 73 | 20 mg | 2-chloro nicotinic acid | 33 mg | EDCI 28 mg, DMAP 8 mg | DMF | 13.1 mg | FAB | 709 (M+H)+ |

Table 17

| Compound No. | Starting material (Compound No.) | Amount | Reaction reagent 1 | Amount | Reaction reagent 2 | Solvent | Yield | Mass spectrometric data Measuring Method | Data |
|---|---|---|---|---|---|---|---|---|---|
| 248 | 73 | 20 mg | 2-chloro-6-methyl nicotinic acid | 36 mg | EDCI 28 mg, DMAP 8 mg | DMF | 17.2 mg | FAB | 723 (M+H)* |
| 249 | 73 | 20 mg | methoxymethyl bromide | 31 mg | [(CH$_3$)$_2$CH]$_2$NEt 18 mg | DMF | 1.2 mg | ESI | 614 (M+H)* |
| 250 | 102 | 20 mg | 2,2-difluorocyclopropane carboxylic acid | 106 mg | EDCI 84 mg, DMAP 5 mg | DMF | 23.2 mg | ESI | 770 (M+H)* |
| 251 | 73 | 20 mg | 3-tert-buthylthio-2-carboxy piridine | 44 mg | EDCI 28 mg, DMAP 8 mg | DMF | 7.6 mg | ESI | 763 (M+H)* |
| 252 | 73 | 20 mg | 3,5-difluoropyridine-2-carboxylic acid | 33 mg | EDCI 28 mg, DMAP 8 mg | DMF | 10.9 mg | ESI | 711 (M+H)* |
| 253 | 73 | 20 mg | pyrazine carboxylic acid | 26 mg | EDCI 28 mg, DMAP 8 mg | DMF | 10.9 mg | ESI | 676 (M+H)* |
| 254 | 73 | 20 mg | 4-thiazole carboxylic acid | 27 mg | EDCI 28 mg, DMAP 8 mg | DMF | 18.5 mg | ESI | 681 (M+H)* |
| 255 | 73 | 20 mg | 3-chloro thiophene-2-carboxylic acid | 34 mg | EDCI 28 mg, DMAP 8 mg | DMF | 15.8 mg | ESI | 714 (M+H)* |
| 256 | 73 | 20 mg | 6-methyl nicotinic acid | 29 mg | EDCI 28 mg, DMAP 8 mg | DMF | 15.1 mg | ESI | 689 (M+H)* |
| 257 | 73 | 20 mg | 6-chloro pyridine-2-carboxylic acid | 33 mg | EDCI 28 mg, DMAP 8 mg | DMF | 12.7 mg | ESI | 709 (M+H)* |
| 258 | 73 | 20 mg | 6-fluoro pyridine-2-carboxylic acid | 30 mg | EDCI 28 mg, DMAP 8 mg | DMF | 14.4 mg | ESI | 693 (M+H)* |
| 259 | 73 | 20 mg | 1-methyl indole-2-carboxylic acid | 37 mg | EDCI 28 mg, DMAP 8 mg | DMF | 18.8 mg | ESI | 727 (M+H)* |
| 260 | 73 | 20 mg | 3-chloropyridine-2-carboxylic acid | 33 mg | EDCI 28 mg, DMAP 8 mg | DMF | 14.6 mg | ESI | 709 (M+H)* |
| 262 | 73 | 20 mg | 2-fluoro nicotinic acid | 30 mg | EDCI 28 mg, DMAP 8 mg | DMF | 9.9 mg | ESI | 693 (M+H)* |
| 263 | 73 | 20 mg | 4-cyano benzoic acid | 31 mg | EDCI 28 mg, DMAP 8 mg | DMF | 14.0 mg | ESI | 699 (M+H)* |
| 264 | 73 | 20 mg | 3-cyano benzoic acid | 31 mg | EDCI 28 mg, DMAP 8 mg | DMF | 16.9 mg | ESI | 699 (M+H)* |
| 265 | 73 | 20 mg | 3-(trifluoromethyl)benzoic acid | 40 mg | EDCI 28 mg, DMAP 8 mg | DMF | 14.3 mg | ESI | 742 (M+H)* |
| 266 | 73 | 20 mg | 2-pyridyl acetic acid | 36 mg | EDCI 28 mg, DMAP 8 mg | DMF | 11.7 mg | ESI | 689 (M+H)* |
| 267 | 73 | 20 mg | 3-pyridyl acetic acid | 36 mg | EDCI 28 mg, DMAP 8 mg | DMF | 8.6 mg | ESI | 689 (M+H)* |
| 268 | 73 | 20 mg | (4-pyridylthio) acetic acid | 36 mg | EDCI 28 mg, DMAP 4 mg | DMF | 16.5 mg | ESI | 721 (M+H)* |
| 270 | 261 | 20 mg | 4-(trifluoromethyl)nicotinic acid | 39 mg | EDCI 28 mg, DMAP 4 mg | DMF | 8.3 mg | ESI | 767 (M+H)* |
| 271 | 261 | 20 mg | 3-chloropyridine-2-carboxylic acid | 32 mg | EDCI 26 mg, DMAP 4 mg | DMF | 14.5 mg | ESI | 733 (M+H)* |

Table 18

| Compound No. | $^1$H-NMR δ (ppm) |
|---|---|
| 73 | 0.91 (3H, s), 1.13 (3H, t, J = 5.1 Hz), 1.14 (3H, t, J = 5.1 Hz), 1.26 (1H, s), 1.32-1.40 (1H, m), 1.42 (3H, s), 1.45 (1H, d, J = 2.7 Hz), 1.49-1.51 (2H, m), 1.66 (3H, s), 1.81-1.91 (2H, m), 2.13-2.18 (1H, m), 2.24-2.37 (4H, m), 2.90 (1H, m), 3.79 (3H, m), 4.80 (1H, dd, J = 3.5, 7.6 Hz), 4.99-5.00 (1H, m), 6.52 (1H, s), 7.42 (1H, dd, J = 3.5, 5.4 Hz), 8.11 (1H, dt, J = 1.4, 5.4 Hz), 8.70 (1H, d, J = 2.4 Hz), 9.00 (1H, s) |
| 77 | 0.92 (3H, s), 1.14 (3H, t, J = 7.6 Hz), 1.20 (3H, t, J = 7.6 Hz), 1.26 (1H, s), 1.37-1.46 (1H, m), 1.51 (3H, s), 1.62 (1H, d, J = 3.8 Hz), 1.68-1.82 (2H, m), 1.87 (3H, s), 1.91-2.00 (2H, m), 2.18-2.23 (1H, m), 2.33 (2H, q, J = 7.6 Hz), 2.43 (2H, dq, J = 1.4, 7.6 Hz), 2.97 (1H, s), 3.70 (1H, d, J = 11.9 Hz), 3.84 (1H, d, J = 11.9 Hz), 4.83 (1H, dd, J = 5.1, 11.1 Hz), 5.05 (1H, d, J = 4.3 Hz), 5.27 (1H, dd, J = 4.6, 11.1 Hz), 6.45 (1H, s), 7.39-7.66 (4H, m), 8.05-8.13 (3H, m), 8.70 (1H, d, J = 4.6 Hz), 9.00 (1H, s) |
| 74 | 0.90 (3H, s), 1.12 (3H, t, J = 7.8 Hz), 1.13 (3H, t, J = 7.8 Hz), 1.19 (1H, s), 1.25-1.34 (1H, m), 1.44 (3H, s), 1.53-1.63 (3H, m), 1.69 (3H,s), 1.73-1.90 (2H, m), 2.10 (1H, m), 2.16 (3H, s), 2.33 (2H, dq, J = 2.4, 7.6 Hz), 2.36 (2H, dq, J = 3.2, 7.6 Hz), 2.87 (1H, m), 3.72 (2H, m), 4.81 (1H, dd, J = 4.6, 11.6 Hz), 4.97-5.00 (2H, m), 6.46 (1H, s), 7.40 (1H, dd, J = 4.6, 8.1 Hz), 8.10 (1H, m), 8.69 (1H, d, J = 4.9 Hz), 9.00 (1H, s) |
| 205 | 0.92 (3H, s), 1.14 (3H, t, J = 7.6 Hz), 1.20 (3H, t, J = 7.6 Hz), 1.26 (1H, s), 1.42-1.50 (1H, m), 1.59 (3H, s), 1.61-1.83 (3H, m), 1.85 (3H, s), 1.83-2.00 (2H, m), 2.18-2.23 (1H, m), 2.33 (2H, q, J = 7.6 Hz), 2.43 (2H, q, J = 7.6 Hz), 2.94 (1H, m), 3.72 (1H, d, J = 11.9 Hz), 3.82 (1H, d, J = 12.7 Hz), 4.83 (1H, dd, J = 4.9, 11.3 Hz), 5.03-5.06 (1H, m), 5.27 (1H, dd, J = 4.9, 11.3 Hz), 6.42 (1H, s), 7.38 (1H, dd, J = 4.9, 8.1 Hz), 7.45 (1H, dd, J = 4.9, 8.1 Hz), 8.07 (1H, dt, J = 2.2, 8.1 Hz), 8.36 (1H, dt, J = 1.9, 8.1 Hz), 8.67 (1H, dd, J = 1.9, 5.1 Hz), 8.83 (1H, dd, J = 1.9, 4.9 Hz), 8.97 (1H, d, J = 1.9 Hz), 9.30 (1H, d, J = 1.9 Hz) |
| 206 | 0.90 (3H, s), 1.13 (6H, t, J = 7.6 Hz), 1.19 (1H, s), 1.24 (3H, d, J = 4.6 Hz), 1.26 (3H, d, J = 4.6 Hz), 1.33-1.38 (1H, m), 1.45 (3H, s), 1.54 (1H, d, J = 3.8 Hz), 1.60-1.64 (2H, m), 1.67 (3H,s), 1.75-1.90 (2H, m), 2.15-2.19 (1H, m), 2.32 (2H, q, J = 7.6 Hz), 2.38 (2H, q, J = 7.6 Hz), 2.65 (1H, quint., J = 7.6 Hz), 2.88 (1H, d, J = 1.6 Hz), 3.68 (1H, d, J = 12.4 Hz), 3.83 (1H, d, J = 11.9 Hz), 4.80 (1H, dd, J = 4.9, 11.3 Hz), 5.00 (2H, m), 6.38 (1H, s), 7.40 (1H, dd, J = 4.6, 8.1 Hz), 8.09 (1H, dt, J = 1.9, 8.1 Hz), 8.69 (1H, dd, J = 1.6, 4.6 Hz), 9.00 (1H, d, J = 1.6 Hz) |

Table 19

| Compound No. | $^1$H-NMR δ (ppm) |
|---|---|
| 208 | 0.92 (3H, s), 1.14 (3H, t, J = 7.6 Hz), 1.21 (3H, t, J = 7.6 Hz), 1.26 (1H, s), 1.39-1.47 (1H, m), 1.50 (3H, s), 1.61 (1H, m), 1.68-1.83 (2H, m), 1.86 (3H,s), 1.91-2.05 (2H, m), 2.18-2.23 (1H, m), 2.33 (2H, q, J = 7.6 Hz), 2.43 (2H, dq, J = 1.4, 7.6 Hz), 2.95 (1H, d, J = 2.4 Hz), 3.72 (1H, d, J = 11.9 Hz), 3.82 (1H, d, J = 11.9 Hz), 4.83 (1H, dd, J = 5.1, 11.1 Hz), 5.03-5.06 (1H, m), 5.26 (1H, dd, J = 4.9, 11.1 Hz), 6.40 (1H, s), 7.38 (1H, dd, J = 4.9, 8.4 Hz), 7.76 (2H, d, J = 8.4 Hz), 8.06 (1H, dt, J = 2.2, 8.1 Hz), 8.22 (2H, d, J = 8.4 Hz), 8.66 (1H, dd, J = 1.6, 4.9 Hz), 8.96 (1H, d, J = 2.2 Hz) |
| 211 | 0.90 (3H, s), 1.14 (3H, t, J = 7.6 Hz), 1.15 (3H, t, J = 7.6 Hz), 1.26 (1H, s), 1.29-1.38 (1H, m), 1.41 (3H, s), 1.43-1.71 (5H, m), 1.59 (3H, s), 1.75-1.89 (6H, m), 2.12-2.17 (1H, m), 2.26-2.38 (4H, m), 2.86 (1H, m), 3.45-4.00 (5H, m), 4.82 (1H, dd, J = 5.4, 10.8 Hz), 4.97-5.03 (2H, m), 6.41 (1H, s), 7.40 (1H, dd, J = 4.9, 7.8 Hz), 8.07-8.13 (1H, m), 8.67-8.70 (1H, m), 9.01 (1H, d, J = 2.4 Hz) |
| 212 | 0.92 (3H, s), 1.14 (3H, t, J = 7.6 Hz), 1.20 (3H, t, J = 7.6 Hz), 1.26 (1H, s), 1.38-1.46 (1H, m), 1.50 (3H, s), 1.61 (1H, m), 1.66-1.78 (2H, m), 1.84 (3H, s), 1.87-1.99 (2H, m), 2.12-2.23 (1H, m), 2.31 (2H, q, J = 7.6 Hz), 2.41 (2H, q, J = 7.6 Hz), 2.95 (1H, m), 3.73 (1H, d, J = 11.9 Hz), 3.81 (1H, d, J = 11.9 Hz), 4.83 (1H, dd, J = 4.9, 11.3 Hz), 5.04 (1H, m), 5.25 (1H, dd, J = 4.9, 11.3 Hz), 6.40 (1H, s), 7.38 (1H, dd, J = 4.6, 7.8 Hz), 7.47 (1H, d, J = 8.1 Hz), 8.06 (1H, dt, J = 1.6, 7.8 Hz), 8.30 (1H, dd, J = 2.4, 8.1 Hz), 8.67 (1H, dd, J = 1.4, 4.6 Hz), 8.97 (1H, d, J = 2.4 Hz), 9.06 (1H, d, J = 2.7 Hz) |
| 213 | 0.90 (3H, s), 0.93 (2H, d, J = 2.7 Hz), 0.96 (2H, d, J = 2.7 Hz), 1.03-1.19 (6H, m), 1.26 (1H, s), 1.32-1.39 (1H, m), 1.45 (3H, s), 1.52 (1H, d, J = 3.8 Hz), 1.61-1.69 (3H, m), 1.71 (3H,s), 1.73-1.94 (2H, m), 2.14-2.19 (1H, m), 2.24-2.40 (4H, m), 2.95 (1H, m), 3.68 (1H, d, J = 11.9 Hz), 3.81 (1H, d, J = 11.9 Hz), 4.79 (1H, dd, J = 5.4, 11.3 Hz), 4.96-5.00 (2H, m), 6.45 (1H, s), 7.40 (1H, dd, J = 4.6, 8.1 Hz), 8.10 (1H, dt, J = 1.9, 8.1 Hz), 8.68 (1H, m), 9.01 (1H, m) |
| 214 | 0.90 (3H, s), 1.13 (3H, t, J = 7.6 Hz), 1.17 (3H, t, J = 7.6 Hz), 1.26 (1H, s), 1.34-1.40 (1H, m), 1.44 (3H, s), 1.54 (1H, d, J = 4.3 Hz), 1.61-1.67 (2H, m), 1.69 (3H,s), 1.72-2.42 (13H, m), 2.91 (1H, m), 3.23 (1H, quint., J = 8.1 Hz), 3.69 (1H, d, J = 11.9 Hz), 3.81 (1H, d, J = 11.9 Hz), 4.80 (1H, dd, J = 4.9, 11.3 Hz), 4.99-5.04 (2H, m), 6.40 (1H, s), 7.39 (1H, dd, J = 4.9, 8.1 Hz), 8.09 (1H, dt, J = 1.6, 8.1 Hz), 8.69 (1H, dd, J = 1.6, 4.6 Hz), 9.01 (1H, d, J = 1.6 Hz) |
| 215 | 0.90 (3H, s), 1.13 (3H, t, J = 7.6 Hz), 1.17 (3H, t, J = 7.6 Hz), 1.26 (1H, s), 1.41-1.46 (1H, m), 1.59 (3H, s), 1.65-1.68 (3H, m), 1.73 (3H, s), 1.84-1.90 (2H, m), 2.18 (1H, m), 2.31 (2H, q, J = 7.6 Hz), 2.38 (2H, q, J = 7.6 Hz), 2.93 (1H, m), 3.69 (1H, d, J = 11.9 Hz), 3.81 (1H, d, J = 11.9 Hz), 4.80(1H, m), 5.01-5.09 (2H, m), 5.92 (1H, dd, J = 1.6, 10.5 Hz), 6.15-6.24 (1H, m), 6.45 (1H, s), 6.45-6.53 (1H, m), 7.40 (1H, dd, J = 4.6, 7.8 Hz), 8.07-8.11 (1H, m), 8.68 (1H, dd, J = 1.9, 4.9 Hz), 9.00 (1H, d, J = 2.2 Hz) |

Table20

| Compound No. | $^1$H-NMR $\delta$ (ppm) |
|---|---|
| 216 | 0.92 (3H, s), 1.14 (3H, t, J = 7.6 Hz), 1.20 (3H, t, J = 7.6 Hz), 1.26 (1H, s), 1.38-1.42 (1H, m), 1.50 (3H, s), 1.64-1.78 (3H, m), 1.85 (3H,s), 1.88-2.05 (2H, m), 2.17-2.23 (1H, m), 2.33 (2H, q, J = 7.6 Hz), 2.42 (2H, dq, J = 1.1, 7.6 Hz), 2.99 (1H, m), 3.72 (1H, d, J = 12.4 Hz), 3.81 (1H, d, J = 11.5 Hz), 4.83 (1H, dd, J = 4.9, 11.5 Hz), 5.03-5.05 (1H, m), 5.25 (1H, dd, J = 5.4, 11.5 Hz), 6.41 (1H, s), 7.37 (1H, dd, J = 5.2, 8.1 Hz), 7.91 (2H, dd, J = 1.6, 4.6 Hz), 8.07 (1H, dt, J = 1.6, 8.1 Hz), 8.67 (1H, dd, J = 1.9, 4.9 Hz), 8.83 (2H, dd, J = 1.6, 4.3 Hz), 8.97 (1H, d, J = 1.6 Hz) |
| 217 | 0.91 (3H, s), 1.13 (3H, t, J = 7.6 Hz), 1.20 (3H, t, J = 7.6 Hz), 1.26 (1H, s), 1.37-1.46 (1H, m), 1.50 (3H, s), 1.63-1.75 (3H, m), 1.87 (3H, s), 1.83-1.96 (2H, m), 2.13-2.23 (1H, m), 2.32 (2H, q, J = 7.6 Hz), 2.41 (2H, dq, J = 1.4, 7.6 Hz), 2.99 (1H, m), 3.67 (1H, d, J = 11.9 Hz), 3.83 (1H, d, J = 11.9 Hz), 4.83 (1H, dd, J = 5.4, 11.3 Hz), 4.98-5.06 (1H, m), 5.38 (1H, dd, J = 5.4, 10.8 Hz), 6.43 (1H, s), 7.35-7.44 (1H, m), 7.50-7.55 (1H, m), 7.89 (1H, dt, J = 1.6, 7.6 Hz), 8.07 (1H, dt, J = 1.6, 8.1 Hz), 8.18 (1H, d, J = 7.6 Hz), 8.67 (1H, dd, J = 1.6, 4.9 Hz), 8.82-8.84 (1H, m), 8.97 (1H, d, J = 2.4 Hz) |
| 218 | 0.83-1.12 (12H, m), 0.91 (3H, s), 1.26 (1H, s), 1.33-1.41 (1H, m), 1.45 (3H, s), 1.52-1.69 (6H, m), 1.71 (3H, s), 1.81-1.93 (2H, m), 2.14-2.18 (1H, m), 2.92 (1H, m), 3.72 (1H, d, J = 11.9 Hz), 3.82 (1H, d, J = 11.9 Hz), 4.80 (1H, dd, J = 4.9, 11.4 Hz), 4.99-5.04 (2H, m), 6.46 (1H, s), 7.41 (1H, dd, J = 4.9, 8.3 Hz), 8.10 (1H, dt, J = 1.7, 8.3 Hz), 8.69 (1H, dd, J = 1.5, 4.9 Hz), 9.01 (1H, d, J = 1.4 Hz) |
| 219 | 0.90 (3H, s), 1.26 (1H, s), 1.32-1.41 (1H, m), 1.44 (3H, s), 1.51-1.63 (3H, m), 1.69 (3H, s), 1.79-2.04 (8H, m), 2.17-2.40 (14H, m), 2.89 (1H, m), 3.08-3.26 (3H, m), 3.67 (1H, d, J = 11.9 Hz), 3.78 (1H, d, J = 11.9 Hz), 4.79 (1H, dd, J = 5.4, 11.1 Hz), 4.97-5.00 (2H, m), 6.41 (1H, s), 7.41 (1H, dd, J = 4.9, 8.1 Hz), 8.09 (1H, dt, J = 1.9, 8.4 Hz), 8.68 (1H, m), 9.00(1H, m) |
| 220 | 1.17 (3H, s), 1.26 (1H, s), 1.57 (3H, s), 1.65 (1H, m), 1.77-1.82 (2H, m), 1.88 (3H, s), 1.94-2.05 (3H, m), 2.13-2.31 (1H, m), 2.95 (1H, m), 4.16 (2H, s), 5.06 (1H, dd, J = 2.4, 6.5 Hz), 5.17-5.32 (2H, m), 6.42 (1H, s), 7.34-7.64 (10H, m), 8.01-8.12 (7H, m), 8.66 (1H, dd, J = 1.6, 5.1 Hz), 8.97 (1H, d, J = 1.9 Hz) |
| 221 | 0.92 (3H, s), 1.14 (3H, t, J = 7.6 Hz), 1.21 (3H, t, J = 7.6 Hz), 1.26 (1H, s), 1.44 (1H, m), 1.50 (3H, s), 1.57-1.62 (1H, m), 1.67-1.80 (2H, m), 1.85 (3H, s), 1.91-1.95 (2H, m), 2.17-2.24 (1H, m), 2.33 (2H, q, J = 7.6 Hz), 2.42 (2H, q, J = 7.6 Hz), 2.92 (1H, m), 3.74 (1H, d, J = 11.9 Hz), 3.81 (1H, d, J = 11.9 Hz), 4.84 (1H, dd, J = 4.9, 11.1 Hz), 5.04 (1H, m), 5.27 (1H, dd, J = 4.9, 11.1 Hz), 6.40 (1H, s), 7.38 (1H, dd, J = 4.9, 8.1 Hz), 7.84 (1H, d, J = 8.4 Hz), 8.05-8.08(1H, m), 8.54 (1H, d, J = 8.1 Hz), 8.67 (1H, d, J = 4.6 Hz), 8.96 (1H, d, J = 2.2 Hz), 9.38 (1H, s) |

Table21

| Compound No. | $^1$H-NMR $\delta$ (ppm) |
|---|---|
| 222 | 0.94 (3H, s), 1.14 (3H, t, J = 7.6 Hz), 1.19 (3H, t, J = 7.6 Hz), 1.26 (1H, s), 1.38-1.47 (1H, m), 1.48 (3H, s), 1.57-1.71 (3H, m), 1.75 (3H, s), 1.83-1.97 (2H, m), 2.10-2.22 (1H, m), 2.33 (2H, q, J = 7.6 Hz), 2.41 (2H, dq, J = 1.6, 7.6 Hz), 2.96 (1H, m), 3.74-3.80 (2H, m), 4.83 (1H, dd, J = 5.7, 11.6 Hz), 5.02-5.03 (1H, m), 5.28 (1H, dd, J = 5.4, 11.6 Hz), 6.41 (1H, s), 7.40 (1H, dd, J = 5.4, 7.6 Hz), 7.69 (1H, d, J = 5.4 Hz), 8.08 (1H, dt, J = 2.2, 8.1 Hz), 8.69 (1H, dd, J = 1.6, 4.9 Hz), 8.97 (1H, d, J = 4.6 Hz), 9.00 (1H, d, J = 2.4 Hz), 9.16 (1H, s) |
| 223 | 0.94 (3H, s), 1.26 (1H, s), 1.37 (1H, m), 1.47 (3H, s), 1.48-1.66 (3H, m), 1.71 (3H, s), 1.75-1.96 (2H, m), 2.17-2.24 (1H, m), 2.96 (1H, m), 3.14-3.35 (6H, m), 3.85 (1H, d, J = 12.2 Hz), 3.93 (1H, d, J = 12.2 Hz), 4.87 (1H, dd, J = 5.7, 10.8 Hz), 4.99-5.08 (2H, m), 6.41 (1H, s), 7.41 (1H, dd, J = 4.6, 8.1 Hz), 8.09 (1H, m), 8.69 (1H, m), 9.02 (1H, m) |
| 224 | 0.91 (3H, s), 1.13 (3H, t, J = 7.3 Hz), 1.17 (3H, t, J = 7.3 Hz), 1.26 (1H, s), 1.40 (1H, m), 1.45 (3H, s), 1.58-1.63 (3H, m), 1.70 (3H, s), 1.73-1.89 (2H, m), 2.10-2.18 (1H, m), 2.32 (2H, q, J = 7.6 Hz), 2.36 (2H, q, J = 7.6 Hz), 2.96 (1H, m), 3.25 (1H, d, J = 9.7 Hz), 3.32 (1H, d, J = 9.7 Hz), 3.69-3.81 (2H, m), 4.80 (1H, dd, J = 5.4, 11.3 Hz), 5.00-5.08 (2H, m), 6.40 (1H, s), 7.41 (1H, dd, J = 4.9, 8.1 Hz), 8.09 (1H, m), 8.69 (1H, dd, J = 1.4, 5.1 Hz), 9.01 (1H, d, J = 2.4 Hz) |
| 225 | 0.88 (3H, s), 1.13 (3H, t, J = 7.6 Hz), 1.19 (3H, t, J = 7.5 Hz), 1.22 (3H, t, J = 7.6 Hz), 1.24 (3H, s), 1.26 (1H, m), 1.50-1.55 (1H, m), 1.56 (3H, s), 1.55-1.64 (3H, m), 1.70-1.84 (2H, m), 2.31 (2H, dq, J = 1.2, 7.8 Hz), 2.42 (2H, dq, J = 3.4, 13.6 Hz), 2.44 (2H, dq, J = 2.0, 7.5 Hz), 2.79 (1H, dt, J = 1.4, 5.1 Hz), 3.69 (1H, d, J = 11.9 Hz), 3.79 (1H, d, J = 11.9 Hz), 4.79 (1H, dd, J = 4.9, 11.4 Hz), 5.24 (1H, dd, J = 4.9, 11.4 Hz), 6.45 (1H, s), 7.47 (1H, d, J = 8.5 Hz), 8.12 (1H, dd, J = 2.7, 8.5 Hz), 8.83 (1H, d, J = 2.7 Hz) |
| 226 | 0.89 (3H, s), 1.13 (3H, t, J = 7.6 Hz), 1.19 (3H, t, J = 7.6 Hz), 1.10-1.24 (3H, m), 1.26 (1H, s), 1.31-1.39 (1H, m), 1.44 (3H, s), 1.53 (1H, d, J = 3.8 Hz), 1.61-1.67 (2H, m), 1.69 (3H, s), 1.72-1.92 (2H, m), 2.08-2.18 (1H, m), 2.31 (2H, dq, J = 2.7, 7.6 Hz), 2.44 (2H, dq, J = 1.6, 7.6 Hz), 2.26-2.64 (2H, m), 2.85 (1H, s), 3.69 (1H, d, J = 11.9 Hz), 3.80 (1H, d, J = 11.9 Hz), 4.80 (1H, dd, J = 5.4, 11.3 Hz), 4.92-5.10 (2H, m), 6.41 (1H, s), 7.44 (1H, d, J = 8.4 Hz), 8.05 (1H, dd, J = 2.4, 8.4 Hz), 8.78 (1H, d, J = 2.4 Hz) |
| 227 | 0.88 (3H, s), 1.14 (3H, t, J = 7.6 Hz), 1.20 (3H, t, J = 7.6 Hz), 1.23-1.33 (1H, m), 1.43 (1H, m), 1.49 (3H, s), 1.61-1.74 (3H, m), 1.82 (3H, s), 1.87-2.23 (3H, m), 2.33 (2H, q, J = 7.6 Hz), 2.42 (2H, q, J = 7.6 Hz), 2.96 (1H, m), 3.73 (1H, d, J = 12.4 Hz), 3.82 (1H, d, J = 12.4 Hz), 4.83 (1H, dd, J = 5.4, 11.3 Hz), 5.03 (1H, m), 5.26 (1H, dd, J = 5.4, 11.3 Hz), 6.43 (1H, s), 7.39 (1H, dd, J = 4.9, 8.1 Hz), 7.86 (1H, t, J = 5.4 Hz), 8.08 (1H, dt, J = 1.9, 7.8 Hz), 8.60 (1H, d, J = 2.2 Hz), 8.66-8.68 (2H, m), 8.98 (1H, d, J = 2.2 Hz) |

Table 22

| Compound No. | $^1$H-NMR δ (ppm) |
|---|---|
| 228 | 0.93 (3H, s), 1.14 (3H, t, J = 7.6 Hz), 1.20 (3H, t, J = 7.6 Hz), 1.26 (1H, s), 1.32-1.44 (1H, m), 1.49 (3H, s), 1.61 (1H, d, J = 4.1 Hz), 1.67-1.75 (2H, m), 1.81 (3H,s), 1.79-2.05 (2H, m), 2.13-2.22 (1H, m), 2.33 (2H, q, J = 7.6 Hz), 2.42 (2H, dq, J = 1.4, 7.6 Hz), 2.92 (1H, m), 3.74 (1H, d, J = 11.9 Hz), 3.82 (1H, d, J = 11.9 Hz), 4.84 (1H, dd, J = 5.4, 10.8 Hz), 5.04 (1H, m), 5.27 (1H, dd, J = 5.4, 10.8 Hz), 6.43 (1H, s), 7.40 (1H, dd, J = 4.9, 8.1 Hz), 7.74 (1H, d, J = 5.1 Hz), 8.08 (1H, dt, J = 2.2, 8.1 Hz), 8.65 (1H, d, J = 4.9 Hz), 8.69 (1H, dd, J = 4.1, 7.6 Hz), 8.78 (1H, s), 8.99 (1H, d, J = 1.9 Hz) |
| 229 | 0.92 (3H, s), 1.14 (3H, t, J = 7.6 Hz), 1.19 (3H, t, J = 6.5 Hz), 1.26 (1H, s), 1.34-1.45 (1H, m), 1.49 (3H, s), 1.62 (1H, m), 1.71-1.77 (2H, m), 1.83 (3H, s), 1.88-2.01 (2H, m), 2.14-2.22 (1H, m), 2.33 (2H, q, J = 7.6 Hz), 2.42 (2H, dq, J = 2.2, 7.6 Hz), 2.64 (3H, s), 2.96 (1H, m), 3.72 (1H, d, J = 11.9Hz), 3.84 (1H, d, J = 11.9 Hz), 4.84 (1H, dd, J = 5.4, 11.3 Hz), 5.04 (1H, m), 5.36 (1H, dd, J = 5.4, 10.8 Hz), 6.42 (1H, s), 7.35-7.42 (2H, m), 7.66 (1H, d, J = 7.8 Hz), 8.08 (1H, dt, J = 1.9, 7.8 Hz), 8.60 (1H, d, J = 4.1 Hz), 8.68 (1H, dd, J = 1.6, 4.9 Hz), 8.98 (1H, d, J = 2.4 Hz), |
| 230 | 0.78 (3H, s), 1.09 (3H, t, J = 7.8 Hz), 1.12 (3H, t, J = 7.8 Hz), 1.26 (1H, s), 1.33 (3H, s), 1.36-1.38 (1H, m), 1.40-1.48 (2H, m), 1.55 (3H, s), 1.59-1.85 (2H, m), 2.09-2.18 (1H, m), 2.32 (4H, q, J = 7.6 Hz), 2.96 (1H, m), 3.40 (1H, d, J = 11.9 Hz), 3.75 (1H, d, J = 11.9 Hz), 4.72 (1H, dd, J = 4.9, 11.3 Hz), 4.95 (1H, m), 5.17 (1H, dd, J = 5.4, 11.9 Hz), 6.45 (1H, s), 7.40 (1H, dd, J = 4.9, 8.1 Hz), 7.49-7.67 (3H, m), 7.83-7.88 (4H, m), 8.02 (1H, s), 8.07 (1H, dt, J = 2.2, 8.1 Hz), 8.68 (1H, dd, J = 1.4, 4.6 Hz), 8.95 (1H, dd, J = 1.6, 4.6 Hz), 8.99 (1H, d, J = 1.9 Hz) |
| 231 | 0.91 (3H, s), 1.09 (3H, t, J = 7.6 Hz), 1.14 (3H, t, J = 7.6 Hz), 1.18 (3H, t, J = 7.6 Hz), 1.26 (1H, s), 1.34-1.43 (1H, m), 1.48 (3H, s), 1.63 (1H, m), 1.67-1.75 (2H, m), 1.80 (3H, s), 1.83-2.08 (4H, m), 2.17-2.25 (1H, m), 2.32 (2H, q, J = 7.6 Hz), 2.40 (2H, dq, J = 7.6, 1.9 Hz), 2.96 (1H, m), 3.64 (1H, d, J = 11.9 Hz), 3.87 (1H, d, J = 11.9 Hz), 4.05 (2H, t, J = 6.2 Hz), 4.82 (1H, dd, J = 5.4, 10.8 Hz), 5.04 (1H, m), 5.40 (1H, dd, J = 5.4, 10.8 Hz), 6.47 (1H, s), 7.19-7.44 (3H, m), 8.08 (1H, dt, J = 1.9, 8.1 Hz), 8.32 (1H, dd, J = 1.6, 4.3 Hz), 8.68 (1H, dd, J = 4.6, 1.6 Hz), 8.98 (1H, d, J = 1.6 Hz) |
| 232 | 0.92 (3H, s), 1.14 (3H, t, J = 7.6 Hz), 1.20 (3H, t, J = 7.6 Hz), 1.26 (1H, s), 1.34-1.43 (1H, m), 1.50 (3H, s), 1.61 (1H, m), 1.67-1.78 (2H, m), 1.84 (3H, s), 1.87-1.97 (2H, m), 2.13-2.23 (1H, m), 2.18 (1H,s), 2.32 (2H, q, J = 7.6 Hz), 2.42 (2H, dq, J = 1.4, 7.6 Hz), 3.73 (1H, d, J = 11.9 Hz), 3.80 (1H, d, J = 11.9 Hz), 4.83 (1H, dd, J = 5.4, 11.1 Hz), 5.04 (1H, d, J = 3.8 Hz), 5.25 (1H, dd, J = 5.1, 11.1 Hz), 6.41 (1H, s), 7.06 (1H, dd, J = 3.0, 8.6 Hz), 7.38 (1H, dd, J = 4.9, 8.1 Hz), 8.08 (1H, dt, J = 1.9, 8.1 Hz), 8.43-8.50 (1H, m), 8.67 (1H, dd, J = 1.6, 4.6 Hz), 8.95-8.98 (2H, m) |

Table 23

| Compound No. | $^1$H-NMR δ (ppm) |
|---|---|
| 233 | 0.91 (3H, s), 1.26 (1H, s), 1.45 (3H, s), 1.70 (3H, s), 1.32-1.97 (29H, m), 2.14-2.19 (1H, m), 2.66-2.90 (3H, m), 3.06 (1H, s), 3.67 (1H, d, J = 11.9 Hz), 3.78 (1H, d, J = 11.9 Hz), 4.78 (1H, dd, J = 5.4, 10.8 Hz), 4.98-5.01 (2H, m), 6.40 (1H, s), 7.42 (1H, dd, J = 4.9, 8.1 Hz), 8.11 (1H, dt, J = 1.6, 8.1 Hz), 8.69 (1H, d, J = 4.6 Hz), 9.01 (1H, s) |
| 234 | 0.91 (3H, s), 1.45 (3H, s), 1.70 (3H, s), 1.10-2.05 (37H, m), 2.14-2.49 (3H, m), 3.04 (1H, s), 3.65 (1H, d, J = 11.3 Hz), 3.77 (1H, d, J = 11.9 Hz), 4.78 (1H, dd, J = 5.4, 10.8 Hz), 4.97-5.01 (2H, m), 6.41 (1H, s), 7.42 (1H, dd, J = 4.9, 8.1 Hz), 8.11 (1H, dd, J = 1.9, 8.1 Hz), 8.69 (1H, d, J = 4.3 Hz), 9.01 (1H, s) |
| 235 | 1.00 (3H, s), 1.25-1.33 (3H, m), 1.48 (3H, s), 1.55 (1H, m), 1.71 (1H, m), 1.75 (3H, s), 1.79-1.98 (2H, m), 2.11-2.21 (1H, m), 3.48 (2H, s), 3.54 (2H, s), 3.60 (2H, s), 3.90 (1H, d, J = 11.9 Hz), 3.99 (1H, d, J = 11.9 Hz), 4.86 (1H, m), 4.98 (1H, m), 5.07-5.12 (1H, m), 6.53 (1H, s), 7.53 (1H, dd, J = 4.9, 8.1 Hz), 8.23 (1H, m), 8.30 (1H, m), 8.70 (1H, m), 9.05 (1H, m) |
| 236 | 0.11-0.27 (8H, m), 0.52-0.65 (8H, m), 0.88 (3H, s), 0.99-1.14 (5H, m), 1.15 (3H, s), 1.25-1.43 (2H, m), 1.61-1.76 (4H, m), 1.72 (3H, s), 2.18-2.54 (9H, m), 3.74 (1H, d, J = 11.9 Hz), 3.83 (1H, d, J = 11.9 Hz), 4.86 (1H, dd, J = 4.6, 11.6 Hz), 5.01-5.12 (2H, m), 6.41 (1H, s), 7.45 (1H, dd, J = 4.9, 7.8 Hz), 8.16 (1H, m), 8.71 (1H, m), 9.02 (1H, s) |
| 237 | 0.14-0.26 (6H, m), 0.52-0.64 (6H, m), 0.92 (3H, s), 0.97-1.16 (4H, m), 1.26-1.38 (1H, m), 1.45 (3H, s), 1.52 (1H, m), 1.63-1.70 (2H, m), 1.70 (3H, s), 1.82-1.91 (2H, m), 2.12-2.41 (7H, m), 2.96 (1H, m), 3.74 (1H, d, J = 11.9 Hz), 3.86 (1H, d, J = 11.9 Hz), 4.84 (1H, dd, J = 4.9, 11.3 Hz), 5.00-5.03 (2H, m), 6.43 (1H, s), 7.42 (1H, dd, J = 4.6, 7.8 Hz), 8.11 (1H, m), 8.70 (1H, d, J = 4.3 Hz), 9.01 (1H, s) |
| 238 | 0.91 (3H, s), 1.26 (1H, s), 1.44 (3H, s), 1.45 (3H, s), 1.46 (3H, s), 1.34-1.53 (7H, m), 1.52 (3H, s), 1.70 (3H, s), 1.81-2.02 (2H, m), 2.15-2.31 (3H, m), 2.96 (1H, s), 3.67 (1H, m), 4.00 (1H, m), 4.85-5.00 (3H, m), 6.46 (1H, s), 7.45 (1H, dd, J = 4.9, 8.1 Hz), 8.13 (1H, m), 8.70 (1H, m), 9.02 (1H, s) |
| 239 | 0.93 (3H, s), 1.14 (3H, t, J = 7.6 Hz), 1.20 (3H, t, J = 7.6 Hz), 1.26 (1H, s), 1.33-1.44 (1H, m), 1.50 (3H, s), 1.61 (1H, m), 1.68-1.77 (2H, m), 1.84 (3H, s), 1.91-1.99 (2H, m), 2.17-2.23 (1H, m), 2.32 (2H, q, J = 7.6 Hz), 2.43 (2H, dq, J = 3.0, 7.6 Hz), 2.69 (3H, s), 2.96 (1H, m), 3.75 (1H, d, J = 12.2 Hz), 3.80 (1H, d, J = 12.2 Hz), 4.48 (1H, dd, J = 5.1, 11.1 Hz), 5.04 (1H, d, J = 4.1 Hz), 5.23 (1H, d, J = 5.4, 10.8 Hz), 6.42 (1H, s), 7.24 (1H, d, J = 5.9 Hz), 7.39 (1H, dd, J = 4.9, 8.1 Hz), 8.08 (1H, d, J = 8.4 Hz), 8.61 (1H, d, J = 5.1 Hz), 8.67 (1H, d, J = 3.5 Hz), 8.98 (1H, s), 9.17 (1H, s) |

Table 24

| Compound No. | $^1$H-NMR δ (ppm) |
|---|---|
| 240 | 0.93 (3H, s), 1.13 (3H, t, J = 7.9 Hz), 1.19 (3H, t, J = 7.9 Hz), 1.26 (1H, s), 1.39-1.43 (1H, m), 1.49 (3H, s), 1.61 (1H, m), 1.68-1.79 (2H, m), 1.82 (3H, s), 1.88-2.04 (2H, m), 2.17-2.23 (1H, m), 2.32 (2H, q, J = 7.6 Hz), 2.42 (2H, dq, J = 1.9, 7.6 Hz), 2.96 (1H, s), 3.74 (1H, d, J = 11.9 Hz), 3.83 (1H, d, J = 11.9 Hz), 4.83 (1H, dd, J = 1.6, 5.4 Hz), 5.04 (1H, d, J = 4.1 Hz), 5.27 (1H, dd, J = 5.4, 11.6 Hz), 6.43 (1H, s), 7.39 (1H, dd, J = 4.9, 8.1 Hz), 7.47 (1H, d, J = 5.1 Hz), 8.08 (1H, dt, J = 1.9, 8.1 Hz), 8.68 (1H, dd, J = 1.4, 4.6 Hz), 8.64 (1H, d, J = 5.1 Hz), 8.99 (1H, d, J = 1.9 Hz), 9.14 (1H, s) |
| 241 | 0.93 (3H, s), 1.14 (3H, t, J = 7.6 Hz), 1.19 (3H, t, J = 7.6 Hz), 1.26 (1H, s), 1.38-1.43 (1H, m), 1.49 (3H, s), 1.59 (1H, d, J = 4.4 Hz), 1.66-1.73 (2H, m), 1.78 (3H, s), 1.82-2.05 (2H, m), 2.18-2.23 (1H, m), 2.31 (2H, q, J = 7.6 Hz), 2.41 (2H, dq, J = 1.4, 7.6 Hz), 2.96 (1H, s), 3.72 (1H, d, J = 7.6 Hz), 3.81 (1H, d, J = 7.6 Hz), 3.98 (3H, s), 4.84 (1H, dd, J = 5.4, 11.3 Hz), 5.04 (1H, m), 5.24 (1H, dd, J = 4.9, 10.8 Hz), 6.54 (1H, s), 7.39 (1H, dd, J = 4.9, 8.1 Hz), 7.53 (1H, d, J = 4.9 Hz), 8.08 (1H, dt, J = 1.9, 8.1 Hz), 8.68 (1H, d, J = 4.1 Hz), 8.88 (1H, d, J = 4.9 Hz), 9.00 (1H, s), 9.17 (1H, s) |
| 242 | 0.95 (3H, s), 1.15 (3H, t, J = 7.6 Hz), 1.20 (3H, t, J = 7.6 Hz), 1.26 (1H, s), 1.38-1.44 (1H, m), 1.49 (3H, s), 1.61 (1H, d, J = 4.1 Hz), 1.68-1.72 (2H, m), 1.76 (3H, s), 1.82-2.06 (2H, m), 2.18-2.23 (1H, m), 2.34 (2H, q, J = 7.6 Hz), 2.43 (2H, dq, J = 2.2, 7.6 Hz), 2.96 (1H, s), 3.78 (1H, d, J = 12.2 Hz), 3.83 (1H, d, J = 12.2 Hz), 4.84 (1H, dd, J = 5.4, 11.3 Hz), 5.04 (1H, d, J = 4.1 Hz), 5.2-5.34 (1H, m), 6.40 (1H, s), 7.40 (1H, dd, J = 4.9, 8.1 Hz), 7.76 (1H, d, J = 5.4 Hz), 8.02-8.11 (2H, m), 8.69 (1H, d, J = 4.3 Hz), 8.74 (1H, s), 9.00 (1H, s) |
| 243 | 0.93 (3H, s), 1.14 (3H, t, J = 7.6 Hz), 1.20 (3H, t, J = 7.6 Hz), 1.26 (1H, s), 1.39-1.44 (1H, m), 1.50 (3H, s), 1.62 (1H, m), 1.68-1.75 (2H, m), 1.84 (3H, s), 1.93-1.96 (2H, m), 2.14-2.23 (1H, m), 2.33 (2H, q, J = 7.6 Hz), 2.42 (2H, dq, J = 2.4, 7.6 Hz), 2.96 (1H, s), 3.72 (1H, d, J = 11.9 Hz), 3.83 (1H, d, J = 11.9 Hz), 4.83 (1H, dd, J = 1.6, 5.4 Hz), 5.04 (1H, m), 5.36 (1H, dd, J = 4.9, 11.3 Hz), 6.46 (1H, s), 7.38 (1H, dd, J = 5.4, 7.6 Hz), 7.68-7.78 (2H, m), 7.83-7.88 (1H, m), 8.07 (1H, dt, J = 1.9, 8.1 Hz), 8.19-8.23 (1H, m), 8.67 (1H, dd, J = 1.6, 4.9 Hz), 8.98 (1H, d, J = 2.2 Hz) |
| 244 | 0.93 (3H, s), 1.14 (3H, t, J = 7.6 Hz), 1.19 (3H, t, J = 7.6 Hz), 1.26 (1H, s), 1.34-1.43 (1H, m), 1.48 (3H, s), 1.60 (1H, d, J = 4.1 Hz), 1.66-2.02 (4H, m), 1.73 (3H, s), 2.11-2.23 (1H, m), 2.33 (2H, q, J = 7.6 Hz), 2.41 (2H, dq, J = 2.2, 7.6 Hz), 2.90 (1H, s), 3.74 (1H, d, J = 11.9 Hz), 5.83 (1H, d, J = 11.9 Hz), 4.82 (1H, dd, J = 4.9, 11.1 Hz), 5.03 (1H, m), 5.27 (1H, dd, J = 5.1, 11.6 Hz), 6.43 (1H, s), 7.41 (1H, dd, J = 4.9, 8.1 Hz), 7.65-7.70 (2H, m), 7.78-7.86 (2H, m), 8.09 (1H, dt, J = 1.9, 8.1 Hz), 8.69 (1H, d, J = 3.8 Hz), 9.00 (1H, s) |

Table 25

| Compound No. | $^1$H-NMR δ (ppm) |
|---|---|
| 245 | 0.92 (3H, s), 1.14 (3H, t, J = 7.5 Hz), 1.20 (3H, t, J = 7.5 Hz), 1.26 (1H, s), 1.39-1.46 (1H, m), 1.49 (3H, s), 1.62 (1H, d, J= 4.1 Hz), 1.83 (3H, s), 1.66-2.02 (4H, m), 2.11-2.23 (1H, m), 2.33 (2H, dq, J = 1.2, 7.6 Hz), 2.42 (2H, dq, J = 3.2, 7.6 Hz), 2.96 (1H, m), 3.70 (1H, d, J = 12.0 Hz), 3.85 (1H, d, J = 12.0 Hz), 4.83 (1H, dd, J = 4.9, 11.7 Hz), 5.04 (1H, m), 5.27 (1H, dd, J = 5.1, 11.9 Hz), 6.45 (1H, s), 7.18 (1H, dd, J = 8.5, 10.9 Hz), 7.27 (1H, m), 7.38 (1H, dd, J = 4.8, 8.1 Hz), 7.55-7.61 (1H, m), 8.03 (1H, dt, J = 1.7, 7.3 Hz), 8.08 (1H, dt, J = 1.7, 8.3 Hz), 8.67 (1H, d, J = 3.9 Hz), 8.98 (1H, s) |
| 246 | 0.93 (3H, s), 1.14 (3H, t, J = 7.5 Hz), 1.19 (3H, t, J = 7.5 Hz), 1.26 (1H, s), 1.32-1.42 (1H, m), 1.45 (3H, s), 1.59 (1H, d, J = 3.0 Hz), 1.66 (3H, s), 1.69-1.92 (4H, m), 2.02-2.21 (1H, m), 2.33 (2H, dq, J = 1.1, 5.1 Hz), 2.42 (2H, dq, J = 2.2, 5.1 Hz), 2.96 (1H, m), 3.76 (1H, d, J = 11.9 Hz), 3.84 (1H, d, J = 12.0 Hz), 4.83 (1H, dd, J = 4.9, 11.7 Hz), 5.03 (1H, d, J = 4.2 Hz), 5.19 (1H, dd, J = 5.4, 11.7 Hz), 6.60 (1H, s), 7.42 (1H, dd, J = 4.6, 8.1 Hz), 7.66-7.76 (2H, m), 7.84 (1H, dd, J = 1.5, 7.5 Hz), 7.93 (1H, dd, J = 1.5, 7.8 Hz), 8.11 (1H, dt, J = 2.1, 8.1 Hz), 8.69 (1H, d, J = 4.6 Hz), 9.03 (1H, s) |
| 247 | 0.93 (3H, s), 1.14 (3H, t, J = 7.6 Hz), 1.20 (3H, t, J = 7.6 Hz), 1.26 (1H, s), 1.42-1.46 (1H, m), 1.49 (3H, s), 1.61 (1H, d, J = 3.0 Hz), 1.68-1.79 (2H, m), 1.82 (3H, s), 1.86-2.02 (2H, m), 2.16-2.22 (1H, m), 2.33 (2H, dq, J = 1.1, 5.1 Hz), 2.42 (2H, dq, J = 2.4, 5.1 Hz); 2.96 (1H, m), 3.74 (1H, d, J = 12.0 Hz), 3.82 (1H, d, J = 12.0 Hz), 4.83 (1H, dd, J = 4.9, 11.7 Hz), 5.04 (1H, m), 5.27 (1H, dd, J = 5.1, 11.7 Hz), 6.44 (1H, s), 7.40 (1H, dd, J = 4.6, 7.8 Hz), 7.72 (1H, dd, J = 1.7, 8.3 Hz), 8.08 (1H, dt, J = 2.2, 8.5 Hz), 8.26 (1H, dd, J = 1.9, 7.8 Hz), 8.58 (1H, dd, J = 1.9, 4.9 Hz), 8.68 (1H, d, J = 3.6 Hz), 9.03 (1H, d, J = 1.7 Hz) |
| 248 | 0.93 (3H, s), 1.16 (3H, t, J = 7.6 Hz), 1.22 (3H, t, J = 7.6 Hz), 1.26 (1H, s), 1.42-1.46 (1H, m), 1.49 (3H, s), 1.61 (1H, d, J = 3.0 Hz), 1.68-1.78 (2H, m), 1.82 (3H, s), 1.86-2.01 (2H, m), 2.17-2.22 (1H, m), 2.33 (2H, dq, J = 1.1, 5.1 Hz), 2.42 (2H, dq, J = 2.4, 5.1 Hz), 2.62 (3H, s), 2.98 (1H, m), 3.73 (1H, d, J = 12.0 Hz), 3.84 (1H, d, J = 11.9 Hz), 4.83 (1H, dd, J = 4.8, 11.5 Hz), 5.04 (1H, d, J = 3.4 Hz), 5.25 (1H, dd, J = 5.1, 11.4 Hz), 6.44 (1H, s), 7.22 (1H, d, J = 7.8 Hz), 7.40 (1H, dd, J = 4.9, 8.0 Hz), 8.08 (1H, dt, J = 2.2, 8.0 Hz), 8.18 (1H, d, J = 7.8 Hz), 8.69 (1H, d, J = 3.7 Hz), 8.99 (1H, d, J = 1.7 Hz) |
| 249 | 0.91 (3H, s), 1.14 (3H, t, J = 7.8 Hz), 1.15 (3H, t, J = 7.8 Hz), 1.26 (1H, s), 1.29-1.39 (1H, m), 1.42 (3H, s), 1.45 (1H, m), 1.57-1.64 (2H, m), 1.66 (3H, s), 1.81-1.88 (2H, m), 2.14-2.18 (1H, m), 2.33 (2H, q, J = 7.8 Hz), 2.35 (2H, q, J = 7.8 Hz), 2.84 (1H, m), 3.46 (3H, s), 3.68 (1H, d, J = 11.7 Hz), 3.93 (1H, d, J = 11.9 Hz), 4.73-4.87 (4H, m), 4.95-5.00 (1H, m), 6.43 (1H, s), 7.42 (1H, dd, J = 4.8, 8.0 Hz), 8.12 (1H, m), 8.69 (1H, m), 9.01 (1H, d, J = 2.2Hz) |
| 250 | 0.92 (3H, s), 1.26 (1H, s), 1.34-1.55 (3H, m), 1.46 (3H, s), 1.71 (3H, s), 1.66-1.92 (6H, m), 2.01-2.18 (4H, m), 2.38-2.57 (3H, m), 3.66-3.78 (1H, m), 3.95-4.13 (1H, m), 4.73-4.84 (1H, m), 4.89-4.95 (1H, m), 4.99-5.10 (1H, m), 6.45 (1H, s), 7.43 (1H, dd, J = 4.9, 8.3 Hz), 8.11 (1H, m), 8.70 (1H, d, J = 4.9 Hz), 9.02 (1H, s) |

Table 26

| Compound No. | $^1$H-NMR δ (ppm) |
|---|---|
| 251 | 0.93 (3H, s), 1.14 (3H, t, J = 7.5 Hz), 1.17 (3H, t, J = 7.5 Hz), 1.26 (1H, s), 1.36 (9H, s), 1.42 (1H, m), 1.47 (3H, s), 1.62–1.70 (3H, m), 1.75 (3H, s), 1.80–1.95 (2H, m), 2.07–2.21 (1H, m), 2.32 (2H, dq, J = 1.5, 7.5 Hz), 2.40 (2H, dq, J = 3.9, 7.6 Hz), 2.96 (1H, m), 3.69 (1H, d, J = 11.9 Hz), 3.87 (1H, d, J = 11.9 Hz), 4.83 (1H, dd, J = 4.9, 11.7 Hz), 5.04 (1H, m), 5.36 (1H, dd, J = 5.1, 11.7 Hz), 6.53 (1H, s), 7.39–7.43 (1H, m), 7.98 (1H, dd, J = 1.7, 8.0 Hz), 8.02 (1H, s), 8.10 (1H, dt, J = 1.7, 8.0 Hz), 8.65 (1H, dd, J = 1.5, 4.7 Hz), 8.69 (1H, d, J = 3.7 Hz), 8.99 (1H, s) |
| 252 | 0.92 (3H, s), 1.14 (3H, t, J = 7.5 Hz), 1.19 (3H, t, J = 7.5 Hz), 1.26 (1H, s), 1.42–1.45 (1H, m), 1.49 (3H, s), 1.62–1.73 (3H, m), 1.82 (3H, s), 1.84–2.00 (2H, m), 2.18–2.22 (1H, m), 2.32 (2H, dq, J = 1.5, 7.5 Hz), 2.41 (2H, dq, J = 2.5, 7.5 Hz), 2.96 (1H, m), 3.68 (1H, d, J = 11.9 Hz), 3.85 (1H, d, J = 11.9 Hz), 4.82 (1H, dd, J = 4.9, 11.7 Hz), 5.04 (1H, m), 5.37 (1H, dd, J = 4.8, 11.7 Hz), 6.44 (1H, s), 7.36–7.41 (2H, m), 8.08 (1H, dt, J = 1.7, 8.0 Hz), 8.53 (1H, d, J = 2.0 Hz), 8.68 (1H, dd, J = 0.7, 4.9 Hz), 8.98 (1H, d, J = 2.6 Hz) |
| 253 | 0.92 (3H, s), 1.14 (3H, t, J = 7.5 Hz), 1.20 (3H, t, J = 7.5 Hz), 1.26 (1H, s), 1.40–1.47 (1H, m), 1.51 (3H, s), 1.64 (1H, d, J = 2.4 Hz), 1.73 (2H, m), 1.87 (3H, s), 1.85–2.00 (2H, m), 2.18–2.23 (1H, m), 2.32 (2H, q, J = 7.6 Hz), 2.42 (2H, dq, J = 1.5, 7.6 Hz), 2.96 (1H, m), 3.71 (1H, d, J = 12.0 Hz), 3.83 (1H, d, J = 11.9 Hz), 4.84 (1H, dd, J = 4.9, 11.7 Hz), 5.05 (1H, m), 5.39 (1H, dd, J = 5.2, 11.6 Hz), 6.42 (1H, s), 7.39 (1H, dd, J = 4.9, 8.1 Hz), 8.02 (1H, s), 8.07 (1H, m), 8.68 (1H, d, J = 4.4 Hz), 8.80–8.83 (1H, m), 8.97 (1H, m), 9.38 (1H, m) |
| 254 | 0.91 (3H, s), 1.14 (3H, t, J = 7.6 Hz), 1.19 (3H, t, J = 7.6 Hz), 1.26 (1H, s), 1.39–1.46 (1H, m), 1.49 (3H, s), 1.63 (1H, d, J = 2.7 Hz), 1.70–1.73 (2H, m), 1.85 (3H, s), 1.88–2.01 (2H, m), 2.18–2.22 (1H, m), 2.32 (2H, q, J = 7.5 Hz), 2.41 (2H, dq, J = 2.2, 7.6 Hz), 2.97 (1H, m), 3.68 (1H, d, J = 11.7 Hz), 3.83 (1H, d, J = 11.9 Hz), 4.83 (1H, dd, J = 4.9, 11.7 Hz), 5.04 (1H, m), 5.34 (1H, dd, J = 5.4, 11.5 Hz), 6.44 (1H, s), 7.39 (1H, dd, J = 4.9, 8.0 Hz), 8.07 (1H, dt, J = 1.9, 6.3 Hz), 8.32 (1H, d, J = 2.0 Hz), 8.67 (1H, d, J = 4.1 Hz), 8.92 (1H, d, J = 2.0 Hz), 8.98 (1H, s) |
| 255 | 0.92 (3H, s), 1.14 (3H, t, J = 7.5 Hz), 1.19 (3H, t, J = 7.5 Hz), 1.26 (1H, s), 1.38–1.45 (1H, m), 1.49 (3H, s), 1.60 (1H, d, J = 3.0 Hz), 1.68–1.70 (2H, m), 1.83 (3H, s), 1.75–1.98 (2H, m), 2.17–2.21 (1H, m), 2.33 (2H, dq, J = 1.7, 7.5 Hz), 2.41 (2H, dq, J = 2.2, 7.5 Hz), 2.97 (1H, m), 3.67 (1H, d, J = 12.0 Hz), 3.87 (1H, d, J = 11.9 Hz), 4.81 (1H, dd, J = 4.9, 11.7 Hz), 5.03 (1H, m), 5.23 (1H, dd, J = 5.1, 11.5 Hz), 6.46 (1H, s), 7.07 (1H, d, J = 5.2 Hz), 7.39 (1H, dd, J = 4.9, 8.1 Hz), 7.54 (1H, d, J = 5.3 Hz), 8.08 (1H, dt, J = 2.2, 8.1 Hz), 8.67 (1H, dd, J = 1.4, 4.9 Hz), 8.99 (1H, d, J = 2.2 Hz) |

Table 27

| Compound No. | $^1$H-NMR $\delta$ (ppm) |
|---|---|
| 256 | 0.92 (3H, s), 1.12 (3H, t, J = 7.8 Hz), 1.15 (3H, t, J = 7.7 Hz), 1.26 (1H, s), 1.39-1.47 (1H, m), 1.50 (3H, s), 1.61 (1H, d, J = 2.4 Hz), 1.69-1.81 (2H, m), 1.85 (3H, s), 1.90-1.99 (2H, m), 2.18-2.21 (1H, m), 2.33 (2H, dq, J = 1.2, 7.7 Hz), 2.41 (2H, dq, J = 2.7, 7.6 Hz), 2.66 (3H, s), 2.96 (1H, m), 3.72 (1H, d, J = 11.7 Hz), 3.83 (1H, d, J = 12.0 Hz), 4.83 (1H, dd, J = 4.9, 11.4 Hz), 5.04 (1H, m), 5.25 (1H, dd, J = 5.3, 11.7 Hz), 6.41 (1H, s), 7.30 (1H, d, J = 8.0 Hz), 7.38 (1H, dd, J = 4.9, 8.1 Hz), 8.07 (1H, dt, J = 2.2, 8.1 Hz), 8.24 (1H, dd, J = 2.2, 8.0 Hz), 8.67 (1H, dd, J = 1.5, 4.9 Hz), 8.97 (1H, d, J = 2.2 Hz), 9.18 (1H, d, J = 2.2 Hz) |
| 257 | 0.91 (3H, s), 1.14 (3H, t, J = 7.5 Hz), 1.19 (3H, t, J = 7.5 Hz), 1.26 (1H, s), 1.38-1.46 (1H, m), 1.50 (3H, s), 1.63 (1H, d, J = 2.4 Hz), 1.70-1.73 (2H, m), 1.86 (3H, s), 1.83-1.98 (2H, m), 2.18-2.22 (1H, m), 2.32 (2H, dq, J = 1.5, 7.7 Hz), 2.41 (2H, dq, J = 2.2, 7.7 Hz), 2.96 (1H, d, J = 1.9 Hz), 3.68 (1H, d, J = 11.9 Hz), 3.84 (1H, d, J = 12.0 Hz), 4.83 (1H, dd, J = 4.9, 11.7 Hz), 5.05 (1H, m), 5.32 (1H, dd, J = 5.3, 11.7 Hz), 6.43 (1H, s), 7.39 (1H, dd, J = 4.9, 8.0 Hz), 7.56 (1H, d, J = 8.1 Hz), 7.85 (1H, t, J = 7.8 Hz), 8.07 (2H, m), 8.67 (1H, dd, J = 1.7, 4.9 Hz), 8.98 (1H, d, J = 2.0 Hz) |
| 258 | 0.91 (3H, s), 1.14 (3H, t, J = 7.5 Hz), 1.19 (3H, t, J = 7.5 Hz), 1.26 (1H, s), 1.38-1.46 (1H, m), 1.50 (3H, s), 1.62 (1H, d, J = 2.4 Hz), 1.69-1.72 (2H, m), 1.86 (3H, s), 1.80-1.96 (2H, m), 2.18-2.22 (1H, m), 2.32 (2H, q, J = 7.5 Hz), 2.41 (2H, dq, J = 2.2, 7.5 Hz), 2.93 (1H, d, J = 1.9 Hz), 3.68 (1H, d, J = 11.9 Hz), 3.83 (1H, d, J = 12.0 Hz), 4.83 (1H, dd, J = 4.9, 11.4 Hz), 5.04 (1H, m), 5.33 (1H, dd, J = 5.3, 11.5 Hz), 6.42 (1H, s), 7.20 (1H, dd, J = 2.9, 8.0 Hz), 7.38 (1H, dd, J = 4.9, 8.3 Hz), 8.00 (1H, q, J = 7.8 Hz), 8.08 (2H, m), 8.67 (1H, dd, J = 1.4, 4.6 Hz), 8.97 (1H, d, J = 2.2 Hz) |
| 259 | 0.93 (3H, s), 1.14 (3H, t, J = 7.5 Hz), 1.21 (3H, t, J = 7.5 Hz), 1.26 (1H, s), 1.40-1.47 (1H, m), 1.51 (3H, s), 1.61 (1H, d, J = 3.0 Hz), 1.70-1.83 (2H, m), 1.86 (3H, s), 1.92-1.98 (2H, m), 2.17-2.22 (1H, m), 2.32 (2H, q, J = 7.3 Hz), 2.43 (2H, dq, J = 1.4, 5.3 Hz), 2.97 (1H, d, J = 2.0 Hz), 3.74 (1H, d, J = 11.7 Hz), 3.83 (1H, d, J = 11.7 Hz), 4.13 (3H, s), 4.84 (1H, dd, J = 4.9, 11.4 Hz), 5.05 (1H, m), 5.24 (1H, dd, J = 5.3, 11.7 Hz), 6.43 (1H, s), 7.16-7.20 (1H, m), 7.35-7.44 (4H, m), 7.70 (1H, d, J = 8.1 Hz), 8.05 (1H, dt, J = 1.7, 8.3 Hz), 8.66 (1H, dd, J = 1.5, 4.9 Hz), 8.96 (1H, d, J = 2.2 Hz) |
| 260 | 0.93 (3H, s), 1.14 (3H, t, J = 7.5 Hz), 1.19 (3H, t, J = 7.5 Hz), 1.26 (1H, s), 1.40-1.46 (1H, m), 1.48 (3H, s), 1.63 (1H, d, J = 3.0 Hz), 1.71-1.74 (2H, m), 1.80 (3H, s), 1.83-1.95 (1H, m), 2.02-2.06 (1H, m), 2.18-2.22 (1H, m), 2.32 (2H, dq, J = 1.7, 7.6 Hz), 2.41 (2H, dq, J = 3.4, 7.5 Hz), 2.96 (1H, m), 3.70 (1H, d, J = 12.0 Hz), 3.87 (1H, d, J = 11.9 Hz), 4.83 (1H, dd, J = 4.8, 11.5 Hz), 5.05 (1H, m), 5.37 (1H, dd, J = 4.9, 11.7 Hz), 6.46 (1H, s), 7.39-7.45 (2H, m), 7.87 (1H, dd, J = 1.5, 8.3 Hz), 8.08 (1H, dt, J = 1.5, 8.3 Hz), 8.64 (1H, dd, J = 1.2, 4.6 Hz), 8.69 (1H, d, J = 4.9 Hz), 8.97 (1H, d, J = 2.2 Hz) |
| 261 | 0.85-1.06 (8H, m), 0.92 (3H, s), 1.26 (1H, s), 1.30-1.40 (1H, m), 1.42 (3H, s), 1.45-1.63 (5H, m), 1.67 (3H, s), 1.81-1.92 (2H, m), 2.14-2.25 (2H, m), 2.88 (1H, d, J = 1.4 Hz), 3.75 (1H, d, J = 11.9 Hz), 3.86 (1H, d, J = 11.6 Hz), 3.78-3.82 (1H, m), 4.82 (1H, dd, J = 5.1, 11.4 Hz), 5.00 (1H, m), 6.52 (1H, s), 7.42 (1H, dd, J = 4.9, 8.0 Hz), 8.11 (1H, dt, J = 1.7, 8.0 Hz), 8.69 (1H, dd, J = 1.5, 4.9 Hz), 9.01 (1H, d, J = 1.9 Hz) |

Table 28

| Compound No. | $^1$H-NMR δ (ppm) |
|---|---|
| 262 | 0.92 (3H, s), 1.14 (3H, t, J = 7.5 Hz), 1.20 (3H, t, J = 7.5 Hz), 1.26 (1H, s), 1.39-1.47 (1H, m), 1.49 (3H, s), 1.61 (1H, d, J = 2.7 Hz), 1.66-1.71 (2H, m), 1.84 (3H, s), 1.76-1.99 (2H, m), 2.18-2.22 (1H, m), 2.32 (2H, dq, J = 1.0, 7.5 Hz), 2.42 (2H, dq, J = 2.7, 7.5 Hz), 2.96 (1H, m), 3.73 (1H, d, J = 11.9 Hz), 3.82 (1H, d, J = 11.9 Hz), 4.83 (1H, dd, J = 4.9, 11.7 Hz), 5.04 (1H, m), 5.26 (1H, dd, J = 5.1, 11.7 Hz), 6.44 (1H, s), 7.35-7.41 (2H, m), 8.07 (1H, dt, J = 1.7, 8.0 Hz), 8.44-8.50 (2H, m), 8.67 (1H, d, J = 4.9 Hz), 8.98 (1H, d, J = 1.7 Hz) |
| 263 | 0.92 (3H, s), 1.12 (3H, t, J = 7.5 Hz), 1.20 (3H, t, J = 7.5 Hz), 1.26 (1H, s), 1.30-1.47 (1H, m), 1.50 (3H, s), 1.62 (1H, d, J = 2.4 Hz), 1.69-1.71 (2H, m), 1.85 (3H, s), 1.75-1.97 (2H, m), 2.18-2.22 (1H, m), 2.33 (2H, dq, J = 0.9, 7.6 Hz), 2.42 (2H, dq, J = 2.4, 7.6 Hz), 2.98 (1H, m), 3.73 (1H, d, J = 11.6 Hz), 3.81 (1H, d, J = 11.9 Hz), 4.84 (1H, dd, J = 4.9, 11.7 Hz), 5.05 (1H, m), 5.26 (1H, dd, J = 5.1, 11.5 Hz), 6.40 (1H, s), 7.38 (1H, dd, J = 4.9, 8.0 Hz), 7.80 (2H, d, J = 8.8 Hz), 8.06 (1H, dt, J = 1.7, 8.0 Hz), 8.21 (2H, d, J = 8.8 Hz), 8.67 (1H, dd, J = 1.5, 4.9 Hz), 8.96 (1H, d, J = 1.7 Hz) |
| 264 | 0.92 (3H, s), 1.14 (3H, t, J = 7.5 Hz), 1.20 (3H, t, J = 7.5 Hz), 1.26 (1H, s), 1.39-1.47 (1H, m), 1.51 (3H, s), 1.62 (1H, d, J = 2.4 Hz), 1.68-1.82 (2H, m), 1.86 (3H, s), 1.93-2.01 (2H, m), 2.19-2.23 (1H, m), 2.32 (2H, dq, J = 1.0, 7.6 Hz), 2.42 (2H, dq, J = 2.4, 7.5 Hz), 2.97 (1H, m), 3.73 (1H, d, J = 11.9 Hz), 3.80 (1H, d, J = 11.9 Hz), 4.84 (1H, dd, J = 4.9, 11.7 Hz), 5.05 (1H, m), 5.26 (1H, dd, J = 5.1, 11.5 Hz), 6.41 (1H, s), 7.38 (1H, dd, J = 4.1, 8.0 Hz), 7.65 (1H, m), 7.90 (1H, dt, J = 1.5, 7.8 Hz), 8.07 (1H, dt, J = 2.2, 8.0 Hz), 8.34 (1H, dt, J = 1.5, 7.8 Hz), 8.38 (1H, t, J = 1.5 Hz), 8.67 (1H, dd, J = 1.5, 4.9 Hz), 8.96 (1H, d, J = 2.4 Hz) |
| 265 | 0.92 (3H, s), 1.14 (3H, t, J = 7.5 Hz), 1.21 (3H, t, J = 7.5 Hz), 1.26 (1H, s), 1.39-1.48 (1H, m), 1.51 (3H, s), 1.63 (1H, d, J = 2.7 Hz), 1.63-1.83 (2H, m), 1.86 (3H, s), 1.90-1.98 (2H, m), 2.18-2.23 (1H, m), 2.33 (2H, q, J = 7.5 Hz), 2.43 (2H, dq, J = 2.5, 7.6 Hz), 2.97 (1H, m), 3.72 (1H, d, J = 11.9 Hz), 3.82 (1H, d, J = 12.0 Hz), 4.84 (1H, dd, J = 4.9, 11.4 Hz), 5.05 (1H, d, J = 4.1 Hz), 5.28 (1H, dd, J = 5.1, 11.5 Hz), 6.42 (1H, s), 7.38 (1H, dd, J = 4.9, 8.0 Hz), 7.65 (1H, t, J = 7.8 Hz), 7.88 (1H, d, J = 7.8 Hz), 8.06 (1H, dt, J = 1.8, 8.0 Hz), 8.30 (1H, d, J = 8.1 Hz), 8.36 (1H, s), 8.67 (1H, dd, J = 1.5, 4.9 Hz), 8.97 (1H, d, J = 2.2 Hz) |
| 266 | 0.89 (3H, s), 1.13 (3H, t, J = 7.6 Hz), 1.14 (3H, t, J = 7.6 Hz), 1.26 (1H, s), 1.33-1.37 (1H, m), 1.42 (3H, s), 1.46-1.55 (1H, m), 1.58 (3H, s), 1.60-1.70 (2H, m), 1.78-1.91 (2H, m), 2.13-2.17 (1H, m), 2.32 (2H, dq, J = 1.7, 7.3 Hz), 2.35 (2H, q, J = 7.3 Hz), 2.89 (1H, m), 3.66 (1H, d, J = 11.4 Hz), 3.81 (1H, d, J = 12.0 Hz), 3.96 (2H, s), 4.76-4.82 (1H, m), 4.98-5.06 (2H, m), 6.38 (1H, s), 7.17-7.25 (1H, m), 7.36-7.46 (2H, m), 7.69-7.73 (1H, m), 8.08-8.12 (1H, m), 8.60 (1H, dt, J = 1.0, 4.9 Hz), 8.70 (1H, dd, J = 1.7, 4.9 Hz), 9.00 (1H, d, J = 1.4 Hz) |

Table 29

| Compound No. | $^1$H–NMR δ (ppm) |
|---|---|
| 267 | 0.89 (3H, s), 1.13 (3H, t, J = 7.6 Hz), 1.15 (3H, t, J = 7.6 Hz), 1.26 (1H, s), 1.43 (3H, s), 1.50 (3H, d, J = 3.0 Hz), 1.61 (3H, s), 1.58–1.70 (2H, m), 1.75–1.93 (2H, m), 2.14–2.18 (1H, m), 2.32 (2H, q, J = 7.6 Hz), 2.36 (2H, q, J =7.6 Hz), 2.90 (1H, d, J = 1.9 Hz), 3.70 (1H, d, J = 12.0 Hz), 3.74 (2H, s), 3.77 (1H, d, J = 11.9 Hz), 4.79 (1H, dd, J = 4.9, 11.4 Hz), 4.96–5.00 (2H, m), 6.37 (1H, s), 7.32 (1H, dd, J = 4.8, 7.6 Hz), 7.42 (1H, dd, J = 4.9, 8.1 Hz), 7.71 (1H, d, J = 7.8 Hz), 8.12 (1H, dt, J = 1.9, 8.1 Hz), 8.57 (1H, dd, J = 1.6, 4.8 Hz), 8.65 (1H, d, J = 1.9 Hz), 8.70 (1H, dd, J = 1.6, 4.7 Hz), 9.04 (1H, d, J = 4.2 Hz) |
| 269 | 0.85–1.11 (8H, m), 0.93 (3H, s), 1.26 (1H, s), 1.39–1.47 (1H, m), 1.50 (3H, s), 1.55–1.68 (5H, m), 1.87 (3H, s), 1.83–2.02 (2H, m), 2.17–2.22 (1H, m), 2.96 (1H, s), 3.79 (1H, d, J = 12.2 Hz), 3.83 (1H, d, J = 12.1 Hz), 4.85 (1H, dd, J = 4.9, 11.5 Hz), 5.04 (1H, m), 5.38 (1H, dd, J = 5.12, 11.6 Hz), 6.46 (1H, s), 7.38 (1H, dd, J = 4.8, 8.2 Hz), 7.69–7.80 (2H, m), 7.87 (1H, m), 8.08 (1H, dt, J = 2.2, 8.0 Hz), 8.22 (1H, dd, J = 1.7, 7.5 Hz), 8.67 (1H, dd, J = 1.5, 4.9 Hz), 8.98 (1H, d, J = 2.4 Hz) |
| 270 | 0.86–1.10 (8H, m), 0.94 (3H, s), 1.26 (1H, s), 1.38–1.46 (1H, m), 1.49 (3H, s), 1.57–1.69 (5H, m), 1.75 (3H, s), 1.78–2.05 (2H, m), 2.18–2.21 (1H, m), 2.93 (1H, m), 3.80 (1H, d, J = 11.9 Hz), 3.84 (1H, d, J = 11.9 Hz), 4.84 (1H, dd, J = 5.0, 11.6 Hz), 5.04 (1H, m), 5.31 (1H, dd, J = 5.0, 11.8 Hz), 6.42 (1H, s), 7.40 (1H, dd, J = 4.9, 8.3 Hz), 7.70 (1H, d, J = 5.3 Hz), 8.09 (1H, dt, J = 1.7, 8.1 Hz), 8.69 (1H, dd, J = 1.6, 4.7 Hz), 8.97 (1H, d, J = 5.1 Hz), 9.00 (1H, d, J = 2.2 Hz), 9.17 (1H, s) |
| 271 | 0.85–1.08 (8H, m), 0.92 (3H, s), 1.26 (1H, s), 1.38–1.46 (1H, m), 1.48 (3H, s), 1.56–1.68 (5H, m), 1.79 (3H, s), 1.83–2.08 (2H, m), 2.18–2.21 (1H, m), 2.95 (1H, m), 3.76 (1H, d, J = 11.9 Hz), 3.86 (1H, d, J = 11.9 Hz), 4.83 (1H, dd, J = 4.9, 11.5 Hz), 5.04 (1H, m), 5.39 (1H, dd, J = 5.1, 11.9 Hz), 646 (1H, s), 7.34–7.45 (2H, m), 7.86 (1H, dd, J = 1.3, 8.0 Hz), 8.08 (1H, dt, J = 2.0, 8.0 Hz), 8.64 (1H, dd, J = 1.2, 4.7 Hz), 8.68 (1H, dd, J = 1.5, 4.9 Hz), 9.00 (1H, d, J = 2.2 Hz) |

Example 11
Preparation Example 1 [Wettable powder]
Compound according to the present invention

| | |
|---|---|
| (Compound No. 82) | 30 wt% |
| Clay | 30 wt% |
| Diatomaceous earth | 35 wt% |
| Calcium lignin sulfonate | 4 wt% |
| Sodium laurylsulfate | 1 wt% |

The above ingredients were homogeneously mixed together, and the mixture was ground to prepare wettable powder.

Preparation Example 2 [Dust]
Compound according to the present invention

| | |
|---|---|
| (Compound No. 82) | 2 wt% |
| Clay | 60 wt% |
| Talc | 37 wt% |
| Calcium stearate | 1 wt% |

The above ingredients were homogeneously mixed together to prepare dust.

Preparation Example 3 [Emulsifiable concentrate]
Compound according to the present invention

| | |
|---|---|
| (Compound No. 82) | 20 wt% |
| N,N-Dimethylformamide | 20 wt% |
| Solvesso 150 (Exxon Mobil Corporation) | 50 wt% |
| Polyoxyethylene alkylaryl ether | 10 wt% |

The above ingredients were homogeneously mixed and dissolved to prepare emulsifiable concentrate.

Preparation Example 4 [Granules]
Compound according to the present invention

| | |
|---|---|
| (Compound No. 28) | 5 wt% |
| Bentonite | 40 wt% |
| Talc | 10 wt% |
| Clay | 43 wt% |
| Calcium lignin sulfonate | 2 wt% |

The above ingredients were homogeneously ground and homogeneously mixed together. Water was added to the mixture, followed by thorough kneading. Thereafter, the kneaded product was granulated and dried to prepare granules.

Preparation Example 5 [Floables]
Compound according to the present invention

| | |
|---|---|
| (Compound No. 28) | 25 wt% |
| POE polystyrylphenyl ether sulfate | 5 wt% |
| Propylene glycol | 6 wt% |
| Bentonite | 1 wt% |
| 1% aqueous xanthan gum solution | 3 wt% |
| PRONAL EX-300 (Toho Chemical Industry Co., Ltd.) | 0.05 wt% |
| ADDAC 827 (K.I. Chemical Industry Co., Ltd.) | 0.02 wt% |
| Water | To 100 wt% |

All the above ingredients except for the 1% aqueous xanthan gum solution and a suitable amount of water were premixed together, and the mixture was then ground by a wet grinding mill. Thereafter, the 1% aqueous xanthan gum solution and the remaining water were added to the ground product to prepare 100 wt% floables.

Test Example 1: Pesticidal effect against Myzus persicae

Among the compounds of formula (I) produced by the conventional method described above, the compounds shown in Tables 1 to 14 and pyripyropene A were tested for pesticidal effect.

A leaf disk having a diameter of 2.8 cmφ was cut out from a cabbage grown in a pot and was placed in a 5.0 cm-Schale. Four adult aphids of Myzus persicae were released in the Schale. One day after the release of the adult aphids, the adult aphids were removed. The number of larvae at the first instar born in the leaf disk was adjusted to 10, and a test solution, which had been adjusted to a concentration of 20 ppm by the addition of a 50% aqueous acetone solution (0.05% Tween 20 added) was spread over the cabbage leaf disk. The cabbage leaf disk was then air dried. Thereafter, the Schale was lidded and was allowed to stand in a temperature-controlled room (light period 16 hr – dark period 8 hr) (25°C). Three days after the initiation of standing of the Schale, the larvae were observed for survival or death, and the death rate of larvae was calculated by the following equation.

Death rate (%) = {number of dead larvae/(number of survived larvae + number of dead larvae)} x 100

As result, it was found that the death rate was not less than 80% for compounds of Nos. 1, 6, 8, 9, 10, 12, 14, 16, 18, 20, 23, 25, 28, 34, 35, 36, 37, 38, 39, 40, 44, 45, 49, 54, 56, 57, 61, 69, 76, 82, 85, 86, 88, 90, 91, 98, 103, 106, 107, 108, 109, 111, 125, 128, 133, 135, 137, 139, 142, 153, 160, 161, 162, 164, 167, 169, 170, 171, 172, 176, 180, 182, 183, 186, 187, 190, 196, 201, 205, 206, 207, 208, 209, 210, 211, 212, 213, 214, 215, 216, 217, 218, 219, 220, 221, 222, 223, 226, 227, 228, 229, 230, 231, 232, 233, 236, 237, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, and 274 and pyripyropene A.

Test Example 2: Pesticidal effect against Myzus persicae

Among the compounds of formula (I) produced by the conventional method described above, the compounds shown in Tables 1 to 14 and pyripyropene A were tested for pesticidal effect.
A leaf disk having a diameter of 2.8 cmφ was cut out from a cabbage grown in a pot and was placed in a 5.0 cm-Schale. Four adult aphids of Myzus persicae were released in the Schale. One day after the release of the adult aphids, the adult aphids were removed. The number of larvae at the first instar born in the leaf disk was adjusted to 10, and a test solution, which had been adjusted to a concentration of 0.156 ppm by the addition of a 50% aqueous acetone solution (0.05% Tween 20 added) was spread over the cabbage leaf disk. The cabbage leaf disk was then air dried. Thereafter, the Schale was lidded and was allowed to stand in a temperature-controlled room (light period 16 hr – dark period 8 hr) (25°C). Three days after the initiation of standing, the larvae were observed for survival or death, and the death rate of larvae was calculated in the same manner as in Test Example 1.

As result, it was found that the death rate was not less than 80% for compounds of Nos. 12, 23, 28, 45, 54, 56, 76, 82, 85, 86, 90, 164, 201, 205, 206, 207, 212, 213, 217, 218, 219, 222, 227, 228, 229, 231, 232, 233, 237, 239, 240, 242, 246, 247, 249, 250, 252, 253, 256, 258, 261, 262, 264, 265, 266, 267, 269, 270, and 271.

Test Example 3: Pesticidal effect against Plutella xylostella

A cabbage leaf disk having a diameter of 5 cm was placed in a plastic cup. Test compounds, which had been diluted to a predetermined concentration by the addition of a 50 % aqueous acetone solution (Tween 20, 0.05% added), were spreaded over the cabbage leaf disk by means of a spray gun, and the cabbage leaf disk was then air dried. Five larvae at the second instar of Plutella xylostella were released in the cup. The cup was then lidded, and the larvae were reared in the temperature-controlled room (25°C). Three days after the treatment, the larvae were observed for survival or death, and the death rate of the larvae was calculated in the same manner as in Test Example 1.

As a results, it was found that the death rate was not less than 80% for compounds of Nos. 76, 213, 218, 237 and 250 at a concentration of 500 ppm.

Test Example 4: Pesticidal effect against Helicoverpa armigera

A cabbage leaf disk having a diameter of 2.8 cm was placed in a plastic cup. Test compounds, which had been diluted to a predetermined concentration by the addition of a 50 % aqueous acetone solution (Tween 20, 0.05% added), were spreaded over the cabbage leaf disk by means of a spray gun, and the cabbage leaf disk was then air dried. A larva at the third instar of Helicoverpa armigera was released in the cup. The cup was then lidded, and the larva was reared in the temperature-controlled room (25°C). Three days after the treatment, the larva was observed for survival or death. The test was repeated 5 times. Further, the death rate of the larvae were calculated in the same manner as in Test Example 1.

As a result, it was found that the death rate was not less than 80% for the compound of No. 219 at a concentration of 100 ppm.

Test Example 5: Pesticidal effect against Trigonotylus caelestialium

A wheat seedling was immersed for 30 seconds in a solution, in which each test compound had been diluted to a predetermined concentration by the addition of a 50 % aqueous acetone solution (Tween 20, 0.05% added). The wheat seedling was air dried, and then placed in a glass cylinder. Further, two larvae at the second instar of Trigonotylus caelestialium were released in the glass cylinder. The glass cylinder was then lidded, and the larvae were reared in the temperature-controlled room (25°C). During the test, the wheat seedling was supplid with water from the bottom of the glass cylinder. Three days after the treatment, the larvae were observed for survival or death, and the death rate of the larvae were calculated in the same manner as in Test Example 1.

As a result, it was found that the death rate was not less than 80% for compound of Nos. 218 and 261 at a concentration of 100 ppm.

What is claimed is:

[1]     A composition for use as a pest control agent, comprising a compound represented by formula (I) or an agriculturally and horticulturally acceptable salt thereof as active ingredient and an agriculturally and horticulturally acceptable carreir:

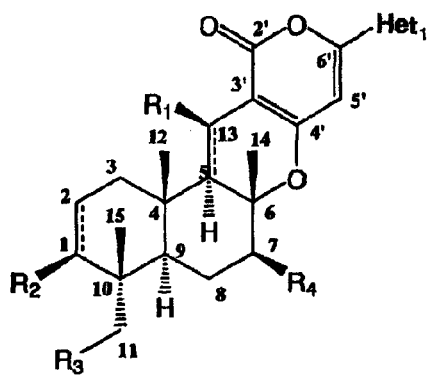

(I)

where

Het₁ represents optionally substituted 3-pyridyl,

R₁ represents hydroxyl,
optionally substituted $C_{1-6}$ alkylcarbonyloxy,
optionally substituted $C_{2-6}$ alkenylcarbonyloxy,
optionally substituted $C_{2-6}$ alkynylcarbonyloxy,
optionally substituted $C_{1-6}$ alkyloxy,
optionally substituted $C_{2-6}$ alkenyloxy,
optionally substituted $C_{2-6}$ alknyloxy,
optionally substituted benzyloxy, or
oxo in the absenace of a hydrogen atom at the
13-position, or the bond between 5-position and 13-position represents a double bond in the absence of R₁ and a hydrogen atom at the 5-position, R₂ represents hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy, or
optionally substituted $C_{1-6}$ alkylsulfonyloxy, R₃ represents a hydrogen atom,
hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy,
optionally substituted $C_{1-6}$ alkylsulfonyloxy,
optionally substituted benzenesulfonyloxy, or
optionally substituted five- or six-membered
heterocyclic thiocarbonyloxy, or R₂ and R₃ together represent -O-CR₂'R₃'-O- wherein R₂' and R₃' which may be the same or different, represent a hydrogen atom. $C_{1-6}$ alkyl, $C_{1-8}$ alkyloxy, $C_{2-6}$ alkenly, optionally substituted phenyl, or optionally substituted benzyl, or $R_2'$ and $R_3'$ together represent oxo or $C_{2-6}$ alkylene, and $\quad\quad R_4$ represents a hydrogen atom, $\quad\quad\quad\quad$ hydroxyl, $\quad\quad\quad\quad\quad\quad$ optionally substituted $C_{1-18}$ alkylcarbonyloxy, $\quad\quad\quad\quad\quad\quad$ optionally substituted $C_{2-6}$ alkenylcarbonyloxy, $\quad\quad\quad\quad\quad\quad$ optionally substituted $C_{2-6}$ alkynylcarbonyloxy, $\quad\quad\quad\quad\quad\quad$ optionally substituted benzoyloxy, $\quad\quad\quad\quad\quad\quad$ optionally substituted $C_{1-6}$ alkylsulfonyloxy, $\quad\quad\quad\quad\quad\quad$ optionally substituted benzenesulfonyloxy, $\quad\quad\quad\quad\quad\quad$ optionally substituted benzyloxy, $\quad\quad\quad\quad\quad\quad$ optionally substituted $C_{1-6}$ alkyloxy, $\quad\quad\quad\quad\quad\quad$ optionally substituted $C_{2-6}$ alkenyloxy, $\quad\quad\quad\quad\quad\quad$ optionally substituted $C_{2-6}$ alkynyloxy, $\quad\quad\quad\quad\quad\quad$ $C_{1-6}$ alkyloxy-$C_{1-6}$ alkyloxy, $\quad\quad\quad\quad\quad\quad$ $C_{1-6}$ alkylthio-$C_{1-6}$ alkyloxy, $\quad\quad\quad\quad\quad\quad$ $C_{1-6}$ alkyloxy-$C_{1-6}$ alkyloxy-$C_{1-6}$ alkyloxy, $\quad\quad\quad\quad\quad\quad$ optionally substituted $C_{1-6}$ alkyloxycarbonyloxy, $\quad\quad\quad\quad\quad\quad$ optionally substituted $C_{1-6}$ alkylaminocarbonyloxy, $\quad\quad\quad\quad\quad\quad$ optionally substituted saturated or unsaturated five- or six-membered heterocyclic oxy, $\quad\quad\quad\quad\quad\quad$ optionally substituted saturated or unsaturated five- or six-membered heterocyclic carbonyloxy, $\quad\quad\quad\quad\quad\quad$ optionally substituted thieno[3,2-b]pyridylcarbonyloxy, $\quad\quad\quad\quad\quad\quad$ optionally substituted 1H-indolylcarbonyloxy, $\quad\quad\quad\quad\quad\quad$ optionally substituted saturated or unsaturated five- or six-membered heterocyclic thiocarbonyloxy, or $\quad\quad\quad\quad\quad\quad$ oxo in the absence of a hydrogen atom at the 7-position, $\quad\quad\quad\quad$ provided that $\quad\quad\quad\quad$ a compound wherein $\quad\quad\quad\quad$ $Het_1$ represents 3-pyridyl, $\quad\quad\quad\quad$ $R_1$ represents hydroxyl, and $\quad\quad\quad\quad$ all of $R_2$, $R_3$, and $R_4$ represent acetyloxy, is excluded.

[2] The composition according to claim 1, wherein $\quad\quad\quad\quad$ $Het_1$ represents 3-pyridyl, $\quad\quad\quad\quad$ $R_1$ represents hydroxyl or $C_{1-6}$ alkylcarbonyloxy, or $\quad\quad\quad\quad$ the bond between 5-position and 13-position represents a double bond in the absence of $R_1$ and a hydrogen atom at the 5-position, $\quad\quad\quad\quad$ $R_2$ represents optionally substituted $C_{1-6}$ alkylcarbonyloxy, $\quad\quad\quad\quad$ $R_3$ represents optionally substituted $C_{1-6}$ alkylcarbonyloxy or $C_{1-6}$ alkylsulfonyloxy, or $R_2$ and $R_3$ together represent $-O-CR_2'R_3'-O-$ wherein $R_2'$ and $R_3'$, which may be the same or different, represent a hydrogen atom, $C_{1-6}$ alkyl, or optionally substituted phenyl, or $R_2'$ and $R_3'$ together represent oxo or $C_{2-6}$ alkylene, and $R_4$ represents hydroxyl,
optionally substituted $C_{1-6}$ alkylcarbonyloxy,
saturated or unsaturated five- or six-membered heterocyclic oxy,
optionally substituted benzoyloxy,
$C_{1-3}$ alkyloxy-$C_{1-3}$ alkyloxy,
optionally substituted $C_{1-6}$ alkylaminocarbonyloxy,
optionally substituted saturated or unsaturated five- or six-membered heterocyclic carbonyloxy,
optionally substituted thieno[3,2-b]pyridylcarbonyloxy,
optionally substituted 1H-indolylcarbonyloxy,
saturated or unsaturated five- or six-membered heterocyclic thiocarbonyloxy, or
oxo in the absence of a hydrogen atom at the 7-position.

[3] The compositon according to claim 1, wherein $Het_1$ represents 3-pyridyl,
$R_1$ represents hydroxyl,
$R_2$ represents optionally substituted $C_{1-6}$ alkylcarbonyloxy, and
$R_3$ represents optionally substituted $C_{1-6}$ alkylcarbonyloxy or $C_{1-6}$ alkylsulfonyloxy, and
$R_4$ represents hydroxyl,
optionally substituted $C_{1-6}$ alkylcarbonyloxy,
saturated or unsaturated five- or six-membered heterocyclic oxy,
optionally substituted benzoyloxy,
$C_{1-3}$ alkyloxy-$C_{1-3}$ alkyloxy,
optionally substituted $C_{1-6}$ alkylaminocarbonyloxy,
optionally substituted saturated or unsaturated five- or six-membered heterocyclic carbonyloxy,
optionally substituted thieno[3,2-b]pyridylcarbonyloxy,
optionally substituted 1H-indolylcarbonyloxy,
saturated or unsaturated five- or six-membered heterocyclic thiocarbonyloxy, or
oxo in the absence of a hydrogen atom at the 7-position.

[4] The compositon according to claim 1, wherein $Het_1$ represents 3-pyridyl,
$R_1$ represents hydroxyl, R₂ represents optionally substituted $C_{1-6}$ alkylcarbonyloxy, R₃ represents optionally substituted $C_{1-6}$ alkylcarbonyloxy or $C_{1-6}$ alkylsulfonyloxy, and R₄ represents hydroxyl, optionally substituted $C_{1-6}$ alkylcarbonyloxy, saturated or unsaturated five- or six-membered heterocyclic oxy, optionally substituted benzoyloxy, optionally substituted saturated or unsaturated five- or six-membered heterocyclic carbonyloxy, or saturated or unsaturated five- or six-membered heterocyclic thiocarbonyloxy.

[5] The compositon according to claim 1, wherein

Het₁ represents 3-pyridyl,

R₁ represents hydroxyl, and

R₂ and R₃ represent optionally substituted cyclic $C_{3-6}$ alkylcarbonyloxy.

[6] A composition for use as a pest control agent, comprising a compound represented by formula (Ia) or an agriculturally and horticulturally acceptable salt thereof as active ingredient and an agriculturally and horticulturally acceptable carrier:

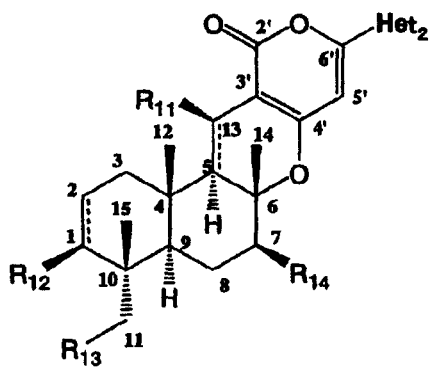

( I a )

wherein

Het₂ represents optionally substituted 3-pyridyl,

R₁₁ represents hydroxyl, optionally substituted $C_{1-6}$ alkylcarbonyloxy, optionally substituted $C_{2-6}$ alkenylcarbonyloxy, optionally substituted $C_{2-6}$ alkynylcarbonyloxy, optionally substituted $C_{1-6}$ alkyloxy, optionally substituted $C_{2-6}$ alkenyloxy, optionally substituted $C_{2-6}$ alkynyloxy, optionally substituted benzyloxy, or oxo in the absence of a hydrogen atom at the 13-position, or the bond between 5-position and 13-position represents a double bond in the absence of $R_{11}$ and a hydrogen atom at the 5-position, $R_{12}$ represents hydroxyl, optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy, or
optionally substituted $C_{1-6}$ alkylsulfonyloxy, $R_{13}$ represents a hydrogen atom, hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy,
optionally substituted $C_{1-6}$ alkylsulfonyloxy,
optionally substituted benzenesulfonyloxy, or
optionally substituted five- or six-membered heterocyclic thiocarbonyloxy, or $R_{12}$ and $R_{13}$ together represent -O-$CR_{12}'R_{13}'$-O- wherein $R_{12}'$ and $R_{13}'$, which may be the same or different, represent a hydrogen atom, $C_{1-6}$ alkyl, $C_{1-6}$ alkyloxy, $C_{2-6}$ alkenyl, optionally substituted phenyl, or optionally substituted benzyl, or $R_{12}'$ and $R_{13}'$ together represent oxo or $C_{2-6}$ alkylene, and $R_{14}$ represents a hydrogen atom, hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy,
optionally substituted $C_{1-6}$ alkylsulfonyloxy,
optionally substituted benzenesulfonyloxy,
optionally substituted benzyloxy,
optionally substituted $C_{1-6}$ alkyloxy,
optionally substituted $C_{2-6}$ alkenyloxy,
optionally substituted $C_{2-6}$ alkynyloxy,
$C_{1-6}$ alkyloxy-$C_{1-6}$ alkyloxy,
$C_{1-6}$ alkylthio-$C_{1-6}$ alkyloxy,
$C_{1-6}$ alkyloxy-$C_{1-6}$ alkyloxy-$C_{1-6}$ alkyloxy,
optionally substituted $C_{1-6}$ alkyloxycarbonyloxy,
optionally substituted $C_{1-6}$ alkylaminocarbonyloxy,
optionally substituted saturated or unsaturated five- or six-membered heterocyclic oxy, optionally substituted saturated or unsaturated five- or six-membered heterocyclic carbonyloxy,
    optionally substituted thieno[3,2-b]pyridylcarbonyloxy,
    optionally substituted 1H-indolylcarbonyloxy,
    optionally substituted saturated or unsaturated five- or
six-membered heterocyclic thiocarbonyloxy, or
    oxo in the absence of a hydrogen atom at the
7-position.

[7]   The composition according to claim 6,
wherein
    $Het_2$ represents 3-pyridyl,
    $R_{11}$ represents hydroxyl or $C_{1-6}$ alkylcarbonyloxy, or
    the bond between 5-position and 13-position represents a
double bond in the absence of R11 and a hydrogen atom at the
5-position,
    $R_{12}$ represents optionally substituted $C_{1-6}$ alkylcarbonyloxy,
    $R_{13}$ represents optionally substituted $C_{1-6}$ alkylcarbonyloxy or
$C_{1-6}$ alkylsulfonyloxy, or
    $R_{12}$ and $R_{13}$ together represent -O-$CR_{12}'R_{13}'$-O- wherein $R_{12}'$
and $R_{13}'$, which may be the same or different, represent a
hydrogen atom, $C_{1-6}$ alkyl, or optionally substituted phenyl, or $R_{12}'$
and $R_{13}'$ together represent oxo or $C_{2-6}$ alkylene, and
    $R_{14}$ represents hydroxyl,
        optionally substituted $C_{1-6}$ alkylcarbonyloxy,
        saturated or unsaturated five- or six-membered
    heterocyclic oxy,
        optionally substituted benzoyloxy,
        $C_{1-3}$ alkyloxy-$C_{1-3}$ alkyloxy,
        optionally substituted $C_{1-6}$ alkylaminocarbonyloxy,
        optionally substituted saturated or unsaturated five- or
    six-membered heterocyclic carbonyloxy,
        optionally substituted thieno[3,2-b]pyridylcarbonyloxy,
        optionally substituted 1H-indolylcarbonyloxy,
        saturated or unsaturated five- or six-membered
    heterocyclic thiocarbonyloxy, or
        oxo in the absence of a hydrogen atom at the
    7-position.

[8]   The composition according to claim 6,
wherein
    $Het_2$ represents 3-pyridyl,
    $R_{11}$ represents hydroxyl,
    $R_{12}$ represents optionally substituted $C_{1-6}$ alkylcarbonyloxy,
and
    $R_{13}$ represents optionally substituted $C_{1-6}$ alkylcarbonyloxy or
$C_{1-6}$ alkylsulfonyloxy, and
    $R_{14}$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

[9] The composition according to claim 6, wherein $Het_2$ represents 3-pyridyl, $R_{11}$ represents hydroxyl, $R_{12}$ represents optionally substituted $C_{1-6}$ alkylcarbonyloxy, $R_{13}$ represents optionally substituted $C_{1-6}$ alkylcarbonyloxy or $C_{1-6}$ alkylsulfonyloxy, and $R_{14}$ represents hydroxyl, optionally substituted $C_{1-6}$ alkylcarbonyloxy, saturated or unsaturated five- or six-membered heterocyclic oxy, optionally substituted benzoyloxy, optionally substituted saturated or unsaturated five- or six-membered heterocyclic carbonyloxy, or saturated or unsaturated five- or six-membered heterocyclic thiocarbonyloxy.

[10] The composition according to claim 6, wherein $Het_2$ represents 3-pyridyl, $R_{11}$ represents hydroxyl, and $R_{12}$ and $R_{13}$ represent optionally substituted cyclic $C_{3-6}$ alkylcarbonyloxy.

[11] The composition according to claim 6, wherein said hemipteran pest is selected from Aphidoidea, Coccoidea, or Aleyrodidae.

[12] The composition according to claim 6, wherein said hemipteran pest is at least one pest selected from the group consisting of Myzus persicae, Aphis gossypii, Aphis fabae, Aphis maidis (corn-leaf aphid), Acyrthosiphon pisum, Aulacorthum solani, Aphis craccivora, Macrosiphum euphorbiae, Macrosiphum avenae, Metopolophium dirhodum, Rhopalosiphum padi, Schizaphis graminum, Brevicoryne brassicae, Lipaphis erysimi, Aphis citricola, Rosy apple aphid, Eriosoma lanigerum, Toxoptera aurantii, Toxoptera citricidus, and Pseudococcus comstocki.

[13] A compound represented by formula (Ib) or an agriculturally and horticulturally acceptable salt thereof:

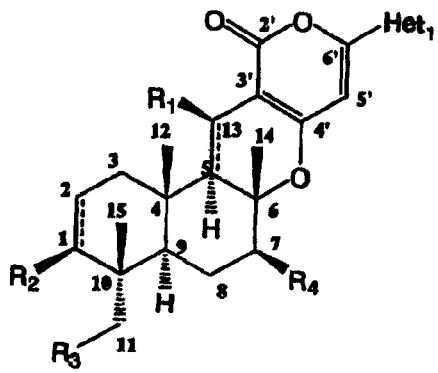

( I b )

wherein
  $Het_1$ represents 3-pyridyl,
  $R_1$ represents hydroxyl,
  $R_2$ and $R_3$ represent propionyloxy or optionally substituted cyclic $C_{3-6}$ alkylcarbonyloxy, and
  $R_4$ represents hydroxyl,
    optionally substituted cyclic $C_{3-6}$ alkylcarbonyloxy,
    optionally substituted benzoyloxy, or
optionally substituted saturated or unsaturated five- or six-membered heterocyclic carbonyloxy, provided that
  a compound wherein
  $Het_1$ represents 3-pyridyl,
  $R_1$ represents hydroxyl,
  $R_2$ and $R_3$ represent propionyloxy, and
  $R_4$ represents hydroxyl,
is excluded.

[14] The compound according to claim 13 or an agriculturally and horticulturally acceptable salt thereof, wherein
  $R_2$ and $R_3$ represent optionally substituted cyclic $C_{3-6}$ alkylcarbonyloxy, and
  $R_4$ represents hydroxyl, optionally substituted cyclic $C_{3-6}$ alkylcarbonyloxy, or optionally substituted benzoyloxy.

[15] The compound according to claim 13 or an agriculturally and horticulturally acceptable salt thereof, wherein
  $R_2$ and $R_3$ represent propionyloxy, and
  $R_4$ represents optionally substituted cyclic $C_{3-6}$ alkylcarbonyloxy or optionally substituted saturated or unsaturated five- or six-membered heterocyclic carbonyloxy.

[16] A composition for use as a pest control agent comprising the compound accoridng to claim 13 or an agriculturally and horticulturally acceptable salt thereof as active ingredient and an agriculturally and horticulturally acceptable carrier.

[17] A method for controlling a pest, comprising applying an effective amount of a compound represented by formula (I) accoding to claim 1 or an agriculturally and horticulturally acceptable salt thereof to a plant or soil.

[18] A method for controlling a hemipteran pest, comprising applying an effective amount of a compound represented by formula (Ia) accoding to claim 6 or an agriculturally and horticulturally acceptable salt thereof to a plant or soil.

[19] A method for controlling an pest, comprising applying an effective amount of a compound represented by formula (Ib) according to claim 13 or an agriculturally and horticulturally acceptable salt thereof to a plant or soil.

UNITED STATES PATENT AND TRADEMARK OFFICE
CERTIFICATE OF CORRECTION

| | | |
|---|---|---|
| PATENT NO. | : 7,491,738 B2 | |
| APPLICATION NO. | : 11/443299 | |
| DATED | : February 17, 2009 | |
| INVENTOR(S) | : Kimihiko Goto et al. | |

It is certified that error appears in the above-identified patent and that said Letters Patent is hereby corrected as shown below:

<u>In the specification, abstract and claims:</u>

*Please replace the specification and abstract of the subject patent with the attached specification and abstract.*

ABSTRACT

Disclosed is a composition for use as a pest control agent, comprising a compound represented by formula (I) or an agriculturally and horticulturally acceptable salt thereof as active ingredient and an agriculturally and horticulturally acceptable carrier:

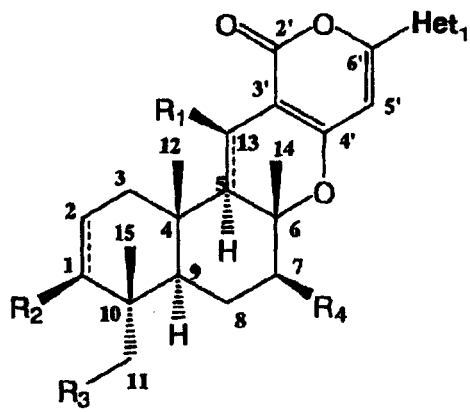

(I)

This certificate supersedes the Certificate of Correction issued April 26, 2011.

Signed and Sealed this
Seventh Day of June, 2011

David J. Kappos
*Director of the United States Patent and Trademark Office*

[BACKGROUND OF THE INVENTION]

Field of Invention

The present invention relates to a composition for use as a pest control agent comprising a pyripyropene derivative as active ingredient.

Background Art

Pyripyropene A has inhibitory activity against ACAT (acyl-CoA: cholesterol acyltransferase) and is expected to be applied, for example, to the treatment of diseases induced by cholesterol accumulation, as described in Japanese Patent No. 2993767 (Japanese Patent Laid-Open Publication No. 360895/1992) and Journal of Antibiotics (1993), 46(7), 1168-9.

Further, pyripyropene analogues and derivatives and ACAT inhibitory activity thereof are described in Journal of Society of Synthetic Organic Chemistry, Japan (1998), Vol. 56, No. 6, pp. 478-488, WO 94/09417, Japanese Patent Laid-Open Publication No. 184158/1994, Japanese Patent Laid-Open Publication No. 239385/1996, Japanese Patent Laid-Open Publication No. 259569/1996, Japanese Patent Laid-Open Publication No. 269062/1996, Japanese Patent Laid-Open Publication No. 269063/1996, Japanese Patent Laid-Open Publication No. 269064/1996, Japanese Patent Laid-Open Publication No. 269065/1996, Japanese Patent Laid-Open Publication No. 269066/1996, Japanese Patent Laid-Open Publication No. 291164/1996, and Journal of Antibiotics (1997), 50(3), 229-36.

Furthermore, Applied and Environmental Microbiology (1995), 61(12), 4429-35 describes that pyripyropene A has insecticidal activity against larvae of Helicoverpa zea. Furthermore, WO 2004/060065 describes that pyripyropene A has insecticidal activity against Plutella xylostella L larvae and Tenebrio molitor L. In these documents, however, there is no specific description on insecticidal activity of pyripyropene A against other pests.

Further, none of the above documents describes insecticidal activity of pyripyropene analogues and derivatives.

Up to now, many compounds having insecticidal activity have been reported and have been used as pest control agents. However, the presence of insect species, which are resistant to or can be hardly controlled by these compounds, has posed a problem. Accordingly, the development of a novel pest control agent having excellent insectidal activity has still been desired.

[SUMMARY OF THE INVENTION]

The present inventors have now found that pyripyropene derivatives represented by formula (I) have significant insecticidal activity.

The present inventors further found that pyripyropene A and its derivatives represented by formula (Ia) have significant insecticidal activity against hemipteran pests.

Furthermore, the present inventors have found novel pyripyropene derivatives represented by formula (Ib) having significant insecticidal activity.

The present invention has been made based on such finding.

Accordingly, an object of the present invention is to provide a composition useful as a pest control agent, that comprises a pyripyropene derivative having significant insecticidal activity as active ingredient and can reliably exhibit the contemplated effect and can be used safely. Another object of the present invention is to provide a hemipteran pest control agent that comprises pyripyropene A and its derivative as active ingredient and can reliably exhibit the contemplated effect and can be used safely. A further object of the present invention is to provide a novel pyripyropene derivative having significant insecticidal activity.

According to one aspect of the present invention, there is provided a composition for use as a pest control agent, comprising a compound represented by formula (I) or an agriculturally and horticulturally acceptable salt thereof as active ingredient and an agriculturally and horticulturally acceptable carrier:

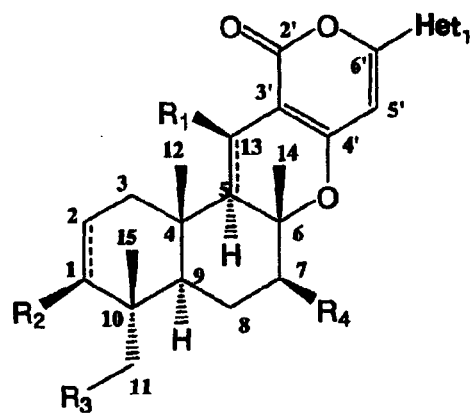

(I)

wherein
    $Het_1$ represents optionally substituted 3-pyridyl,
    $R_1$ represents hydroxyl,
        optionally substituted $C_{1-6}$ alkylcarbonyloxy,
        optionally substituted $C_{2-6}$ alkenylcarbonyloxy,
        optionally substituted $C_{2-6}$ alkynylcarbonyloxy,
        optionally substituted $C_{1-6}$ alkyloxy,
        optionally substituted $C_{2-6}$ alkenyloxy,
        optionally substituted $C_{2-6}$ alkynyloxy,
        optionally substituted benzyloxy, or
        oxo in the absence of a hydrogen atom at the 13-position, or the bond between 5-position and 13-position represents a double bond in the absence of $R_1$ and a hydrogen atom at the 5-position, $R_2$ represents hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy, or
optionally substituted $C_{1-6}$ alkylsulfonyloxy, $R_3$ represents a hydrogen atom,
hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy,
optionally substituted $C_{1-6}$ alkylsulfonyloxy,
optionally substituted benzenesulfonyloxy, or
optionally substituted five- or six-membered heterocyclic thiocarbonyloxy, or $R_2$ and $R_3$ together represent -O-$CR_2'R_3'$-O- wherein $R_2'$ and $R_3'$, which may be the same or different, represent a hydrogen atom, $C_{1-6}$ alkyl, $C_{1-6}$ alkyloxy, $C_{2-6}$ alkenyl, optionally substituted phenyl, or optionally substituted benzyl, or $R_2'$ and $R_3'$ together represent oxo or $C_{2-6}$ alkylene, and $R_4$ represents a hydrogen atom,
hydroxyl,
optionally substituted $C_{1-18}$ alkylcarbonyloxy,
optionally substituted $C_{2-6}$ alkenylcarbonyloxy,
optionally substituted $C_{2-6}$ alkynylcarbonyloxy,
optionally substituted benzoyloxy,
optionally substituted $C_{1-6}$ alkylsulfonyloxy,
optionally substituted benzenesulfonyloxy,
optionally substituted benzyloxy,
optionally substituted $C_{1-6}$ alkyloxy,
optionally substituted $C_{2-6}$ alkenyloxy,
optionally substituted $C_{2-6}$ alkynyloxy,
$C_{1-6}$ alkyloxy-$C_{1-6}$ alkyloxy,
$C_{1-6}$ alkylthio-$C_{1-6}$ alkyloxy,
$C_{1-6}$ alkyloxy-$C_{1-6}$ alkyloxy-$C_{1-6}$ alkyloxy,
optionally substituted $C_{1-6}$ alkyloxycarbonyloxy,
optionally substituted $C_{1-6}$ alkylaminocarbonyloxy,
optionally substituted saturated or unsaturated five- or six-membered heterocyclic oxy,
optionally substituted saturated or unsaturated five- or six-membered heterocyclic carbonyloxy, optionally substituted thieno[3,2-b]pyridylcarbonyloxy,
optionally substituted 1H-indolylcarbonyloxy,
optionally substituted saturated or unsaturated five- or six-membered heterocyclic thiocarbonyloxy, or
oxo in the absence of a hydrogen atom at the 7-position,
provided that
a compound wherein
$Het_1$ represents 3-pyridyl,
$R_1$ represents hydroxyl, and
all of $R_2$, $R_3$, and $R_4$ represent acetyloxy,
is excluded.

Further, according to another aspect of the present invention, there is provided a composition for use as a a hemipteran pest control agent, comprising a compound represented by formula (Ia) or an agriculturally and horticulturally acceptable salt thereof as active ingredient and an agriculturally and horticulturally acceptable carrier:

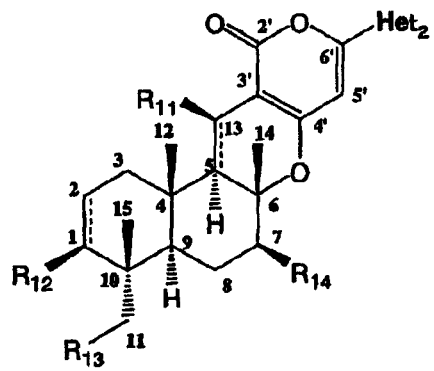

(Ia)

wherein
$Het_2$ represents optionally substituted 3-pyridyl,
$R_{11}$ represents hydroxyl,
optionally substituted $C_{1-6}$ alkylcarbonyloxy,
optionally substituted $C_{2-6}$ alkenylcarbonyloxy,
optionally substituted $C_{2-6}$ alkynylcarbonyloxy,
optionally substituted $C_{1-6}$ alkyloxy,
optionally substituted $C_{2-6}$ alkenyloxy,
optionally substituted $C_{2-6}$ alkynyloxy,
optionally substituted benzyloxy, or
oxo in the absence of a hydrogen atom at the 13-position,
or
the bond between 5-position and 13-position represents a double bond in the absence of $R_{11}$ and a hydrogen atom at the 5-position, $R_{12}$ represents hydroxyl,
- optionally substituted $C_{1-18}$ alkylcarbonyloxy,
- optionally substituted $C_{2-6}$ alkenylcarbonyloxy,
- optionally substituted $C_{2-6}$ alkynylcarbonyloxy,
- optionally substituted benzoyloxy, or
- optionally substituted $C_{1-6}$ alkylsulfonyloxy, $R_{13}$ represents a hydrogen atom,
- hydroxyl,
- optionally substituted $C_{1-18}$ alkylcarbonyloxy,
- optionally substituted $C_{2-6}$ alkenylcarbonyloxy,
- optionally substituted $C_{2-6}$ alkynylcarbonyloxy,
- optionally substituted benzoyloxy,
- optionally substituted $C_{1-6}$ alkylsulfonyloxy,
- optionally substituted benzenesulfonyloxy, or
- optionally substituted five- or six-membered heterocyclic thiocarbonyloxy, or $R_{12}$ and $R_{13}$ together represent -O-$CR_{12}'R_{13}'$-O- wherein $R_{12}'$ and $R_{13}'$, which may be the same or different, represent a hydrogen atom, $C_{1-6}$ alkyl, $C_{1-6}$ alkyloxy, $C_{2-6}$ alkenyl, optionally substituted phenyl, or optionally substituted benzyl, or $R_{12}'$ and $R_{13}'$ together represent oxo or $C_{2-6}$ alkylene, and $R_{14}$ represents a hydrogen atom,
- hydroxyl,
- optionally substituted $C_{1-18}$ alkylcarbonyloxy,
- optionally substituted $C_{2-6}$ alkenylcarbonyloxy,
- optionally substituted $C_{2-6}$ alkynylcarbonyloxy,
- optionally substituted benzoyloxy,
- optionally substituted $C_{1-6}$ alkylsulfonyloxy,
- optionally substituted benzenesulfonyloxy,
- optionally substituted benzyloxy,
- optionally substituted $C_{1-6}$ alkyloxy,
- optionally substituted $C_{2-6}$ alkenyloxy,
- optionally substituted $C_{2-6}$ alkynyloxy,
- $C_{1-6}$ alkyloxy-$C_{1-6}$ alkyloxy,
- $C_{1-6}$ alkylthio-$C_{1-6}$ alkyloxy,
- $C_{1-6}$ alkyloxy-$C_{1-6}$ alkyloxy-$C_{1-6}$ alkyloxy,
- optionally substituted $C_{1-6}$ alkyloxycarbonyloxy,
- optionally substituted $C_{1-6}$ alkylaminocarbonyloxy,
- optionally substituted saturated or unsaturated five- or six-membered heterocyclic oxy,
- optionally substituted saturated or unsaturated five- or six-membered heterocyclic carbonyloxy,
- optionally substituted thieno[3,2-b]pyridylcarbonyloxy,
- optionally substituted 1H-indolylcarbonyloxy, optionally substituted saturated or unsaturated five- or six-membered heterocyclic thiocarbonyloxy, or oxo in the absence of a hydrogen atom at the 7-position.

Further, the pyripyropene derivative according to the present invention comprises a compound represented by formula (Ib) or an agriculturally and horticulturally acceptable salt thereof.

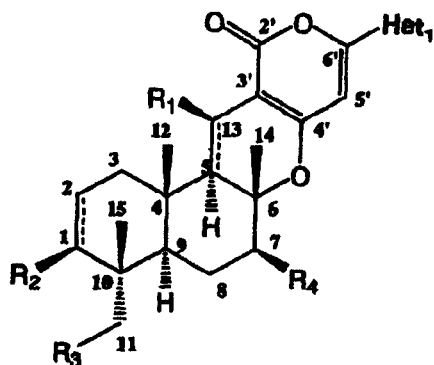

(Ib)

wherein $Het_1$ represents 3-pyridyl, $R_1$ represents hydroxyl, $R_2$ and $R_3$ represent propionyloxy or optionally substituted cyclic $C_{3-6}$ alkylcarbonyloxy, and $R_4$ represents hydroxyl, optionally substituted cyclic $C_{3-6}$ alkylcarbonyloxy, optionally substituted benzoyloxy, or optionally substituted saturated or unsaturated five- or six-membered heterocyclic carbonyloxy.

The pyripyropene derivatives reprsented by formula (I) or formula (Ib) according to the present invention have excellent control effect against agricultural and horiticultural pests, sanitary pests, parasites of animals, stored grain pests, clothing pests, and house pests and a compositions comprising the pyripyropene derivatives as active ingredient can be advantageously utilized as a novel pest control agent.

Further, it is surprising that, among the compounds represented by formula (Ia), pyripyropene A has excellent control effect against hemipteran pests. Accordingly, a composition according to the present invention comprising the compounds represented by formula (Ia) including pyripyropene A, can be advantageously utilized particularly a hemipteran pest control agent.

[DETAILED DESCRIPTION OF THE INVENTION]

The term "halogen" as used herein means fluorine, chlorine, bromine, or iodine, preferably fluorine, chlorine, or bromine.

The terms "alkyl," "alkenyl," and "alkynyl" as used herein as a group or a part of a group respectively mean alkyl, alkenyl, and alkynyl that the group is of a straight chain, branched chain, or cyclic type or a type of a combination thereof unless otherwise specified. Further, for example, "$C_{1-6}$" in "$C_{1-6}$ alkyl" as used herein as a group or a part of a group means that the number of carbon atoms in the alkyl group is 1 to 6. Further, in the case of cyclic alkyl, the number of carbon atoms is at least three.

The term "heterocyclic ring" as used herein means a heterocyclic ring containing one or more, preferably one to four, heteroatoms, which may be the same or different, selected from the group consisting of nitrogen, oxygen, and sulfur atoms. Further, the expression "optionally substituted" alkyl as used herein means that one or more hydrogen atoms on the alkyl group may be substituted by one or more substituents which may be the same or different. It will be apparent to a person having ordinary skill in the art that the maximum number of substituents may be determined depending upon the number of substitutable hydrogen atoms on the alkyl group. This is true of functional groups other than the alkyl group.

3-Pyridyl represented by $Het_1$ and $Het_2$ is optionally substituted, and substituents include halogen atoms, $C_{1-4}$ alkyl, $C_{1-4}$ alkyloxy, nitro, cyano, formyl, trifluoromethyl, trifluoromethoxy, trifluoromethylthio, trifluoromethylsulfinyl, trifluoromethylsulfonyl, acetyl, and acetyloxy. Preferred are halogen atoms and trifluoromethyl. A chlorine atom and trifluoromethyl are more preferred.

"$C_{1-6}$ alkylcarbonyloxy" represented by $R_1$ and $R_{11}$ is optionally substituted, and substituents include halogen atoms, cyano, phenyl, trifluoromethoxy, and trifluoromethylthio.

"$C_{1-18}$ alkylcarbonyloxy" represented by $R_2$, $R_3$ and $R_4$, and $R_{12}$, $R_{13}$ and $R_{14}$ is preferably $C_{1-6}$ alkylcarbonyloxy, more preferably propionyloxy or cyclic $C_{3-6}$ alkylcarbonyloxy. The $C_{1-18}$ alkylcarbonyloxy group is optionally substituted, and substituents include halogen atoms, cyano, cyclic $C_{3-6}$ alkyl, phenyl, trifluoromethoxy, trifluoromethylthio, pyridyl, and pyridylthio. More preferred are halogen atoms, cyclic $C_{3-6}$ alkyl, and pyridyl.

"$C_{2-6}$ alkenylcarbonyloxy" represented by $R_1$, $R_2$, $R_3$ and $R_4$, and $R_{11}$, $R_{12}$, $R_{13}$ and $R_{14}$ is optionally substituted, and substituents include halogen atoms, cyano, phenyl, trifluoromethoxy, and trifluoromethylthio.

"$C_{2-6}$ alkynylcarbonyloxy" represented by $R_1$, $R_2$, $R_3$ and $R_4$, and $R_{11}$, $R_{12}$, $R_{13}$ and $R_{14}$ is optionally substituted, and substituents include halogen atoms, cyano, phenyl, trifluoromethoxy, and trifluoromethylthio.

"$C_{1-6}$ alkyloxy" represented by $R_1$ and $R_4$, and $R_{11}$ and $R_{14}$ is optionally substituted, and substituents include halogen atoms; cyano; phenyl; trifluoromethoxy; trifluoromethylthio; $C_{1-6}$ alkylcarbonyl optionally substituted by a halogen atom; and $C_{1-6}$ alkylcarbonyloxy optionally substituted by a halogen atom.

"$C_{2-6}$ alkenyloxy" represented by $R_1$ and $R_4$, and $R_{11}$ and $R_{14}$ is optionally substituted, and substituents include halogen atoms; cyano; phenyl; trifluoromethoxy; trifluoromethylthio; $C_{1-6}$ alkylcarbonyl optionally substituted by a halogen atom; and $C_{1-6}$ alkylcarbonyloxy optionally substituted by a halogen atom.

"$C_{2-6}$ alkynyloxy" represented by $R_1$ and $R_4$, and $R_{11}$ and $R_{14}$ is optionally substituted, and substituents include halogen atoms; cyano; phenyl; trifluoromethoxy; trifluoromethylthio; $C_{1-6}$ alkylcarbonyl optionally substituted by a halogen atom; and $C_{1-6}$ alkylcarbonyloxy optionally substituted by a halogen atom.

Phenyl in "benzyloxy" represented by $R_1$ and $R_4$, and $R_{11}$ and $R_{14}$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; formyl; azide; guanidyl; group -C(=NH)-NH$_2$; and group -CH=N-O-CH$_3$.

Phenyl in "benzoyloxy" represented by $R_2$, $R_3$ and $R_4$, and $R_{12}$, $R_{13}$ and $R_{14}$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; nitro; formyl; azide; guanidyl; group -C(=NH)-NH$_2$; and group -CH=N-O-CH$_3$. Preferred are halogen atoms, $C_{1-6}$ alkyl substituted by a halogen atom, cyano, and nitro.

Phenyl in "benzenesulfonyloxy" represented by $R_3$ and $R_4$, and $R_{13}$ and $R_{14}$ is optionally substituted, and substituents include halogen atoms; $C_{1-6}$ alkyloxy optionally substituted by a halogen atom; $C_{1-6}$ alkyl optionally substituted by a halogen atom; $C_{1-6}$ alkylcarbonyl optionally substituted by a halogen atom; $C_{1-6}$ alkylcarbonyloxy optionally substituted by a halogen atom; $C_{1-6}$ alkylcarbonylamino optionally substituted by a halogen atom; $C_{1-6}$ alkylaminocarbonyloxy optionally substituted by a halogen atom; $C_{1-6}$ alkylaminocarbonyl optionally substituted by a halogen atom; $C_{1-6}$ alkylsulfonyloxy optionally substituted by a halogen atom; $C_{1-6}$ alkylthio optionally substituted by a halogen atom; $C_{1-6}$ alkylsulfinyl optionally substituted by a halogen atom; $C_{1-6}$ alkylsulfonyl optionally substituted by a halogen atom; cyano; formyl; azide; guanidyl; group -C(=NH)-NH$_2$; and group -CH=N-O-CH$_3$.

"$C_{1-6}$ alkylsulfonyloxy" represented by $R_2$, $R_3$ and $R_4$, and $R_{12}$, $R_{13}$ and $R_{14}$ is optionally substituted, and substituents include halogen atoms, cyano, phenyl, trifluoromethoxy, and trifluoromethylthio.

"$C_{1-6}$ alkyloxycarbonyloxy" represented by $R_4$ and $R_{14}$ is optionally substituted, and substituents include halogen atoms, cyano, phenyl, trifluoromethoxy, and trifluoromethylthio.

"$C_{1-6}$ alkylaminocarbonyloxy" represented by $R_4$ and $R_{14}$ is optionally substituted, and substituents include halogen atoms, cyano, phenyl, trifluoromethoxy, and trifluoromethylthio.

"Phenyl" represented by $R_2'$ and $R_3'$, and $R_{12}'$ and $R_{13}'$ and phenyl in "benzyl" represented by $R_2'$ and $R_3'$, and $R_{12}'$ and $R_{13}'$ is optionally substituted, and substituents include halogen atoms, $C_{1-4}$ alkyl, $C_{1-4}$ alkyloxy, nitro, cyano, formyl, trifluoromethoxy, acetyl, and acetyloxy.

"Saturated or unsaturated five- or six-membered heterocyclic ring" in "saturated or unsaturated five- or six-membered heterocyclic thiocarbonyloxy" represented by $R_3$ and $R_{13}$, and "saturated or unsaturated five- or six-membered heterocyclic oxy," "saturated or unsaturated five- or six-membered heterocyclic carbonyloxy," and "saturated or unsaturated five- or six-membered heterocyclic thiocarbonyloxy" represented by $R_4$ and $R_{14}$, is preferably, saturated or unsaturated five- or six-membered heterocyclic ring containing one to three heteroatoms selected from the group consisting of nitrogen, oxygen, and sulfur atoms, more preferably, saturated or unsaturated five- or six-membered heterocyclic ring containing one or two heteroatoms selected from the group consisting of nitrogen, oxygen, and sulfur atoms, more preferably, saturated or unsaturated five- or six-membered heterocyclic ring containing one or two nitrogen atoms, saturated or unsaturated five- or six-membered heterocyclic ring containing one or two oxygen atoms, saturated or unsaturated five- or six-membered heterocyclic ring containing one or two sulfur atoms, saturated or unsaturated five- or six-membered heterocyclic ring containing one nitrogen atom and one oxigen atom, or saturated or unsaturated five- or six-membered heterocyclic ring containing one nitrogen atom and one sulfur atom.

More specifically, examples of the "saturated or unsaturated five- or six-membered heterocyclic ring" include thienyl, furyl, pyrrolyl, imidazolyl, pyrazolyl, isothiazoyl, isoxazolyl, thiazolyl, oxazolyl, pyridyl, pyrimidinyl, pyrazinyl, pyridazinyl, tetrahydropyranyl, piperidinyl, piperazinyl, morpholinyl, and mannosyl. Preferred are pyridyl, furanyl, thiazolyl, imidazolyl, tetrahydropyranyl, and mannosyl. More specific examples thereof include (2- or 3-)thienyl, (2- or 3-)furyl, (1-, 2- or 3-)pyrrolyl, (1-, 2-, 4- or 5-)imidazolyl, (1-, 3-, 4- or 5-)pyrazolyl, (3-, 4- or 5-)isothiazoyl, (3-, 4- or 5-)isoxazolyl, (2-, 4- or 5-)thiazolyl, (2-, 4- or 5-)oxazolyl, (2-, 3- or 4-)pyridyl or, (2-, 4-, 5- or 6-)pyrimidinyl, (2- or 3-)pyrazinyl, (3- or 4-)pyridazinyl, (2-, 3- or 4-)tetrahydropyranyl, (1-, 2-, 3- or 4-)piperidinyl, (1-, 2- or 3-)piperazinyl, and (2-, 3- or 4-)morpholinyl, preferably 3-pyridyl, 2-franyl, 5-thiazolyl, 1-imidazolyl, 5-imidazolyl, and 2-tetrahydropyranyl, more preferably 2-tetrahydropyranyl, 2-pyrazinyl, and 3-pyridyl, particularly preferably 3-pyridyl.

The heterocyclic ring in the "saturated or unsaturated five- or six-membered heterocyclic carbonyloxy" and "saturated or unsaturated five- or six-membered heterocyclic thiocarbonyloxy" and "thieno[3,2-b]pyridylcarbonyloxy" and "1H-indolylcarbonyloxy" represented by $R_4$ and $R_{14}$ are optionally substituted, and substituents include halogen atoms, $C_{1-4}$ alkyl, $C_{1-4}$ alkyloxy, $C_{1-4}$ alkylthio, nitro, cyano, formyl, trifluoromethoxy, trifluoromethyl, trifluoromethylthio, trifluoromethylsulfinyl, trifluoromethylsulfonyl, acetyl, acetyloxy, benzoyl, and $C_{1-4}$ alkyloxycarbonyl. Preferred are halogen atoms, $C_{1-4}$ alkyl, $C_{1-4}$ alkyloxy, and trifluoromethyl.

The heterocyclic ring in the "saturated or unsaturated five- or six-membered heterocyclic oxy" is optionally substituted, and substituents include hydroxyl, benzyloxy, a halogen atom, $C_{1-4}$ alkyl, $C_{1-4}$ alkyloxy, nitro, cyano, formyl, trifluoromethoxy, trifluoromethyl, trifluoromethylthio, trifluoromethylsulfinyl, trifluoromethylsulfonyl, acetyl, and acetyloxy. Preferred are hydroxyl and benzyloxy.

<u>A composition for use as a pest control agent, comprising a compound represented by formula (I)</u>

According to a preferred embodiment of the present invention, in the compound represented by formula (I), preferably, $Het_1$ represents 3-pyridyl.

Further, according to a preferred embodiment of the present invention, in the compound represented by formula (I), $R_1$ represents hydroxyl, $C_{1-6}$ alkylcarbonyloxy, $C_{1-3}$ alkyloxy, or benzyloxy, or oxo in the absence of a hydrogen atom at the 13-position, or the bond between 5-position and 13-position represents a double bond in the absence of $R_1$ and a hydrogen atom at the 5-position. More preferably, $R_1$ represents hydroxyl or $C_{1-6}$ alkylcarbonyloxy, or the bond between 5-position and 13-position represents a double bond in the absence of $R_1$ and a hydrogen atom at the 5-position, still more preferably $R_1$ represents hydroxyl.

According to a preferred embodiment of the present invention, in the compound represented by formula (I), $R_2$ represents hydroxyl, optionally substituted $C_{1-18}$ alkylcarbonyloxy, optionally substituted benzoyloxy, or $C_{1-3}$ alkylsulfonyloxy, more preferably optionally substituted $C_{1-18}$ alkylcarbonyloxy, still more preferably optionally substituted $C_{1-6}$ alkylcarbonyloxy, still more preferably straight chain or branched chain $C_{1-6}$ alkylcarbonyloxy (particularly propionyloxy) or optionally substituted cyclic $C_{3-6}$ alkylcarbonyloxy.

In a preferred embodiment of the present invention, in the compound represented by formula (I), $R_3$ represents a hydrogen atom, hydroxyl, optionally substituted $C_{1-18}$ alkylcarbonyloxy, optionally substituted benzoyloxy, $C_{1-6}$ alkylsulfonyloxy, optionally substituted benzenesulfonyloxy, or saturated or unsaturated five- or six-membered heterocyclic thiocarbonyloxy, more preferably optionally substituted $C_{1-6}$ alkylcarbonyloxy or $C_{1-6}$ alkylsulfonyloxy, still more preferably optionally substituted $C_{1-6}$ alkylcarbonyloxy, still more preferably straight chain or branched chain $C_{2-4}$ alkylcarbonyloxy (particularly propionyloxy) or optionally substituted cyclic $C_{3-6}$ alkylcarbonyloxy.

According to a preferred embodiment of the present invention, in the compound represented by formula (I), $R_2$ and $R_3$ together represent -O-CR$_2$'R$_3$'-O-, wherein $R_2$' and $R_3$' which may be the same or different, represent a hydrogen atom, $C_{1-6}$ alkyl, $C_{1-3}$ alkyloxy, $C_{2-3}$ alkenyl, benzyl, or optionally substituted phenyl, or $R_2$' and $R_3$' together represent oxo or $C_{2-6}$ alkylene. More preferably, $R_2$ and $R_3$ together represent -O-CR$_2$'R$_3$'-O-, wherein $R_2$' and $R_3$' which may be the same or different, represent a hydrogen atom, $C_{1-6}$ alkyl, or optionally substituted phenyl, or $R_2$' and $R_3$' together represent oxo or $C_{2-6}$ alkylene.

According to a preferred embodiment of the present invention, in the compound represented by formula (I), $R_4$ represents a hydrogen atom, hydroxyl, optionally substituted $C_{1-18}$ alkylcarbonyloxy, $C_{2-6}$ alkenylcarbonyloxy, $C_{2-6}$ alkynyl carbonyloxy, $C_{1-6}$ alkylsulfonyloxy, benzenesulfonyloxy, benzyloxy, $C_{1-3}$ alkyloxy, $C_{1-3}$ alkyloxy-$C_{1-3}$ alkyloxy, $C_{1-3}$ alkylthio-$C_{1-3}$ alkyloxy, $C_{1-3}$ alkyloxy-$C_{1-3}$ alkyloxy-$C_{1-3}$ alkyloxy, optionally substituted $C_{1-3}$ alkyloxycarbonyloxy, optionally substituted $C_{1-6}$ alkylaminocarbonyloxy, optionally substituted benzoyloxy, saturated or unsaturated five- or six-membered heterocyclic oxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. More preferably, $R_4$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. Still more preferably, $R_4$ represents hydroxyl, optionally substituted $C_{1-6}$ alkylcarbonyloxy, saturated or unsaturated five- or six-membered heterocyclic oxy, optionally substituted benzoyloxy, optionally substituted saturated or unsaturated five- or six-membered heterocyclic carbonyloxy, or saturated or unsaturated five- or six-membered heterocyclic thiocarbonyloxy. Still more preferably, $R_4$ represents hydroxyl, straight chain or branched chain $C_{2-4}$ alkylcarbonyloxy (particularly propionyloxy), optionally substituted cyclic $C_{3-6}$ alkylcarbonyloxy, or optionally substituted saturated or unsaturated five- or six-membered heterocyclic carbonyloxy.

According to another preferred embodiment of the present invention, in the compound represented by formula (I), $Het_1$ represents 3-pyridyl, $R_1$ represents hydroxyl or $C_{1-6}$ alkylcarbonyloxy, or the bond between 5-position and 13-position represents a double bond in the absence of and a hydrogen atom at the 5-position, $R_2$ represents optionally substituted $C_{1-6}$ alkylcarbonyloxy, $R_3$ represents optionally substituted $C_{1-6}$ alkylcarbonyloxy or $C_{1-6}$ alkylsulfonyloxy, or $R_2$ and $R_3$ together represent -O-$CR_2'R_3'$-O- wherein $R_2'$ and $R_3'$, which may be the same or different, represent a hydrogen atom, $C_{1-6}$ alkyl, or optionally substituted phenyl, or $R_2'$ and $R_3'$ together represent oxo or $C_{2-6}$ alkylene, and $R_4$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (I), $Het_1$ represents 3-pyridyl, $R_1$ represents hydroxyl, $R_2$ represents optionally substituted $C_{1-6}$ alkylcarbonyloxy, and $R_3$ represents optionally substituted $C_{1-6}$ alkylcarbonyloxy or $C_{1-6}$ alkylsulfonyloxy, and $R_4$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six- membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (I), $Het_1$ represents 3-pyridyl, represents hydroxyl, $R_2$ represents optionally substituted $C_{1-6}$ alkylcarbonyloxy, $R_3$ represents optionally substituted $C_{1-6}$ alkylcarbonyloxy or $C_{1-6}$ alkylsulfonyloxy, and $R_4$ represents hydroxyl, optionally substituted $C_{1-6}$ alkylcarbonyloxy, optionally substituted benzoyloxy, saturated or unsaturated five- or six-membered heterocyclic oxy, optionally substituted saturated or unsaturated five- or six-membered heterocyclic carbonyloxy, or saturated or unsaturated five- or six-membered heterocyclic thiocarbonyloxy.

According to another preferred embodiment of the present invention, in the compound represented by formula (I), $Het_1$ represents 3-pyridyl, $R_1$ represents hydroxyl, and $R_2$ and $R_3$ represent optionally substituted cyclic $C_{3-6}$ alkylcarbonyloxy.

According to another preferred embodiment of the present invention, in the compound represented by formula (I),
    $Het_1$ represents 3-pyridyl,
    $R_1$ represents hydroxyl or
        optionally substituted $C_{1-6}$ alkylcarbonyloxy or
    the bond between 5-position and 13-position represents a double bond in the absence of $R_1$ and a hydrogen atom at the 5-position,
    $R_2$ represents optionally substituted $C_{1-18}$ alkylcarbonyloxy or
        optionally substituted benzoyloxy,
    $R_3$ represents optionally substituted $C_{1-18}$ alkylcarbonyloxy or
        optionally substituted $C_{1-6}$ alkylsulfonyloxy, and
    $R_4$ represents hydroxyl,
        optionally substituted $C_{1-18}$ alkylcarbonyloxy,
        optionally substituted $C_{2-6}$ alkenylcarbonyloxy,
        optionally substituted benzoyloxy,
        optionally substituted $C_{1-6}$ alkylaminocarbonyloxy,
        optionally substituted saturated or unsaturated five- or six-membered heterocyclic oxy,
        optionally substituted saturated or unsaturated five- or six-membered heterocyclic carbonyloxy,
        optionally substituted thieno[3,2-b]pyridylcarbonyloxy
        optionally substituted 1H-indolylcarbonyloxy, or
        oxo in the absence of a hydrogen atom at the 7-position.

According to another preferred embodiment of the present invention, in the compound represented by formula (I), Het$_1$ represents 3-pyridyl, R$_1$ represents hydroxyl or
    optionally substituted C$_{1-6}$ alkylcarbonyloxy, or the bond between 5-position and 13-position represents a double bond in the absence of R$_1$ and a hydrogen atom at the 5-position, R$_2$ represents optionally substituted C$_{1-18}$ alkylcarbonyloxy, R$_3$ represents optionally substituted C$_{1-18}$ alkylcarbonyloxy or
    optionally substituted C$_{1-6}$ alkylsulfonyloxy, and R$_4$ represents hydroxyl,
    optionally substituted C$_{1-18}$ alkylcarbonyloxy,
    optionally substituted C$_{2-6}$ alkenylcarbonyloxy,
    optionally substituted benzoyloxy,
    optionally substituted C$_{1-6}$ alkylaminocarbonyloxy,
    optionally substituted saturated or unsaturated five- or six-membered heterocyclic oxy,
    optionally substituted saturated or unsaturated five- or six-membered heterocyclic carbonyloxy, or
    oxo in the absence of a hydrogen atom at the 7-position.

According to another preferred embodiment of the present invention, in the compound represented by formula (I), Het$_1$ represents 3-pyridyl, R$_1$ represents hydroxyl or
    optionally substituted C$_{1-6}$ alkylcarbonyloxy, or the bond between 5-position and 13-position represents a double bond in the absence of R$_1$ and a hydrogen atom at the 5-position, R$_2$ represents optionally substituted C$_{1-18}$ alkylcarbonyloxy, R$_3$ represents optionally substituted C$_{1-18}$ alkylcarbonyloxy, R$_4$ represents hydroxyl,
    optionally substituted C$_{1-18}$ alkylcarbonyloxy,
    optionally substituted benzoyloxy,
    optionally substituted saturated or unsaturated five- or six-membered heterocyclic oxy, or
    optionally substituted saturated or unsaturated five- or six-membered heterocyclic carbonyloxy.

According to another preferred embodiment of the present invention, in the compound represented by formula (I), Het$_1$ represents 3-pyridyl, R$_1$ represents hydroxyl, R$_2$ represents C$_{1-6}$ alkylcarbonyloxy, and R$_3$ and/or R$_4$ represent C$_{2-4}$ alkylcarbonyloxy.

Further, an agriculturally and horticulturally acceptable salt of the compound represented by formula (I) include the same as that of the compound represented by formula (Ib) described below.

A composition for use as a hemipteran pest control agent, comprising a compound represented by formula (Ia)

According to a preferred embodiment of the present invention, in the compound represented by formula (Ia), preferably, $Het_2$ represents 3-pyridyl.

Further, according to a preferred embodiment of the present invention, in the compound represented by formula (Ia), $R_{11}$ represents hydroxyl, $C_{1-6}$ alkylcarbonyloxy, $C_{1-3}$ alkyloxy, or benzyloxy, or oxo in the absence of a hydrogen atom at the 13-position, or the bond between 5-position and 13-position represents a double bond in the absence of $R_{11}$ and a hydrogen atom at the 5-position. More preferably, $R_{11}$ represents hydroxyl or $C_{1-6}$ alkylcarbonyloxy, or the bond between 5-position and 13-position represents a double bond in the absence of $R_{11}$ and a hydrogen atom at the 5-position, still more preferably $R_{11}$ represents hydroxyl.

According to a preferred embodiment of the present invention, in the compound represented by formula (Ia), $R_{12}$ represents hydroxyl, optionally substituted $C_{1-18}$ alkylcarbonyloxy, optionally substituted benzoyloxy, or $C_{1-3}$ alkylsulfonyloxy, more preferably optionally substituted $C_{1-18}$ alkylcarbonyloxy, still more preferably optionally substituted $C_{1-6}$ alkylcarbonyloxy, still more preferably straight chain or branched chain $C_{1-6}$ alkylcarbonyloxy (particularly propionyloxy) or optionally substituted cyclic $C_{3-6}$ alkylcarbonyloxy.

In a preferred embodiment of the present invention, in the compound represented by formula (Ia), $R_{13}$ represents a hydrogen atom, hydroxyl, optionally substituted $C_{1-18}$ alkylcarbonyloxy, optionally substituted benzoyloxy, $C_{1-6}$ alkylsulfonyloxy, optionally substituted benzenesulfonyloxy, or saturated or unsaturated five- or six-membered heterocyclic thiocarbonyloxy, more preferably optionally substituted $C_{1-6}$ alkylcarbonyloxy or $C_{1-6}$ alkylsulfonyloxy, still more preferably optionally substituted $C_{1-6}$ alkylcarbonyloxy, still more preferably straight chain or branched chain $C_{2-4}$ alkylcarbonyloxy (particularly propionyloxy) or optionally substituted cyclic $C_{3-6}$ alkylcarbonyloxy.

According to a preferred embodiment of the present invention, in the compound represented by formula (Ia), $R_{12}$ and $R_{13}$ together represent -O-$CR_{12}'R_{13}'$-O-, wherein $R_{12}'$ and $R_{13}'$, which may be the same or different, represent a hydrogen atom, $C_{1-6}$ alkyl, $C_{1-3}$ alkyloxy, $C_{2-3}$ alkenyl, benzyl, or optionally substituted phenyl, or $R_{12}'$ and $R_{13}'$ together represent oxo or $C_{2-6}$ alkylene. More preferably, $R_{12}$ and $R_{13}$ together represent -O-$CR_{12}'R_{13}'$-O-, wherein $R_{12}'$ and $R_{13}'$, which may be the same or different, represent a hydrogen atom, $C_{1-6}$ alkyl, or optionally substituted phenyl, or $R_{12}'$ and $R_{13}'$ together represent oxo or $C_{2-6}$ alkylene.

According to a preferred embodiment of the present invention, in the compound represented by formula (Ia), $R_{14}$ represents a hydrogen atom, hydroxyl, optionally substituted $C_{1-18}$ alkylcarbonyloxy, $C_{2-6}$ alkenylcarbonyloxy, $C_{2-6}$ alkynyl carbonyloxy, $C_{1-6}$ alkylsulfonyloxy, benzenesulfonyloxy, benzyloxy, $C_{1-3}$ alkyloxy, $C_{1-3}$ alkyloxy-$C_{1-3}$ alkyloxy, $C_{1-3}$ alkylthio-$C_{1-3}$ alkyloxy, $C_{1-3}$ alkyloxy-$C_{1-3}$ alkyloxy-$C_{1-3}$ alkyloxy, optionally substituted $C_{1-3}$ alkyloxycarbonyloxy, optionally substituted $C_{1-6}$ alkylaminocarbonyloxy, optionally substituted benzoyloxy, saturated or unsaturated five- or six-membered heterocyclic oxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. More preferably, $R_{14}$ represents hydroxyl, optionally substituted $C_{1-6}$ alkylcarbonyloxy, optionally substituted benzoyloxy, saturated or unsaturated five- or six-membered heterocyclic oxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, or saturated or unsaturated five- or six-membered heterocyclic thiocarbonyloxy, or oxo in the absence of a hydrogen atom at the 7-position. Still more preferably, $R_{14}$ represents hydroxyl, optionally substituted $C_{1-6}$ alkylcarbonyloxy, saturated or unsaturated five- or six-membered heterocyclic oxy, optionally substituted benzoyloxy, optionally substituted saturated or unsaturated five- or six-membered heterocyclic carbonyloxy, or saturated or unsaturated five- or six-membered heterocyclic thiocarbonyloxy. Still more preferably, $R_{14}$ represents straight chain or branched chain $C_{2-4}$ alkylcarbonyloxy (particularly propionyloxy), optionally substituted cyclic $C_{3-6}$ alkylcarbonyloxy, or optionally substituted saturated or unsaturated five- or six-membered heterocyclic carbonyloxy.

According to another preferred embodiment of the present invention, in the compound represented by formula (Ia), $Het_2$ represents 3-pyridyl, $R_{11}$ represents hydroxyl or $C_{1-6}$ alkylcarbonyloxy, or the bond between 5-position and 13-position represents a double bond in the absence of $R_{11}$ and a hydrogen atom at the 5-position, $R_{12}$ represents optionally substituted $C_{1-6}$ alkylcarbonyloxy, $R_{13}$ represents optionally substituted $C_{1-6}$ alkylcarbonyloxy or $C_{1-6}$ alkylsulfonyloxy, or $R_{12}$ and $R_{13}$ together represent -O-CR$_{12}$'R$_{13}$'-O- wherein $R_{12}$' and $R_{13}$', which may be the same or different, represent a hydrogen atom, $C_{1-6}$ alkyl, or optionally substituted phenyl, or $R_{12}$' and $R_{13}$' together represent oxo or $C_{2-6}$ alkylene, and $R_{14}$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six-membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (Ia), $Het_2$ represents 3-pyridyl, $R_{11}$ represents hydroxyl, $R_{12}$ represents optionally substituted $C_{1-6}$ alkylcarbonyloxy, and $R_{13}$ represents optionally substituted $C_{1-6}$ alkylcarbonyloxy or $C_{1-6}$ alkylsulfonyloxy, and $R_{14}$ represents hydroxyl, optionally substituted $C_{1-6}$ alkylcarbonyloxy, saturated or unsaturated five- or six-membered heterocyclic oxy, optionally substituted benzoyloxy, $C_{1-3}$ alkyloxy-$C_{1-3}$ alkyloxy, optionally substituted $C_{1-6}$ alkylaminocarbonyloxy, optionally substituted saturated or unsaturated five- or six- membered heterocyclic carbonyloxy, optionally substituted thieno[3,2-b]pyridylcarbonyloxy, optionally substituted 1H-indolylcarbonyloxy, saturated or unsaturated five- or six-membered heterocyclic thiocarbonyloxy, or oxo in the absence of a hydrogen atom at the 7-position.

According to another preferred embodiment of the present invention, in the compound represented by formula (Ia), $Het_2$ represents 3-pyridyl, $R_{11}$ represents hydroxyl, $R_{12}$ represents optionally substituted $C_{1-6}$ alkylcarbonyloxy, $R_{13}$ represents optionally substituted $C_{1-6}$ alkylcarbonyloxy or $C_{1-6}$ alkylsulfonyloxy, and $R_{14}$ represents hydroxyl, optionally substituted $C_{1-6}$ alkylcarbonyloxy, optionally substituted benzoyloxy, saturated or unsaturated five- or six-membered heterocyclic oxy, optionally substituted saturated or unsaturated five- or six-membered heterocyclic carbonyloxy, or saturated or unsaturated five- or six-membered heterocyclic thiocarbonyloxy.

According to another preferred embodiment of the present invention, in the compound represented by formula (Ia), $Het_2$ represents 3-pyridyl, $R_{11}$ represents hydroxyl, and $R_{12}$ and $R_{13}$ represent optionally substituted cyclic $C_{3-6}$ alkylcarbonyloxy.

According to another preferred embodiment of the present invention, in the compound represented by formula (Ia),
    $Het_2$ represents 3-pyridyl,
    $R_{11}$ represents hydroxyl or
        optionally substituted $C_{1-6}$ alkylcarbonyloxy, or
    the bond between 5-position and 13-position represents a double bond in the absence of $R_{11}$ and a hydrogen atom at the 5-position, $R_{12}$ represents optionally substituted $C_{1-18}$ alkylcarbonyloxy or
  optionally substituted benzoyloxy,
$R_{13}$ represents optionally substituted $C_{1-18}$ alkylcarbonyloxy or
  optionally substituted $C_{1-6}$ alkylsulfonyloxy, and
$R_{14}$ represents hydroxyl,
  optionally substituted $C_{1-18}$ alkylcarbonyloxy,
  optionally substituted $C_{2-6}$ alkenylcarbonyloxy,
  optionally substituted benzoyloxy,
  optionally substituted $C_{1-6}$ alkylaminocarbonyloxy,
  optionally substituted saturated or unsaturated five- or
six-membered heterocyclic oxy,
  optionally substituted saturated or unsaturated five- or
six-membered heterocyclic carbonyloxy,
  optionally substituted thieno[3,2-b]pyridylcarbonyloxy,
  optionally substituted 1H-indolylcarbonyloxy, or
  oxo in the absence of a hydrogen atom at the 7-position.

According to another preferred embodiment of the present invention, in the compound represented by formula (Ia),
$Het_2$ represents 3-pyridyl,
$R_{11}$ represents hydroxyl or
  optionally substituted $C_{1-6}$ alkylcarbonyloxy, or
the bond between 5-position and 13-position represents a double bond in the absence of $R_{11}$ and a hydrogen atom at the 5-position,
$R_{12}$ represents optionally substituted $C_{1-18}$ alkylcarbonyloxy,
$R_{13}$ represents optionally substituted $C_{1-18}$ alkylcarbonyloxy or
  optionally substituted $C_{1-6}$ alkylsulfonyloxy, and
$R_{14}$ represents hydroxyl,
  optionally substituted $C_{1-18}$ alkylcarbonyloxy,
  optionally substituted $C_{2-6}$ alkenylcarbonyloxy,
  optionally substituted benzoyloxy,
  optionally substituted $C_{1-6}$ alkylaminocarbonyloxy,
  optionally substituted saturated or unsaturated five- or
six-membered heterocyclic oxy,
  optionally substituted saturated or unsaturated five- or
six-membered heterocyclic carbonyloxy, or
  oxo in the absence of a hydrogen atom at the 7-position.

According to another preferred embodiment of the present invention, in the compound represented by formula (Ia),
$Het_2$ represents 3-pyridyl,
$R_{11}$ represents hydroxyl or
  optionally substituted $C_{1-6}$ alkylcarbonyloxy, or
the bond between 5-position and 13-position represents a double bond in the absence of $R_{11}$ and a hydrogen atom at the 5-position, $R_{12}$ represents optionally substituted $C_{1-18}$ alkylcarbonyloxy, $R_{13}$ represents optionally substituted $C_{1-18}$ alkylcarbonyloxy, $R_{14}$ represents hydroxyl,
- optionally substituted $C_{1-18}$ alkylcarbonyloxy,
- optionally substituted benzoyloxy,
- optionally substituted saturated or unsaturated five- or six-membered heterocyclic oxy, or
- optionally substituted saturated or unsaturated five- or six-membered heterocyclic carbonyloxy.

According to another preferred embodiment of the present invention, in the compound represented by formula (Ia), $Het_2$ represents 3-pyridyl, $R_{11}$ represents hydroxyl, $R_{12}$ represents $C_{1-6}$ alkylcarbonyloxy, and $R_{13}$ and/or $R_{14}$ represent $C_{2-4}$ alkylcarbonyloxy.

Further, an agriculturally and horticulturally acceptable salt of the compound represented by formula (Ia) include the same as that of the compound represented by formula (Ib) described below.

Compunds of formula (Ib) or its agriculturally and horticulturally acceptable salts Compounds of formula (Ib) are novel pyripyropene derivatives that are comprised as a part in the compound represented by formula (I). In particular, they have significant insecticidal activity.

According to an embodiment of the present invention, there is provided the compounds of formula (Ib), excluding a compound wherein $Het_1$ represents 3-pyridyl, $R_1$ represents hydroxyl, and $R_2$ and $R_3$ represent propionyloxy, and $R_4$ represents hydroxyl.

According to another preferred embodiment of the present invention, in the compound represented by formula (Ib), $R_2$ and $R_3$ represent optionally substituted cyclic $C_{3-6}$ alkylcarbonyloxy, $R_4$ represents hydroxyl, optionally substituted cyclic $C_{3-6}$ alkylcarbonyloxy, or optionally substituted benzoyloxy. Alternatively, $R_2$ and $R_3$ represent propionyloxy, $R_4$ represents optionally substituted cyclic $C_{3-6}$ alkylcarbonyloxy, or optionally substituted saturated or unsaturated five- or six-membered heterocyclic carbonyloxy.

According to another preferred embodiment of the present invention, in the compounds represented by formula (Ib), $R_2$ and $R_3$ represent optionally substituted cyclic $C_{3-6}$ alkylcarbonyloxy, $R_4$ represents hydroxyl, optionally substituted cyclic $C_{3-6}$ alkylcarbonyloxy, or optionally substituted benzoyloxy.

According to another preferred embodiment of the present invention, in the compounds represented by formula (Ib), $R_2$ and $R_3$ represent propionyloxy, $R_4$ represents optionally substituted cyclic $C_{3-6}$ alkylcarbonyloxy or optionally substituted saturated or unsaturated five- or six-membered heterocyclic carbonyloxy.

According to still another preferred embodiment of the present invention, there is provided a pest control agent comprising a compound represented by formula (Ib) or an agriculturally and horticulturally acceptable salt thereof as an active ingredient.

Agriculturally and horticulturally acceptable salts in the compounds of formula (Ib) include, for example, acid addition salts such as hydrochlorides, nitrates, sulfates, phosphates, or acetates.

Specific examples of the compounds represented by formula (I), (Ia), or (Ib) include compounds shown in Tables 1 to 14 below. In the following tables, H(=) means that the bond between 5-position and 13-position represents a double bond in the absence of $R_1$ and a hydrogen atom at the 5-position.

Table 1

| Compound No. | $R_1$ | $R_2$ | $R_3$ | $R_4$ | $Het_1$ |
|---|---|---|---|---|---|
| 1 | OH | $OCOCH_3$ | $OCOCH_3$ | $OCOCH_2CH_3$ | 3-pyridyl |
| 2 | OH | $OCOCH_3$ | $OCOCH_3$ | $OCOCH_2CF_3$ | 3-pyridyl |
| 3 | OH | $OCOCH_3$ | $OCOCH_3$ | $OCOCH_2OCH_3$ | 3-pyridyl |
| 4 | OH | $OCOCH_3$ | $OCOCH_3$ | $OCOCH_2OCOCH_3$ | 3-pyridyl |
| 5 | OH | $OCOCH_3$ | $OCOCH_3$ | $OCOCH_2CH_2CN$ | 3-pyridyl |
| 6 | OH | $OCOCH_3$ | $OCOCH_3$ | $OCO(CH_2)_2CH_3$ | 3-pyridyl |
| 7 | OH | $OCOCH_3$ | $OCOCH_3$ | $OCO(CH_2)_3CH_3$ | 3-pyridyl |
| 8 | OH | $OCOCH_3$ | $OCOCH_3$ | $OCO(CH_2)_4CH_3$ | 3-pyridyl |
| 9 | OH | $OCOCH_3$ | $OCOCH_3$ | $OCO(CH_2)_5CH_3$ | 3-pyridyl |
| 10 | OH | $OCOCH_3$ | $OCOCH_3$ | $OCO(CH_2)_6CH_3$ | 3-pyridyl |
| 11 | OH | $OCOCH_3$ | $OCOCH_3$ | $OCO(CH_2)_{16}CH_3$ | 3-pyridyl |
| 12 | OH | $OCOCH_3$ | $OCOCH_3$ | $OCOCH(CH_3)_2$ | 3-pyridyl |
| 13 | OH | $OCOCH_3$ | $OCOCH_3$ | $OCOC(CH_3)_3$ | 3-pyridyl |
| 14 | OH | $OCOCH_3$ | $OCOCH_3$ | $OCOCH_2CH(CH_3)_2$ | 3-pyridyl |
| 15 | OH | $OCOCH_3$ | $OCOCH_3$ | $OCO(CH_2)_2CH(CH_3)_2$ | 3-pyridyl |
| 16 | OH | $OCOCH_3$ | $OCOCH_3$ | OCO-trans-$CH=CHCH_2CH_3$ | 3-pyridyl |
| 17 | OH | $OCOCH_3$ | $OCOCH_3$ | $OCOCH_2C\equiv CCH_3$ | 3-pyridyl |
| 18 | OH | $OCOCH_3$ | $OCOCH_3$ | $OCOC\equiv CCH_2CH_3$ | 3-pyridyl |
| 19 | OH | $OCOCH_3$ | $OCOCH_3$ | $OCO(CH_2)_2C\equiv CH$ | 3-pyridyl |
| 20 | OH | $OCOCH_3$ | $OCOCH_3$ | $OCO(CH_2)_2CH=CH_2$ | 3-pyridyl |

Table 2

| Compound No. | $R_1$ | $R_2$ | $R_3$ | $R_4$ | $Het_1$ |
|---|---|---|---|---|---|
| 21 | OH | OCOCH$_3$ | OCOCH$_3$ | OCOCH$_2$C$_6$H$_5$ | 3-pyridyl |
| 22 | OH | OCOCH$_3$ | OCOCH$_3$ | OCO(CH$_2$)$_2$C$_6$H$_5$ | 3-pyridyl |
| 23 | OH | OCOCH$_3$ | OCOCH$_3$ | OCOC$_6$H$_5$ | 3-pyridyl |
| 24 | OH | OCOCH$_3$ | OCOCH$_3$ | OCO-(4-Br-C$_6$H$_4$) | 3-pyridyl |
| 25 | OH | OCOCH$_3$ | OCOCH$_3$ | OCO-(4-N$_3$-C$_6$H$_4$) | 3-pyridyl |
| 26 | OH | OCOCH$_3$ | OCOCH$_3$ | OCO-(4-OCF$_3$-C$_6$H$_4$) | 3-pyridyl |
| 27 | OH | OCOCH$_3$ | OCOCH$_3$ | OCO-(4-SO$_2$CF$_3$-C$_6$H$_4$) | 3-pyridyl |
| 28 | OH | OCOCH$_3$ | OCOCH$_3$ | OCO-(3-pyridyl) | 3-pyridyl |
| 29 | OH | OCOCH$_3$ | OCOCH$_3$ | OCO-(2-Cl-3-pyridyl) | 3-pyridyl |
| 30 | OH | OCOCH$_3$ | OCOCH$_3$ | OCO-(2-franyl) | 3-pyridyl |
| 31 | OH | OCOCH$_3$ | OCOCH$_3$ | OCO-(2-thiazolyl) | 3-pyridyl |
| 32 | OH | OCOCH$_3$ | OCOCH$_3$ | OCO-(2-Cl-5-thiazolyl) | 3-pyridyl |
| 33 | OH | OCOCH$_3$ | OCOCH$_3$ | OCO-(5-imidazolyl) | 3-pyridyl |
| 34 | OH | OCOCH$_3$ | OCOCH$_3$ | OCS-(1-imidazolyl) | 3-pyridyl |
| 35 | OH | OCOCH$_3$ | OCOCH$_3$ | OCOOCH$_2$C$_6$H$_5$ | 3-pyridyl |
| 36 | OH | OCOCH$_3$ | OCOCH$_3$ | OSO$_2$CH$_3$ | 3-pyridyl |
| 37 | OH | OCOCH$_3$ | OCOCH$_3$ | OSO$_2$C$_6$H$_5$ | 3-pyridyl |
| 38 | OH | OCOCH$_3$ | OCOCH$_3$ | OCONHCH$_2$CH$_3$ | 3-pyridyl |
| 39 | OH | OCOCH$_3$ | OCOCH$_3$ | OCONH(CH$_2$)$_2$CH$_3$ | 3-pyridyl |
| 40 | OH | OCOCH$_3$ | OCOCH$_3$ | OCONHCH$_2$C$_6$H$_5$ | 3-pyridyl |

Table 3

| Compound No. | $R_1$ | $R_2$ | $R_3$ | $R_4$ | $Het_1$ |
|---|---|---|---|---|---|
| 41 | OH | OCOCH$_3$ | OCOCH$_3$ | OCH$_2$C$_6$H$_5$ | 3-pyridyl |
| 42 | OH | OCOCH$_3$ | OCOCH$_3$ | OCH$_2$SCH$_3$ | 3-pyridyl |
| 43 | OH | OCOCH$_3$ | OCOCH$_3$ | OCH$_2$OCH$_3$ | 3-pyridyl |
| 44 | OH | OCOCH$_3$ | OCOCH$_3$ | OCH$_2$OCH$_2$CH$_2$OCH$_3$ | 3-pyridyl |
| 45 | OH | OCOCH$_3$ | OCOCH$_3$ | O-(2-tetrahydropyranyl) | 3-pyridyl |
| 46 | OH | OCOCH$_3$ | OCOCH$_3$ | O-(tetra-O-benzyl-mannosyl) | 3-pyridyl |
| 47 | OH | OCOCH$_3$ | OCOCH$_3$ | H | 3-pyridyl |
| 48 | OH | OCOCH$_3$ | OCOCH$_3$ | OCO-c-C$_3$H$_5$ | 3-pyridyl |
| 49 | OH | OCOCH$_3$ | OCOCH$_3$ | OH | 3-pyridyl |
| 50 | OH | OCOCH$_3$ | OCOCH$_3$ | =O | 3-pyridyl |
| 51 | OH | OCOCH$_3$ | OCOCH2CH3 | OCOCH$_3$ | 3-pyridyl |
| 52 | OH | OCOCH$_3$ | OCOCH2CH3 | OCOCH$_2$CH$_3$ | 3-pyridyl |

| | | | | | |
|---|---|---|---|---|---|
| 53 | OH | OCOCH₃ | OCOCH₂CH₃ | H | 3-pyridyl |
| 54 | OH | OCOCH₃ | OCO(CH₂)₂CH₃ | OCOCH₃ | 3-pyridyl |
| 55 | OH | OCOCH₃ | OCO(CH₂)₂CH₃ | OH | 3-pyridyl |
| 56 | OH | OCOCH₃ | OCO(CH₂)₃CH₃ | OCOCH₃ | 3-pyridyl |
| 57 | OH | OCOCH₃ | OCOCH(CH₃)₂ | OCOCH₃ | 3-pyridyl |
| 58 | OH | OCOCH₃ | OCOC₆H₅ | OCOCH₃ | 3-pyridyl |
| 59 | OH | OCOCH₃ | OCOC₆H₅ | OH | 3-pyridyl |
| 60 | OH | OCOCH₃ | OCS-(1-imidazolyl) | OCOCH₃ | 3-pyridyl |

Table 4

| Compound No. | R₁ | R₂ | R₃ | R₄ | Het₁ |
|---|---|---|---|---|---|
| 61 | OH | OCOCH₃ | OSO₂CH₃ | OCOCH₃ | 3-pyridyl |
| 62 | OH | OCOCH₃ | OSO₂CH₃ | OCO(CH₂)₃CH₃ | 3-pyridyl |
| 63 | OH | OCOCH₃ | OSO₂C₆H₅ | OCOCH₃ | 3-pyridyl |
| 64 | OH | OCOCH₃ | OSO₂CH₂CH₃ | OCOCH₃ | 3-pyridyl |
| 65 | OH | OCOCH₃ | OSO₂CH₂CH₂CH₃ | OCOCH₃ | 3-pyridyl |
| 66 | OH | OCOCH₃ | OSO₂CH₂CH₃ | OH | 3-pyridyl |
| 67 | OH | OCOCH₃ | OSO₂CH₂CH₂CH₃ | OH | 3-pyridyl |
| 68 | OH | OCOCH₃ | OH | OH | 3-pyridyl |
| 69 | OH | OCOCH₃ | OH | OCOCH₃ | 3-pyridyl |
| 70 | OH | OCOCH₃ | H | H | 3-pyridyl |
| 71 | OH | OCOCH₃ | H | OCOCH₂CH₃ | 3-pyridyl |
| 72 | OH | OCOCH₂CH₃ | OCOCH₃ | OCOCH₃ | 3-pyridyl |
| 73 | OH | OCOCH₂CH₃ | OCOCH₂CH₃ | OH | 3-pyridyl |
| 74 | OH | OCOCH₂CH₃ | OCOCH₂CH₃ | OCOCH₃ | 3-pyridyl |
| 75 | OH | OCOCH₂CH₃ | OCOCH₃ | OCOCH₂CH₃ | 3-pyridyl |
| 76 | OH | OCOCH₂CH₃ | OCOCH₂CH₃ | OCOCH₂CH₃ | 3-pyridyl |
| 77 | OH | OCOCH₂CH₃ | OCOCH₂CH₃ | OCOC₆H₅ | 3-pyridyl |
| 78 | OH | OCOCH₂CH₃ | OCOCH₂CH₃ | H | 3-pyridyl |
| 79 | OH | OCOCH₂CH₃ | H | H | 3-pyridyl |
| 80 | OH | OCO(CH₂)₂CH₃ | OCOCH₃ | OCOCH₃ | 3-pyridyl |

Table 5

| Compound No. | R₁ | R₂ | R₃ | R₄ | Het₁ |
|---|---|---|---|---|---|
| 81 | OH | OCO(CH₂)₂CH₃ | OCO(CH₂)₂CH₃ | OH | 3-pyridyl |
| 82 | OH | OCO(CH₂)₂CH₃ | OCO(CH₂)₂CH₃ | OCO(CH₂)₂CH₃ | 3-pyridyl |
| 83 | OH | OCO(CH₂)₂CH₃ | OCO(CH₂)₂CH₃ | OCOCH₃ | 3-pyridyl |
| 84 | OH | OCO(CH₂)₃CH₃ | OCOCH₃ | OCOCH₃ | 3-pyridyl |
| 85 | OH | OCO(CH₂)₃CH₃ | OCO(CH₂)₃CH₃ | OCO(CH₂)₃CH₃ | 3-pyridyl |
| 86 | OH | OCO(CH₂)₃CH₃ | OSO₂CH₃ | OCO(CH₂)₃CH₃ | 3-pyridyl |
| 87 | OH | OCO(CH₂)₃CH₃ | OSO₂CH₃ | OH | 3-pyridyl |

| | | | | | |
|---|---|---|---|---|---|
| 88 | OH | OCO(CH$_2$)$_{16}$CH$_3$ | OCO(CH$_2$)$_{16}$CH$_3$ | OCO(CH$_2$)$_{16}$CH$_3$ | 3-pyridyl |
| 89 | OH | OCOCH(CH$_3$)$_2$ | OCOCH$_3$ | OCOCH$_3$ | 3-pyridyl |
| 90 | OH | OCOCH(CH$_3$)$_2$ | OCOCH(CH$_3$)$_2$ | OCOCH(CH$_3$)$_2$ | 3-pyridyl |
| 91 | OH | OCOC(CH$_3$)$_3$ | OCOC(CH$_3$)$_3$ | OCOC(CH$_3$)$_3$ | 3-pyridyl |
| 92 | OH | OCOC$_6$H$_5$ | OCOCH$_3$ | OCOCH$_3$ | 3-pyridyl |
| 93 | OH | OCOC$_6$H$_5$ | OSO$_2$CH$_3$ | OH | 3-pyridyl |
| 94 | OH | OCOC$_6$H$_5$ | OSO$_2$CH$_3$ | OCOCH$_3$ | 3-pyridyl |
| 95 | OH | OCOC$_6$H$_5$ | OSO$_2$CH$_3$ | OCO(CH$_2$)$_3$CH$_3$ | 3-pyridyl |
| 96 | OH | OCO-(4-Br-C$_6$H$_4$) | OCO-(4-Br-C$_6$H$_4$) | OCO-(4-Br-C$_6$H$_4$) | 3-pyridyl |
| 97 | OH | OCO-(4-N$_3$-C$_6$H$_4$) | OSO$_2$CH$_3$ | OCOCH$_3$ | 3-pyridyl |
| 98 | OH | OSO$_2$CH$_3$ | OSO$_2$CH$_3$ | OH | 3-pyridyl |
| 99 | OH | OSO$_2$CH$_3$ | OSO$_2$CH$_3$ | OSO$_2$CH$_3$ | 3-pyridyl |
| 100 | OH | OSO$_2$CH$_3$ | OSO$_2$CH$_3$ | OCOCH$_3$ | 3-pyridyl |

Table 6

| Compound No. | R$_1$ | R$_2$ | R$_3$ | R$_4$ | Het$_1$ |
|---|---|---|---|---|---|
| 101 | OH | OSO$_2$CH$_3$ | OH | OH | 3-pyridyl |
| 102 | OH | OH | OH | OH | 3-pyridyl |
| 103 | OH | OH | OH | OCOCH$_3$ | 3-pyridyl |
| 104 | OH | OH | OH | OCO(CH$_2$)$_3$CH$_3$ | 3-pyridyl |
| 105 | OH | OH | OH | OCH$_2$OCH$_2$CH$_2$OCH$_3$ | 3-pyridyl |
| 106 | OH | OH | OCOCH$_3$ | OH | 3-pyridyl |
| 107 | OH | OH | OCOCH$_2$CH$_3$ | OH | 3-pyridyl |
| 108 | OH | OH | OCO(CH$_2$)$_2$CH$_3$ | OH | 3-pyridyl |
| 109 | OH | OH | OCO(CH$_2$)$_3$CH$_3$ | OH | 3-pyridyl |
| 110 | OH | OH | OCOCH(CH$_3$)$_2$ | OH | 3-pyridyl |
| 111 | OH | OH | OSO$_2$CH$_3$ | OH | 3-pyridyl |
| 112 | OH | OH | OSO$_2$CH$_2$CH$_3$ | OH | 3-pyridyl |
| 113 | OH | OH | OSO$_2$CH$_2$CH$_2$CH$_3$ | OH | 3-pyridyl |
| 114 | OH | OH | OSO$_2$CH(CH$_3$)$_2$ | OH | 3-pyridyl |
| 115 | OH | OH | OSO$_2$C$_6$H$_5$ | OH | 3-pyridyl |
| 116 | OH | OH | OSO$_2$-(4-CH$_3$-C$_6$H$_4$) | OH | 3-pyridyl |
| 117 | OH | OH | OCO-(4-Br-C$_6$H$_4$) | OH | 3-pyridyl |
| 118 | OH | OH | OCO(CH$_2$)$_3$CH$_3$ | OCO(CH$_2$)$_3$CH$_3$ | 3-pyridyl |
| 119 | OH | OH | OSO$_2$CH$_3$ | OSO$_2$CH$_3$ | 3-pyridyl |
| 120 | OH | OH | OSO$_2$CH$_3$ | OCOCH$_3$ | 3-pyridyl |

Table 7

| Compound No. | R$_1$ | R$_2$ | R$_3$ | R$_4$ | Het$_1$ |
|---|---|---|---|---|---|
| 121 | OH | OH | OSO$_2$CH$_3$ | OCOCH$_3$ | 3-pyridyl |
| 122 | OH | OH | OSO$_2$CH$_3$ | OCO(CH$_2$)$_3$CH$_3$ | 3-pyridyl |
| 123 | OH | OH | OSO$_2$C$_6$H$_5$ | OCOCH$_3$ | 3-pyridyl |

| | | | | | |
|---|---|---|---|---|---|
| 124 | OH | OH | $OSO_2C_6H_5$ | $OSO_2C_6H_5$ | 3-pyridyl |
| 125 | OH | | $-O-CH(CH_3)-O-$ | $OCO(CH_2)_3CH_3$ | 3-pyridyl |
| 126 | OH | | $-O-CH(C_2H_5)-O-$ | OH | 3-pyridyl |
| 127 | OH | | $-O-CH(C_2H_5)-O-$ | $OCO(CH_2)_3CH_3$ | 3-pyridyl |
| 128 | OH | | $-O-CH(CH=CH_2)-O-$ | OH | 3-pyridyl |
| 129 | OH | | $-O-CH(CH=CH_2)-O-$ | $OCO(CH_2)_3CH_3$ | 3-pyridyl |
| 130 | OH | | $-O-CH(CH(CH_3)_2)-O-$ | OH | 3-pyridyl |
| 131 | OH | | $-O-CH(CH(CH_3)_2)-O-$ | $OCO(CH_2)_3CH_3$ | 3-pyridyl |
| 132 | OH | | $-O-CH(OCH_3)-O-$ | OH | 3-pyridyl |
| 133 | OH | | $-O-CH(C(CH_3)_3)-O-$ | $OCO(CH_2)_3CH_3$ | 3-pyridyl |
| 134 | OH | | $-O-CH(CH_2C_6H_5)-O-$ | OH | 3-pyridyl |
| 135 | OH | | $-O-C(CH_3)_2-O-$ | OH | 3-pyridyl |
| 136 | OH | | $-O-C(CH_3)_2-O-$ | $OCOCH_3$ | 3-pyridyl |
| 137 | OH | | $-O-C(CH_3)_2-O-$ | $OCO(CH_2)_3CH_3$ | 3-pyridyl |
| 138 | OH | | $-O-C(CH_3)(C_6H_5)-O-$ | OH | 3-pyridyl |
| 139 | OH | | $-O-C(CH_3)(C_6H_5)-O-$ | $OCO(CH_2)_3CH_3$ | 3-pyridyl |
| 140 | OH | | $-O-CH(C_6H_5)-O-$ | OH | 3-pyridyl |

Table 8

| Compound No. | $R_1$ | $R_2$ | $R_3$ | $R_4$ | $Het_1$ |
|---|---|---|---|---|---|
| 141 | OH | | $-O-CH(C_6H_5)-O-$ | $OCOCH_3$ | 3-pyridyl |
| 142 | OH | | $-O-CH(OCH_3)-O-$ | $OCO(CH_2)_3CH_3$ | 3-pyridyl |
| 143 | OH | | $-O-CH(C_6H_5)-O-$ | $OCO(CH_2)_3CH_3$ | 3-pyridyl |
| 144 | OH | | $-O-CH(3-CH_3-C_6H_4)-O-$ | OH | 3-pyridyl |
| 145 | OH | | $-O-CH(3-CH_3-C_6H_4)-O-$ | $OCO(CH_2)_3CH_3$ | 3-pyridyl |
| 146 | OH | | $-O-CH(2-CH_3-C_6H_4)-O-$ | OH | 3-pyridyl |
| 147 | OH | | $-O-CH(4-CH_3-C_6H_4)-O-$ | $OCO(CH_2)_3CH_3$ | 3-pyridyl |
| 148 | OH | | $-O-CH(3-F-C_6H_4)-O-$ | OH | 3-pyridyl |
| 149 | OH | | $-O-CH(2-F-C_6H_4)-O-$ | $OCO(CH_2)_3CH_3$ | 3-pyridyl |
| 150 | OH | | $-O-CH(4-F-C_6H_4)-O-$ | $OCO(CH_2)_3CH_3$ | 3-pyridyl |
| 151 | OH | | $-O-CH(4-NO_2-C_6H_4)-O-$ | OH | 3-pyridyl |
| 152 | OH | | $-O-CH(4-NO_2-C_6H_4)-O-$ | $OCO(CH_2)_3CH_3$ | 3-pyridyl |
| 153 | OH | | $-O-CH(4-OCH_3-C_6H_4)-O-$ | OH | 3-pyridyl |
| 154 | OH | | $-O-CH(4-OCH_3-C_6H_4)-O-$ | $OCO(CH_2)_3CH_3$ | 3-pyridyl |
| 155 | OH | | $-O-C(spiro-c-C_5H_8)-O-$ | OH | 3-pyridyl |
| 156 | OH | | $-O-C(spiro-c-C_5H_8)-O-$ | $OCO(CH_2)_3CH_3$ | 3-pyridyl |
| 157 | OH | | $-O-C(spiro-c-C_6H_{10})-O-$ | OH | 3-pyridyl |
| 158 | OH | | $-O-C(spiro-c-C_6H_{10})-O-$ | $OCO(CH_2)_3CH_3$ | 3-pyridyl |
| 159 | OH | | $-O-CO-O-$ | OH | 3-pyridyl |
| 160 | OH | | $-O-CO-O-$ | OCO-1-imidazolyl | 3-pyridyl |

Table 9

| Compound No. | $R_1$ | $R_2$ | $R_3$ | $R_4$ | $Het_1$ |
|---|---|---|---|---|---|
| 161 | OH | -O-CO-O- | | $OCO(CH_2)_3CH_3$ | 3-pyridyl |
| 162 | $OCOCH_3$ | $OCOCH_3$ | $OCOCH_3$ | $OCOCH_3$ | 3-pyridyl |
| 163 | $OCOCH_3$ | $OCOCH_3$ | $OCOCH_3$ | OH | 3-pyridyl |
| 164 | $OCOCH_3$ | $OCOCH_3$ | $OCO(CH_2)_2CH_3$ | $OCOCH_3$ | 3-pyridyl |
| 165 | $OCOCH_3$ | OH | OH | $OCOCH_3$ | 3-pyridyl |
| 166 | $OCOCH_3$ | $OCOCH_2CH_3$ | $OCOCH_2CH_3$ | $OCOCH_2CH_3$ | 3-pyridyl |
| 167 | $OCOCH_2CH_3$ | $OCOCH_2CH_3$ | $OCOCH_2CH_3$ | $OCOCH_2CH_3$ | 3-pyridyl |
| 168 | $OCOCH_2CH_3$ | $OCOCH_3$ | $OCOCH_3$ | $OCOCH_3$ | 3-pyridyl |
| 169 | $OCO(CH_2)_3CH_3$ | $OCOCH_3$ | $OCOCH_3$ | $OCOCH_3$ | 3-pyridyl |
| 170 | $OCO(CH_2)_3CH_3$ | $OCOCH_3$ | $OCOCH_3$ | $OCO(CH_2)_3CH_3$ | 3-pyridyl |
| 171 | $OCO(CH_2)_2CH_3$ | $OCOCH_3$ | $OCOCH_3$ | $OCOCH_3$ | 3-pyridyl |
| 172 | $OCH_3$ | $OCOCH_3$ | $OCOCH_3$ | $OCOCH_3$ | 3-pyridyl |
| 173 | H(=) | $OSO_2CH_3$ | $OSO_2CH_3$ | OH | 3-pyridyl |
| 174 | H(=) | $OCOC_6H_5$ | $OSO_2CH_3$ | $OCOCH_3$ | 3-pyridyl |
| 175 | H(=) | OH | OH | $OCOCH_3$ | 3-pyridyl |
| 176 | H(=) | $OCOCH_3$ | $OCOCH_3$ | =O | 3-pyridyl |
| 177 | H(=) | $-O-CH(C_6H_5)-O-$ | | $OCOCH_3$ | 3-pyridyl |
| 178 | H(=) | $-O-CH(CH(CH_3)_2)-O-$ | | OH | 3-pyridyl |
| 179 | H(=) | $-O-CH(4-NO_2-C_6H_4)-O-$ | | OH | 3-pyridyl |
| 180 | H(=) | $OCOCH_3$ | $OCOCH_3$ | $OCOCH_3$ | 3-pyridyl |

Table 10

| Compound No. | $R_1$ | $R_2$ | $R_3$ | $R_4$ | $Het_1$ |
|---|---|---|---|---|---|
| 181 | H(=) | OH | OH | OH | 3-pyridyl |
| 182 | H(=) | $OCOCH_3$ | $OCOCH_3$ | OH | 3-pyridyl |
| 183 | H(=) | $OCOCH_3$ | $OCOCH_3$ | $OCH_2SCH_3$ | 3-pyridyl |
| 184 | H(=) | $OCOCH_3$ | $OCOCH_3$ | $OCH_2OCH_3$ | 3-pyridyl |
| 185 | H(=) | $OCOCH_3$ | $OCOCH_3$ | $OCO(CH_2)_3CH_3$ | 3-pyridyl |
| 186 | H(=) | $OCOCH_3$ | $OCOCH_3$ | $OCO(CH_2)_2Ph$ | 3-pyridyl |
| 187 | H(=) | $OCOCH_3$ | $OSO_2CH_3$ | $OCOCH_3$ | 3-pyridyl |
| 188 | H(=) | $OCOCH_2CH_3$ | $OCOCH_2CH_3$ | $OCOCH_2CH_3$ | 3-pyridyl |
| 189 | H(=) | $OCOCH_2CH_3$ | $OCOCH_2CH_3$ | OH | 3-pyridyl |
| 190 | H(=) | OH | $OSO_2CH_3$ | OH | 3-pyridyl |
| 191 | H(=) | OH | OH | $OCO(CH_2)_3CH_3$ | 3-pyridyl |
| 192 | H(=) | $-O-C(CH_3)_2-O-$ | | OH | 3-pyridyl |
| 193 | H(=) | $-O-C(CH_3)_2-O-$ | | $OCO(CH_2)_3CH_3$ | 3-pyridyl |
| 194 | H(=) | $-O-CH(C_6H_5)-O-$ | | OH | 3-pyridyl |
| 195 | H(=) | $-O-CH(C_6H_5)-O-$ | | $OCO(CH_2)_3CH_3$ | 3-pyridyl |
| 196 | H(=) | $-O-CH(4-OCH_3-C_6H_4)-O-$ | | OH | 3-pyridyl |
| 197 | H(=) | $-O-CH(C_2H_5)-O-$ | | OH | 3-pyridyl |
| 198 | H(=) | $-O-CH(C(CH_3)_3)-O-$ | | OH | 3-pyridyl |
| 199 | H(=) | $-O-CH(CH_2C_6H_5)-O-$ | | OH | 3-pyridyl |
| 200 | =O | OH | OH | OH | 3-pyridyl |

Table 11

| Compound No. | $R_1$ | $R_2$ | $R_3$ | $R_4$ | $Het_1$ |
|---|---|---|---|---|---|
| 201 | =O | OCOCH$_3$ | OCOCH$_3$ | =O | 3-pyridyl |
| 202 | =O | OCOCH$_3$ | OCOCH$_3$ | OH | 3-pyridyl |
| 203 | =O | OCOCH$_3$ | OCOCH$_3$ | OCOCH$_3$ | 3-pyridyl |
| 204 | =O | OCOCH$_2$CH$_3$ | OCOCH$_2$CH$_3$ | OCOCH$_2$CH$_3$ | 3-pyridyl |
| 205 | OH | OCOCH$_2$CH$_3$ | OCOCH$_2$CH$_3$ | OCO-(3-Pyridyl) | 3-pyridyl |
| 206 | OH | OCOCH$_2$CH$_3$ | OCOCH$_2$CH$_3$ | OCOCH(CH$_3$)$_2$ | 3-pyridyl |
| 207 | OH | OCOCH$_2$CH$_3$ | OCOCH$_2$CH$_3$ | OCOC(CH$_3$)$_3$ | 3-pyridyl |
| 208 | OH | OCOCH$_2$CH$_3$ | OCOCH$_2$CH$_3$ | OCO-(4-CF$_3$-C$_6$H$_4$) | 3-pyridyl |
| 209 | OH | OCOCH$_2$CH$_3$ | OCOCH$_2$CH$_3$ | OCO-(1-imidazolyl) | 3-pyridyl |
| 210 | OH | OCOCH$_2$CH$_3$ | OCOCH$_2$CH$_3$ | OCONH(CH$_2$)$_2$CH$_3$ | 3-pyridyl |
| 211 | OH | OCOCH$_2$CH$_3$ | OCOCH$_2$CH$_3$ | O-(2-tetrahydropyranyl) | 3-pyridyl |
| 212 | OH | OCOCH$_2$CH$_3$ | OCOCH$_2$CH$_3$ | OCO-(6-Cl-3-pyridyl) | 3-pyridyl |
| 213 | OH | OCOCH$_2$CH$_3$ | OCOCH$_2$CH$_3$ | OCO-c-C$_3$H$_5$ | 3-pyridyl |
| 214 | OH | OCOCH$_2$CH$_3$ | OCOCH$_2$CH$_3$ | OCO-c-C$_4$H$_7$ | 3-pyridyl |
| 215 | OH | OCOCH$_2$CH$_3$ | OCOCH$_2$CH$_3$ | OCOCH=CH | 3-pyridyl |
| 216 | OH | OCOCH$_2$CH$_3$ | OCOCH$_2$CH$_3$ | OCO-(4-pyridyl) | 3-pyridyl |
| 217 | OH | OCOCH$_2$CH$_3$ | OCOCH$_2$CH$_3$ | OCO-(2-pyridyl) | 3-pyridyl |
| 218 | OH | OCO-c-C$_3$H$_5$ | OCO-c-C$_3$H$_5$ | OCO-c-C$_3$H$_5$ | 3-pyridyl |
| 219 | OH | OCO-c-C$_4$H$_7$ | OCO-c-C$_4$H$_7$ | OCO-c-C$_4$H$_7$ | 3-pyridyl |
| 220 | OH | OCOC$_6$H$_5$ | OCOC$_6$H$_5$ | OCOC$_6$H$_5$ | 3-pyridyl |

Table 12

| Compound No. | $R_1$ | $R_2$ | $R_3$ | $R_4$ | $Het_1$ |
|---|---|---|---|---|---|
| 221 | OH | OCOCH$_2$CH$_3$ | OCOCH$_2$CH$_3$ | OCO-(6-CF$_3$-3-pyridyl) | 3-pyridyl |
| 222 | OH | OCOCH$_2$CH$_3$ | OCOCH$_2$CH$_3$ | OCO-(4-CF$_3$-3-pyridyl) | 3-pyridyl |
| 223 | OH | OCOCH$_2$CF$_3$ | OCOCH$_2$CF$_3$ | OCOCH$_2$CF$_3$ | 3-pyridyl |
| 224 | OH | OCOCH$_2$CH$_3$ | OCOCH$_2$CH$_3$ | OCOCH$_2$CF$_3$ | 3-pyridyl |
| 225 | =O | OCOCH$_2$CH$_3$ | OCOCH$_2$CH$_3$ | OCOCH$_2$CH$_3$ | 6-Cl-3-pyridyl |
| 226 | OH | OCOCH$_2$CH$_3$ | OCOCH$_2$CH$_3$ | OCOCH$_2$CH$_3$ | 6-Cl-3-pyridyl |
| 227 | OH | OCOCH$_2$CH$_3$ | OCOCH$_2$CH$_3$ | OCO-(3-F-4-pyridyl) | 3-pyridyl |
| 228 | OH | OCOCH$_2$CH$_3$ | OCOCH$_2$CH$_3$ | OCO-(3-Cl-4-pyridyl) | 3-pyridyl |
| 229 | OH | OCOCH$_2$CH$_3$ | OCOCH$_2$CH$_3$ | OCO-(3-CH$_3$-2-pyridyl) | 3-pyridyl |
| 230 | OH | OCOCH$_2$CH$_3$ | OCOCH$_2$CH$_3$ | OCO-(3-COC$_6$H$_5$-2-pyridyl) | 3-pyridyl |
| 231 | OH | OCOCH$_2$CH$_3$ | OCOCH$_2$CH$_3$ | OCO-(3-OCH$_2$CH$_2$CH$_3$-2-pyridyl) | 3-pyridyl |
| 232 | OH | OCOCH$_2$CH$_3$ | OCOCH$_2$CH$_3$ | OCO-(6-F-3-pyridyl) | 3-pyridyl |
| 233 | OH | OCO-c-C$_5$H$_9$ | OCO-c-C$_5$H$_9$ | OCO-c-C$_5$H$_9$ | 3-pyridyl |
| 234 | OH | OCO-c-C$_6$H$_{11}$ | OCO-c-C$_6$H$_{11}$ | OCO-c-C$_6$H$_{11}$ | 3-pyridyl |
| 235 | OH | OCOCH$_2$CN | OCOCH$_2$CN | OCOCH$_2$CN | 3-pyridyl |

| | | | | | |
|---|---|---|---|---|---|
| 236 | OCOCH$_2$-c-C$_3$H$_5$ | OCOCH$_2$-c-C$_3$H$_5$ | OCOCH$_2$-c-C$_3$H$_5$ | OCOCH$_2$-c-C$_3$H$_5$ | 3-pyridyl |
| 237 | OH | OCOCH$_2$-c-C$_3$H$_5$ | OCOCH$_2$-c-C$_3$H$_5$ | OCOCH$_2$-c-C$_3$H$_5$ | 3-pyridyl |
| 238 | OH | OCO-(1-CH$_3$-2,2-diF-c-C$_3$H$_2$) | OCO-(1-CH$_3$-2,2-diF-c-C$_3$H$_2$) | OCO-(1-CH$_3$-2,2-diF-c-C$_3$H$_2$) | 3-pyridyl |
| 239 | OH | OCOCH$_2$CH$_3$ | OCOCH$_2$CH$_3$ | OCO-(4-CH$_3$-3-pyridyl) | 3-pyridyl |
| 240 | OH | OCOCH$_2$CH$_3$ | OCOCH$_2$CH$_3$ | OCO-(4-Cl-3-pyridyl) | 3-pyridyl |

Table 13

| Compound No. | R$_1$ | R$_2$ | R$_3$ | R$_4$ | Het$_1$ |
|---|---|---|---|---|---|
| 241 | OH | OCOCH$_2$CH$_3$ | OCOCH$_2$CH$_3$ | OCO-(4-COOCH$_3$-3-pyridyl) | 3-pyridyl |
| 242 | OH | OCOCH$_2$CH$_3$ | OCOCH$_2$CH$_3$ | OCO-{5-(CF$_3$)-thieno[3,2-b]pyridin-6-yl} | 3-pyridyl |
| 243 | OH | OCOCH$_2$CH$_3$ | OCOCH$_2$CH$_3$ | OCO-(2-CN-C$_6$H$_4$) | 3-pyridyl |
| 244 | OH | OCOCH$_2$CH$_3$ | OCOCH$_2$CH$_3$ | OCO-(2-CF$_3$-C$_6$H$_4$) | 3-pyridyl |
| 245 | OH | OCOCH$_2$CH$_3$ | OCOCH$_2$CH$_3$ | OCO-(2-F-C$_6$H$_4$) | 3-pyridyl |
| 246 | OH | OCOCH$_2$CH$_3$ | OCOCH$_2$CH$_3$ | OCO-(2-NO$_2$-C$_6$H$_4$) | 3-pyridyl |
| 247 | OH | OCOCH$_2$CH$_3$ | OCOCH$_2$CH$_3$ | OCO-(2-Cl-3-pyridyl) | 3-pyridyl |
| 248 | OH | OCOCH$_2$CH$_3$ | OCOCH$_2$CH$_3$ | OCO(2-Cl-6-CH$_3$-3-pyridyl) | 3-pyridyl |
| 249 | OH | OCOCH$_2$CH$_3$ | OCOCH$_2$CH$_3$ | OCH$_2$OCH$_3$ | 3-pyridyl |
| 250 | OH | OCO-(2,2-diF-c-C$_3$H$_3$) | OCO-(2,2-diF-c-C$_3$H$_3$) | OCO-(2,2-diF-c-C$_3$H$_3$) | 3-pyridyl |
| 251 | OH | OCOCH$_2$CH$_3$ | OCOCH$_2$CH$_3$ | OCO-(3-SC(CH$_3$)$_3$-2-pyridyl) | 3-pyridyl |
| 252 | OH | OCOCH$_2$CH$_3$ | OCOCH$_2$CH$_3$ | OCO-(3,5-diF-2-pyridyl) | 3-pyridyl |
| 253 | OH | OCOCH$_2$CH$_3$ | OCOCH$_2$CH$_3$ | OCO-2-pyrazinyl | 3-pyridyl |
| 254 | OH | OCOCH$_2$CH$_3$ | OCOCH$_2$CH$_3$ | OCO-4-thiazolyl | 3-pyridyl |
| 255 | OH | OCOCH$_2$CH$_3$ | OCOCH$_2$CH$_3$ | OCO-(3-Cl-2-thienyl) | 3-pyridyl |
| 256 | OH | OCOCH$_2$CH$_3$ | OCOCH$_2$CH$_3$ | OCO-(6-CH$_3$-3-pyridyl) | 3-pyridyl |
| 257 | OH | OCOCH$_2$CH$_3$ | OCOCH$_2$CH$_3$ | OCO-(6-Cl-2-pyridyl) | 3-pyridyl |
| 258 | OH | OCOCH$_2$CH$_3$ | OCOCH$_2$CH$_3$ | OCO-(6-F-2-pyridyl) | 3-pyridyl |
| 259 | OH | OCOCH$_2$CH$_3$ | OCOCH$_2$CH$_3$ | OCO-(1-CH$_3$-1H-indolyl) | 3-pyridyl |
| 260 | OH | OCOCH$_2$CH$_3$ | OCOCH$_2$CH$_3$ | OCO-(3-Cl-2-pyridyl) | 3-pyridyl |

Table 14

| Compound No. | R$_1$ | R$_2$ | R$_3$ | R$_4$ | Het$_1$ |
|---|---|---|---|---|---|
| 261 | OH | OCO-c-C$_3$H$_5$ | OCO-c-C$_3$H$_5$ | OH | 3-pyridyl |
| 262 | OH | OCOCH$_2$CH$_3$ | OCOCH$_2$CH$_3$ | OCO-(2-F-3-pyridyl) | 3-pyridyl |
| 263 | OH | OCOCH$_2$CH$_3$ | OCOCH$_2$CH$_3$ | OCO-(4-CN-C$_6$H$_4$) | 3-pyridyl |
| 264 | OH | OCOCH2CH3 | OCOCH$_2$CH$_3$ | OCO-(3-CN-C$_6$H$_4$) | 3-pyridyl |
| 265 | OH | OCOCH$_2$CH$_3$ | OCOCH$_2$CH$_3$ | OCO-(3-CF$_3$-C$_6$H$_4$) | 3-pyridyl |
| 266 | OH | OCOCH$_2$CH$_3$ | OCOCH$_2$CH$_3$ | OCOCH$_2$(2-pyridyl) | 3-pyridyl |
| 267 | OH | OCOCH$_2$CH$_3$ | OCOCH$_2$CH$_3$ | OCOCH$_2$(3-pyridyl) | 3-pyridyl |
| 268 | OH | OCOCH$_2$CH$_3$ | OCOCH$_2$CH$_3$ | OCOCH$_2$S(4-pyridyl) | 3-pyridyl |
| 269 | OH | OCO-c-C$_3$H$_5$ | OCO-c-C$_3$H$_5$ | OCO-(2-CN- | 3-pyridyl |

| | | | | $C_6H_4$) | |
|---|---|---|---|---|---|
| 270 | OH | OCO-c-$C_3H_5$ | OCO-c-$C_3H_5$ | OCO(4-$CF_3$-3-pyridyl) | 3-pyridyl |
| 271 | OH | OCO-c-$C_3H_5$ | OCO-c-$C_3H_5$ | OCO(3-Cl-2-pyridyl) | 3-pyridyl |
| 272 | OH | -O-CH($C_6H_5$)-O- | | =O | 3-pyridyl |
| 273 | OH | -O-CH(4-$OCH_3$-$C_6H_4$)-O- | | =O | 3-pyridyl |
| 274 | OCO($CH_2$)$_3CH_3$ | -O-CO-O- | | OCO($CH_2$)$_3$CH3 | 3-pyridyl |
| 275 | $OCOCH_3$ | -O-CH($C_6H_5$)-O- | | $OCOCH_3$ | 3-pyridyl |
| 276 | =O | -O-CH(4-$OCH_3$-$C_6H_4$)-O- | | OH | 3-pyridyl |

Production process

The compositon according to the present invention can be prepared by mixing the compound represented by formula (I), (Ia), or (Ib) as active ingredient with an agriculturally and horticulturally acceptable carrier. The compound represented by formula (I), (Ia), or (Ib) according to the present invention can be produced according to the following procedure.

Among the compounds according to the present invention, the compounds represented by formula (II) can be synthesized by the method described in Japanese Patent Laid-Open Publication No. 259569/1996, Japanese Patent Laid-Open Publication No. 269062/1996, Japanese Patent Laid-Open Publication No. 269065/1996, or Journal of Antibiotics (1997), 50(3), pp. 229-36. When pyripyropene A is used as a starting material, pyripyropene A, produced by the method described in Journal of SoClety of Synthetic Organic Chemistry, Japan (1998), Vol. 56, No. 6, pp. 478-488 or WO 94/09417, may be used as the starting material.

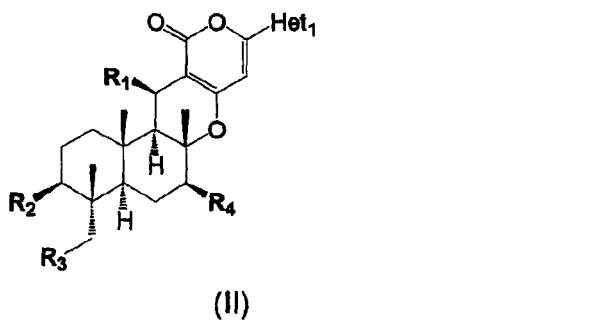

(II)

wherein $R_1$ represents hydroxyl, optionally substituted $C_{1-6}$ alkylcarbonyloxy, optionally substituted $C_{2-6}$ alkenylcarbonyloxy, optionally substituted $C_{2-6}$ alkynyl carbonyloxy, optionally substituted $C_{1-6}$ alkyloxy, optionally substituted $C_{2-6}$ alkenyloxy, optionally substituted $C_{2-6}$ alkynyloxy, optionally substituted benzyloxy, or oxo in the absence of a hydrogen atom at the 13-position, and $R_2$, $R_3$ and $R_4$ are as defined in formula (I).

Further, among the compounds according to the present invention, the compounds represented by formula (III) can be synthesized by the method described in Japanese Patent Laid-Open Publication No. 269063/1996, or Japanese Patent Laid-Open Publication No. 269066/1996.

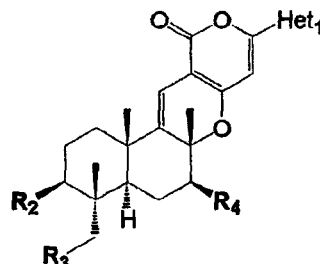

(III)

wherein $R_2$, $R_3$ and $R_4$ are as defined in formula (I).

Use

Insect species against which pyripyropene derivatives of formula (I) or (Ib) according to the present invention have control effect include: lepidopteran pests, for example, Spodoptera litura, Mamestra brassicae, Pseudaletia separata, green caterpillar, Plutella xylostella, Spodoptera exigua, Chilo suppressalis, Cnaphalocrocis medinalis, Tortricidae, Carposinidae, Lyonetiidae, Lymantriidae, pests belonging to the genus Agrotis spp., pests belonging to the genus Helicoverpa spp., and pests belonging to the genus Heliothis spp.; hemipteran pests, for example, Aphidoidea including Aphididae, Adelgidae and Phylloxeridae such as Myzus persicae, Aphis gossypii, Aphis fabae, Aphis maidis (corn-leaf aphid), Acyrthosiphon pisum, Aulacorthum solani, Aphis craccivora, Macrosiphum euphorbiae, Macrosiphum avenae, Metopolophium dirhodum, Rhopalosiphum padi, Schizaphis graminum, Brevicoryne brassicae, Lipaphis erysimi, Aphis citricola, Rosy apple aphid, Eriosoma lanigerum, Toxoptera aurantii, and Toxoptera citricidus; Deltocephalidae such as Nephotettix cincticeps, Delphacidae such as Laodelphax striatellus, Nilaparvata lugens, and Sogatella furcifera; Pentatomidae such as Eysarcoris ventralis, Nezara viridula, and Trigonotylus coelestialium; Aleyrodidae such as Bemisia argentifolii, Bemisia tabaci, and Trialeurodes vaporariorum; Diaspididae, Margarodidae, Ortheziidae, Aclerdiae, Dactylopiidae, Kerridae, Pseudococcidae, Coccidae, Eriococcidae, Asterolecaniidae, Beesonidae, Lecanodiaspididae, or Cerococcidae, such as Pseudococcus comstocki and Planococcus citri Risso; Coleoptera pests, for example, Lissorhoptrus oryzophilus, Callosobruchuys chienensis, Tenebrio molitor, Diabrotica virgifera virgifera, Diabrotica undecimpunctata howardi, Anomala cuprea, Anomala rufocuprea, Phyllotreta striolata, Aulacophora femoralis, Leptinotarsa decemlineata, Oulema oryzae, Carposinidae, and Cerambycidae; Acari, for example, Tetranychus urticae, Tetranychus kanzawai, and Panonychus citri; Hymenopteran pests, for example, Tenthredinidae; Orthopteran pests, for example, Acrididae; Dipteran pests, for example, Muscidae and Agromyzidae; Thysanopteran pests, for example, Thrips palmi and Frankliniella occidentalis; Plant Parasitic Nematodes, for example, Meloidogyne hapla, Pratylenchus spp., Aphelenchoides besseyi and Bursaphelenchus xylophilus; and parasites of animals, for example, Siphonaptera, Anoplura, mites such as Boophilus microplus, Haemaphysalis longicornis, Rhipicephalus sanguineus, and Scarcoptes scabiei. Preferred are hemipteran pests.

The compound represented by formula (Ia) accordingly to the present invention has significant control effect against hemipteran pests. Preferred hemipteran pests are selected from Aphidoidea such as Aphididae, Adelgidae, and Phylloxeridae, particularly preferably Aphididae; Coccoidea such as Diaspididae, Margarodidae, Ortheziidae, Aclerdiae, Dactylopiidae, Kerridae, Pseudococcidae, Coccidae, Eriococcidae, Asterolecaniidae, Beesonidae, Lecanodiaspididae, and Cerococcidae; and Aleyrodidae. More preferred are Myzus persicae, Aphis gossypii, Aphis fabae, Aphis maidis (corn-leaf aphid), Acyrthosiphon pisum, Aulacorthum solani, Aphis craccivora, Macrosiphum euphorbiae, Macrosiphum avenae, Metopolophium dirhodum, Rhopalosiphum padi, Schizaphis graminum, Brevicoryne brassicae, Lipaphis erysimi, Aphis citricola, Rosy apple aphid, Eriosoma lanigerum, Toxoptera aurantii, Toxoptera citricidus, and Pseudococcus comstocki.

The composition according to the present invention can be prescribed in any suitable formulation, such as emulsifiable concentrates, liquid formulations, suspension, wettable powder, flowables, dust, granules, tablets, oil solutions, aerosols, or smoking agents by using suitable agriculturally and horticulturally acceptable carriers. Accordingly, the carrier include solid carriers, liquid carriers, gaseous carriers, surfactants, dispersants and/or other adjuvants for formulations, and the like.

Solid carriers usable herein include, for example, talc, bentonite, clay, kaolin, diatomaceous earth, vermiculite, white carbon, and calcium carbonate.

Examples of liquid carriers include: alcohols, such as methanol, n-hexanol, and ethylene glycol; ketones, such as acetone, methyl ethyl ketone, and cyclohexanone; aliphatic hydrocarbons, such as n-hexane, kerosine, and kerosene; aromatic hydrocarbons, such as toluene, xylene, and methylnaphthalene; ethers, such as diethyl ether, dioxane, and tetrahydrofuran; esters, such as ethyl acetate; nitriles, such as acetonitrile and isobutyronitrile; acid amides, such as dimethylformamide and dimethylacetamide; vegetable oils, such as soy bean oil and cotton seed oil; dimethylsulfoxide; and water.

Gaseous carriers include, for example, LPG, air, nitrogen, carbon dioxide, and dimethyl ether.

Surfactants or dispersants usable, for example, for emulsifying, dispersing, or spreading include, for example, alkylsulfonic esters, alkyl(aryl)sulfonic acid salts, polyoxyalkylene alkyl(aryl) ethers, polyhydric alcohol esters, and lignin sulfonic acid salts.

Adjuvants usable for improving the properties of formulations include, for example, carboxymethylcellulose, gum arabic, polyethylene glycol, and calcium stearate.

The above carriers, surfactants, dispersants, and adjuvant may be used either solely or in combination according to need.

The content of the active ingredient in the formulation is not particularly limited. In general, however, the content of the active ingredient is 1 to 75% by weight for emulsifiable concentrates, 0.3 to 25% by weight for dust, 1 to 90% by weight for wettable powder, and 0.5 to 10% by weight for granules.

The compound represented by formula (I), (Ia), (Ib), or an agriculturally and horticulturally acceptable salt thereof and the above formualtions comprising the same may be applied as such or after dilution to plants or soil. Therefore, according to another aspect of the present invention, there is provided a method for controlling a pest, comprising applying an effective amount of a compound represented by formula (I) or an agriculturally and horticulturally acceptable salt thereof to a plant or soil. According to still another aspect of the present invention, there is provided a method for controlling a hemipteran pest, comprising applying an effective amount of a compound represented by formula (Ia) or an agriculturally and horticulturally acceptable salt thereof to a plant or soil. According to a further aspect of the present invention, there is provided a method for controlling a pest, comprising applying an effective amount of a compound represented by formula (Ib) or an agriculturally and horticulturally acceptable salt thereof to a plant or soil. Preferred methods usable for applying the compound or formulation to plants or soil include spreading treatment, soil treatment, surface treatment, and fumigation treatment.

Spreading treatments include, for example, spreading, spraying, misting, atomizing, granule application, and submerged application. Soil treatments include, for example, soil affusion and soil mixing. Examples of surface treatments include, for example, coating, dust coating, and covering. Fumigation treatments include, for example, covering of soil with a polyethylene film after soil injection. Accordingly, the control method according to the present invention comprises a method in which the compound represented by formula (I), (Ia), or (Ib) or a formulation comprising the same is applied by fumigation in a sealed space.

The composition according to the present invention may be used as a mixture or in a combination with, for example, other insecticides, fungicides, miticides, herbicides, plant growth-regulating agents, or fertilizers. Agents which may be mixed or used in combination include those described, for example, in The Pesticide Manual, 13th edition, published by The British Crop Protection Council; and SHIBUYA INDEX, the 10th edition, 2005, published by SHIBUYA INDEX RESEARCH GROUP. More specifically, insecticides usable herein include, for example, organophosphate ester compounds such as acephate, dichlorvos, EPN, fenitrothion, fenamifos, prothiofos, profenofos, pyraclofos, chlorpyrifos-methyl, and diazinon; carbamate compounds such as methomyl, thiodicarb, aldicarb, oxamyl, propoxur, carbaryl, fenobucarb, ethiofencarb, fenothiocarb, pirimicarb, carbofuran, and benfuracarb; nereistoxin derivatives such as cartap and thiocyclam; organochlorine compounds such as dicofol and tetradifon; pyrethroid compounds such as permethrin, tefluthrin, cypermethrin, deltamethrin, cyhalothrin, fenvalerate, fluvalinate, ethofenprox, and silafluofen; benzoylurea compounds such as diflubenzuron, teflubenzuron, flufenoxuron, and chlorfluazuron; juvenile hormone-like compounds such as methoprene; and molting hormone-like compounds such as chromafenozide. Other compounds usable herein include buprofezin, hexythiazox, amitraz, chlordimeform, pyridaben, fenpyroximate, pyrimidifen, tebufenpyrad, fluacrypyrim, acequinocyl, cyflumetofen, flubendiamide, ethiprole, fipronil, ethoxazole, imidacloprid, chlothianidin, pymetrozine, bifenazate, spirodiclofen, spiromesifen, flonicamid, chlorfenapyr, pyriproxyfene, indoxacarb, pyridalyl, or spinosad, avermectin, milbemycin, organometallic compounds, dinitro compounds, organosulfur compounds, urea compounds, triazine compounds, hydrazine compounds.

The composition according to the present invention may also be used as a mixture or in a combination with microbial pesticides such as BT formulations and entomopathogenic viral agents.

Fungicides usable herein include, for example, strobilurin compounds such as azoxystrobin, kresoxym-methyl, and trifloxystrobin; anilinopyrimidine compounds such as mepanipyrim, pyrimethanil, and cyprodinil; azole compounds such as triadimefon, bitertanol, triflumizole, etaconazole, propiconazole, penconazole, flusilazole, myclobutanil, cyproconazole, tebuconazole, hexaconazole, prochloraz, and simeconazole; quinoxaline compounds such as quinomethionate; dithiocarbamate compounds such as maneb, zineb, mancozeb, polycarbamate, and propineb; phenylcarbamate compounds such as diethofencarb; organochlorine compounds such as chlorothalonil and quintozene; benzimidazole compounds such as benomyl, thiophanate-methyl, and carbendazole; phenylamide compounds such as metalaxyl, oxadixyl, ofurace, benalaxyl, furalaxyl, and cyprofuram; sulfenic acid compounds such as dichlofluanid; copper compounds such as copper hydroxide and oxine-copper; isoxazole compounds such as hydroxyisoxazole; organophosphorus compounds such as fosetyl-aluminium and tolclofos-methyl; N-halogenothioalkyl compounds such as captan, captafol, and folpet; dicarboxyimide compounds such as procymidone, iprodione, and vinchlozolin; benzanilide compounds such as flutolanil and mepronil; morpholine comopounds such as fenpropimorph and dimethomorph; organotin compounds such as fenthin hydroxide, and fenthin acetate; and cyanopyrrole compounds such as fludioxonil and fenpiclonil. Other compounds usable herein include fthalide, fluazinam, cymoxanil, triforine, pyrifenox, fenarimol, fenpropidin, pencycuron, cyazofamid, iprovalicarb, and benthiavalicarb-isopropyl and the like.

According to another aspect of the present invention, there is provided use of a compound represented by formula (I) or an agriculturally and horticulturally acceptable salt thereof as a pest control agent. According to still another aspect of the present invention, there is provided use of a compound represented by formula (Ia) or an agriculturally and horticulturally acceptable salt thereof as a hemipteran pest control agent. According to still another aspect of the present invention, there is provided use of a compound represented by formula (Ib) or an agriculturally and horticulturally acceptable salt thereof as a pest control agent.

[EXAMPLES]

The present invention is further illustrated by the following Examples that are not intended as a limitation of the invention. The compound Nos. correspond to the compound Nos. in Tables 1 to 14.

Example 1: Synthesis of compound 73

Compound 76 (890 mg) synthesized by the method described in Japanese Patent Laid-Open Publication No. 259569/1996 was dissolved in an 80% aqueous methanol solution. Next, 1,8-diazabicyclo[5.4.0]-undeca-7-ene (216 mg) was added to the solution, and the mixture was stirred at room temperature for 1.5 hr. The reaction mixture was added with acetic acid to quench the reaction, and the solvent was removed by evaporation under the reduced pressure. Water was added to the precipitated crystal, followed by extraction with chloroform. The chloroform layer was washed with saturated brine, was dried over anhydrous magnesium sulfate, and the solvent was removed by evaporation under the reduced pressure to give a crude product of compound 73. The crude product was purified by chromatography on silica gel (Mega Bond Elut (Varian), acetone : hexane = 1 : 1) to give compound 73 (451 mg).

Mass spectrometric data (FAB$^+$): 570(M+H)$^+$

Example 2: Synthesis of compound 218

Compound 102 (30 mg) synthesized by the method described in Japanese Patent Laid-Open Publication No. 259569/1996 and cyclopropanecarboxylic acid (112 mg) were dissolved in anhydrous N,N-dimethylformamide (2 ml), and 1-ethyl-3-(3-dimethylaminopropyl)-carbodiimide hydrochloride (76 mg) and 4-(dimethylamino)pyridine (32 mg) were added to the solution. The reaction solution was stirred at room temperature for 68 hr and was then poured into water, followed by extraction with ethyl acetate. The ethyl acetate layer was washed with saturated brine and was dried over anhydrous magnesium sulfate, and the solvent was removed by evaporation under the reduced pressure to give a crude product of compound 218. The crude product was purified by preparative thin-layer chromatography (Merck Silica Gel 60 $F_{254}$ 0.5mm, acetone : hexane = 1 : 1) to give compound 218 (33 mg).
Mass spectrometric data ($FAB^+$): $662(M+H)^+$ Example 3: Synthesis of compound 261

Compound 218 (1.07 g) prepared in Example 2 was dissolved in an 80% aqueous methanol solution. 1,8-Diazabicyclo[5.4.0]-undeca-7-ene (271 mg) was added to the solution, and the mixture was stirred at room temperature for 24.5 hr. The reaction mixture was added with acetic acid to quench the reaction, and the solvent was removed by evaporation under the reduced pressure. Water was added to the precipitated crystal, followed by extraction with chloroform. The chloroform layer was washed with saturated brine and was dried over anhydrous magnesium sulfate, and the solvent was removed by evaporation under the reduced pressure to give a crude product of compound 261.   The crude product was purified by chromatography on silica gel (Mega Bond Elut (Varian), acetone : hexane = 1 : 1) to give compound 261 (233 mg).
Mass spectrometric data ($ESI^+$): $594(M+H)^+$ Example 4: Synthesis of compound 222

Compound 73 (30 mg) prepared in Example 1 and 4-(trifluoromethyl)nicotinic acid (30 mg) was dissolved in anhydrous N,N-dimethylformamide (3 ml). Next, 1-ethyl-3-(3-dimethylaminopropyl)-carbodiimide hydrochloride (15 mg) and 4-(dimethylamino)pyridine (4 mg) were added to the solution, and the reaction solution was stirred at room temperature for 15 hr and was then poured into water, followed by extraction with ethyl acetate. The ethyl acetate layer was washed with saturated brine and was dried over anhydrous magnesium sulfate, and the solvent was removed by evaporation under the reduced pressure to give a crude produce of compound 222. The crude product was purified by preparative thin-layer chromatography (Merck Silica Gel 60 $F_{254}$ 0.5mm, acetone : hexane = 1 : 1) to give compound 222 (19 mg).
Mass spectrometric data ($FAB^+$): $743(M+H)^+$ Example 5: Synthesis of compound 269

Compound 261 (20 mg) prepared in Example 3 and 2-cyanobenzoic acid (30 mg) were dissolved in anhydrous N,N-dimethylformamide (1 ml), and 1-ethyl-3-(3-dimethylaminopropyl)-carbodiimide hydrochloride (26 mg) and 4-(dimethylamino)pyridine (4 mg) were added to the solution. The reaction solution was stirred at room temperature for 12 hr, and the reaction solution was added to water, followed by extraction with ethyl acetate. The ethyl acetate layer was washed with saturated brine and was dried over anhydrous magnesium sulfate. The solvent was removed by evaporation under the reduced pressure to give a crude product of compound 269. The crude product was purified by preparative thin-layer chromatography (Merck Silica Gel 60 $F_{254}$ 0.5mm, acetone : hexane = 1 :1) to give compound 269 (18 mg).
Mass spectrometric data (ESI$^+$): 723 (M+H)$^+$ Example 6: Synthesis of compound 225

1,7,11-Trideacetyl-13-oxo-6"-chloropyripyropene A (10 mg) described in Journal of Antibiotics (1997), 50 (3), 229-36 was dissolved in anhydrous N,N-dimethylformamide (1 ml). Triethylamine (24 mg) and 4-(dimethylamino)pyridine (0.5 mg) were added to the solution, and the mixture was stirred at room temperature for 30 min. Thereafter, propionic acid anhydride (8 mg) was added. The reaction solution was stirred at the same temperature for 4 hr. The reaction solution was added to water, and the mixture was extracted with ethyl acetate. The ethyl acetate layer was washed with saturated brine and was dried over anhydrous magnesium sulfate, and the solvent was then removed by evaporation under the reduced pressure to give a crude product of compound 225. The crude product was purified by preparative thin-layer chromatography (Merck Silica Gel 60 $F_{254}$ 0.5mm, acetone: hexane = 1 : 1) to give compound 225 (5.6 mg).
Mass spectrometric data (ESI$^+$): 658 (M+H)$^+$ Example 7: Synthesis of compound 226

Compound 225 (10 mg) prepared in Example 6 was dissolved in methanol (1 ml). Cerium(III) chloride heptahydrate (57 mg) and sodium borohydride (6 mg) were added to the solution. The mixture was stirred at 0°C for 7 hr, and water was added to the reaction solution, followed by extraction with ethyl acetate. The ethyl acetate layer was washed with saturated brine and was dried over anhydrous magnesium sulfate, and the solvent was removed by evaporation under the reduced pressure to give a crude product of compound 226. The crude product was purified by preparative thin-layer chromatography (Merck Silica Gel 60 $F_{254}$ 0.5mm, acetone : hexane = 1 :1) to give compound 226 (8.5 mg).
Mass spectrometric data (ESI$^+$): 660 (M+H)$^+$ Example 8: Synthesis of compound 273

1,7,11-Trideacetyl-1,11-o-p-methoxybenzylidene pyripyropen A (10 mg) described in Japanese Patent Laid-Open Publication No. 269065/1996 was dissolved in anhydrous dichloromethane (0.5 ml), and pyridinium dichromate (PDC) (39 mg) was added to the solution. The reaction solution was stirred at room temperature for 4 hr, and the reaction solution was added to water. The dichloromethane layer was washed with saturated brine, and was dried over anhydrous sodium sulfate, and the solvent was then removed by evaporation under the reduced pressure to give a crude product of compound 273. The crude product was purified by preparative thin-layer chromatography (Merck Silica Gel 60 $F_{254}$ 0.5mm, chloroform : methanol = 12.5 :1) to give compound 273 (4.4 mg).
Mass spectrometric data ($ESI^+$): 574 $(M+H)^+$ Example 9: Synthesis of compound 274

1,11-o-Cyclic carbonate1,7,11-trideacetyl-pyripyropene A (4 mg) described in Japanese Patent Laid-Open Publication No. 269065/1996 was dissolved in anhydrous dichloromethane (1 ml). Triethylamine (5 μl) and 4-(dimethylamino)pyridine (1 mg) were added to the solution. The reaction solution was stirred at room temperature for 30 min, and valeric acid anhydride (5 μl) was added thereto. Next, the reaction solution was stirred at room temperature for 3 hr. The reaction solution was added to water, and the dichloromethane layer was washed with saturated brine and was dried over anhydrous sodium sulfate. The solvent was then removed by evaporation under the reduced pressure to give a crude product of compound 274. The crude product was purified by preparative thin-layer chromatography (Merck Silica Gel 60 $F_{254}$ 0.5mm, chloroform : methanol = 25 :1) to give compound 274 (0.1 mg).
Mass spectrometric data ($ESI^+$): 652 $(M+H)^+$ Example 10

Compounds shown in Tables 15 to 17 were synthesized using starting materials, reaction reagents 1 and 2 and solvents described in these tables. Further, the $^1$H-NMR data about some of the compounds in Tables 15 to 17 was described in Tables 18 to 29. In addition, $CDCl_3$ was used as the solvent for the $^1$H-NMR measurement. Tetramethylsilane was used as a standard substance for the $^1$H-NMR measurement.

Table 15

| Compound No. | Starting material (Compound No.) | Amount | Reaction reagent 1 | Amount | Reaction reagent 2 | Solvent | Yield | Mass spectrometric data Measuring Method | Data |
|---|---|---|---|---|---|---|---|---|---|
| 74 | 73 | 30 mg | acetic anhydride | 32.7 mg | Et$_3$N 64.0 mg, DMAP 12.8 mg | DMF | 13.6 mg | FAB | 612 (M+H)$^+$ |
| 77 | 73 | 30 mg | benzoic acid | 84.8 mg | EDCl 49.2 mg, DMAP 46.4 mg | DMF | 36.4 mg | FAB | 674 (M+H)$^+$ |
| 91 | 102 | 30 mg | pivalic anhydride | 220 mg | Et$_3$N 60.0 mg, DMAP 8.0 mg | DMF | 27.7 mg | FAB | 710 (M+H)$^+$ |
| 205 | 73 | 30 mg | nicotinic acid | 12.9 mg | EDCl 15.1 mg, DMAP 6.4 mg | DMF | 27.1 mg | FAB | 675 (M+H)$^+$ |
| 206 | 73 | 30 mg | isobutyric anhydride | 50.0 mg | Et$_3$N 64.0 mg, DMAP 12.8 mg | DMF | 11.4 mg | FAB | 640 (M+H)$^+$ |
| 207 | 73 | 30 mg | pivalic anhydride | 58.9 mg | Et$_3$N 64.0 mg, DMAP 12.8 mg | DMF | 23.4 mg | FAB | 654 (M+H)$^+$ |
| 208 | 73 | 30 mg | 4-(trifluoromethyl)benzoic anhydride | 114 mg | Et$_3$N 64.0 mg, DMAP 12.8 mg | DMF | 32.2 mg | FAB | 742 (M+H)$^+$ |
| 209 | 73 | 40 mg | 1,1-carbonyl diimidazole | 34.0 mg | | toluene | 5.1 mg | FAB | 664 (M+H)$^+$ |
| 210 | 73 | 30 mg | propyl isocyanate | 26.9 mg | Et$_3$N 64.0 mg, DMAP 12.8 mg | DMF | 3.2 mg | FAB | 655 (M+H)$^+$ |
| 211 | 73 | 30 mg | 3,4-dihydro-2H-pyran | 155 mg | pyridine hydrochloride | CH$_2$Cl$_2$ | 22.7 mg | FAB | 654 (M+H)$^+$ |
| 212 | 73 | 30 mg | 6-chloro nicotinic acid | 16.5 mg | EDCl 15.2 mg, DMAP 6.4 mg | DMF | 39.8 mg | FAB | 709 (M+H)$^+$ |
| 213 | 73 | 30 mg | cyclopropane carboxylic acid | 27 mg | EDCl 15.2 mg, DMAP 6.4 mg | DMF | 18.2 mg | FAB | 638 (M+H)$^+$ |
| 214 | 73 | 30 mg | cyclobutane carboxylic acid | 31 mg | EDCl 15.2 mg, DMAP 6.4 mg | DMF | 14.9 mg | FAB | 652 (M+H)$^+$ |
| 215 | 73 | 30 mg | acrylic acid | 22.5 mg | EDCl 15.2 mg, DMAP 6.4 mg | DMF | 5.6 mg | FAB | 624 (M+H)$^+$ |
| 216 | 73 | 30 mg | isonicotinic acid | 12.9 mg | EDCl 15.2 mg, DMAP 6.4 mg | DMF | 8.2 mg | FAB | 675 (M+H)$^+$ |
| 217 | 73 | 30 mg | picolinic acid | 12.9 mg | EDCl 15.2 mg, DMAP 8.4 mg | DMF | 40.6 mg | FAB | 675 (M+H)$^+$ |
| 219 | 102 | 30 mg | cyclobutane carboxylic acid | 131 mg | EDCl 76 mg, DMAP 32 mg | DMF | 38.9 mg | FAB | 704 (M+H)$^+$ |
| 220 | 102 | 30 mg | benzoic acid | 160 mg | EDCl 126 mg, DMAP 80 mg | DMF | 37.9 mg | FAB | 770 (M+H)$^+$ |
| 221 | 73 | 30 mg | 6-(trifluoromethyl)nicotinic acid | 30 mg | EDCl 15.2 mg, DMAP 6.4 mg | DMF | 35.4 mg | FAB | 743 (M+H)$^+$ |
| 223 | 102 | 30 mg | 3,3,3-trifluoropropionic acid | 168 mg | EDCl 126 mg, DMAP 80 mg | DMF | 10.4 mg | FAB | 788 (M+H)$^+$ |
| 224 | 73 | 30 mg | 3,3,3-trifluoropropionic acid | 20 mg | EDCl 15.2 mg, DMAP 6.4 mg | DMF | 8.0 mg | FAB | 680 (M+H)$^+$ |

Table16

| Compound No. | Starting material (Compound No.) | Amount | Reaction reagent 1 | Amount | Reaction reagent 2 | Solvent | Yield | Mass spectrometric data Measuring Method | Data |
|---|---|---|---|---|---|---|---|---|---|
| 227 | 73 | 20 mg | 3-fluoro-isonicotinic acid | 15 mg | EDCI 14 mg, DMAP 4 mg | DMF | 5.4 mg | FAB | 693 (M+H)+ |
| 228 | 73 | 20 mg | 3-chloro-isonicotinic acid | 17 mg | EDCI 14 mg, DMAP 4 mg | DMF | 7.8 mg | FAB | 709 (M+H)+ |
| 229 | 73 | 20 mg | 3-methyl picolinic acid | 14 mg | EDCI 28 mg, DMAP 8 mg | DMF | 16.7 mg | FAB | 689 (M+H)+ |
| 230 | 73 | 20 mg | 3-benzoyl-2-pyridine carboxylic acid | 48 mg | EDCI 28 mg, DMAP 8 mg | DMF | 16.4 mg | FAB | 779 (M+H)+ |
| 231 | 73 | 20 mg | 3-n-propoxy picolinic acid | 38 mg | EDCI 28 mg, DMAP 8 mg | DMF | 17.3 mg | FAB | 733 (M+H)+ |
| 232 | 73 | 20 mg | 6-fluoro nicotinic acid | 30 mg | EDCI 28 mg, DMAP 8 mg | DMF | 5.3 mg | FAB | 693 (M+H)+ |
| 233 | 102 | 20 mg | cyclopentane carboxylic acid | 99 mg | EDCI 84 mg, DMAP 5 mg | DMF | 28.3 mg | FAB | 746 (M+H)+ |
| 234 | 102 | 20 mg | cyclohexane carboxylic acid | 112 mg | EDCI 84 mg, DMAP 5 mg | DMF | 21.5 mg | FAB | 788 (M+H)+ |
| 235 | 102 | 20 mg | cyano acetic acid | 74 mg | EDCI 84 mg, DMAP 5 mg | DMF | 3.3 mg | FAB | 659 (M+H)+ |
| 236 | 102 | 20 mg | cyclopropyl acetic acid | 87 mg | EDCI 84 mg, DMAP 5 mg | DMF | 16.7 mg | FAB | 786 (M+H)+ |
| 237 | 102 | 20 mg | cyclopropyl acetic acid | 87 mg | EDCI 84 mg, DMAP 5 mg | DMF | 8.2 mg | FAB | 704 (M+H)+ |
| 238 | 102 | 20 mg | 2,2-difluoro-1-methylcyclopropanecarboxylic acid | 118 mg | EDCI 84 mg, DMAP 5 mg | DMF | 6.1 mg | FAB | 812 (M+H)+ |
| 239 | 73 | 20 mg | 4-methyl nicotinic acid | 36 mg | EDCI 28 mg, DMAP 8 mg | DMF | 16.1 mg | FAB | 689 (M+H)+ |
| 240 | 73 | 20 mg | 4-chloro nicotinic acid | 33 mg | EDCI 28 mg, DMAP 8 mg | DMF | 13.8 mg | FAB | 709 (M+H)+ |
| 241 | 73 | 20 mg | (4-methoxy carbonyl) nicotinic acid | 38 mg | EDCI 28 mg, DMAP 8 mg | DMF | 18.8 mg | FAB | 733 (M+H)+ |
| 242 | 73 | 20 mg | 5-(trifluoromethyl)thieno[3,2-b]pyridine-6-carboxylic acid | 38 mg | EDCI 28 mg, DMAP 8 mg | DMF | 20.3 mg | FAB | 799 (M+H)+ |
| 243 | 73 | 20 mg | 2-cyano benzoic acid | 31 mg | EDCI 28 mg, DMAP 8 mg | DMF | 6.8 mg | FAB | 699 (M+H)+ |
| 244 | 73 | 20 mg | 2-(trifluoromethyl)benzoic acid | 40 mg | EDCI 28 mg, DMAP 8 mg | DMF | 10.2 mg | FAB | 742 (M+H)+ |
| 245 | 73 | 20 mg | 2-fluoro benzoic acid | 29 mg | EDCI 28 mg, DMAP 8 mg | DMF | 16.1 mg | FAB | 692 (M+H)+ |
| 246 | 73 | 20 mg | 2-nitro benzoic acid | 35 mg | EDCI 28 mg, DMAP 8 mg | DMF | 9.8 mg | FAB | 719 (M+H)+ |
| 247 | 73 | 20 mg | 2-chloro nicotinic acid | 33 mg | EDCI 28 mg, DMAP 8 mg | DMF | 13.1 mg | FAB | 709 (M+H)+ |

Table 17

| Compound No. | Starting material (Compound No.) | Amount | Reaction reagent 1 | Amount | Reaction reagent 2 | Solvent | Yield | Mass spectrometric data Measuring Method | Data |
|---|---|---|---|---|---|---|---|---|---|
| 248 | 73 | 20 mg | 2-chloro-6-methyl nicotinic acid | 36 mg | EDCl 28 mg, DMAP 8 mg | DMF | 17.2 mg | FAB | 723 (M+H)* |
| 249 | 73 | 20 mg | methoxymethyl bromide | 31 mg | [(CH₃)₂CH]₂NEt 18 mg | DMF | 1.2 mg | ESI | 614 (M+H)* |
| 250 | 102 | 20 mg | 2,2-difluorocyclopropane carboxylic acid | 106 mg | EDCl 84 mg, DMAP 5 mg | DMF | 23.2 mg | ESI | 770 (M+H)* |
| 251 | 73 | 20 mg | 3-tert-buthylthio-2-carboxy pyridine | 44 mg | EDCl 28 mg, DMAP 8 mg | DMF | 7.6 mg | ESI | 763 (M+H)* |
| 252 | 73 | 20 mg | 3,5-difluoropyridine-2-carboxylic acid | 33 mg | EDCl 28 mg, DMAP 8 mg | DMF | 10.9 mg | ESI | 711 (M+H)* |
| 253 | 73 | 20 mg | pyrazine carboxylic acid | 26 mg | EDCl 28 mg, DMAP 8 mg | DMF | 10.9 mg | ESI | 676 (M+H)* |
| 254 | 73 | 20 mg | 4-thiazole carboxylic acid | 27 mg | EDCl 28 mg, DMAP 8 mg | DMF | 18.5 mg | ESI | 681 (M+H)* |
| 255 | 73 | 20 mg | 3-chloro thiophene-2-carboxylic acid | 34 mg | EDCl 28 mg, DMAP 8 mg | DMF | 15.8 mg | ESI | 714 (M+H)* |
| 256 | 73 | 20 mg | 6-methyl nicotinic acid | 29 mg | EDCl 28 mg, DMAP 8 mg | DMF | 15.1 mg | ESI | 689 (M+H)* |
| 257 | 73 | 20 mg | 6-chloro pyridine-2-carboxylic acid | 33 mg | EDCl 28 mg, DMAP 8 mg | DMF | 12.7 mg | ESI | 709 (M+H)* |
| 258 | 73 | 20 mg | 6-fluoro pyridine-2-carboxylic acid | 30 mg | EDCl 28 mg, DMAP 8 mg | DMF | 14.4 mg | ESI | 693 (M+H)* |
| 259 | 73 | 20 mg | 1-methyl indole-2-carboxylic acid | 37 mg | EDCl 28 mg, DMAP 8 mg | DMF | 18.8 mg | ESI | 727 (M+H)* |
| 260 | 73 | 20 mg | 3-chloropyridine-2-carboxylic acid | 33 mg | EDCl 28 mg, DMAP 8 mg | DMF | 14.6 mg | ESI | 709 (M+H)* |
| 262 | 73 | 20 mg | 2-fluoro nicotinic acid | 30 mg | EDCl 28 mg, DMAP 8 mg | DMF | 9.9 mg | ESI | 693 (M+H)* |
| 263 | 73 | 20 mg | 4-cyano benzoic acid | 31 mg | EDCl 28 mg, DMAP 8 mg | DMF | 14.0 mg | ESI | 699 (M+H)* |
| 264 | 73 | 20 mg | 3-cyano benzoic acid | 31 mg | EDCl 28 mg, DMAP 8 mg | DMF | 16.9 mg | ESI | 699 (M+H)* |
| 265 | 73 | 20 mg | 3-(trifluoromethyl)benzoic acid | 40 mg | EDCl 28 mg, DMAP 8 mg | DMF | 14.3 mg | ESI | 742 (M+H)* |
| 266 | 73 | 20 mg | 2-pyridyl acetic acid | 36 mg | EDCl 28 mg, DMAP 8 mg | DMF | 11.7 mg | ESI | 689 (M+H)* |
| 267 | 73 | 20 mg | 3-pyridyl acetic acid | 36 mg | EDCl 28 mg, DMAP 8 mg | DMF | 8.6 mg | ESI | 689 (M+H)* |
| 268 | 73 | 20 mg | (4-pyridylthio) acetic acid | 36 mg | EDCl 28 mg, DMAP 4 mg | DMF | 16.5 mg | ESI | 721 (M+H)* |
| 270 | 261 | 20 mg | 4-(trifluoromethyl)nicotinic acid | 39 mg | EDCl 28 mg, DMAP 4 mg | DMF | 8.3 mg | ESI | 767 (M+H)* |
| 271 | 261 | 20 mg | 3-chloropyridine-2-carboxylic acid | 32 mg | EDCl 28 mg, DMAP 4 mg | DMF | 14.5 mg | ESI | 733 (M+H)* |

Table 18

| Compound No. | $^1$H-NMR δ (ppm) |
|---|---|
| 73 | 0.91 (3H, s), 1.13 (3H, t, J = 5.1 Hz), 1.14 (3H, t, J = 5.1 Hz), 1.26 (1H, s), 1.32-1.40 (1H, m), 1.42 (3H, s), 1.45 (1H, d, J = 2.7 Hz), 1.49-1.51 (2H, m), 1.66 (3H, s), 1.81-1.91 (2H, m), 2.13-2.18 (1H, m), 2.24-2.37 (4H, m), 2.90 (1H, m), 3.79 (3H, m), 4.80 (1H, dd, J = 3.5, 7.6 Hz), 4.99-5.00 (1H, m), 6.52 (1H, s), 7.42 (1H, dd, J = 3.5, 5.4 Hz), 8.11 (1H, dt, J = 1.4, 5.4 Hz), 8.70 (1H, d, J = 2.4 Hz), 9.00 (1H, s) |
| 77 | 0.92 (3H, s), 1.14 (3H, t, J = 7.6 Hz), 1.20 (3H, t, J = 7.6 Hz), 1.26 (1H, s), 1.37-1.46 (1H, m), 1.51 (3H, s), 1.62 (1H, d, J = 3.8 Hz), 1.68-1.82 (2H, m), 1.87 (3H, s), 1.91-2.00 (2H, m), 2.18-2.23 (1H, m), 2.33 (2H, q, J = 7.6 Hz), 2.43 (2H, dq, J = 1.4, 7.6 Hz), 2.97 (1H, s), 3.70 (1H, d, J = 11.9 Hz), 3.84 (1H, d, J = 11.9 Hz), 4.83 (1H, dd, J = 5.1, 11.1 Hz), 5.05 (1H, d, J = 4.3 Hz), 5.27 (1H, dd, J = 4.6, 11.1 Hz), 6.45 (1H, s), 7.39-7.66 (4H, m), 8.05-8.13 (3H, m), 8.70 (1H, d, J = 4.6 Hz), 9.00 (1H, s) |
| 74 | 0.90 (3H, s), 1.12 (3H, t, J = 7.8 Hz), 1.13 (3H, t, J = 7.8 Hz), 1.19 (1H, s), 1.25-1.34 (1H, m), 1.44 (3H, s), 1.53-1.63 (3H, m), 1.69 (3H,s), 1.73-1.90 (2H, m), 2.10 (1H, m), 2.16 (3H, s), 2.33 (2H, dq, J = 2.4, 7.6 Hz), 2.36 (2H, dq, J = 3.2, 7.6 Hz), 2.87 (1H, m), 3.72 (2H, m), 4.81 (1H, dd, J = 4.6, 11.6 Hz), 4.97-5.00 (2H, m), 6.46 (1H, s), 7.40 (1H, dd, J = 4.6, 8.1 Hz), 8.10 (1H, m), 8.69 (1H, d, J = 4.9 Hz), 9.00 (1H, s) |
| 205 | 0.92 (3H, s), 1.14 (3H, t, J = 7.6 Hz), 1.20 (3H, t, J = 7.6 Hz), 1.26 (1H, s), 1.42-1.50 (1H, m), 1.59 (3H, s), 1.61-1.83 (3H, m), 1.85 (3H, s), 1.83-2.00 (2H, m), 2.18-2.23 (1H, m), 2.33 (2H, q, J = 7.6 Hz), 2.43 (2H, q, J = 7.6 Hz), 2.94 (1H, m), 3.72 (1H, d, J = 11.9 Hz), 3.82 (1H, d, J = 12.7 Hz), 4.83 (1H, dd, J = 4.9, 11.3 Hz), 5.03-5.06 (1H, m), 5.27 (1H, dd, J = 4.9, 11.3 Hz), 6.42 (1H, s), 7.38 (1H, dd, J = 4.9, 8.1 Hz), 7.45 (1H, dd, J = 4.9, 8.1 Hz), 8.07 (1H, dt, J = 2.2, 8.1 Hz), 8.36 (1H, dt, J = 1.9, 8.1 Hz), 8.67 (1H, dd, J = 1.9, 5.1 Hz), 8.83 (1H, dd, J = 1.9, 4.9 Hz), 8.97 (1H, d, J = 1.9 Hz), 9.30 (1H, d, J = 1.9 Hz) |
| 206 | 0.90 (3H, s), 1.13 (6H, t, J = 7.6 Hz), 1.19 (1H, s), 1.24 (3H, d, J = 4.6 Hz), 1.26 (3H, d, J = 4.6 Hz), 1.33-1.38 (1H, m), 1.45 (3H, s), 1.54 (1H, d, J = 3.8 Hz), 1.60-1.64 (2H, m), 1.67 (3H,s), 1.75-1.90 (2H, m), 2.15-2.19 (1H, m), 2.32 (2H, q, J = 7.6 Hz), 2.38 (2H, q, J = 7.6 Hz), 2.65 (1H, quint., J = 7.6 Hz), 2.88 (1H, d, J = 1.6 Hz), 3.68 (1H, d, J = 12.4 Hz), 3.83 (1H, d, J = 11.9 Hz), 4.80 (1H, dd, J = 4.9, 11.3 Hz), 5.00 (2H, m), 6.38 (1H, s), 7.40 (1H, dd, J = 4.6, 8.1 Hz), 8.09 (1H, dt, J = 1.9, 8.1 Hz), 8.69 (1H, dd, J = 1.6, 4.6 Hz), 9.00 (1H, d, J = 1.6 Hz) |

Table 19

| Compound No. | $^1$H-NMR δ (ppm) |
|---|---|
| 208 | 0.92 (3H, s), 1.14 (3H, t, J = 7.6 Hz), 1.21 (3H, t, J = 7.6 Hz), 1.26 (1H, s), 1.39-1.47 (1H, m), 1.50 (3H, s), 1.61 (1H, m), 1.68-1.83 (2H, m), 1.86 (3H,s), 1.91-2.05 (2H, m), 2.18-2.23 (1H, m), 2.33 (2H, q, J = 7.6 Hz), 2.43 (2H, dq, J = 1.4, 7.6 Hz), 2.95 (1H, d, J = 2.4 Hz), 3.72 (1H, d, J = 11.9 Hz), 3.82 (1H, d, J = 11.9 Hz), 4.83 (1H, dd, J = 5.1, 11.1 Hz), 5.03-5.06 (1H, m), 5.26 (1H, dd, J = 4.9, 11.1 Hz), 6.40 (1H, s), 7.38 (1H, dd, J = 4.9, 8.4 Hz), 7.76 (2H, d, J = 8.4 Hz), 8.06 (1H, dt, J = 2.2, 8.1 Hz), 8.22 (2H, d, J = 8.4 Hz), 8.66 (1H, dd, J = 1.6, 4.9 Hz), 8.96 (1H, d, J = 2.2 Hz) |
| 211 | 0.90 (3H, s), 1.14 (3H, t, J = 7.6 Hz), 1.15 (3H, t, J = 7.6 Hz), 1.26 (1H, s), 1.29-1.38 (1H, m), 1.41 (3H, s), 1.43-1.71 (5H, m), 1.59 (3H, s), 1.75-1.89 (6H, m), 2.12-2.17 (1H, m), 2.26-2.38 (4H, m), 2.86 (1H, m), 3.45-4.00 (5H, m), 4.82 (1H, dd, J = 5.4, 10.8 Hz), 4.97-5.03 (2H, m), 6.41 (1H, s), 7.40 (1H, dd, J = 4.9, 7.8 Hz), 8.07-8.13 (1H, m), 8.67-8.70 (1H, m), 9.01 (1H, d, J = 2.4 Hz) |
| 212 | 0.92 (3H, s), 1.14 (3H, t, J = 7.6 Hz), 1.20 (3H, t, J = 7.6 Hz), 1.26 (1H, s), 1.38-1.46 (1H, m), 1.50 (3H, s), 1.61 (1H, m), 1.66-1.78 (2H, m), 1.84 (3H, s), 1.87-1.99 (2H, m), 2.12-2.23 (1H, m), 2.31 (2H, q, J = 7.6 Hz), 2.41 (2H, q, J = 7.6 Hz), 2.95 (1H, m), 3.73 (1H, d, J = 11.9 Hz), 3.81 (1H, d, J = 11.9 Hz), 4.83 (1H, dd, J = 4.9, 11.3 Hz), 5.04 (1H, m), 5.25 (1H, dd, J = 4.9, 11.3 Hz), 6.40 (1H, s), 7.38 (1H, dd, J = 4.6, 7.8 Hz), 7.47 (1H, d, J = 8.1 Hz), 8.06 (1H, dt, J = 1.6, 7.8 Hz), 8.30 (1H, dd, J = 2.4, 8.1 Hz), 8.67 (1H, dd, J = 1.4, 4.6 Hz), 8.97 (1H, d, J = 2.4 Hz), 9.06 (1H, d, J = 2.7 Hz) |
| 213 | 0.90 (3H, s), 0.93 (2H, d, J = 2.7 Hz), 0.96 (2H, d, J = 2.7 Hz), 1.03-1.19 (6H, m), 1.26 (1H, s), 1.32-1.39 (1H, m), 1.45 (3H, s), 1.52 (1H, d, J = 3.8 Hz), 1.61-1.69 (3H, m), 1.71 (3H,s), 1.73-1.94 (2H, m), 2.14-2.19 (1H, m), 2.24-2.40 (4H, m), 2.95 (1H, m), 3.68 (1H, d, J = 11.9 Hz), 3.81 (1H, d, J = 11.9 Hz), 4.79 (1H, dd, J = 5.4, 11.3 Hz), 4.96-5.00 (2H, m), 6.45 (1H, s), 7.40 (1H, dd, J = 4.6, 8.1 Hz), 8.10 (1H, dt, J = 1.9, 8.1 Hz), 8.68 (1H, m), 9.01 (1H, m) |
| 214 | 0.90 (3H, s), 1.13 (3H, t, J = 7.6 Hz), 1.17 (3H, t, J = 7.6 Hz), 1.26 (1H, s), 1.34-1.40 (1H, m), 1.44 (3H, s), 1.54 (1H, d, J = 4.3 Hz), 1.61-1.67 (2H, m), 1.69 (3H,s), 1.72-2.42 (13H, m), 2.91 (1H, m), 3.23 (1H, quint., J = 8.1 Hz), 3.69 (1H, d, J = 11.9 Hz), 3.81 (1H, d, J = 11.9 Hz), 4.80 (1H, dd, J = 4.9, 11.3 Hz), 4.99-5.04 (2H, m), 6.40 (1H, s), 7.39 (1H, dd, J = 4.9, 8.1 Hz), 8.09 (1H, dt, J = 1.6, 8.1 Hz), 8.69 (1H, dd, J = 1.6, 4.6 Hz), 9.01 (1H, d, J = 1.6 Hz) |
| 215 | 0.90 (3H, s), 1.13 (3H, t, J = 7.6 Hz), 1.17 (3H, t, J = 7.6 Hz), 1.26 (1H, s), 1.41-1.46 (1H, m), 1.59 (3H, s), 1.65-1.68 (3H, m), 1.73 (3H, s), 1.84-1.90 (2H, m), 2.18 (1H, m), 2.31 (2H, q, J = 7.6 Hz), 2.38 (2H, q, J = 7.6 Hz), 2.93 (1H, m), 3.69 (1H, d, J = 11.9 Hz), 3.81 (1H, d, J = 11.9 Hz), 4.80(1H, m), 5.01-5.09 (2H, m), 5.92 (1H, dd, J = 1.6, 10.5 Hz), 6.15-6.24 (1H, m), 6.45 (1H, s), 6.45-6.53 (1H, m), 7.40 (1H, dd, J = 4.6, 7.8 Hz), 8.07-8.11 (1H, m), 8.68 (1H, dd, J = 1.9, 4.9 Hz), 9.00 (1H, d, J = 2.2 Hz) |

Table 20

| Compound No. | $^1$H-NMR $\delta$ (ppm) |
|---|---|
| 216 | 0.92 (3H, s), 1.14 (3H, t, J = 7.6 Hz), 1.20 (3H, t, J = 7.6 Hz), 1.26 (1H, s), 1.38-1.42 (1H, m), 1.50 (3H, s), 1.64-1.78 (3H, m), 1.85 (3H,s), 1.88-2.05 (2H, m), 2.17-2.23 (1H, m), 2.33 (2H, q, J = 7.6 Hz), 2.42 (2H, dq, J = 1.1, 7.6 Hz), 2.99 (1H, m), 3.72 (1H, d, J = 12.4 Hz), 3.81 (1H, d, J = 11.5 Hz), 4.83 (1H, dd, J = 4.9, 11.5 Hz), 5.03-5.05 (1H, m), 5.25 (1H, dd, J = 5.4, 11.5 Hz), 6.41 (1H, s), 7.37 (1H, dd, J = 5.2, 8.1 Hz), 7.91 (2H, dd, J = 1.6, 4.6 Hz), 8.07 (1H, dt, J = 1.6, 8.1 Hz), 8.67 (1H, dd, J = 1.9, 4.9 Hz), 8.83 (2H, dd, J = 1.6, 4.3 Hz), 8.97 (1H, d, J = 1.6 Hz) |
| 217 | 0.91 (3H, s), 1.13 (3H, t, J = 7.6 Hz), 1.20 (3H, t, J = 7.6 Hz), 1.26 (1H, s), 1.37-1.46 (1H, m), 1.50 (3H, s), 1.63-1.75 (3H, m), 1.87 (3H, s), 1.83-1.96 (2H, m), 2.13-2.23 (1H, m), 2.32 (2H, q, J = 7.6 Hz), 2.41 (2H, dq, J = 1.4, 7.6 Hz), 2.99 (1H, m), 3.67 (1H, d, J = 11.9 Hz), 3.83 (1H, d, J = 11.9 Hz), 4.83 (1H, dd, J = 5.4, 11.3 Hz), 4.98-5.06 (1H, m), 5.38 (1H, dd, J = 5.4, 10.8 Hz), 6.43 (1H, s), 7.35-7.44 (1H, m), 7.50-7.55 (1H, m), 7.89 (1H, dt, J = 1.6, 7.6 Hz), 8.07 (1H, dt, J = 1.6, 8.1 Hz), 8.18 (1H, d, J = 7.6 Hz), 8.67 (1H, dd, J = 1.6, 4.9 Hz), 8.82-8.84 (1H, m), 8.97 (1H, d, J = 2.4 Hz) |
| 218 | 0.83-1.12 (12H, m), 0.91 (3H, s), 1.26 (1H, s), 1.33-1.41 (1H, m), 1.45 (3H, s), 1.52-1.69 (6H, m), 1.71 (3H, s), 1.81-1.93 (2H, m), 2.14-2.18 (1H, m), 2.92 (1H, m), 3.72 (1H, d, J = 11.9 Hz), 3.82 (1H, d, J = 11.9 Hz), 4.80 (1H, dd, J = 4.9, 11.4 Hz), 4.99-5.04 (2H, m), 6.46 (1H, s), 7.41 (1H, dd, J = 4.9, 8.3 Hz), 8.10 (1H, dt, J = 1.7, 8.3 Hz), 8.69 (1H, dd, J = 1.5, 4.9 Hz), 9.01 (1H, d, J = 1.4 Hz) |
| 219 | 0.90 (3H, s), 1.26 (1H, s), 1.32-1.41 (1H, m), 1.44 (3H, s), 1.51-1.63 (3H, m), 1.69 (3H, s), 1.79-2.04 (8H, m), 2.17-2.40 (14H, m), 2.89 (1H, m), 3.08-3.26 (3H, m), 3.67 (1H, d, J = 11.9 Hz), 3.78 (1H, d, J = 11.9 Hz), 4.79 (1H, dd, J = 5.4, 11.1 Hz), 4.97-5.00 (2H, m), 6.41 (1H, s), 7.41 (1H, dd, J = 4.9, 8.1 Hz), 8.09 (1H, dt, J = 1.9, 8.4 Hz), 8.68 (1H, m), 9.00(1H, m) |
| 220 | 1.17 (3H, s), 1.26 (1H, s), 1.57 (3H, s), 1.65 (1H, m), 1.77-1.82 (2H, m), 1.88 (3H, s), 1.94-2.05 (3H, m), 2.13-2.31 (1H, m), 2.95 (1H, m), 4.16 (2H, s), 5.06 (1H, dd, J = 2.4, 6.5 Hz), 5.17-5.32 (2H, m), 6.42 (1H, s), 7.34-7.64 (10H, m), 8.01-8.12 (7H, m), 8.66 (1H, dd, J = 1.6, 5.1 Hz), 8.97 (1H, d, J = 1.9 Hz) |
| 221 | 0.92 (3H, s), 1.14 (3H, t, J = 7.6 Hz), 1.21 (3H, t, J = 7.6 Hz), 1.26 (1H, s), 1.44 (1H, m), 1.50 (3H, s), 1.57-1.62 (1H, m), 1.67-1.80 (2H, m), 1.85 (3H, s), 1.91-1.95 (2H, m), 2.17-2.24 (1H, m), 2.33 (2H, q, J = 7.6 Hz), 2.42 (2H, q, J = 7.6 Hz), 2.92 (1H, m), 3.74 (1H, d, J = 11.9 Hz), 3.81 (1H, d, J = 11.9 Hz), 4.84 (1H, dd, J = 4.9, 11.1 Hz), 5.04 (1H, m), 5.27 (1H, dd, J = 4.9, 11.1 Hz), 6.40 (1H, s), 7.38 (1H, dd, J = 4.9, 8.1 Hz), 7.84 (1H, d, J = 8.4 Hz), 8.05-8.08(1H, m), 8.54 (1H, d, J = 8.1 Hz), 8.67 (1H, d, J = 4.6 Hz), 8.96 (1H, d, J = 2.2 Hz), 9.38 (1H, s) |

Table21

| Compound No. | $^1$H-NMR $\delta$ (ppm) |
|---|---|
| 222 | 0.94 (3H, s), 1.14 (3H, t, J = 7.6 Hz), 1.19 (3H, t, J = 7.6 Hz), 1.26 (1H, s), 1.38-1.47 (1H, m), 1.48 (3H, s), 1.57-1.71 (3H, m), 1.75 (3H, s), 1.83-1.97 (2H, m), 2.10-2.22 (1H, m), 2.33 (2H, q, J = 7.6 Hz), 2.41 (2H, dq, J = 1.6, 7.6 Hz), 2.96 (1H, m), 3.74-3.80 (2H, m), 4.83 (1H, dd, J = 5.7, 11.6 Hz), 5.02-5.03 (1H, m), 5.28 (1H, dd, J = 5.4, 11.6 Hz), 6.41 (1H, s), 7.40 (1H, dd, J = 5.4, 7.6 Hz), 7.69 (1H, d, J = 5.4 Hz), 8.08 (1H, dt, J = 2.2, 8.1 Hz), 8.69 (1H, dd, J = 1.6, 4.9 Hz), 8.97 (1H, d, J = 4.6 Hz), 9.00 (1H, d, J = 2.4 Hz), 9.16 (1H, s) |
| 223 | 0.94 (3H, s), 1.26 (1H, s), 1.37 (1H, m), 1.47 (3H, s), 1.48-1.66 (3H, m), 1.71 (3H, s), 1.75-1.96 (2H, m), 2.17-2.24 (1H, m), 2.96 (1H, m), 3.14-3.35 (6H, m), 3.85 (1H, d, J = 12.2 Hz), 3.93 (1H, d, J = 12.2 Hz), 4.87 (1H, dd, J = 5.7, 10.8 Hz), 4.99-5.08 (2H, m), 6.41 (1H, s), 7.41 (1H, dd, J = 4.6, 8.1 Hz), 8.09 (1H, m), 8.69 (1H, m), 9.02 (1H, m) |
| 224 | 0.91 (3H, s), 1.13 (3H, t, J = 7.3 Hz), 1.17 (3H, t, J = 7.3 Hz), 1.26 (1H, s), 1.40 (1H, m), 1.45 (3H, s), 1.58-1.63 (3H, m), 1.70 (3H, s), 1.73-1.89 (2H, m), 2.10-2.18 (1H, m), 2.32 (2H, q, J = 7.6 Hz), 2.36 (2H, q, J = 7.6 Hz), 2.96 (1H, m), 3.25 (1H, d, J = 9.7 Hz), 3.32 (1H, d, J = 9.7 Hz), 3.69-3.81 (2H, m), 4.80 (1H, dd, J = 5.4, 11.3 Hz), 5.00-5.08 (2H, m), 6.40 (1H, s), 7.41 (1H, dd, J = 4.9, 8.1 Hz), 8.09 (1H, m), 8.69 (1H, dd, J = 1.4, 5.1 Hz), 9.01 (1H, d, J = 2.4 Hz) |
| 225 | 0.88 (3H, s), 1.13 (3H, t, J = 7.6 Hz), 1.19 (3H, t, J = 7.5 Hz), 1.22 (3H, t, J = 7.6 Hz), 1.24 (3H, s), 1.26 (1H, m), 1.50-1.55 (1H, m), 1.56 (3H, s), 1.55-1.64 (3H, m), 1.70-1.84 (2H, m), 2.31 (2H, dq, J = 1.2, 7.8 Hz), 2.42 (2H, dq, J = 3.4, 13.6 Hz), 2.44 (2H, dq, J = 2.0, 7.5 Hz), 2.79 (1H, dt, J = 1.4, 5.1 Hz), 3.69 (1H, d, J = 11.9 Hz), 3.79 (1H, d, J = 11.9 Hz), 4.79 (1H, dd, J = 4.9, 11.4 Hz), 5.24 (1H, dd, J = 4.9, 11.4 Hz), 6.45 (1H, s), 7.47 (1H, d, J = 8.5 Hz), 8.12 (1H, dd, J = 2.7, 8.5 Hz), 8.83 (1H, d, J = 2.7 Hz) |
| 226 | 0.89 (3H, s), 1.13 (3H, t, J = 7.6 Hz), 1.19 (3H, t, J = 7.6 Hz), 1.10-1.24 (3H, m), 1.26 (1H, s), 1.31-1.39 (1H, m), 1.44 (3H, s), 1.53 (1H, d, J = 3.8 Hz), 1.61-1.67 (2H, m), 1.69 (3H, s), 1.72-1.92 (2H, m), 2.08-2.18 (1H, m), 2.31 (2H, dq, J = 2.7, 7.6 Hz), 2.44 (2H, dq, J = 1.6, 7.6 Hz), 2.26-2.64 (2H, m), 2.85 (1H, s), 3.69 (1H, d, J = 11.9 Hz), 3.80 (1H, d, J = 11.9 Hz), 4.80 (1H, dd, J = 5.4, 11.3 Hz), 4.92-5.10 (2H, m), 6.41 (1H, s), 7.44 (1H, d, J = 8.4 Hz), 8.05 (1H, dd, J = 2.4, 8.4 Hz), 8.78 (1H, d, J = 2.4 Hz) |
| 227 | 0.88 (3H, s), 1.14 (3H, t, J = 7.6 Hz), 1.20 (3H, t, J = 7.6 Hz), 1.23-1.33 (1H, m), 1.43 (1H, m), 1.49 (3H, s), 1.61-1.74 (3H, m), 1.82 (3H, s), 1.87-2.23 (3H, m), 2.33 (2H, q, J = 7.6 Hz), 2.42 (2H, q, J = 7.6 Hz), 2.96 (1H, m), 3.73 (1H, d, J = 12.4 Hz), 3.82 (1H, d, J = 12.4 Hz), 4.83 (1H, dd, J = 5.4, 11.3 Hz), 5.03 (1H, m), 5.26 (1H, dd, J = 5.4, 11.3 Hz), 6.43 (1H, s), 7.39 (1H, dd, J = 4.9, 8.1 Hz), 7.86 (1H, t, J = 5.4 Hz), 8.08 (1H, dt, J = 1.9, 7.8 Hz), 8.60 (1H, d, J = 2.2 Hz), 8.66-8.68 (2H, m), 8.98 (1H, d, J = 2.2 Hz) |

Table 22

| Compound No. | $^1$H-NMR δ (ppm) |
|---|---|
| 228 | 0.93 (3H, s), 1.14 (3H, t, J = 7.6 Hz), 1.20 (3H, t, J = 7.6 Hz), 1.26 (1H, s), 1.32-1.44 (1H, m), 1.49 (3H, s), 1.61 (1H, d, J = 4.1 Hz), 1.67-1.75 (2H, m), 1.81 (3H,s), 1.79-2.05 (2H, m), 2.13-2.22 (1H, m), 2.33 (2H, q, J = 7.6 Hz), 2.42 (2H, dq, J = 1.4, 7.6 Hz), 2.92 (1H, m), 3.74 (1H, d, J = 11.9 Hz), 3.82 (1H, d, J = 11.9 Hz), 4.84 (1H, dd, J = 5.4, 10.8 Hz), 5.04 (1H, m), 5.27 (1H, dd, J = 5.4, 10.8 Hz), 6.43 (1H, s), 7.40 (1H, dd, J = 4.9, 8.1 Hz), 7.74 (1H, d, J = 5.1 Hz), 8.08 (1H, dt, J = 2.2, 8.1 Hz), 8.65 (1H, d, J = 4.9 Hz), 8.69 (1H, dd, J = 4.1, 7.6 Hz), 8.78 (1H, s), 8.99 (1H, d, J = 1.9 Hz) |
| 229 | 0.92 (3H, s), 1.14 (3H, t, J = 7.6 Hz), 1.19 (3H, t, J = 6.5 Hz), 1.26 (1H, s), 1.34-1.45 (1H, m), 1.49 (3H, s), 1.62 (1H, m), 1.71-1.77 (2H, m), 1.83 (3H, s), 1.88-2.01 (2H, m), 2.14-2.22 (1H, m), 2.33 (2H, q, J = 7.6 Hz), 2.42 (2H, dq, J = 2.2, 7.6 Hz), 2.64 (3H, s), 2.96 (1H, m), 3.72 (1H, d, J = 11.9Hz), 3.84 (1H, d, J = 11.9 Hz), 4.84 (1H, dd, J = 5.4, 11.3 Hz), 5.04 (1H, m), 5.36 (1H, dd, J = 5.4, 10.8 Hz), 6.42 (1H, s), 7.35-7.42 (2H, m), 7.66 (1H, d, J = 7.8 Hz), 8.08 (1H, dt, J = 1.9, 7.8 Hz), 8.60 (1H, d, J = 4.1 Hz), 8.68 (1H, dd, J = 1.6, 4.9 Hz), 8.98 (1H, d, J = 2.4 Hz), |
| 230 | 0.78 (3H, s), 1.09 (3H, t, J = 7.8 Hz), 1.12 (3H, t, J = 7.8 Hz), 1.26 (1H, s), 1.33 (3H, s), 1.36-1.38 (1H, m), 1.40-1.48 (2H, m), 1.55 (3H, s), 1.59-1.85 (2H, m), 2.09-2.18 (1H, m), 2.32 (4H, q, J = 7.6 Hz), 2.96 (1H, m), 3.40 (1H, d, J = 11.9 Hz), 3.75 (1H, d, J = 11.9 Hz), 4.72 (1H, dd, J = 4.9, 11.3 Hz), 4.95 (1H, m), 5.17 (1H, dd, J = 5.4, 11.9 Hz), 6.45 (1H, s), 7.40 (1H, dd, J = 4.9, 8.1 Hz), 7.49-7.67 (3H, m), 7.83-7.88 (4H, m), 8.02 (1H, s), 8.07 (1H, dt, J = 2.2, 8.1 Hz), 8.68 (1H, dd, J = 1.4, 4.6 Hz), 8.95 (1H, dd, J = 1.6, 4.6 Hz), 8.99 (1H, d, J = 1.9 Hz) |
| 231 | 0.91 (3H, s), 1.09 (3H, t, J = 7.6 Hz), 1.14 (3H, t, J = 7.6 Hz), 1.18 (3H, t, J = 7.6 Hz), 1.26 (1H, s), 1.34-1.43 (1H, m), 1.48 (3H, s), 1.63 (1H, m), 1.67-1.75 (2H, m), 1.80 (3H, s), 1.83-2.08 (4H, m), 2.17-2.25 (1H, m), 2.32 (2H, q, J = 7.6 Hz), 2.40 (2H, dq, J = 7.6, 1.9 Hz), 2.96 (1H, m), 3.64 (1H, d, J = 11.9 Hz), 3.87 (1H, d, J = 11.9 Hz), 4.05 (2H, t, J = 6.2 Hz), 4.82 (1H, dd, J = 5.4, 10.8 Hz), 5.04 (1H, m), 5.40 (1H, dd, J = 5.4, 10.8 Hz), 6.47 (1H, s), 7.19-7.44 (3H, m), 8.08 (1H, dt, J = 1.9, 8.1 Hz), 8.32 (1H, dd, J = 1.6, 4.3 Hz), 8.68 (1H, dd, J = 4.6, 1.6 Hz), 8.98 (1H, d, J = 1.6 Hz) |
| 232 | 0.92 (3H, s), 1.14 (3H, t, J = 7.6 Hz), 1.20 (3H, t, J = 7.6 Hz), 1.26 (1H, s), 1.34-1.43 (1H, m), 1.50 (3H, s), 1.61 (1H, m), 1.67-1.78 (2H, m), 1.84 (3H, s), 1.87-1.97 (2H, m), 2.13-2.23 (1H, m), 2.18 (1H,s), 2.32 (2H, q, J = 7.6 Hz), 2.42 (2H, dq, J = 1.4, 7.6 Hz), 3.73 (1H, d, J = 11.9 Hz), 3.80 (1H, d, J = 11.9 Hz), 4.83 (1H, dd, J = 5.4, 11.1 Hz), 5.04 (1H, d, J = 3.8 Hz), 5.25 (1H, dd, J = 5.1, 11.1 Hz), 6.41 (1H, s), 7.06 (1H, dd, J = 3.0, 8.6 Hz), 7.38 (1H, dd, J = 4.9, 8.1 Hz), 8.08 (1H, dt, J = 1.9, 8.1 Hz), 8.43-8.50 (1H, m), 8.67 (1H, dd, J = 1.6, 4.6 Hz), 8.95-8.98 (2H, m) |

Table 23

| Compound No. | $^1$H-NMR δ (ppm) |
|---|---|
| 233 | 0.91 (3H, s), 1.26 (1H, s), 1.45 (3H, s), 1.70 (3H, s), 1.32-1.97 (29H, m), 2.14-2.19 (1H, m), 2.66-2.90 (3H, m), 3.06 (1H, s), 3.67 (1H, d, J = 11.9 Hz), 3.78 (1H, d, J = 11.9 Hz), 4.78 (1H, dd, J = 5.4, 10.8 Hz), 4.98-5.01 (2H, m), 6.40 (1H, s), 7.42 (1H, dd, J = 4.9, 8.1 Hz), 8.11 (1H, dt, J = 1.6, 8.1 Hz), 8.69 (1H, d, J = 4.6 Hz), 9.01 (1H, s) |
| 234 | 0.91 (3H, s), 1.45 (3H, s), 1.70 (3H, s), 1.10-2.05 (37H, m), 2.14-2.49 (3H, m), 3.04 (1H, s), 3.65 (1H, d, J = 11.3 Hz), 3.77 (1H, d, J = 11.9 Hz), 4.78 (1H, dd, J = 5.4, 10.8 Hz), 4.97-5.01 (2H, m), 6.41 (1H, s), 7.42 (1H, dd, J = 4.9, 8.1 Hz), 8.11 (1H, dd, J = 1.9, 8.1 Hz), 8.69 (1H, d, J = 4.3 Hz), 9.01 (1H, s) |
| 235 | 1.00 (3H, s), 1.25-1.33 (3H, m), 1.48 (3H, s), 1.55 (1H, m), 1.71 (1H, m), 1.75 (3H, s), 1.79-1.98 (2H, m), 2.11-2.21 (1H, m), 3.48 (2H, s), 3.54 (2H, s), 3.60 (2H, s), 3.90 (1H, d, J = 11.9 Hz), 3.99 (1H, d, J = 11.9 Hz), 4.86 (1H, m), 4.98 (1H, m), 5.07-5.12 (1H, m), 6.53 (1H, s), 7.53 (1H, dd, J = 4.9, 8.1 Hz), 8.23 (1H, m), 8.30 (1H, m), 8.70 (1H, m), 9.05 (1H, m) |
| 236 | 0.11-0.27 (8H, m), 0.52-0.65 (8H, m), 0.88 (3H, s), 0.99-1.14 (5H, m), 1.15 (3H, s), 1.25-1.43 (2H, m), 1.61-1.76 (4H, m), 1.72 (3H, s), 2.18-2.54 (9H, m), 3.74 (1H, d, J = 11.9 Hz), 3.83 (1H, d, J = 11.9 Hz), 4.86 (1H, dd, J = 4.6, 11.6 Hz), 5.01-5.12 (2H, m), 6.41 (1H, s), 7.45 (1H, dd, J = 4.9, 7.8 Hz), 8.16 (1H, m), 8.71 (1H, m), 9.02 (1H, s) |
| 237 | 0.14-0.26 (6H, m), 0.52-0.64 (6H, m), 0.92 (3H, s), 0.97-1.16 (4H, m), 1.26-1.38 (1H, m), 1.45 (3H, s), 1.52 (1H, m), 1.63-1.70 (2H, m), 1.70 (3H, s), 1.82-1.91 (2H, m), 2.12-2.41 (7H, m), 2.96 (1H, m), 3.74 (1H, d, J = 11.9 Hz), 3.86 (1H, d, J = 11.9 Hz), 4.84 (1H, dd, J = 4.9, 11.3 Hz), 5.00-5.03 (2H, m), 6.43 (1H, s), 7.42 (1H, dd, J = 4.6, 7.8 Hz), 8.11 (1H, m), 8.70 (1H, d, J = 4.3 Hz), 9.01 (1H, s) |
| 238 | 0.91 (3H, s), 1.26 (1H, s), 1.44 (3H, s), 1.45 (3H, s), 1.46 (3H, s), 1.34-1.53 (7H, m), 1.52 (3H, s), 1.70 (3H, s), 1.81-2.02 (2H, m), 2.15-2.31 (3H, m), 2.96 (1H, s), 3.67 (1H, m), 4.00 (1H, m), 4.85-5.00 (3H, m), 6.46 (1H, s), 7.45 (1H, dd, J = 4.9, 8.1 Hz), 8.13 (1H, m), 8.70 (1H, m), 9.02 (1H, s) |
| 239 | 0.93 (3H, s), 1.14 (3H, t, J = 7.6 Hz), 1.20 (3H, t, J = 7.6 Hz), 1.26 (1H, s), 1.33-1.44 (1H, m), 1.50 (3H, s), 1.61 (1H, m), 1.68-1.77 (2H, m), 1.84 (3H, s), 1.91-1.99 (2H, m), 2.17-2.23 (1H, m), 2.32 (2H, q, J = 7.6 Hz), 2.43 (2H, dq, J = 3.0, 7.6 Hz), 2.69 (3H, s), 2.96 (1H, m), 3.75 (1H, d, J = 12.2 Hz), 3.80 (1H, d, J = 12.2 Hz), 4.48 (1H, dd, J = 5.1, 11.1 Hz), 5.04 (1H, d, J = 4.1 Hz), 5.23 (1H, d, J = 5.4, 10.8 Hz), 6.42 (1H, s), 7.24 (1H, d, J = 5.9 Hz), 7.39 (1H, dd, J = 4.9, 8.1 Hz), 8.08 (1H, d, J = 8.4 Hz), 8.61 (1H, d, J = 5.1 Hz), 8.67 (1H, d, J = 3.5 Hz), 8.98 (1H, s), 9.17 (1H, s) |

Table 24

| Compound No. | $^1$H-NMR δ (ppm) |
|---|---|
| 240 | 0.93 (3H, s), 1.13 (3H, t, J = 7.9 Hz), 1.19 (3H, t, J = 7.9 Hz), 1.26 (1H, s), 1.39-1.43 (1H, m), 1.49 (3H, s), 1.61 (1H, m), 1.68-1.79 (2H, m), 1.82 (3H, s), 1.88-2.04 (2H, m), 2.17-2.23 (1H, m), 2.32 (2H, q, J = 7.6 Hz), 2.42 (2H, dq, J = 1.9, 7.6 Hz), 2.96 (1H, s), 3.74 (1H, d, J = 11.9 Hz), 3.83 (1H, d, J = 11.9 Hz), 4.83 (1H, dd, J = 1.6, 5.4 Hz), 5.04 (1H, d, J = 4.1 Hz), 5.27 (1H, dd, J = 5.4, 11.6 Hz), 6.43 (1H, s), 7.39 (1H, dd, J = 4.9, 8.1 Hz), 7.47 (1H, d, J = 5.1 Hz), 8.08 (1H, dt, J = 1.9, 8.1 Hz), 8.68 (1H, dd, J = 1.4, 4.6 Hz), 8.64 (1H, d, J = 5.1 Hz), 8.99 (1H, d, J = 1.9 Hz), 9.14 (1H, s) |
| 241 | 0.93 (3H, s), 1.14 (3H, t, J = 7.6 Hz), 1.19 (3H, t, J = 7.6 Hz), 1.26 (1H, s), 1.38-1.43 (1H, m), 1.49 (3H, s), 1.59 (1H, d, J = 4.4 Hz), 1.66-1.73 (2H, m), 1.78 (3H, s), 1.82-2.05 (2H, m), 2.18-2.23 (1H, m), 2.31 (2H, q, J = 7.6 Hz), 2.41 (2H, dq, J = 1.4, 7.6 Hz), 2.96 (1H, s), 3.72 (1H, d, J = 7.6 Hz), 3.81 (1H, d, J = 7.6 Hz), 3.98 (3H, s), 4.84 (1H, dd, J = 5.4, 11.3 Hz), 5.04 (1H, m), 5.24 (1H, dd, J = 4.9, 10.8 Hz), 6.54 (1H, s), 7.39 (1H, dd, J = 4.9, 8.1 Hz), 7.53 (1H, d, J = 4.9 Hz), 8.08 (1H, dt, J = 1.9, 8.1 Hz), 8.68 (1H, d, J = 4.1 Hz), 8.88 (1H, d, J = 4.9 Hz), 9.00 (1H, s), 9.17 (1H, s) |
| 242 | 0.95 (3H, s), 1.15 (3H, t, J = 7.6 Hz), 1.20 (3H, t, J = 7.6 Hz), 1.26 (1H, s), 1.38-1.44 (1H, m), 1.49 (3H, s), 1.61 (1H, d, J = 4.1 Hz), 1.68-1.72 (2H, m), 1.76 (3H, s), 1.82-2.06 (2H, m), 2.18-2.23 (1H, m), 2.34 (2H, q, J = 7.6 Hz), 2.43 (2H, dq, J = 2.2, 7.6 Hz), 2.96 (1H, s), 3.78 (1H, d, J = 12.2 Hz), 3.83 (1H, d, J = 12.2 Hz), 4.84 (1H, dd, J = 5.4, 11.3 Hz), 5.04 (1H, d, J = 4.1 Hz), 5.2-5.34 (1H, m), 6.40 (1H, s), 7.40 (1H, dd, J = 4.9, 8.1 Hz), 7.76 (1H, d, J = 5.4 Hz), 8.02-8.11 (2H, m), 8.69 (1H, d, J = 4.3 Hz), 8.74 (1H, s), 9.00 (1H, s) |
| 243 | 0.93 (3H, s), 1.14 (3H, t, J = 7.6 Hz), 1.20 (3H, t, J = 7.6 Hz), 1.26 (1H, s), 1.39-1.44 (1H, m), 1.50 (3H, s), 1.62 (1H, m), 1.68-1.75 (2H, m), 1.84 (3H, s), 1.93-1.96 (2H, m), 2.14-2.23 (1H, m), 2.33 (2H, q, J = 7.6 Hz), 2.42 (2H, dq, J = 2.4, 7.6 Hz), 2.96 (1H, s), 3.72 (1H, d, J = 11.9 Hz), 3.83 (1H, d, J = 11.9 Hz), 4.83 (1H, dd, J = 1.6, 5.4 Hz), 5.04 (1H, m), 5.36 (1H, dd, J = 4.9, 11.3 Hz), 6.46 (1H, s), 7.38 (1H, dd, J = 5.4, 7.6 Hz), 7.68-7.78 (2H, m), 7.83-7.88 (1H, m), 8.07 (1H, dt, J = 1.9, 8.1 Hz), 8.19-8.23 (1H, m), 8.67 (1H, dd, J = 1.6, 4.9 Hz), 8.98 (1H, d, J = 2.2 Hz) |
| 244 | 0.93 (3H, s), 1.14 (3H, t, J = 7.6 Hz), 1.19 (3H, t, J = 7.6 Hz), 1.26 (1H, s), 1.34-1.43 (1H, m), 1.48 (3H, s), 1.60 (1H, d, J = 4.1 Hz), 1.66-2.02 (4H, m), 1.73 (3H, s), 2.11-2.23 (1H, m), 2.33 (2H, q, J = 7.6 Hz), 2.41 (2H, dq, J = 2.2, 7.6 Hz), 2.90 (1H, s), 3.74 (1H, d, J = 11.9 Hz), 5.83 (1H, d, J = 11.9 Hz), 4.82 (1H, dd, J = 4.9, 11.1 Hz), 5.03 (1H, m), 5.27 (1H, dd, J = 5.1, 11.6 Hz), 6.43 (1H, s), 7.41 (1H, dd, J = 4.9, 8.1 Hz), 7.65-7.70 (2H, m), 7.78-7.86 (2H, m), 8.09 (1H, dt, J = 1.9, 8.1 Hz), 8.69 (1H, d, J = 3.8 Hz), 9.00 (1H, s) |

Table 25

| Compound No. | $^1$H-NMR δ (ppm) |
|---|---|
| 245 | 0.92 (3H, s), 1.14 (3H, t, J = 7.5 Hz), 1.20 (3H, t, J = 7.5 Hz), 1.26 (1H, s), 1.39-1.46 (1H, m), 1.49 (3H, s), 1.62 (1H, d, J= 4.1 Hz), 1.83 (3H, s), 1.66-2.02 (4H, m), 2.11-2.23 (1H, m), 2.33 (2H, dq, J = 1.2, 7.6 Hz), 2.42 (2H, dq, J = 3.2, 7.6 Hz), 2.96 (1H, m), 3.70 (1H, d, J = 12.0 Hz), 3.85 (1H, d, J = 12.0 Hz), 4.83 (1H, dd, J = 4.9, 11.7 Hz), 5.04 (1H, m), 5.27 (1H, dd, J = 5.1, 11.9 Hz), 6.45 (1H, s), 7.18 (1H, dd, J = 8.5, 10.9 Hz), 7.27 (1H, m), 7.38 (1H, dd, J = 4.8, 8.1 Hz), 7.55-7.61 (1H, m), 8.03 (1H, dt, J = 1.7, 7.3 Hz), 8.08 (1H, dt, J = 1.7, 8.3 Hz), 8.67 (1H, d, J = 3.9 Hz), 8.98 (1H, s) |
| 246 | 0.93 (3H, s), 1.14 (3H, t, J = 7.5 Hz), 1.19 (3H, t, J = 7.5 Hz), 1.26 (1H, s), 1.32-1.42 (1H, m), 1.45 (3H, s), 1.59 (1H, d, J = 3.0 Hz), 1.66 (3H, s), 1.69-1.92 (4H, m), 2.02-2.21 (1H, m), 2.33 (2H, dq, J = 1.1, 5.1 Hz), 2.42 (2H, dq, J = 2.2, 5.1 Hz), 2.96 (1H, m), 3.76 (1H, d, J = 11.9 Hz), 3.84 (1H, d, J = 12.0 Hz), 4.83 (1H, dd, J = 4.9, 11.7 Hz), 5.03 (1H, d, J = 4.2 Hz), 5.19 (1H, dd, J = 5.4, 11.7 Hz), 6.60 (1H, s), 7.42 (1H, dd, J = 4.6, 8.1 Hz), 7.66-7.76 (2H, m), 7.84 (1H, dd, J = 1.5, 7.5 Hz), 7.93 (1H, dd, J = 1.5, 7.8 Hz), 8.11 (1H, dt, J = 2.1, 8.1 Hz), 8.69 (1H, d, J = 4.6 Hz), 9.03 (1H, s) |
| 247 | 0.93 (3H, s), 1.14 (3H, t, J = 7.6 Hz), 1.20 (3H, t, J = 7.6 Hz), 1.26 (1H, s), 1.42-1.46 (1H, m), 1.49 (3H, s), 1.61 (1H, d, J = 3.0 Hz), 1.68-1.79 (2H, m), 1.82 (3H, s), 1.86-2.02 (2H, m), 2.16-2.22 (1H, m), 2.33 (2H, dq, J = 1.1, 5.1 Hz), 2.42 (2H, dq, J = 2.4, 5.1 Hz); 2.96 (1H, m), 3.74 (1H, d, J = 12.0 Hz), 3.82 (1H, d, J = 12.0 Hz), 4.83 (1H, dd, J = 4.9, 11.7 Hz), 5.04 (1H, m), 5.27 (1H, dd, J = 5.1, 11.7 Hz), 6.44 (1H, s), 7.40 (1H, dd, J = 4.6, 7.8 Hz), 7.72 (1H, dd, J = 1.7, 8.3 Hz), 8.08 (1H, dt, J = 2.2, 8.5 Hz), 8.26 (1H, dd, J = 1.9, 7.8 Hz), 8.58 (1H, dd, J = 1.9, 4.9 Hz), 8.68 (1H, d, J = 3.6 Hz), 9.03 (1H, d, J = 1.7 Hz) |
| 248 | 0.93 (3H, s), 1.16 (3H, t, J = 7.6 Hz), 1.22 (3H, t, J = 7.6 Hz), 1.26 (1H, s), 1.42-1.46 (1H, m), 1.49 (3H, s), 1.61 (1H, d, J = 3.0 Hz), 1.68-1.78 (2H, m), 1.82 (3H, s), 1.86-2.01 (2H, m), 2.17-2.22 (1H, m), 2.33 (2H, dq, J = 1.1, 5.1 Hz), 2.42 (2H, dq, J = 2.4, 5.1 Hz), 2.62 (3H, s), 2.98 (1H, m), 3.73 (1H, d, J = 12.0 Hz), 3.84 (1H, d, J = 11.9 Hz), 4.83 (1H, dd, J = 4.8, 11.5 Hz), 5.04 (1H, d, J = 3.4 Hz), 5.25 (1H, dd, J = 5.1, 11.4 Hz), 6.44 (1H, s), 7.22 (1H, d, J = 7.8 Hz), 7.40 (1H, dd, J = 4.9, 8.0 Hz), 8.08 (1H, dt, J = 2.2, 8.0 Hz), 8.18 (1H, d, J = 7.8 Hz), 8.69 (1H, d, J = 3.7 Hz), 8.99 (1H, d, J = 1.7 Hz) |
| 249 | 0.91 (3H, s), 1.14 (3H, t, J = 7.8 Hz), 1.15 (3H, t, J = 7.8 Hz), 1.26 (1H, s), 1.29-1.39 (1H, m), 1.42 (3H, s), 1.45 (1H, m), 1.57-1.64 (2H, m), 1.66 (3H, s), 1.81-1.88 (2H, m), 2.14-2.18 (1H, m), 2.33 (2H, q, J = 7.8 Hz), 2.35 (2H, q, J = 7.8 Hz), 2.84 (1H, m), 3.46 (3H, s), 3.68 (1H, d, J = 11.7 Hz), 3.93 (1H, d, J = 11.9 Hz), 4.73-4.87 (4H, m), 4.95-5.00 (1H, m), 6.43 (1H, s), 7.42 (1H, dd, J = 4.8, 8.0 Hz), 8.12 (1H, m), 8.69 (1H, m), 9.01 (1H, d, J = 2.2Hz) |
| 250 | 0.92 (3H, s), 1.26 (1H, s), 1.34-1.55 (3H, m), 1.46 (3H, s), 1.71 (3H, s), 1.66-1.92 (6H, m), 2.01-2.18 (4H, m), 2.38-2.57 (3H, m), 3.66-3.78 (1H, m), 3.95-4.13 (1H, m), 4.73-4.84 (1H, m), 4.89-4.95 (1H, m), 4.99-5.10 (1H, m), 6.45 (1H, s), 7.43 (1H, dd, J = 4.9, 8.3 Hz), 8.11 (1H, m), 8.70 (1H, d, J = 4.9 Hz), 9.02 (1H, s) |

Table 26

| Compound No. | $^1$H-NMR δ (ppm) |
|---|---|
| 251 | 0.93 (3H, s), 1.14 (3H, t, J = 7.5 Hz), 1.17 (3H, t, J = 7.5 Hz), 1.26 (1H, s), 1.36 (9H, s), 1.42 (1H, m), 1.47 (3H, s), 1.62–1.70 (3H, m), 1.75 (3H, s), 1.80–1.95 (2H, m), 2.07–2.21 (1H, m), 2.32 (2H, dq, J = 1.5, 7.5 Hz), 2.40 (2H, dq, J = 3.9, 7.6 Hz), 2.96 (1H, m), 3.69 (1H, d, J = 11.9 Hz), 3.87 (1H, d, J = 11.9 Hz), 4.83 (1H, dd, J = 4.9, 11.7 Hz), 5.04 (1H, m), 5.36 (1H, dd, J = 5.1, 11.7 Hz), 6.53 (1H, s), 7.39–7.43 (1H, m), 7.98 (1H, dd, J = 1.7, 8.0 Hz), 8.02 (1H, s), 8.10 (1H, dt, J = 1.7, 8.0 Hz), 8.65 (1H, dd, J = 1.5, 4.7 Hz), 8.69 (1H, d, J = 3.7 Hz), 8.99 (1H, s) |
| 252 | 0.92 (3H, s), 1.14 (3H, t, J = 7.5 Hz), 1.19 (3H, t, J = 7.5 Hz), 1.26 (1H, s), 1.42–1.45 (1H, m), 1.49 (3H, s), 1.62–1.73 (3H, m), 1.82 (3H, s), 1.84–2.00 (2H, m), 2.18–2.22 (1H, m), 2.32 (2H, dq, J = 1.5, 7.5 Hz), 2.41 (2H, dq, J = 2.5, 7.5 Hz), 2.96 (1H, m), 3.68 (1H, d, J = 11.9 Hz), 3.85 (1H, d, J = 11.9 Hz), 4.82 (1H, dd, J = 4.9, 11.7 Hz), 5.04 (1H, m), 5.37 (1H, dd, J = 4.8, 11.7 Hz), 6.44 (1H, s), 7.36–7.41 (2H, m), 8.08 (1H, dt, J = 1.7, 8.0 Hz), 8.53 (1H, d, J = 2.0 Hz), 8.68 (1H, dd, J = 0.7, 4.9 Hz), 8.98 (1H, d, J = 2.6 Hz) |
| 253 | 0.92 (3H, s), 1.14 (3H, t, J = 7.5 Hz), 1.20 (3H, t, J = 7.5 Hz), 1.26 (1H, s), 1.40–1.47 (1H, m), 1.51 (3H, s), 1.64 (1H, d, J = 2.4 Hz), 1.73 (2H, m), 1.87 (3H, s), 1.85–2.00 (2H, m), 2.18–2.23 (1H, m), 2.32 (2H, q, J = 7.6 Hz), 2.42 (2H, dq, J = 1.5, 7.6 Hz), 2.96 (1H, m), 3.71 (1H, d, J = 12.0 Hz), 3.83 (1H, d, J = 11.9 Hz), 4.84 (1H, dd, J = 4.9, 11.7 Hz), 5.05 (1H, m), 5.39 (1H, dd, J = 5.2, 11.6 Hz), 6.42 (1H, s), 7.39 (1H, dd, J = 4.9, 8.1 Hz), 8.02 (1H, s), 8.07 (1H, m), 8.68 (1H, d, J = 4.4 Hz), 8.80–8.83 (1H, m), 8.97 (1H, m), 9.38 (1H, m) |
| 254 | 0.91 (3H, s), 1.14 (3H, t, J = 7.6 Hz), 1.19 (3H, t, J = 7.6 Hz), 1.26 (1H, s), 1.39–1.46 (1H, m), 1.49 (3H, s), 1.63 (1H, d, J = 2.7 Hz), 1.70–1.73 (2H, m), 1.85 (3H, s), 1.88–2.01 (2H, m), 2.18–2.22 (1H, m), 2.32 (2H, q, J = 7.5 Hz), 2.41 (2H, dq, J = 2.2, 7.6 Hz), 2.97 (1H, m), 3.68 (1H, d, J = 11.7 Hz), 3.83 (1H, d, J = 11.9 Hz), 4.83 (1H, dd, J = 4.9, 11.7 Hz), 5.04 (1H, m), 5.34 (1H, dd, J = 5.4, 11.5 Hz), 6.44 (1H, s), 7.39 (1H, dd, J = 4.9, 8.0 Hz), 8.07 (1H, dt, J = 1.9, 6.3 Hz), 8.32 (1H, d, J = 2.0 Hz), 8.67 (1H, d, J = 4.1 Hz), 8.92 (1H, d, J = 2.0 Hz), 8.98 (1H, s) |
| 255 | 0.92 (3H, s), 1.14 (3H, t, J = 7.5 Hz), 1.19 (3H, t, J = 7.5 Hz), 1.26 (1H, s), 1.38–1.45 (1H, m), 1.49 (3H, s), 1.60 (1H, d, J = 3.0 Hz), 1.68–1.70 (2H, m), 1.83 (3H, s), 1.75–1.98 (2H, m), 2.17–2.21 (1H, m), 2.33 (2H, dq, J = 1.7, 7.5 Hz), 2.41 (2H, dq, J = 2.2, 7.5 Hz), 2.97 (1H, m), 3.67 (1H, d, J = 12.0 Hz), 3.87 (1H, d, J = 11.9 Hz), 4.81 (1H, dd, J = 4.9, 11.7 Hz), 5.03 (1H, m), 5.23 (1H, dd, J = 5.1, 11.5 Hz), 6.46 (1H, s), 7.07 (1H, d, J = 5.2 Hz), 7.39 (1H, dd, J = 4.9, 8.1 Hz), 7.54 (1H, d, J = 5.3 Hz), 8.08 (1H, dt, J = 2.2, 8.1 Hz), 8.67 (1H, dd, J = 1.4, 4.9 Hz), 8.99 (1H, d, J = 2.2 Hz) |

Table 27

| Compound No. | $^1$H-NMR δ (ppm) |
|---|---|
| 256 | 0.92 (3H, s), 1.12 (3H, t, J = 7.8 Hz), 1.15 (3H, t, J = 7.7 Hz), 1.26 (1H, s), 1.39-1.47 (1H, m), 1.50 (3H, s), 1.61 (1H, d, J = 2.4 Hz), 1.69-1.81 (2H, m), 1.85 (3H, s), 1.90-1.99 (2H, m), 2.18-2.21 (1H, m), 2.33 (2H, dq, J = 1.2, 7.7 Hz), 2.41 (2H, dq, J = 2.7, 7.6 Hz), 2.66 (3H, s), 2.96 (1H, m), 3.72 (1H, d, J = 11.7 Hz), 3.83 (1H, d, J = 12.0 Hz), 4.83 (1H, dd, J = 4.9, 11.4 Hz), 5.04 (1H, m), 5.25 (1H, dd, J = 5.3, 11.7 Hz), 6.41 (1H, s), 7.30 (1H, d, J = 8.0 Hz), 7.38 (1H, dd, J = 4.9, 8.1 Hz), 8.07 (1H, dt, J = 2.2, 8.1 Hz), 8.24 (1H, dd, J = 2.2, 8.0 Hz), 8.67 (1H, dd, J = 1.5, 4.9 Hz), 8.97 (1H, d, J = 2.2 Hz), 9.18 (1H, d, J = 2.2 Hz) |
| 257 | 0.91 (3H, s), 1.14 (3H, t, J = 7.5 Hz), 1.19 (3H, t, J = 7.5 Hz), 1.26 (1H, s), 1.38-1.46 (1H, m), 1.50 (3H, s), 1.63 (1H, d, J = 2.4 Hz), 1.70-1.73 (2H, m), 1.86 (3H, s), 1.83-1.98 (2H, m), 2.18-2.22 (1H, m), 2.32 (2H, dq, J = 1.5, 7.7 Hz), 2.41 (2H, dq, J = 2.2, 7.7 Hz), 2.96 (1H, d, J = 1.9 Hz), 3.68 (1H, d, J = 11.9 Hz), 3.84 (1H, d, J = 12.0 Hz), 4.83 (1H, dd, J = 4.9, 11.7 Hz), 5.05 (1H, m), 5.32 (1H, dd, J = 5.3, 11.7 Hz), 6.43 (1H, s), 7.39 (1H, dd, J = 4.9, 8.0 Hz), 7.56 (1H, d, J = 8.1 Hz), 7.85 (1H, t, J = 7.8 Hz), 8.07 (2H, m), 8.67 (1H, dd, J = 1.7, 4.9 Hz), 8.98 (1H, d, J = 2.0 Hz) |
| 258 | 0.91 (3H, s), 1.14 (3H, t, J = 7.5 Hz), 1.19 (3H, t, J = 7.5 Hz), 1.26 (1H, s), 1.38-1.46 (1H, m), 1.50 (3H, s), 1.62 (1H, d, J = 2.4 Hz), 1.69-1.72 (2H, m), 1.86 (3H, s), 1.80-1.96 (2H, m), 2.18-2.22 (1H, m), 2.32 (2H, q, J = 7.5 Hz), 2.41 (2H, dq, J = 2.2, 7.5 Hz), 2.93 (1H, d, J = 1.9 Hz), 3.68 (1H, d, J = 11.9 Hz), 3.83 (1H, d, J = 12.0 Hz), 4.83 (1H, dd, J = 4.9, 11.4 Hz), 5.04 (1H, m), 5.33 (1H, dd, J = 5.3, 11.5 Hz), 6.42 (1H, s), 7.20 (1H, dd, J = 2.9, 8.0 Hz), 7.38 (1H, dd, J = 4.9, 8.3 Hz), 8.00 (1H, q, J = 7.8 Hz), 8.08 (2H, m), 8.67 (1H, dd, J = 1.4, 4.6 Hz), 8.97 (1H, d, J = 2.2 Hz) |
| 259 | 0.93 (3H, s), 1.14 (3H, t, J = 7.5 Hz), 1.21 (3H, t, J = 7.5 Hz), 1.26 (1H, s), 1.40-1.47 (1H, m), 1.51 (3H, s), 1.61 (1H, d, J = 3.0 Hz), 1.70-1.83 (2H, m), 1.86 (3H, s), 1.92-1.98 (2H, m), 2.17-2.22 (1H, m), 2.32 (2H, q, J = 7.3 Hz), 2.43 (2H, dq, J = 1.4, 5.3 Hz), 2.97 (1H, d, J = 2.0 Hz), 3.74 (1H, d, J = 11.7 Hz), 3.83 (1H, d, J = 11.7 Hz), 4.13 (3H, s), 4.84 (1H, dd, J = 4.9, 11.4 Hz), 5.05 (1H, m), 5.24 (1H, dd, J = 5.3, 11.7 Hz), 6.43 (1H, s), 7.16-7.20 (1H, m), 7.35-7.44 (4H, m), 7.70 (1H, d, J = 8.1 Hz), 8.05 (1H, dt, J = 1.7, 8.3 Hz), 8.66 (1H, dd, J = 1.5, 4.9 Hz), 8.96 (1H, d, J = 2.2 Hz) |
| 260 | 0.93 (3H, s), 1.14 (3H, t, J = 7.5 Hz), 1.19 (3H, t, J = 7.5 Hz), 1.26 (1H, s), 1.40-1.46 (1H, m), 1.48 (3H, s), 1.63 (1H, d, J = 3.0 Hz), 1.71-1.74 (2H, m), 1.80 (3H, s), 1.83-1.95 (1H, m), 2.02-2.06 (1H, m), 2.18-2.22 (1H, m), 2.32 (2H, dq, J = 1.7, 7.6 Hz), 2.41 (2H, dq, J = 3.4, 7.5 Hz), 2.96 (1H, m), 3.70 (1H, d, J = 12.0 Hz), 3.87 (1H, d, J = 11.9 Hz), 4.83 (1H, dd, J = 4.8, 11.5 Hz), 5.05 (1H, m), 5.37 (1H, dd, J = 4.9, 11.7 Hz), 6.46(1H, s), 7.39-7.45 (2H, m), 7.87 (1H, dd, J = 1.5, 8.3 Hz), 8.08 (1H, dt, J = 1.5, 8.3 Hz), 8.64 (1H, dd, J = 1.2, 4.6 Hz), 8.69 (1H, d, J = 4.9 Hz), 8.97 (1H, d, J = 2.2 Hz) |
| 261 | 0.85-1.06 (8H, m), 0.92 (3H, s), 1.26 (1H, s), 1.30-1.40 (1H, m), 1.42 (3H, s), 1.45-1.63 (5H, m), 1.67 (3H, s), 1.81-1.92 (2H, m), 2.14-2.25 (2H, m), 2.88 (1H, d, J = 1.4 Hz), 3.75 (1H, d, J = 11.9 Hz), 3.86 (1H, d, J = 11.6 Hz), 3.78-3.82 (1H, m), 4.82 (1H, dd, J = 5.1, 11.4 Hz), 5.00 (1H, m), 6.52 (1H, s), 7.42 (1H, dd, J = 4.9, 8.0 Hz), 8.11 (1H, dt, J = 1.7, 8.0 Hz), 8.69 (1H, dd, J = 1.5, 4.9 Hz), 9.01 (1H, d, J = 1.9 Hz) |

Table 28

| Compound No. | $^1$H-NMR δ (ppm) |
|---|---|
| 262 | 0.92 (3H, s), 1.14 (3H, t, J = 7.5 Hz), 1.20 (3H, t, J = 7.5 Hz), 1.26 (1H, s), 1.39-1.47 (1H, m), 1.49 (3H, s), 1.61 (1H, d, J = 2.7 Hz), 1.66-1.71 (2H, m), 1.84 (3H, s), 1.76-1.99 (2H, m), 2.18-2.22 (1H, m), 2.32 (2H, dq, J = 1.0, 7.5 Hz), 2.42 (2H, dq, J = 2.7, 7.5 Hz), 2.96 (1H, m), 3.73 (1H, d, J = 11.9 Hz), 3.82 (1H, d, J = 11.9 Hz), 4.83 (1H, dd, J = 4.9, 11.7 Hz), 5.04 (1H, m), 5.26 (1H, dd, J = 5.1, 11.7 Hz), 6.44 (1H, s), 7.35-7.41 (2H, m), 8.07 (1H, dt, J = 1.7, 8.0 Hz), 8.44-8.50 (2H, m), 8.67 (1H, d, J = 4.9 Hz), 8.98 (1H, d, J = 1.7 Hz) |
| 263 | 0.92 (3H, s), 1.12 (3H, t, J = 7.5 Hz), 1.20 (3H, t, J = 7.5 Hz), 1.26 (1H, s), 1.30-1.47 (1H, m), 1.50 (3H, s), 1.62 (1H, d, J = 2.4 Hz), 1.69-1.71 (2H, m), 1.85 (3H, s), 1.75-1.97 (2H, m), 2.18-2.22 (1H, m), 2.33 (2H, dq, J = 0.9, 7.6 Hz), 2.42 (2H, dq, J = 2.4, 7.6 Hz), 2.98 (1H, m), 3.73 (1H, d, J = 11.6 Hz), 3.81 (1H, d, J = 11.9 Hz), 4.84 (1H, dd, J = 4.9, 11.7 Hz), 5.05 (1H, m), 5.26 (1H, dd, J = 5.1, 11.5 Hz), 6.40 (1H, s), 7.38 (1H, dd, J = 4.9, 8.0 Hz), 7.80 (2H, d, J = 8.8 Hz), 8.06 (1H, dt, J = 1.7, 8.0 Hz), 8.21 (2H, d, J = 8.8 Hz), 8.67 (1H, dd, J = 1.5, 4.9 Hz), 8.96 (1H, d, J = 1.7 Hz) |
| 264 | 0.92 (3H, s), 1.14 (3H, t, J = 7.5 Hz), 1.20 (3H, t, J = 7.5 Hz), 1.26 (1H, s), 1.39-1.47 (1H, m), 1.51 (3H, s), 1.62 (1H, d, J = 2.4 Hz), 1.68-1.82 (2H, m), 1.86 (3H, s), 1.93-2.01 (2H, m), 2.19-2.23 (1H, m), 2.32 (2H, dq, J = 1.0, 7.6 Hz), 2.42 (2H, dq, J = 2.4, 7.5 Hz), 2.97 (1H, m), 3.73 (1H, d, J = 11.9 Hz), 3.80 (1H, d, J = 11.9 Hz), 4.84 (1H, dd, J = 4.9, 11.7 Hz), 5.05 (1H, m), 5.26 (1H, dd, J = 5.1, 11.5 Hz), 6.41 (1H, s), 7.38 (1H, dd, J = 4.1, 8.0 Hz), 7.65 (1H, m), 7.90 (1H, dt, J = 1.5, 7.8 Hz), 8.07 (1H, dt, J = 2.2, 8.0 Hz), 8.34 (1H, dt, J = 1.5, 7.8 Hz), 8.38 (1H, t, J = 1.5 Hz), 8.67 (1H, dd, J = 1.5, 4.9 Hz), 8.96 (1H, d, J = 2.4 Hz) |
| 265 | 0.92 (3H, s), 1.14 (3H, t, J = 7.5 Hz), 1.21 (3H, t, J = 7.5 Hz), 1.26 (1H, s), 1.39-1.48 (1H, m), 1.51 (3H, s), 1.63 (1H, d, J = 2.7 Hz), 1.63-1.83 (2H, m), 1.86 (3H, s), 1.90-1.98 (2H, m), 2.18-2.23 (1H, m), 2.33 (2H, q, J = 7.5 Hz), 2.43 (2H, dq, J = 2.5, 7.6 Hz), 2.97 (1H, m), 3.72 (1H, d, J = 11.9 Hz), 3.82 (1H, d, J = 12.0 Hz), 4.84 (1H, dd, J = 4.9, 11.4 Hz), 5.05 (1H, d, J = 4.1 Hz), 5.28 (1H, dd, J = 5.1, 11.5 Hz), 6.42 (1H, s), 7.38 (1H, dd, J = 4.9, 8.0 Hz), 7.65 (1H, t, J = 7.8 Hz), 7.88 (1H, d, J = 7.8 Hz), 8.06 (1H, dt, J = 1.8, 8.0 Hz), 8.30 (1H, d, J = 8.1 Hz), 8.36 (1H, s), 8.67 (1H, dd, J = 1.5, 4.9 Hz), 8.97 (1H, d, J = 2.2 Hz) |
| 266 | 0.89 (3H, s), 1.13 (3H, t, J = 7.6 Hz), 1.14 (3H, t, J = 7.6 Hz), 1.26 (1H, s), 1.33-1.37 (1H, m), 1.42 (3H, s), 1.46-1.55 (1H, m), 1.58 (3H, s), 1.60-1.70 (2H, m), 1.78-1.91 (2H, m), 2.13-2.17 (1H, m), 2.32 (2H, dq, J = 1.7, 7.3 Hz), 2.35 (2H, q, J = 7.3 Hz), 2.89 (1H, m), 3.66 (1H, d, J = 11.4 Hz), 3.81 (1H, d, J = 12.0 Hz), 3.96 (2H, s), 4.76-4.82 (1H, m), 4.98-5.06 (2H, m), 6.38 (1H, s), 7.17-7.25 (1H, m), 7.36-7.46 (2H, m), 7.69-7.73 (1H, m), 8.08-8.12 (1H, m), 8.60 (1H, dt, J = 1.0, 4.9 Hz), 8.70 (1H, dd, J = 1.7, 4.9 Hz), 9.00 (1H, d, J = 1.4 Hz) |

Table 29

| Compound No. | $^1$H-NMR δ (ppm) |
|---|---|
| 267 | 0.89 (3H, s), 1.13 (3H, t, J = 7.6 Hz), 1.15 (3H, t, J = 7.6 Hz), 1.26 (1H, s), 1.43 (3H, s), 1.50 (3H, d, J = 3.0 Hz), 1.61 (3H, s), 1.58-1.70 (2H, m), 1.75-1.93 (2H, m), 2.14-2.18 (1H, m), 2.32 (2H, q, J = 7.6 Hz), 2.36 (2H, q, J =7.6 Hz), 2.90 (1H, d, J = 1.9 Hz), 3.70 (1H, d, J = 12.0 Hz), 3.74 (2H, s), 3.77 (1H, d, J = 11.9 Hz), 4.79 (1H, dd, J = 4.9, 11.4 Hz), 4.96-5.00 (2H, m), 6.37 (1H, s), 7.32 (1H, dd, J = 4.8, 7.6 Hz), 7.42 (1H, dd, J = 4.9, 8.1 Hz), 7.71 (1H, d, J = 7.8 Hz), 8.12 (1H, dt, J = 1.9, 8.1 Hz), 8.57 (1H, dd, J = 1.6, 4.8 Hz), 8.65 (1H, d, J = 1.9 Hz), 8.70 (1H, dd, J = 1.6, 4.7 Hz), 9.04 (1H, d, J = 4.2 Hz) |
| 269 | 0.85-1.11 (8H, m), 0.93 (3H, s), 1.26 (1H, s), 1.39-1.47 (1H, m), 1.50 (3H, s), 1.55-1.68 (5H, m), 1.87 (3H, s), 1.83-2.02 (2H, m), 2.17-2.22 (1H, m), 2.96 (1H, s), 3.79 (1H, d, J = 12.2 Hz), 3.83 (1H, d, J = 12.1 Hz), 4.85 (1H, dd, J = 4.9, 11.5 Hz), 5.04 (1H, m), 5.38 (1H, dd, J = 5.12, 11.6 Hz), 6.46 (1H, s), 7.38 (1H, dd, J = 4.8, 8.2 Hz), 7.69-7.80 (2H, m), 7.87 (1H, m), 8.08 (1H, dt, J = 2.2, 8.0 Hz), 8.22 (1H, dd, J = 1.7, 7.5 Hz), 8.67 (1H, dd, J = 1.5, 4.9 Hz), 8.98 (1H, d, J = 2.4 Hz) |
| 270 | 0.86-1.10 (8H, m), 0.94 (3H, s), 1.26 (1H, s), 1.38-1.46 (1H, m), 1.49 (3H, s), 1.57-1.69 (5H, m), 1.75 (3H, s), 1.78-2.05 (2H, m), 2.18-2.21 (1H, m), 2.93 (1H, m), 3.80 (1H, d, J = 11.9 Hz), 3.84 (1H, d, J = 11.9 Hz), 4.84 (1H, dd, J = 5.0, 11.6 Hz), 5.04 (1H, m), 5.31 (1H, dd, J = 5.0, 11.8 Hz), 6.42 (1H, s), 7.40 (1H, dd, J = 4.9, 8.3 Hz), 7.70 (1H, d, J = 5.3 Hz), 8.09 (1H, dt, J = 1.7, 8.1 Hz), 8.69 (1H, dd, J = 1.6, 4.7 Hz), 8.97 (1H, d, J = 5.1 Hz), 9.00 (1H, d, J = 2.2 Hz), 9.17 (1H, s) |
| 271 | 0.85-1.08 (8H, m), 0.92 (3H, s), 1.26 (1H, s), 1.38-1.46 (1H, m), 1.48 (3H, s), 1.56-1.68 (5H, m), 1.79 (3H, s), 1.83-2.08 (2H, m), 2.18-2.21 (1H, m), 2.95 (1H, m), 3.76 (1H, d, J = 11.9 Hz), 3.86 (1H, d, J = 11.9 Hz), 4.83 (1H, dd, J = 4.9, 11.5 Hz), 5.04 (1H, m), 5.39 (1H, dd, J = 5.1, 11.9 Hz), 646 (1H, s), 7.34-7.45 (2H, m), 7.86 (1H, dd, J = 1.3, 8.0 Hz), 8.08 (1H, dt, J = 2.0, 8.0 Hz), 8.64 (1H, dd, J = 1.2, 4.7 Hz), 8.68 (1H, dd, J = 1.5, 4.9 Hz), 9.00 (1H, d, J = 2.2 Hz) |

Example 11

Preparation Example 1 [Wettable powder]

Compound according to the present invention

| | |
|---|---|
| (Compound No. 82) | 30 wt% |
| Clay | 30 wt% |
| Diatomaceous earth | 35 wt% |
| Calcium lignin sulfonate | 4 wt% |
| Sodium laurylsulfate | 1 wt% |

The above ingredients were homogeneously mixed together, and the mixture was ground to prepare wettable powder.

Preparation Example 2 [Dust]

Compound according to the present invention

| | |
|---|---|
| (Compound No. 82) | 2 wt% |
| Clay | 60 wt% |
| Talc | 37 wt% |
| Calcium stearate | 1 wt% |

The above ingredients were homogeneously mixed together to prepare dust.

Preparation Example 3 [Emulsifiable concentrate]

Compound according to the present invention

| | |
|---|---|
| (Compound No. 82) | 20 wt% |
| N,N-Dimethylformamide | 20 wt% |
| Solvesso 150 (Exxon Mobil Corporation) | 50 wt% |
| Polyoxyethylene alkylaryl ether | 10 wt% |

The above ingredients were homogeneously mixed and dissolved to prepare emulsifiable concentrate.

Preparation Example 4 [Granules]

Compound according to the present invention

| | |
|---|---|
| (Compound No. 28) | 5 wt% |
| Bentonite | 40 wt% |
| Talc | 10 wt% |
| Clay | 43 wt% |
| Calcium lignin sulfonate | 2 wt% |

The above ingredients were homogeneously ground and homogeneously mixed together. Water was added to the mixture, followed by thorough kneading. Thereafter, the kneaded product was granulated and dried to prepare granules.

Preparation Example 5 [Floables]
Compound according to the present invention

| | |
|---|---|
| (Compound No. 28) | 25 wt% |
| POE polystyrylphenyl ether sulfate | 5 wt% |
| Propylene glycol | 6 wt% |
| Bentonite | 1 wt% |
| 1% aqueous xanthan gum solution | 3 wt% |
| PRONAL EX-300 (Toho Chemical Industry Co., Ltd.) | 0.05 wt% |
| ADDAC 827 (K.I. Chemical Industry Co., Ltd.) | 0.02 wt% |
| Water | To 100 wt% |

All the above ingredients except for the 1% aqueous xanthan gum solution and a suitable amount of water were premixed together, and the mixture was then ground by a wet grinding mill. Thereafter, the 1% aqueous xanthan gum solution and the remaining water were added to the ground product to prepare 100 wt% floables.

Test Example 1: Pesticidal effect against Myzus persicae

Among the compounds of formula (I) produced by the conventional method described above, the compounds shown in Tables 1 to 14 and pyripyropene A were tested for pesticidal effect.

A leaf disk having a diameter of 2.8 cmφ was cut out from a cabbage grown in a pot and was placed in a 5.0 cm-Schale. Four adult aphids of Myzus persicae were released in the Schale. One day after the release of the adult aphids, the adult aphids were removed. The number of larvae at the first instar born in the leaf disk was adjusted to 10, and a test solution, which had been adjusted to a concentration of 20 ppm by the addition of a 50% aqueous acetone solution (0.05% Tween 20 added) was spread over the cabbage leaf disk. The cabbage leaf disk was then air dried. Thereafter, the Schale was lidded and was allowed to stand in a temperature-controlled room (light period 16 hr – dark period 8 hr) (25°C). Three days after the initiation of standing of the Schale, the larvae were observed for survival or death, and the death rate of larvae was calculated by the following equation.

Death rate (%) = {number of dead larvae/(number of survived larvae + number of dead larvae)} x 100

As result, it was found that the death rate was not less than 80% for compounds of Nos. 1, 6, 8, 9, 10, 12, 14, 16, 18, 20, 23, 25, 28, 34, 35, 36, 37, 38, 39, 40, 44, 45, 49, 54, 56, 57, 61, 69, 76, 82, 85, 86, 88, 90, 91, 98, 103, 106, 107, 108, 109, 111, 125, 128, 133, 135, 137, 139, 142, 153, 160, 161, 162, 164, 167, 169, 170, 171, 172, 176, 180, 182, 183, 186, 187, 190, 196, 201, 205, 206, 207, 208, 209, 210, 211, 212, 213, 214, 215, 216, 217, 218, 219, 220, 221, 222, 223, 226, 227, 228, 229, 230, 231, 232, 233, 236, 237, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, and 274 and pyripyropene A.

Test Example 2: Pesticidal effect against Myzus persicae

Among the compounds of formula (I) produced by the conventional method described above, the compounds shown in Tables 1 to 14 and pyripyropene A were tested for pesticidal effect.
A leaf disk having a diameter of 2.8 cmφ was cut out from a cabbage grown in a pot and was placed in a 5.0 cm-Schale. Four adult aphids of Myzus persicae were released in the Schale. One day after the release of the adult aphids, the adult aphids were removed. The number of larvae at the first instar born in the leaf disk was adjusted to 10, and a test solution, which had been adjusted to a concentration of 0.156 ppm by the addition of a 50% aqueous acetone solution (0.05% Tween 20 added) was spread over the cabbage leaf disk. The cabbage leaf disk was then air dried. Thereafter, the Schale was lidded and was allowed to stand in a temperature-controlled room (light period 16 hr – dark period 8 hr) (25°C). Three days after the initiation of standing, the larvae were observed for survival or death, and the death rate of larvae was calculated in the same manner as in Test Example 1.

As result, it was found that the death rate was not less than 80% for compounds of Nos. 12, 23, 28, 45, 54, 56, 76, 82, 85, 86, 90, 164, 201, 205, 206, 207, 212, 213, 217, 218, 219, 222, 227, 228, 229, 231, 232, 233, 237, 239, 240, 242, 246, 247, 249, 250, 252, 253, 256, 258, 261, 262, 264, 265, 266, 267, 269, 270, and 271.

Test Example 3: Pesticidal effect against Plutella xylostella

A cabbage leaf disk having a diameter of 5 cm was placed in a plastic cup. Test compounds, which had been diluted to a predetermined concentration by the addition of a 50 % aqueous acetone solution (Tween 20, 0.05% added), were spreaded over the cabbage leaf disk by means of a spray gun, and the cabbage leaf disk was then air dried. Five larvae at the second instar of Plutella xylostella were released in the cup. The cup was then lidded, and the larvae were reared in the temperature-controlled room (25°C). Three days after the treatment, the larvae were observed for survival or death, and the death rate of the larvae was calculated in the same manner as in Test Example 1.

As a results, it was found that the death rate was not less than 80% for compounds of Nos. 76, 213, 218, 237 and 250 at a concentration of 500 ppm.

Test Example 4: Pesticidal effect against Helicoverpa armigera

A cabbage leaf disk having a diameter of 2.8 cm was placed in a plastic cup. Test compounds, which had been diluted to a predetermined concentration by the addition of a 50 % aqueous acetone solution (Tween 20, 0.05% added), were spreaded over the cabbage leaf disk by means of a spray gun, and the cabbage leaf disk was then air dried. A larva at the third instar of Helicoverpa armigera was released in the cup. The cup was then lidded, and the larva was reared in the temperature-controlled room (25°C). Three days after the treatment, the larva was observed for survival or death. The test was repeated 5 times. Further, the death rate of the larvae were calculated in the same manner as in Test Example 1.

As a result, it was found that the death rate was not less than 80% for the compound of No. 219 at a concentration of 100 ppm.

Test Example 5: Pesticidal effect against Trigonotylus caelestialium

A wheat seedling was immersed for 30 seconds in a solution, in which each test compound had been diluted to a predetermined concentration by the addition of a 50 % aqueous acetone solution (Tween 20, 0.05% added). The wheat seedling was air dried, and then placed in a glass cylinder. Further, two larvae at the second instar of Trigonotylus caelestialium were released in the glass cylinder. The glass cylinder was then lidded, and the larvae were reared in the temperature-controlled room (25°C). During the test, the wheat seedling was supplid with water from the bottom of the glass cylinder. Three days after the treatment, the larvae were observed for survival or death, and the death rate of the larvae were calculated in the same manner as in Test Example 1.

As a result, it was found that the death rate was not less than 80% for compound of Nos. 218 and 261 at a concentration of 100 ppm.